(12) United States Patent
Nitsch et al.

(10) Patent No.: US 9,587,014 B2
(45) Date of Patent: Mar. 7, 2017

(54) TDP-43 SPECIFIC BINDING MOLECULES

(71) Applicants: Biogen International Neuroscience GmbH, Zug (CH); University of Zürich, Zürich (CH)

(72) Inventors: Roger Nitsch, Zumikon (CH); Christoph Hock, Erlenbach (CH); Maria Grazia Barenco Montrasio, Schindellegi (CH); Fabio Montrasio, Schindellegi (CH); Jan Grimm, Duebendorf (CH); Jean-Luc Baeriswyl, Zurich (CH); Paul Weinreb, Andover, MA (US); Janaky Coomaraswamy, Zurich (CH); Omar Quintero-Monzon, Waltham, MA (US)

(73) Assignees: Biogen International Neuroscience GmbH, Zug (CH); University of Zürich, Zürich (CH)

( * ) Notice: Subject to any disclaimer, the term of this patent is extended or adjusted under 35 U.S.C. 154(b) by 0 days.

(21) Appl. No.: 14/354,404

(22) PCT Filed: Oct. 26, 2012

(86) PCT No.: PCT/IB2012/002905
§ 371 (c)(1),
(2) Date: Apr. 25, 2014

(87) PCT Pub. No.: WO2013/061163
PCT Pub. Date: May 2, 2013

(65) Prior Publication Data
US 2014/0255304 A1 Sep. 11, 2014

Related U.S. Application Data

(60) Provisional application No. 61/553,113, filed on Oct. 28, 2011.

(51) Int. Cl.
C07K 16/18 (2006.01)
A61K 47/48 (2006.01)
A61K 39/395 (2006.01)
A61K 51/10 (2006.01)

(52) U.S. Cl.
CPC .......... *C07K 16/18* (2013.01); *A61K 39/3955* (2013.01); *A61K 47/48538* (2013.01); *A61K 51/1018* (2013.01); *C07K 2317/21* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| 5,688,511 A | 11/1997 | Gaynor et al. |
| 2009/0263824 A1* | 10/2009 | Lee et al. .................. 435/7.1 |
| 2010/0136573 A1 | 6/2010 | Petrucelli et al. |

FOREIGN PATENT DOCUMENTS

| CN | 101634656 A | 1/2010 |
| EP | 2 189 526 A1 | 5/2010 |
| WO | WO 2008/081008 A1 | 7/2008 |
| WO | WO 2009/008529 | 1/2009 |
| WO | WO 2009/099941 A2 | 8/2009 |
| WO | WO 2010/069603 | 6/2010 |

OTHER PUBLICATIONS

Mayo Clinic reference on Alzheimer's disease; printed on Aug. 8, 2015 from http://www.mayoclinic.org/diseases-conditions/alzheimers-disease/basics/causes/con-20023871.*
NINDS Information Page for Alzheimer's Disease, downloaded on Aug. 8, 2015 from http://www.ninds.nih.gov/disorders/alzheimersdisease/alzheimersdisease.htm.*
NINDS reference on ALS; printed on Aug. 8, 2015 from http://www.ninds.nih.gov/disorders/amyotrophiclateralsclerosis/detail_ALS.htm.*
D'Alton et al (Front Aging Neurosci. Aug. 19, 2014;6:204).*
Ma (Modern Drug Discovery 2004, 7(6)).*
Ittner et al (Nat Rev Neurol. Jun. 2015;11(6):360-6).*
Freskgard et al (Neuropharmacology. Mar. 10, 2016).*
Bond, C.J. et al. (2003) "Contributions of CDR3 to $V_HH$ Domain Stability and the Design of Monobody Scaffolds for Naïve Antibody Libraries" *J. Mol. Biol.*, 332:643-655.
Businesswire (Dec. 20, 2010) "Biogen Idec and Neurimmune Announce Agreement on Three Neurodegenerative Disease Programs" [online]. Retrieved from: http:/www.businesswire.com/news/home/20101220006526/en/Biogen-Idec-Neurimmune-Announce-Agreement-Neurodegenerative-Disease.
Dorfman, T. et al. (Sep. 29, 2006) "A Tyrosine-sulfated Peptide Derived from the Heavy-chain CDR3 Region of an HIV-1-neutralizing Antibody Binds gp120 and Inhibits HIV-1 Infection" *J. Biol. Chem.*, 281(39):28529-28535.
Hosse, R.J. et al. (2006) "A new generation of protein display scaffolds for molecular recognition" *Protein Science*, 15:14-27.
Igarashi, K. et al. (1995) "Specific Binding of a Synthetic Peptide Derived from an Antibody Complementarity Determining Region to Phosphatidylserine" *J. Biochem.*, 117:452-457.
(Continued)

*Primary Examiner* — Brian J Gangle
*Assistant Examiner* — Andrea McCollum
(74) *Attorney, Agent, or Firm* — Fish & Richardson P.C.

(57) ABSTRACT

Provided are novel TAR DNA-binding proteins of 43 kDa ("TDP-43")-specific binding molecules including polypeptides such as human antibodies, as well as fragments, derivatives and variants thereof. Also provided are methods related to these TDP-43 specific binding molecules. Assays, kits, and solid supports related to TDP-43-specific binding molecules, including polypeptides such as, human antibodies are also disclosed. The TDP-43-specific binding molecule, antibody, immunoglobulin chain(s), as well as binding fragments, derivatives and variants thereof can be used in pharmaceutical and diagnostic compositions for TDP-43 targeted immunotherapy and diagnosis, respectively.

33 Claims, 33 Drawing Sheets

(56) References Cited

OTHER PUBLICATIONS

International Search Report and Written Opinion mailed Jan. 16, 2014, in International Patent Application No. PCT/IB2012/002905, filed Oct. 26, 2012, by Biogen Idec International Neuroscience GmbH.

Johnson, B.S. et al. (Apr. 29, 2008) "A yeast TDP-43 proteinopathy model: Exploring the molecular determinants of TDP-43 aggregation and cellular toxicity" PNAS, 105(17):6439-6444.

Levi, M. et al. (May 1993) "A complementarity-determining region synthetic peptide acts as a miniantibody and neutralizes human immunodeficiency virus type 1 in vitro" Proc. Natl. Acad. Sci. USA, 90:4374-4378.

Nicaise, M. et al. (2004) "Affinity transfer by CDR grafting on a nonimmunoglobulin scaffold" Protien Science, 13:1882-1891.

Santa Cruz Biotechnology, Inc. (Mar. 26, 2009) "TARDP (41-7.1): sc-100871" [online]. Retrieved from the Internet: http://datasheets.scbt.com/sc-100871.pdf, on Jun. 3,2013 (1 page).

Shiina. Y. et al. (May 2010) "TDP-43 dimerizes in human cells in culture" Cell Mol. Neurobiol., 30(4):641-652.

Arai, T. et al. (2006) "TDP-43 is a component of ubiquitin-positive tau-negative inclusions in frontotemporal lobar degeneration and amyotrophic lateral sclerosis" Biochem. Biophys. Res. Commun., 351;602-611 (2006).

Caccamo, A. et al. (Jan. 2012) "Cognitive decline typical of frontotemporal lobar degeneration in transgenic mice expressing the 25-kDa C-terminal fragment of TDP-43" Am. J. Pathol., 180(1):293-302.

Cannon, A. et al. (Apr. 2012) "Neuronal sensitivity to TDP-43 overexpression is dependent on timing of induction" Acte Neuropathol., 123(6):807-823.

Custer, S.K. et al. (2010) "Transgenic mice expressing mutant forms VCP/p97 recapitulate the full spectrum of IBMPFD including degeneration in muscle, brain and bone" Hum. Mol. Genet., 19(9):1741-1755 (2010).

De Haard, H.J. et al. (Jun. 1999) "A large non-immunized human Fab fragment phage library that permits rapid isolation and kinetic analysis of high affinity antibodies" J. Biol. Chem., 274(26):18218-18230.

Dennis, J.S. and B.A. CITRON (2009) "Wobbler mice modeling motor neuron disease display elevated transactive response DNA binding protein" Neurosci., 185:745-750.

Duchen, L.W. and S.J. Strich (1968) "An hereditary motor neurone disease with progressive denervation of muscle in the mouse: the mutant 'wobbler'" J. Neurol. Neurosurg. Psychiatry, 31:535-542.

Forman, M.S. et al. (Oct. 2007) "TDP-43: A Novel Neurodegenerative Proteinopathy" Curr. Opin. Neurobiol., 17(5):548-555. NIH Public Access Author Manuscript; available in PMC May 7, 2009 (12 pages).

Furukawa, Y. et al. (May 2011) "A Seeding Reaction Recapitulates Intracellular Formation of Sarkosyl-Insoluble Transactivation Response Element (TAR) DNA-binding Protein-43 Inclusions" J. Biol. Chem., 286(21):18664-18672.

Giordana, M.T. et al. (Mar. 2010) "TDP-43 redistribution is an early event in sporadic amyotrophic lateral sclerosis" Brain Pathol., 20:351-360.

Gurney, M.E. et al. (1994) "Motor neuron degeneration in mice that express a human Cu,Zn superoxide dismutase mutation" Science, 264:1772-1775.

Hasegawa, M. et al. (2008) "Phosphorylated TDP-43 in frontotemporal lobar degeneration and amyotrophic lateral sclerosis" Ann. Neurol., 64(1):60-70. NIH Public Access Author Manuscript: available in PMC Jul. 1, 2009 (19 pages).

IGAZ, L.M. et al. (Feb. 2011) "Dysregulation of the ALS-associated gene TDP-43 leads to neuronal death and degeneration in mice" J. Clin. Invest., 121(2):726-738.

Jucker, M. and L.C. Walker (Oct. 2011) "Pathogenic Protein Seeding in Alzheimer's Disease and Other Neurodegenerative Disorders" Ann. Neurol., 70(4):532-540. NIH Public Access Author Manuscript; available in PMC Sep. 1, 2012 (15 pages).

Kou, P.H. et al. (Jan. 2009) "Structural insights into TDP-43 in nucleic-acid binding and domain interactions" Nucleic Acids Res., 37(6):1799-1808.

Lagier-Tourenne, C. et al. (Apr. 2010) "TDP-43 and FUS/TLS: emerging roles in RNA processing and neurodegeneration" Hum. Mol. Gen., 19:R46-R46.

MacKenzie et al. (Oct. 2010) "TDP-43 and FUS in amyotrophic lateral sclerosis and frontotemporal dementia" Lancet Neurol., 9(10):995-1007.

Neumann, M. et al. (Oct. 2006) "Ubiquilinated TCP-43 in frontotemporal lobar degeneration and amyotrophic lateral sclerosis" Science, 314(5796):130-133.

Neumann, M. et al. (Oct. 2007) "TDP-43 proteinopathy in frontotemporal lobar degeneration and amyotrophic lateral sclerosis: protein misfolding diseases without amyloidosis" Arch. Neurol., 64(10):1388-1394.

Neumann, M. et al. (Mar. 2007) "TDP-43-positive white matter pathology in frontotemporal lobar degeneration with ubiquitin-positive inclusions" J. Neuropath. Exp. Neurol., 66(3):177-183.

Polymenidou, M. and D.W. Cleveland (Oct. 2011) "The Seeds of Neurodegeneration: Prion-like Spreading in ALS" Cell, 147(3):498-508. NIH Public Access Author Manuscript; available in PMC Oct. 28, 2012 (17 pages).

Shan, X. et al. (Jul. 2009) "Mislocalization of TDP-43 in the G93A mutant SOD1 transgenic mouse model of ALS" Neuropharmacol. Lett., 458(2):70-74.

Swarup, V. et al. (Sep. 2011) "Pathological hallmarks of amyotrophic lateral sclerosis/frontotemporal lobar degeneration in transgenic mice produced with TDP-43 genomic fragments" Brain, 134:2610-2626.

Tatom, J.B. et al. (Apr. 2009) "Mimicking aspects of frontotemporal lobar degeneration and Lou Gehrig's disease in rats via TDP-43 overexpression" Mol. Ther., 17:607-613.

Tripathi, V.B. et al. (2014) "Tar DNA-binding protein-43 (TDP-43) regulates axon growth in vitro and in vivo" Neurobiol. Dis., 65:25-34.

Wegorzewska, I. et al. (Nov. 2009) "TDP-43 mutant transgenic mice develop features of ALS and frontotemporal lobar degeneration" Proc. Natl. Acad. Sci. USA, 106(44):18809-18814.

Wils, H. et al. (Feb. 2010) "TDP-43 transgenic mice develop spastic paralysis and neuronal inclusions characteristic of ALS and frontotemporal lobar degeneration" Proc. Natl. Acad. Sci. USA, 107(8):3858-3863.

Zhang, H.-X. et al. (2008) "Epitope mapping of 2E2-D3, a monoclonal antibody directed against human TDP-43" Neurosci. Lett., 434(2):170-174.

Zhang, Y.J. et al. (May 2009) "Aberrant cleavage of TDP-43 enhances aggregation and cellular toxicity" Proc. Natl. Acad. Sci. USA, 106(18):7607-7612.

European Examination Report in European Application No. 12824769.9, dated Oct. 20, 2016, 18 pages.

Goossens et al., "Additional file 1.pdf for: TDP-43 as a possible biomarker for frontotemporal lobar degeneration: a systematic review of existing antibodies," (Apr. 2015) 4 pages.

Goossens et al., "TDP-43 as a possible biomarker for frontotemporal lobar degeneration: a systematic review of existing antibodies," ACTA Neuropathaoglica Communications, Biomed Central LTD, London, UK, 3(1):15 (Apr. 2015).

Kwong et al., "Novel monoclonal antibodies to normal and pathologically altered human TDP-43 proteins," Acta Neuropathologica Communications, Biomed Central LTD., London UK, 2(1):33 (Mar. 2014).

Xu et al., "Wild-Type Human TDP-43 Expression Causes TDP-43 Phosphorylation, Mitochondrial Aggregation, Motor Deficits, and Early Mortality in Transgenic Mice," Journal of Neuroscience, 30(32):10851-10859 (Aug. 2010).

Yang et al., "The C-terminal TDP-43 fragments have a high aggregation propensity and harm neurons by a dominant-negative mechanism," PLOS ONE, 5(12):E15878.1 (Dec. 2010).

Fonnan et al., "Frontotemporal dementia: clinicopathological correlations" Ann. Neurol. 59:952-62 (2006).

(56) References Cited

OTHER PUBLICATIONS

International Preliminary Report on Patentability in International Application No. PCT/IB2012/002905, dated Apr. 29, 2014, 14 pages.
International Search Report and Written Opinion in International Application No. PCT/IB2012/002905, dated Jan. 16, 2014, 20 pages.
Kohler and Milstein, "Continuous cultures of fused cells secreting antibody of predefined specificity" Nature 256(5517):495-497 (1975).

* cited by examiner

NI-205.3F10-VH(variable heavy chain sequence VH (SEQ ID NOS:1, 2))
```
FR1---------------------------CDR1----FR2----------CDR2-----
EVQLLESGGDLVQPGGSLRLSCAASGFTFSSQAMSWVRQAPKGLEWVSALSRTGDYTWYAD
    V
--------------FR3-------------------------CDR3--------------JH-
SVRGRFTVSRDDSKNIFYLEMNSLRAEDTAVYYCAKNYYSSFGYNWAAFHIWGQGTMVTVSS
```

NI-205.3F10-VK(variable light chain sequence VK (SEQ ID NO:6))
```
FR1------------------------CDR1-----------FR2---------CDR2------
EIVLTQSPGTLSLSPGERATLSCRASQDVNNNYLAWYQQKPGQAPRLLIYGASRRATGVPDR
---FR3-------------------------CDR3---------JK----
FSGRGSGTDFTLTINRLEPEDFAMYFCQQYGGSPPYTFGQGTKLEIK
```

Fig. 1B

NI-205.51C1-VH (variable heavy chain sequence VH (SEQ ID NO:10))
```
FR1---------------------------CDR1------FR2----------CDR2---
EVQLVESGGGLVQPGGSLRISCTTSGFIFSDYWMHWVRQAPGKGLTWVSRINLDGSDTI
-----------FR3------------------------------CDR3-----JH-------
YADSVKGRFTISRDNDKNTLYLQMNSLRVEDTAIYYCARSRKSVWGQGTMVTVSS
```

NI-205.51C1-VL (variable light chain sequence VL (SEQ ID NO:14))
```
FR1----------------------CDR1------------FR2-------CDR2-----
QSALTQPASVSGSPGQSITISCTGSNTDVGAYDYVSWSQQLPGKAPKFVIFDVDVRPSGIS
----FR3------------------------CDR3---------JL---
DRFSGSKSGNTASLTISGLQAEDEADYYCSSYTKSGTLVFGGGTKVTVV
```

Fig. 1C

NI-205.21G2-VH (variable heavy chain sequence VH(SEQ ID NO:18))
```
FR1----------------------------CDR1----FR2---------CDR2---
QVQLVQSGAEVKKPGASVKVSCKTSGYSFTSYTLHWVRQAPGHRPEWMGWINAAFINT
-----------FR3----------------------------CDR3-------JH-----
KYSQKFQGRITLTRDTSANIAYLELRSLTTEDTAVYYCARRASGSNGLDVWGQGTTVTVSS
```

NI-205.21G2-VK (variable light chain sequence VK(SEQ ID NO:22)
```
FR1---------------------CDR1--------FR2----------CDR2--
DIQMTQSPSSLSASVGDRITITCQASRDITNYLNWYQQKPGKAPKLLIYDASYLETG
FR3--------------------------CDR3--------JK---
VPSTFSGSGSGTHFTLTISSLQPDDFATYYCQQYDSVPLTFGGGTKVEIK
```

NI-205.8A2-VH (variable heavy chain sequence VH (SEQ ID NOS:26, 27)
```
FR1-------------------------CDR1-----FR2--------CDR2--
QVQLVESGGGVVQPGKSLRLSCAASGFTFRDHGMHWVRQAPGKGLEWVAVIWLDGSS
E
-------------FR3-------------------------------CDR3-----------JH--
RFYADSVEGRFTISRDNSKNTLYLQLTSLRAEDTAIYYCARDRVASEGTAFDVWGQGTMVTVSS
                                                        T
```

NI-205.8A2-VK (variable light chain sequence VK (SEQ ID NO:31))
```
FR1---------------------CDR1---------FR2--------CDR2-----
EIVLTQSPATLSLSPGERATLSCWASQNVNHYLVWYQQRPGQAPRLLLYDTSVRAAGIP
-----FR3------------------------CDR3-----JK--
ARFIGSGSGTHFTLTISSLEPEDSAVYYCQHRSDWTFGQGTKVEIK
```

Fig. 1E

NI-205.15F12-VH (variable heavy chain sequence VH(SEQ ID NO:35, 36))
```
FR1--------------------------CDR1-------FR2------CDR2--
QVQLVQSGTAVKKPGASVKVSCKASGFSFNGYYMHWVRQAPGQGLEWMGVINPNGG
E    E
-------------FR3-----------------------------CDR3--------JH----
STNYAQKFKGRITMSADTPARSVSMELGSLRSDDTAMYYCARLPVNIEVLDLWGQGTLVTVSS
```

NI-205.15F12-VK (variable light chain sequence VK (SEQ ID NOS:40,41))
```
FR1------------------------CDR1-------------FR2------CDR2
DIVMTQSPDSLAVSLGERATINCRSSQTVLFSSNDKNYLAWYQQKPGQPPKLLIYWASV
E    L
------FR3---------------------------CDR3-------JK----
RASGVPDRFSGSGSGTDFSLTINGLQAEDVAVYYCQQSSTAPLTFGGGTKVEIK
```

Fig. 1F

NI-205.113C4-VH (variable heavy chain sequence VH (SEQ ID NO:45))
```
FR1---------------------------CDR1-----FR2---------CDR2--
QVQLVQSGAEVKKPGASVKVSCKASGYTFTNYYMHWVRQAPGQGLEWMGIINPSGGR
-------------FR3-------------------------------CDR3-------
TSYAQKFQGRASMTRDTSTSTVYMEVISLRSEDTAVYYCARQRPSGYSGYGPSESYGNP
-------------JH----
TDDAFDVWGQGTTVTVSS
```

NI-205.113C4-VL (variable light chain sequence VL (SEQ ID NO:49))
```
FR1--------------------CDR1----------FR2-------CDR2---FR3
SYVLTQPPSVSVAPGQTARITCGGNNIGSRGVHWYQQRPGQAPVLVVYDDSDRPSGIPE
-------------------------------CDR3----------JL--
RFSGSNSGDTATLTISRVEVGDEADYYCQVWDNSSDHLVVFGGGTKLTVL
```

Figure 1G-I

Fig. 1G
NI-205.25F3-VH (variable heavy chain sequence VH (SEQ ID NOS:53,129))
```
FR1----------------------------CDR1-----FR2--------CDR2---
QVQLVESGGGVVQPGRSLRLSCAASGFTFSNYVMYWVRQAPGKGLEWVAFISYDGSNK
E
-----------FR3--------------------------------CDR3-------
YYPDSVKGRFTISRDNSMNTLYLQMDSLRAEDTAVYYCARDTYQYDSSTYYPYFYYG
--------JH----
MDVWGQGTTVTVSS
```

NI-205.25F3-VL (variable light chain sequence VL (SEQ ID NO:57))
```
FR1-----------------------CDR1-----------FR2-------CDR2-----
QSALTQPASVSGSPGQSITISCIGTSSDVGGYNYVSWYQQHPGKAPKLMIYEVSNRPSGV
-----FR3--------------------------CDR3----------JL------
SSRFSGSKSGNTASLTISGLQSEDEADYYCSSFASSSTSVTFGGGTKLTVL
```

Fig. 1H
NI-205.87E7-VH (variable heavy chain sequence VH (SEQ ID NO:61))
```
FR1----------------------------CDR1----FR2----------CDR2-----
EVQLLESGGGLVQPGGSLRLSCAASGFTFSSYAMSWVRQAPGKGLEWVSAISGGGDRT
-------------FR3-------------------------------CDR3------
YSADSVKGRFTISRDNSKNTLYLQINSLRVEDTAVYYCAQGGGGEMTAVTMDGTYYG
------JH------
MDVWGQGTTVTVSS
```

NI-205.87E7-VL (variable light chain sequence VL (SEQ ID NO:65))
```
FR1-----------------------CDR1------------FR2------CDR2----
QSALTQPRSVSGSPGQSITISCTGTSSNVGTYKFVSWYQQHPGKAPKLMIYDVTKRPSGV
-FR3----------------------------CDR3--------JL---
PDRFSGSKSGNTASLTISGLQAEDEADYYCCSYAGSYTYVFGSGTKVTVL
```

Fig. 1I
NI-205.21G1-VH (variable heavy chain sequence VH (SEQ ID NO:69))
```
FR1---------------------------CDR1-----FR2--------CDR2---
QVQLVESGGGVVQPGMSLRLSCAASGFSFSSHGMHWVRQTPGKGLEWLAVISYDASNK
-----------FR3---------------------------CDR3--------JH----
SYADSVKGRFTISRDNSKKTLYLQMDSLRVEDTALYYCANAFSSSASGGYWGQGTLVTVSS
```

NI-205.21G1-VK: (variable light chain sequence VK(SEQ ID NO:73))
```
FR1-------------------------CDR1------------FR2-------CDR2-
DVVMTQSPLSLPVTLGQPASISCRSSQSLVHSDGVTYLNWFQQRPGQSPRRLIYKVSNRD
FR3-------------------------------CDR3---------JK--
SGVPDRFSGSGSGTDFTLEISRVEAEDVGIYYCMQGTHWPPWTFGQGTKVEIK
```

NI-205.68G5-VH (variable heavy chain sequence VH (SEQ ID NOS:77,78))
```
FR1---------------------------CDR1----FR2---------CDR2---
QVQLVESGGGVVQPGRSLRLSCAASGFTFSSYGMHWVRQAPGKGLEWVAIIYYDSSQR
                                                         E
------------FR3--------------------------------CDR3--------
YYADSVKGRFTISRDNSKNALYLQMNSLRAEDTALYYCARDLPFHYHRSASFAPSDTW
JH--------
GQGTLVTVSS
```

NI-205.68G5-VK (variable light chain sequence VK( SEQ ID NOS:82,83))
```
FR1------------------------CDR1----------FR2-------CDR2-----
EIVLTQSPGTLSLSPGERATLSCRASQAVTNNYLAWYQQKPGQAPRLLVYAASSRATGIP
    M
FR3--------------------------CDR3---------JK--
RFYGSGSGADFTLTISRLEPEDFAVYYCQQYGTSPITFGQGTRLEIK
```

Fig. 1K

NI-205.20A1-VH (variable heavy chain sequence VH (SEQ ID NO:87))
```
FR1---------------------------CDR1---FR2-----------CDR2---
EVQLVESGGGLVQPGGSLRLSCAASGFTFSSYRMNWVRQAPGKGLEWVSYISTSSSTIY
-----------FR3--------------------------CDR3-----JH----
YADSVKGRFTISRDNAKNSLYLQMNSLRAEDTAVYYCARAFDYWGQGTLVTVSS
```

NI-205.20A1-VK (variable light chain sequence VK (SEQ ID NO:122))
```
FR1----------------------CDR1---------FR2--------CDR2---FR3
EIVLTQSPGTLSLSPGERATLSCRASQSVSSSYLAWYQQKPGQAPRLLIYGASSRATGIPD
---------------------------CDR3-------JK----
RFSGSGSGTDFTLTIIRLEPEDFAVYYCQQYGSSPFTFGQGTKVEIK
```

NI-205.41D1-VH (SEQ ID NO:130):

EVQLVESGGGLVQPGGSLRLSCAAS<u>GFTFSTYYMS</u>WVRQAPGKGLEWVA<u>NIKQDGSEKYYVDSVKG</u>RFTIS
RDNARNSLYLQMHSLRAEDTAVYYCAS<u>PPGW</u>WGQGTLVTVSS

NI-205.41D1-VK (SEQ ID NO:134):

DIVMTQTPLSLSVTPGQPASISC<u>KSSQSLLHSDGKTYLY</u>WYLQKPGQPPQLLIY<u>EVSNRF</u>SGVPDRFSGSGSG
TDFTLKISRVEAEDVGVYYC<u>MQSIQLPVT</u>FGGGTKVEIK

Fig. 3B

NI-205.29E11-VH (SEQ ID NO:138):

QVQLVQSGAEVKKPGASVKVSCKAS<u>GYIFTDYFIH</u>WIRQAPGQGLEWMG<u>WIKPKSGGTDYAEKFQG</u>RVTL
TRDTSITTVYMELSRLNSDDTAVYYCAR<u>LKYSVPDSD</u>YWGQGTLVTVSS

NI-205.29E11-VK (SEQ ID NO:142):

DVVMTQSPLSLPVTLGQSASISC<u>RSSQGLVHSDGNTYLN</u>WFHQRPGQSPRRLIY<u>KVFNRDS</u>GVSDRFSGSGS
GSDFTLMISRVEAEDVGIYYC<u>MQGTLWPLT</u>FGQGTKVEIK

Fig. 3C

NI-205. 9E12-VH (SEQ ID NO:146):

EVQLVESGGGLVKPGGSLRLSCATS<u>GFNFSNVWIS</u>WVRQAPGKGLEWVG<u>RIKSKNDGGTTEYAAPVKG</u>RF
TISRDDSKNTVYLQMNSLKTEDAGVYYCTT<u>DPYHYFDMGGPGFGP</u>WGQGTLVTVSS

NI-205. 9E12A-VK (SEQ ID NO:150):

DIVMTQSPDSLAVSLGERATINC<u>KSGQSVLYRSNNRNYIA</u>WYQQKPGQPPKLLIY<u>WASTRES</u>GVPDRFSGSG
SGTDFTLTISSLQAEDVAVYYC<u>QQYYSNRWT</u>FGQGTKVEIK

NI-205. 9E12D-VK (SEQ ID NO:151):

DIVMTQSPDSLAVSLGERATINC<u>KSSQSVSYSSNNKNFLS</u>WYQQKPGQPPKLLIY<u>WASTRES</u>GVPDRFSGSG
SGTDFTLTISSLQAEDVAVYYC<u>QQYSSLPIS</u>FGQGTRLEIK

NI-205.98H6-VH (SEQ ID NO:155):

EVQLLESGGALVQPGGSLRLSCAASGLTFSRHAFSWVRQAPGKGLEWVAISSGSGGNTYYAASVKGRFTISR
DESKNTLYLQMNSLRVEDTALYYCAKEVLEWSLLSRYMDVWGKGTTVTVSS

NI-205.98H6-VL (SEQ ID NO:159):

QSVLTQPPSASGTPGQRVTISCSGSSSNIGGNTVNWYHQLPGTAPKLLVYSTNQRPSGVPDRFSGSKSGTSA
SLAISGLQAEDEADYYCATWDDSLNGWVFGGGTKLTVL

Fig. 3E

NI-205.10D3-VH (SEQ ID NO:163):

QVQLQESGPGLVKPSETLSLTCTVSGGSITDYYWSWIPQPPGKGLEWIGYIHDSGTTRYNPSLTSRLSMSLDT
STNQVSLRLTSVTAADTAVYYCAKVPDYWGQGTLVTVSS

NI-205.10D3-VK (SEQ ID NO:167):

DIVMTQSPDSLAVSLGERATINCKSSQSVLYNSDNKNYLAWLQQKPGQPPKVLIYWASTREFGVPDRFSGS
GSGTDFTLTISSLQAEDVAVYYCHQYYSVPFTFGGGTKVEIK

Fig. 3F

NI-205.44B2-VH (SEQ ID NO:171):

QVQLQESGPGVVKPSQTLSLTCTVSGVSVGSGDYYWSWIRHHPGKGLEWIGYISFFGSSNYNPSLKGRVSM
SVDTSNNQFSLNLKSVTAADTAVYFCATGNAYSFWGQGTMVTVSS

NI-205.44B2-VL (SEQ ID NO:175):

QSALTQPASVSGSPGQSITISCTGTSSDIGTHNLVSWYQQHPGKAPKLIIYEIFERPSGISSRFTGSKSGNTASLT
ISGLQAEDEADYFCCAYSVTVIFGGGTKLTVL

NI-205.38H2-VH (SEQ ID NO:179):

EVQLVESGGDLVQPGGSLRLSCTAS<u>GFNLGDYWMH</u>WVRQVPGKGLVWVS<u>RISSDGASVSYADFVEGR</u>FTI
SRGNARNTLFLELNSLRLDDTAVYYCAM<u>GVV</u>WGQGTLVTVSS

NI-205.38H2-VL (SEQ ID NO:183):

SYELTQPPSVSVSPGQTATISC<u>SGDALPKRYAY</u>WYKQKSGQVPVLIIY<u>EDNKRPS</u>GIPARFSGSSSGTMATLTI
TGAQVDDEADYYC<u>YSSDNSDTYSV</u>FGGGTKLTVL

Fig. 3H

NI-205.36D5-VH (SEQ ID NO:187):

QVQLVESGGGVVQPGRSLRLSCAAS<u>RFTFSSYGMH</u>WVRQAPGKGLEWVA<u>LIYYDATQKYYADSVKG</u>RFTIS
RDNSKNALYLQMTSLRADDTAVYYCAR<u>DLPYHYHRSASFAPADT</u>WGQGTLVTVSS

NI-205.36D5-VK (SEQ ID NO:191):

EIVLTQSPGTLSLSPGERATLSC<u>RASQTISNNYLA</u>WYQQKPGQAPRLLVY<u>AASSRAT</u>GIPDRFYGSGSGADFTL
TISRLEPEDFVVYYC<u>QQYGSSPIT</u>FGQGTRLEIK

Fig. 3I

NI-205.58E11-VH (SEQ ID NO:195):

EVQLLESGGGLVQPGGSLRLSCAAS<u>GFTFSSYSMS</u>WVRQAPGKGLEWVA<u>TVGYGGTIYYADSVKG</u>RFTISR
DNSKNTLYLEMNSLRAEATAVYYCAK<u>ANYGGNRFGLDV</u>WGQGTTVTVSS

NI-205.58E11-VL (SEQ ID NO:199):

QSALTQPPSASGSPGQSVTISC<u>TGTSSDVGGYNYVS</u>WYQHQPGKAPKLMIY<u>EVSKRPS</u>GVPDRFSGSKSGN
TASLTVSGLQAEDEADYYC<u>SSYAGSNNLGV</u>FGTGTEVTVL

NI-205. 14H5-VH (SEQ ID NO:203):

EVQLLESGGGLVQPGGSLRLSCAASGFTFRNYAMAWVRQAPGKGLEWVSAIPARGDKTYYADSVRGRFTIS
RDISKSALYLQMNSLRVEDTAVYYCAKAHHLYNKNFDYWGQGTLVTVSS

NI-205. 14H5-VK (SEQ ID NO:207):

EIVLTQSPGTLSLSPGETVTLSCRASQSVSSSNLAWYQQKPGQAPRLLIYGASSRATGIPDRFSGRGSGTDFTL
TISRLEPEDFAVYYCQHYGTFGQGTKVDIK

Fig. 3K

NI-205. 31D2-VH (SEQ ID NO:211):

EVQLLESGGGSVQPGGSLRLSCAASGFTFSTYVMSWVRQAPGKGLEWVSAISRRGGSTYYADSVKGRFTISR
DNSKNTLYLQMNSLRAEDTAVYYCAKDRWLTGRTGGVFDIWGQGTMVTVSS

NI-205. 31D2-VK (SEQ ID NO:215):

DIQMTQSPSSLSASVGDRVTITCQASQDISNYLNWYQQKPGKAPKLLIYDASNLETGVPSRFSGSGSGTDFTF
TISSLQPEDTATYYCQQYDNLPLTFGGGTKVEIK

Fig. 3L

NI-205. 8F8-VH (SEQ ID NO:219):

EVQLLESGGGLVQPGGSLRLSCAASGYTFSYYAMSWVRQAPGKGLEWVSTIGDSGSTTHYADSVKGRFTISR
DNSKSTLYLQMNSLRAEDTAVYYCAKGLGPVAAIGDYWGQGTLVTVSS

NI-205. 8F8-VL (SEQ ID NO:223):

QSVLTQPPSASGTPGQRVTISCSGSSSNIGSNNVYWYQQLPGTAPKLLVYRNNQRPSGVPDRVSGSKSGSSA
SLAISGLRSEDEADYYCAAWDDSLRGYVFGTGTKVTVL

NI-205.31C11 VH (SEQ ID NO:227):

QVQLVESGGGVVQPGRSLRLSCVASGFTFD<u>NYGMH</u>WVRQAPGKGLEWLA<u>VISYGGDHQFYGDSVKD</u>RFT
ISRDNSKNTAYLQMHSLRPDDTAVYYCAT<u>GVTPDF</u>WGQGTLVTVSS

NI-205.31C11 VK (SEQ ID NO:231):

DVVMTQSPLSLPVTLGQPASISC<u>RSSQSLVHSDGNTYLN</u>WFQQRPGQSPRRLIY<u>KVSHRDS</u>GVPDRFSGSGS
GTDFTLKISRVEAEDVGVYYC<u>LQGTHWPPFT</u>FGQGTKLEIK

Fig. 3N

NI-205.8C10 VH (SEQ ID NO:235):

EVQLVESGGGLVNPGGSLRLSCTASGFSFS<u>TYSMN</u>WVRQAPGKGLEWVS<u>LITSSGSYIYYADSVKG</u>RFTISRD
DAKNSLYLQMNSLRAEDTAVYYCAN<u>MLAAAGSHYFHY</u>WGQGTLVTVSS

NI-205.8C10 VK (SEQ ID NO:239):

DIVMTQTPLSSPVTLGQPASISC<u>RSSQSLVHSDGNTYLS</u>WLQQRPGQPPRLLIY<u>KISERFS</u>GVPDRFSGSGAG
TDFTLKISRVEAEDVGVYYC<u>MQVTQFPIT</u>FGQGTRLEIK

Fig. 3O

NI-205.10H7 VH (SEQ ID NO:243):

QVQLVESGGGVVQPGRSLRLSCAASGFTFS<u>NYAMH</u>WVRQAPGKGLEWVA<u>VIWYDGSKKYYGDSVKG</u>RFT
ISRDNPKNTLYLQMNSLRVEDTAIYYCVP<u>DAFDM</u>WGQGTMVTVSS

NI-205.10H7 VK (SEQ ID NO:247):

DIVMTQTPLSSPVTLGQPASISC<u>RSSQSLVHTDGKTYLS</u>WLHQRPGQPPRPLIY<u>KMSKRFS</u>GVPDRFSGSGA
ETEFTLKISRVEAEDVGIYYC<u>LQLTQFPIT</u>FGQGTRLEIK

NI-205.1A9 VH (SEQ ID NO:251):

QVQLVQSGSELKKPGASVKVSCKASGYTFTS<u>YAMN</u>WVRQAPGQGLEWMG<u>WINTNTGNPTYAQGFTG</u>RF
VFSLDTSVSTAYLQISSLKAEDTAVYYCAR<u>DRIDGSSWSSWFDP</u>WGQGTLVTVSS

NI-205.1A9 VL (SEQ ID NO:255):

QSVLTQPPSVSGAPGQRVTISC<u>TGSSSNIGAGYDVH</u>WYQQLPGTAPKLLIY<u>GNSNRPS</u>GVPDRFSGSKSGTS
ASLAITGLQAEDEADYYC<u>QSFDSSLSSS</u>VFGGGTKLTVL

Fig. 3Q

NI-205.14W3 VH (SEQ ID NO:259):

QVQLVQSGSELKKPGASVKVSCKASGYPVN<u>NYAIN</u>WVRQAPGQGLEWMG<u>FINTNTGIPTYAQGFTG</u>RFVF
SLDTSVNTAYLQISGLKADDTAVYYCAR<u>VGIVGVIVFDY</u>WGQGTLVTVSS

NI-205.14W3 VK (SEQ ID NO:263):

DVVMTQSPDSLAVSLGERATINC<u>KSSQSVLSSSKNKNHLA</u>WYQQKPGQPPKLLIY<u>WASTRES</u>GYWASTRES
GVPDRFSGSGSGTDFTLTISSLQAEDVAVYYC<u>QQYYSPSVT</u>FGGGTKVEIK

Fig. 3R

NI-205.19G5 VH (SEQ ID NO:267):

QVQLVESGGGVVQPGRSLRLSCAASGFTFS<u>SYGMH</u>WVRQAPGKGLEWVA<u>IIYYDSSQRYYADSVKG</u>RFTIS
RDNSKNALYLQMNSLRAEDTALYYCAR<u>DLPFHYHRSASFAPSDT</u>WGQGTLVTVSS

NI-205.19G5 VK (SEQ ID NO:271):

EIVLTQSPGTLSLSPGERATLSC<u>RASQAVTNNYLA</u>WYQQKPGQAPRLLVY<u>AASSRAT</u>GIPDRFYGSGSGADFT
LTISRLEPEDFAVYYC<u>QQYGTSPIT</u>FGQGTRLEIK

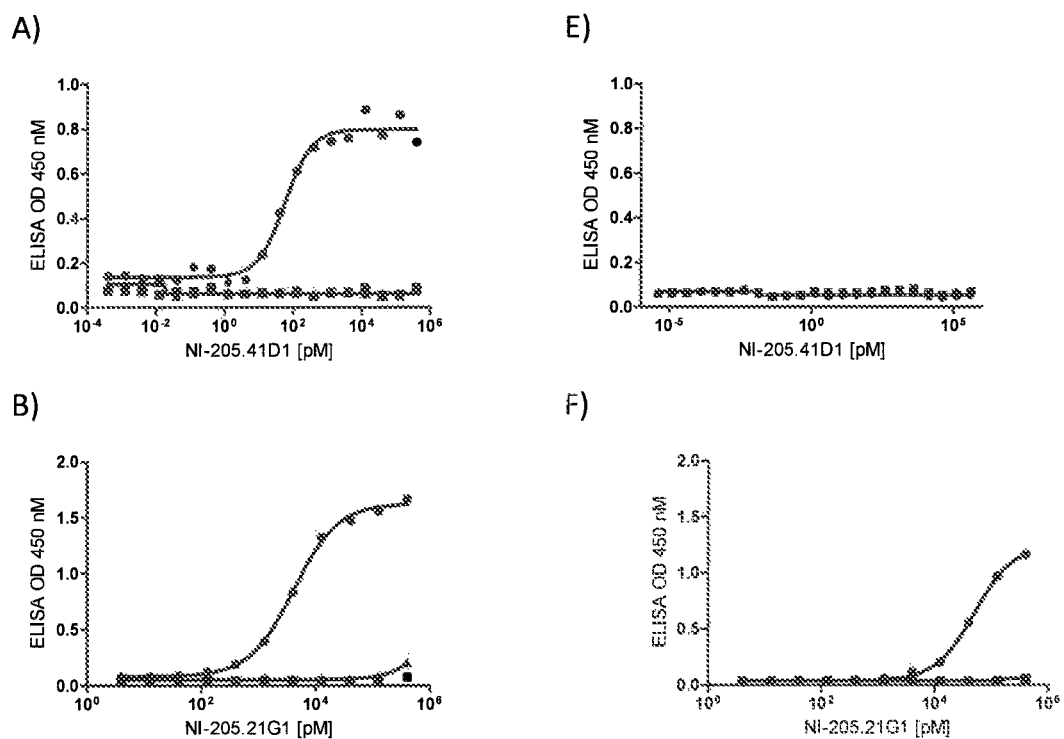
Figure 4A, B, E and F
Determination of binding affinity (EC$_{50}$) for human TDP-43

Figure 4C, D, G, and H
Determination of binding affinity (EC$_{50}$) for human TDP-43
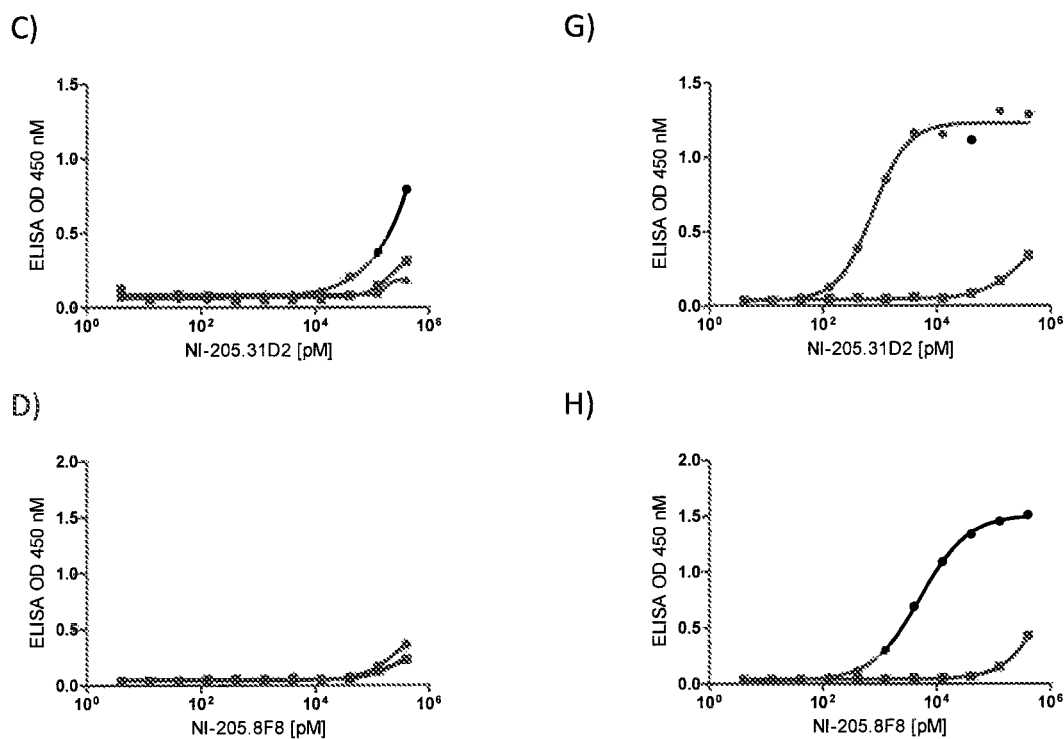

Figure 5A-I
Binding to distinct TDP-43 domains
A)
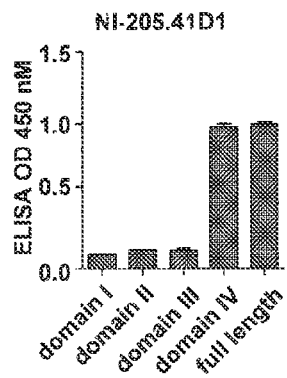
B)
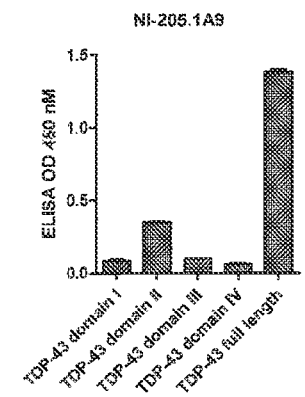
C)
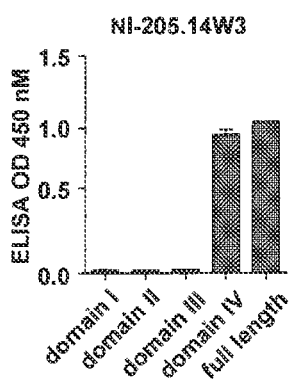
D)
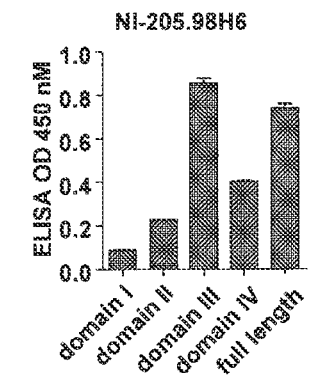
E)
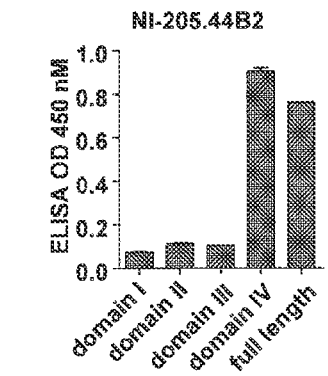
F)
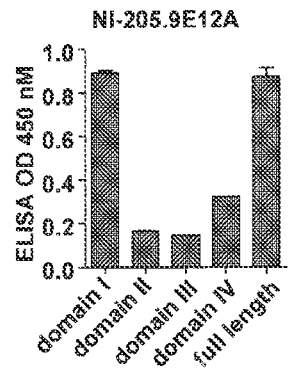
G)
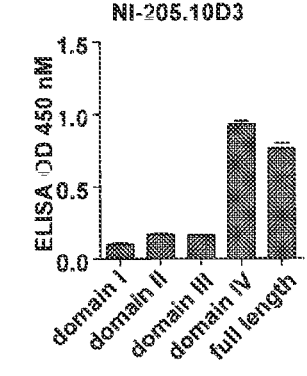
H)
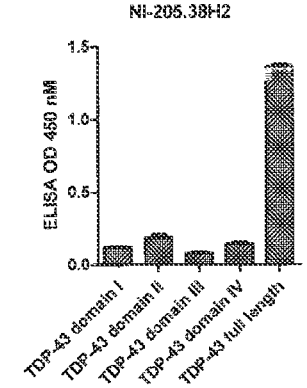
I)
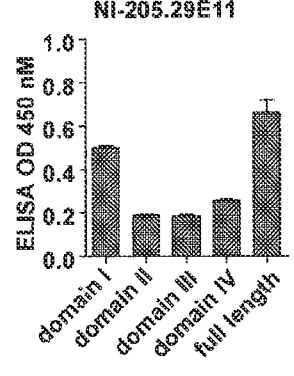

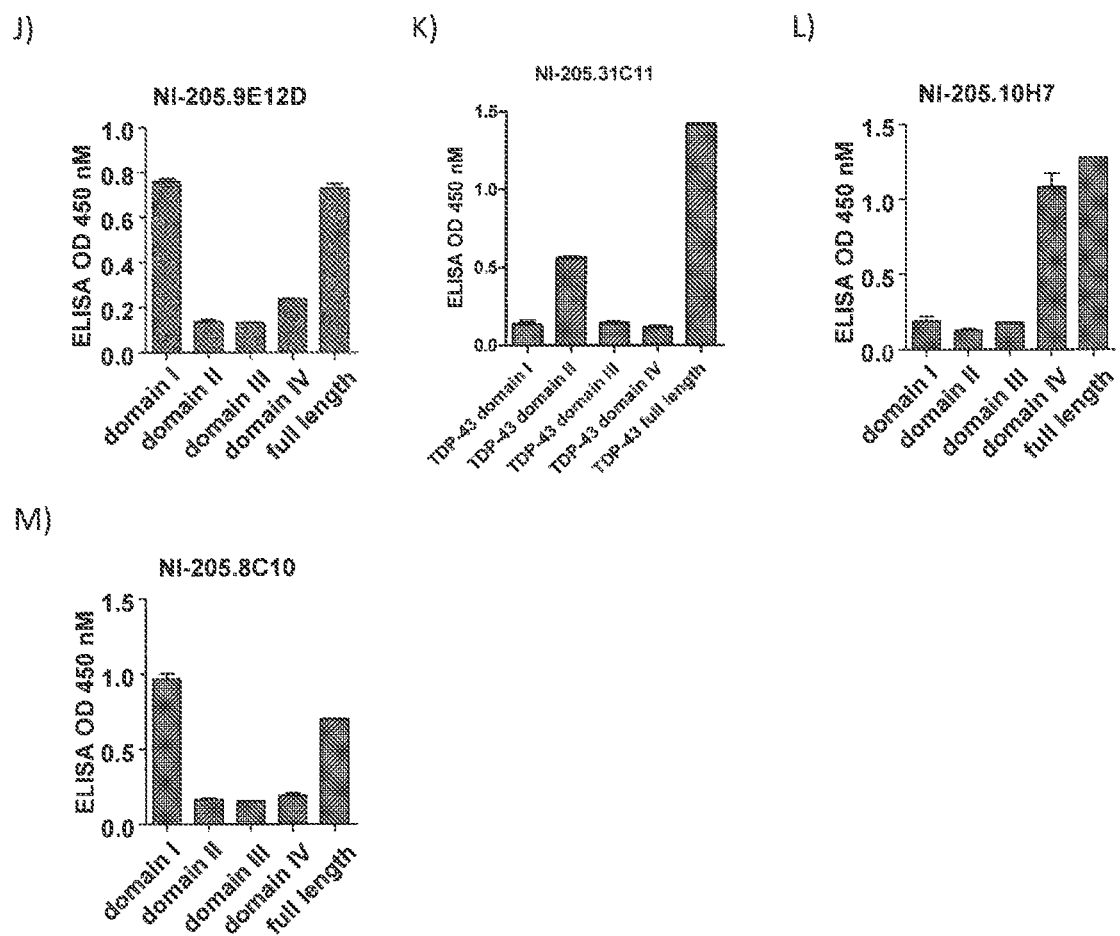
Figure 5J-M
Binding to distinct TDP-43 domains

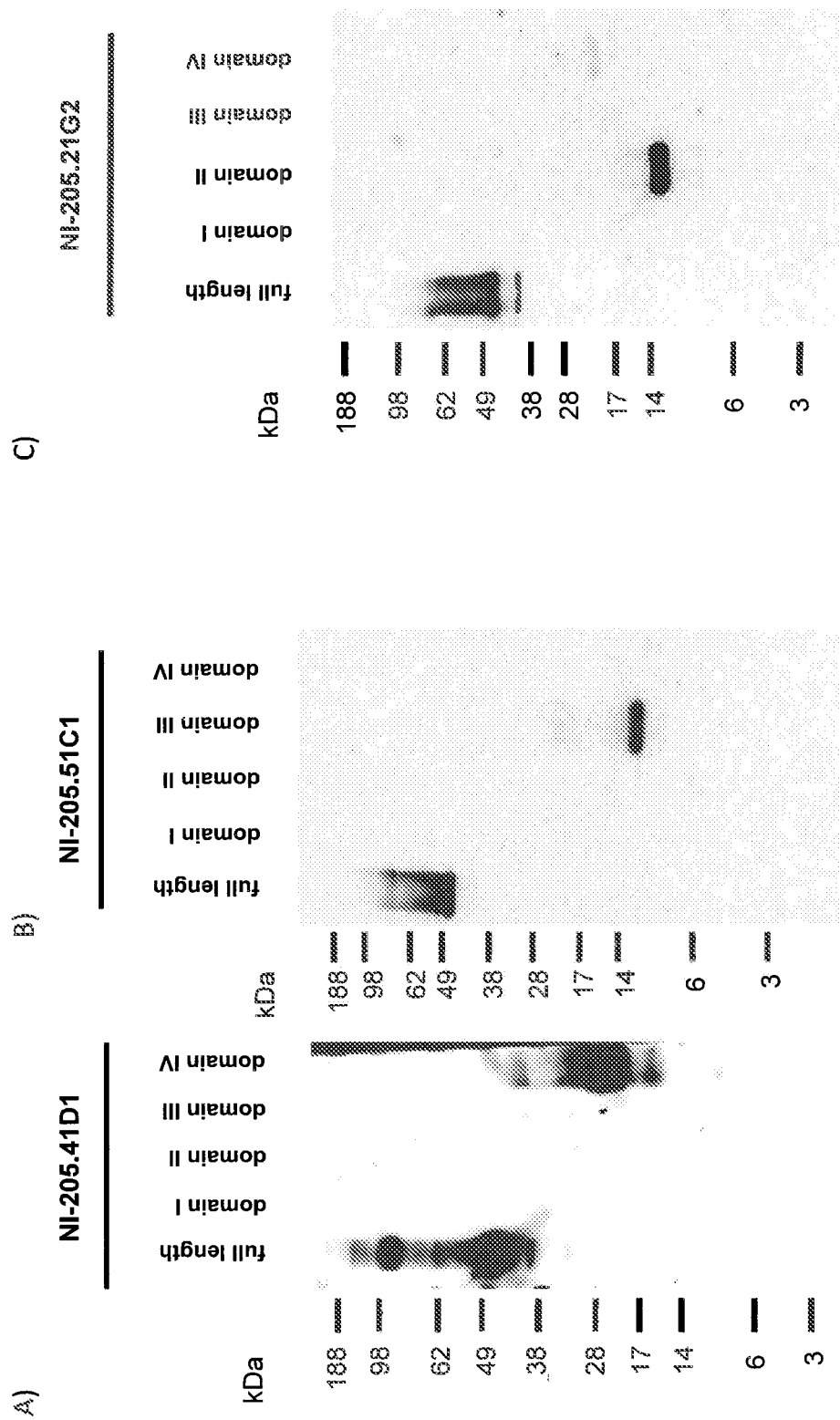
Figure 6A-C
Binding to distinct TDP-43 domains by immunoblot

Figure 6D-F
Binding to distinct TDP-43 domains by immunoblot
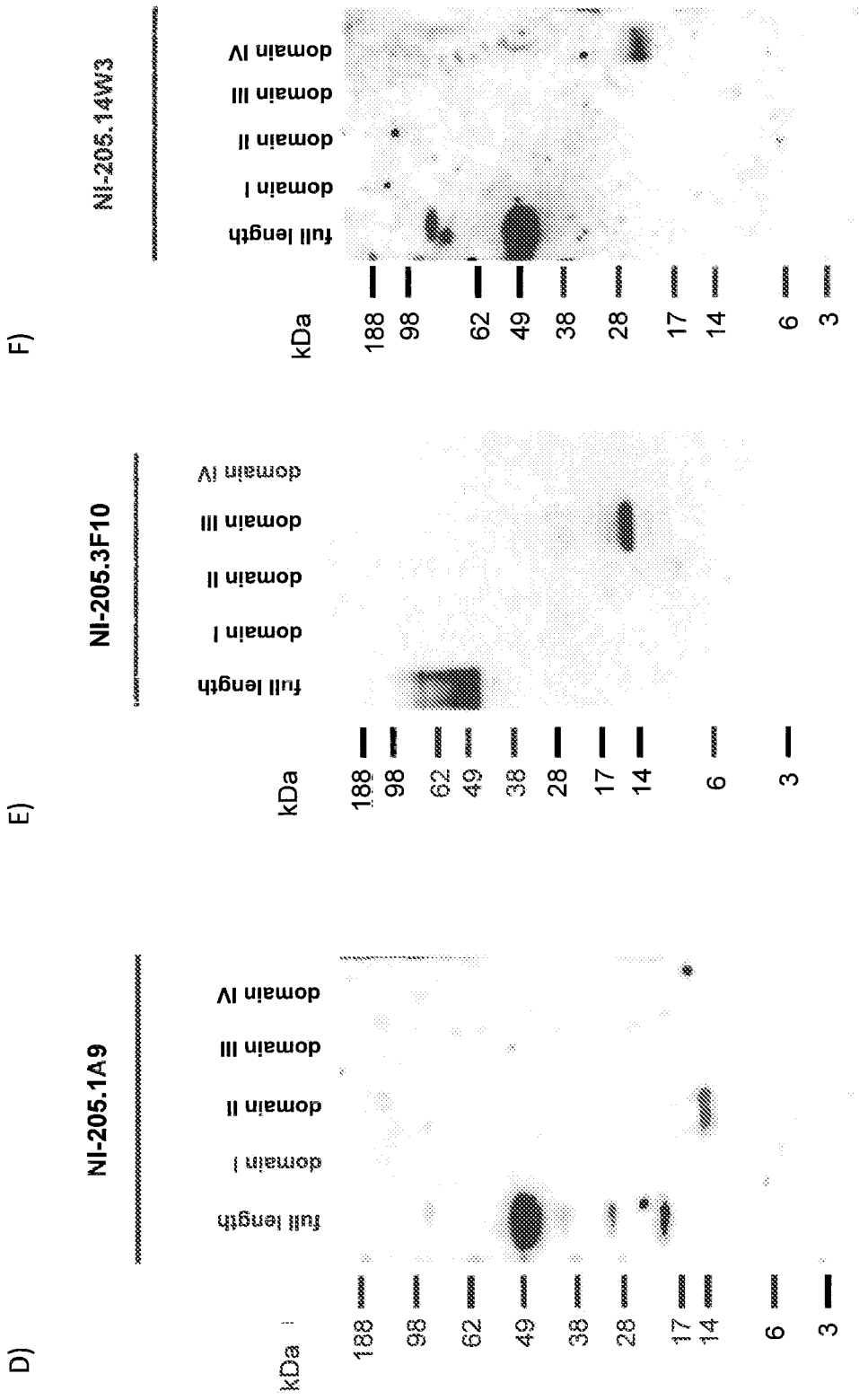

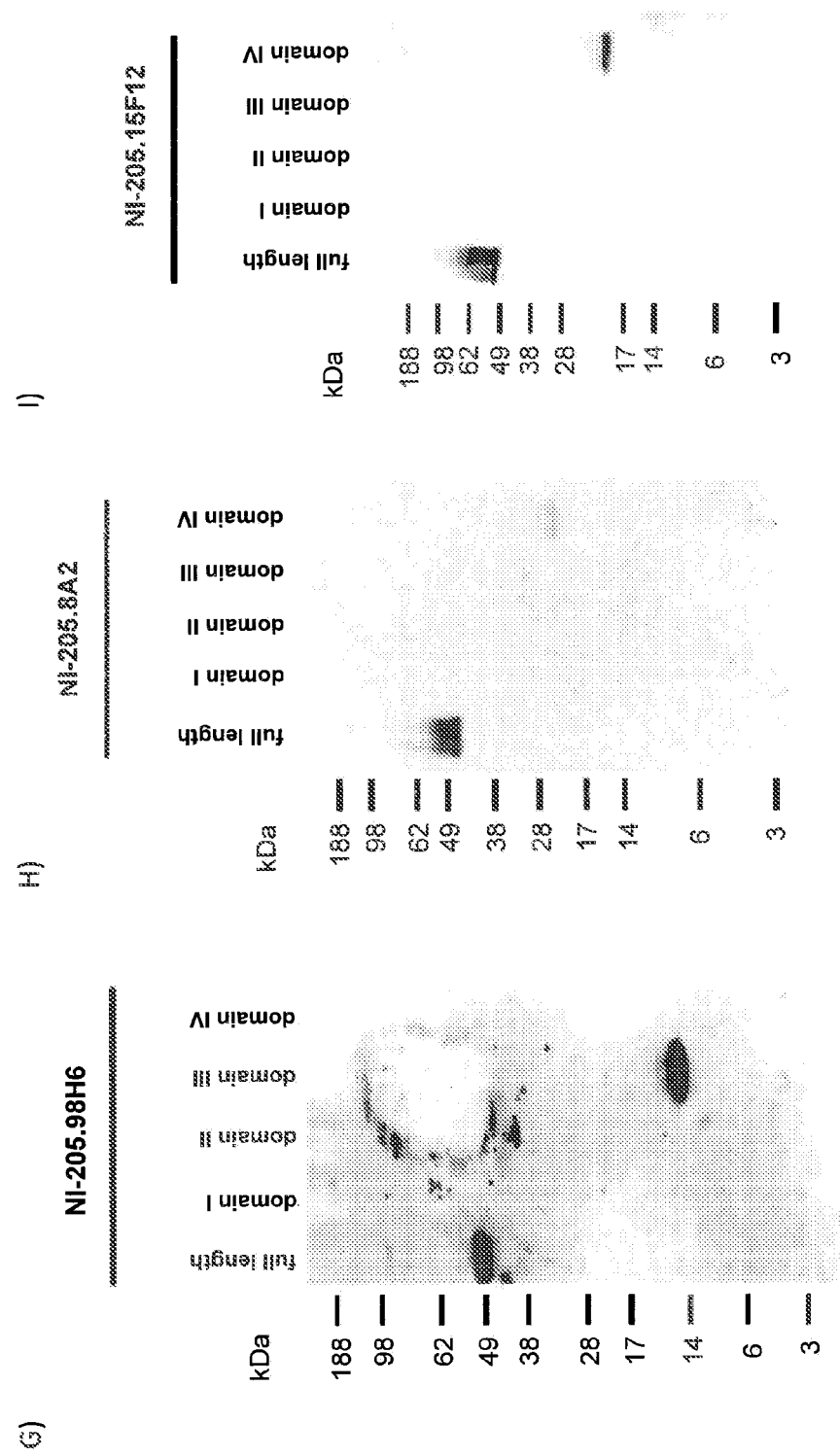
Figure 6G-I
Binding to distinct TDP-43 domains by immunoblot

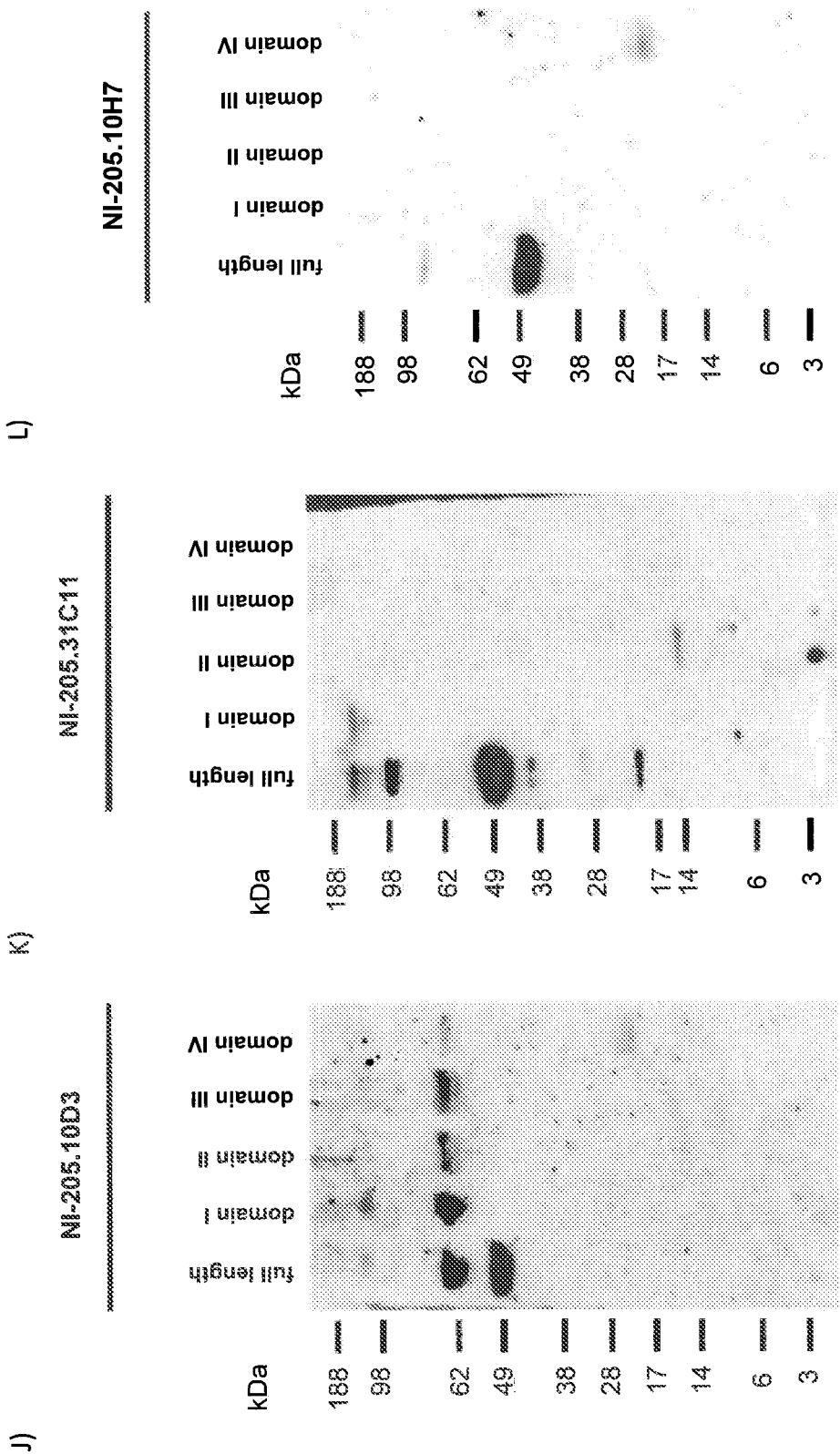
Figure 6J-L.
Binding to distinct TDP-43 domains by immunoblot

Figure 6M-O
Binding to distinct TDP-43 domains by immunoblot
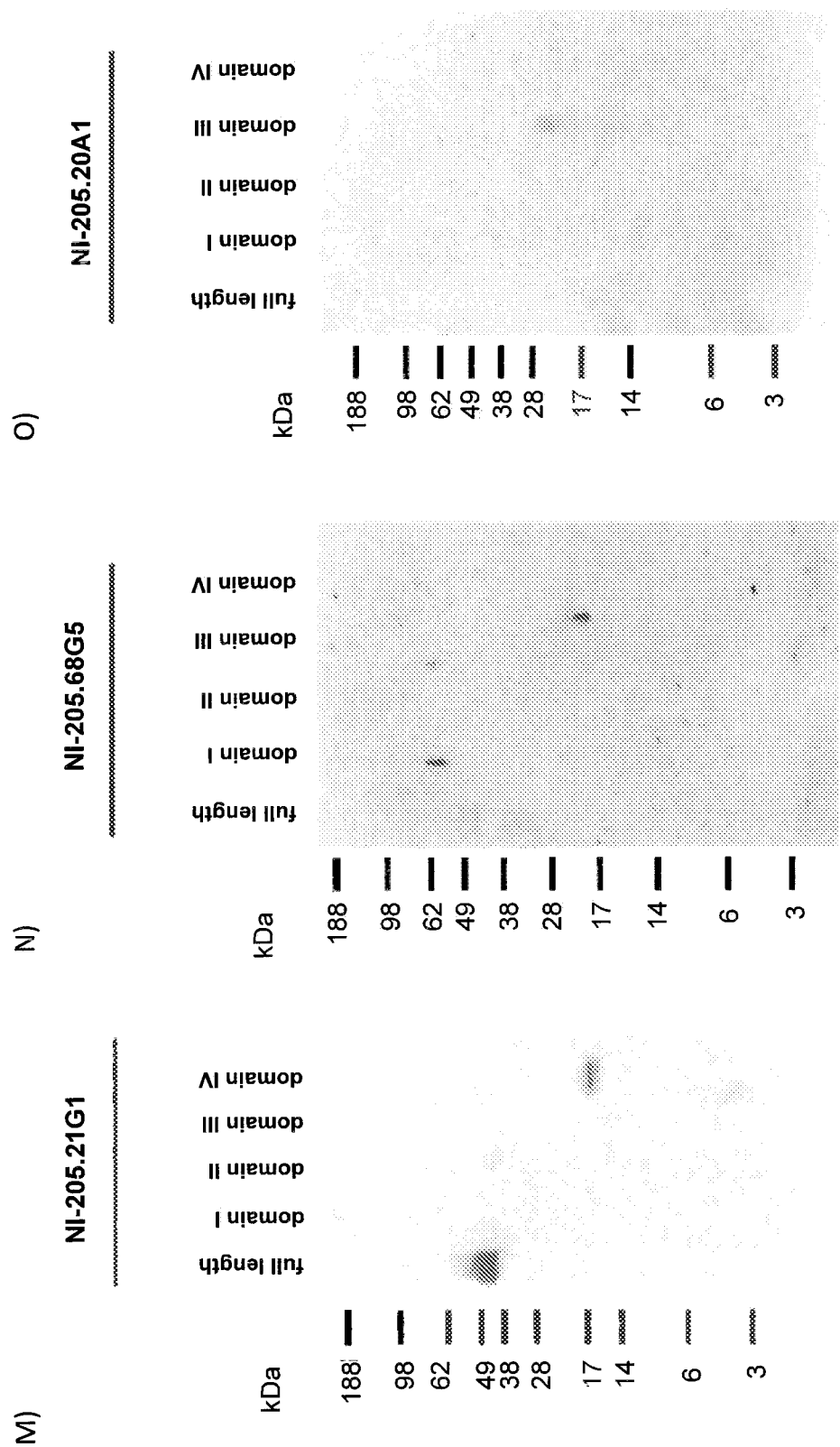

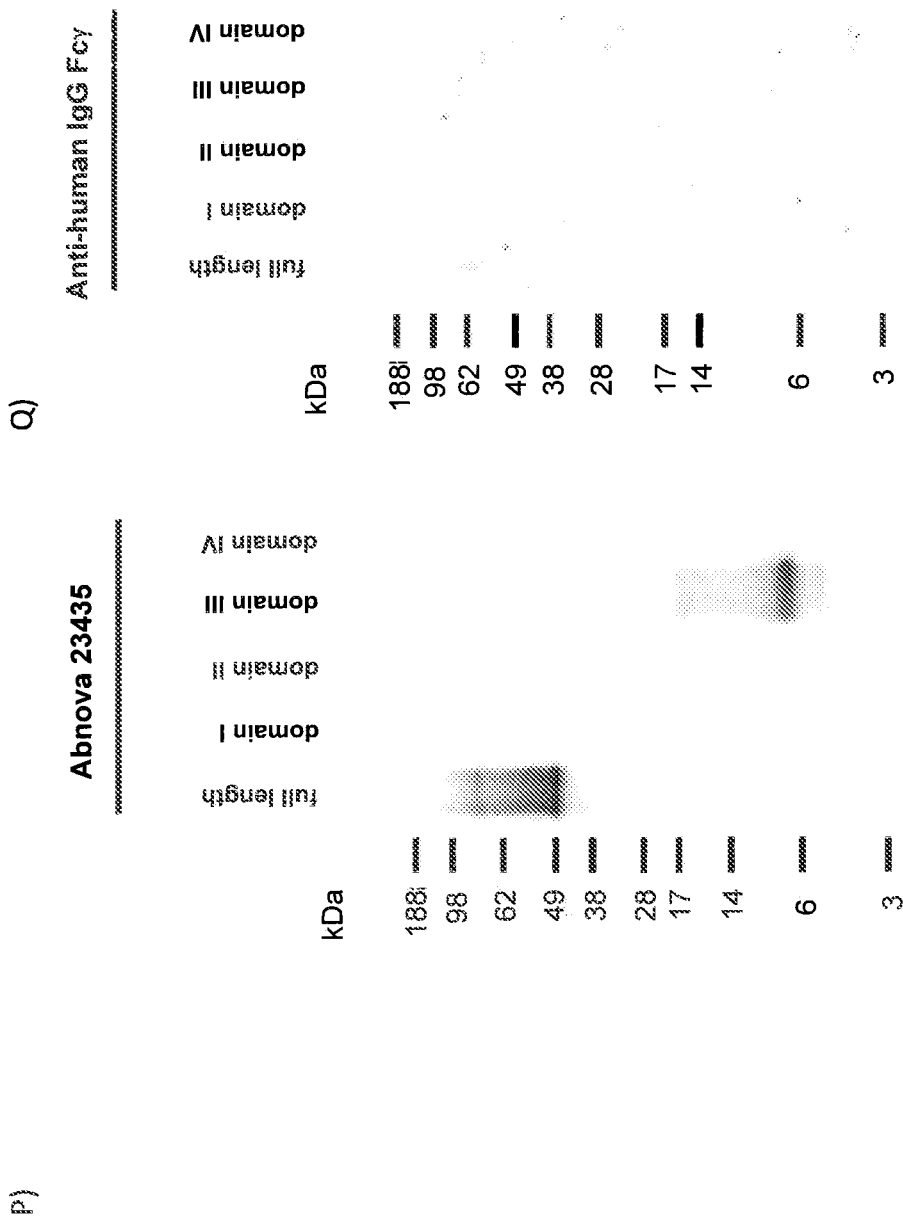
Figure 6P-Q
Binding to distinct TDP-43 domains by immunoblot

Figure 7AB
Determination of NI-205.41D1 binding epitope
A)
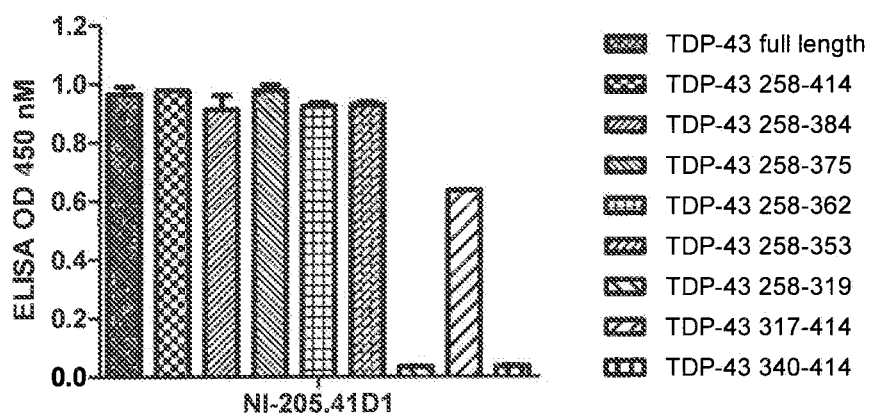
B)
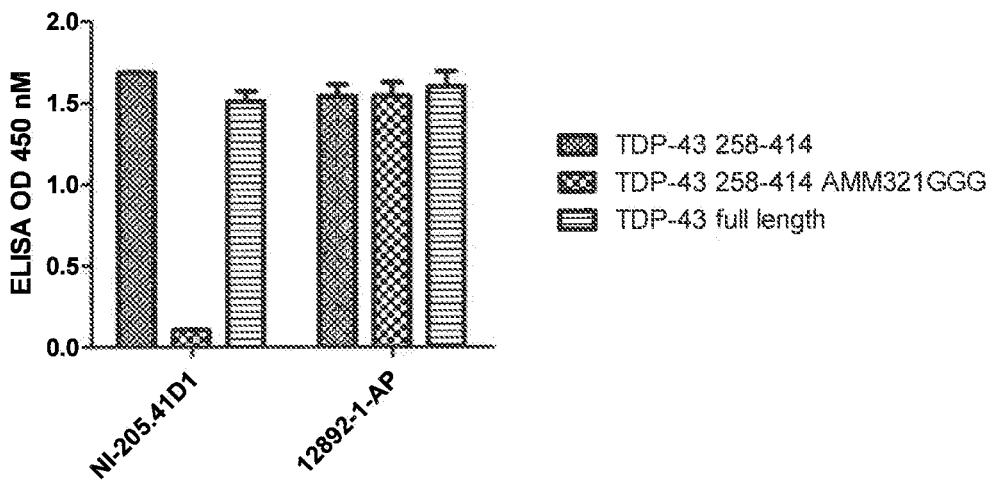

Determination of NI-205.41D1 binding epitope

Figure 8AB
Purification of monomeric forms of TDP-43 using mild chaotropic conditions
A
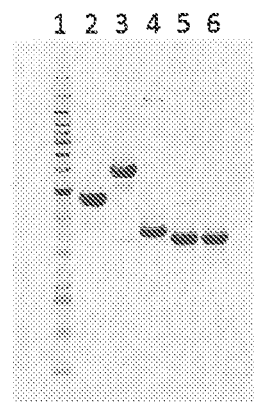
B
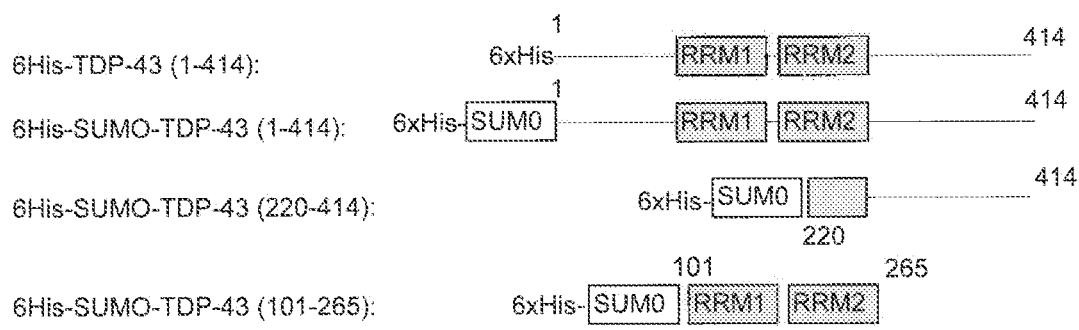

Purification of monomeric forms of TDP-43 using mild chaotropic conditions

Figure 10AB
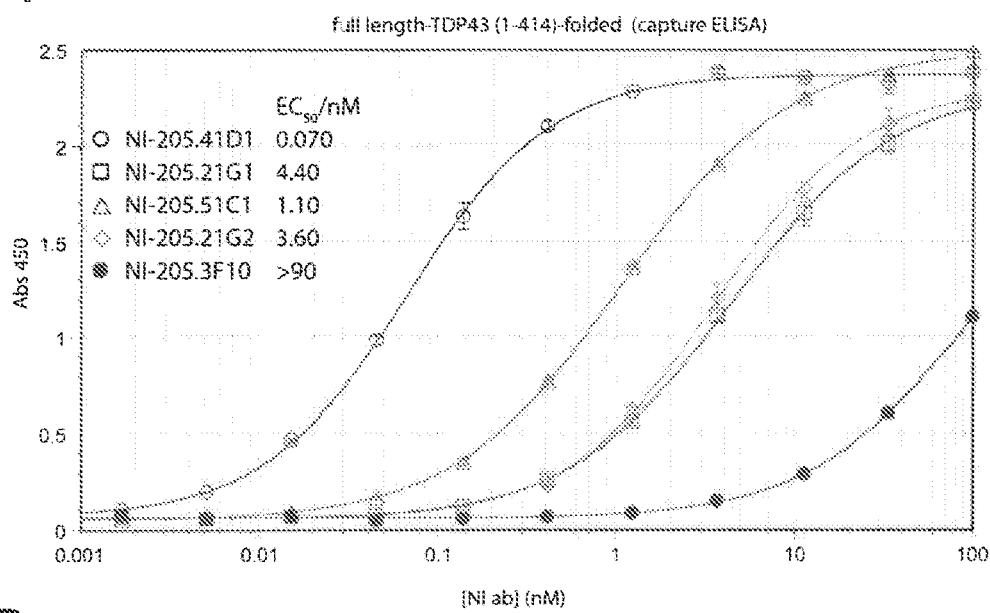
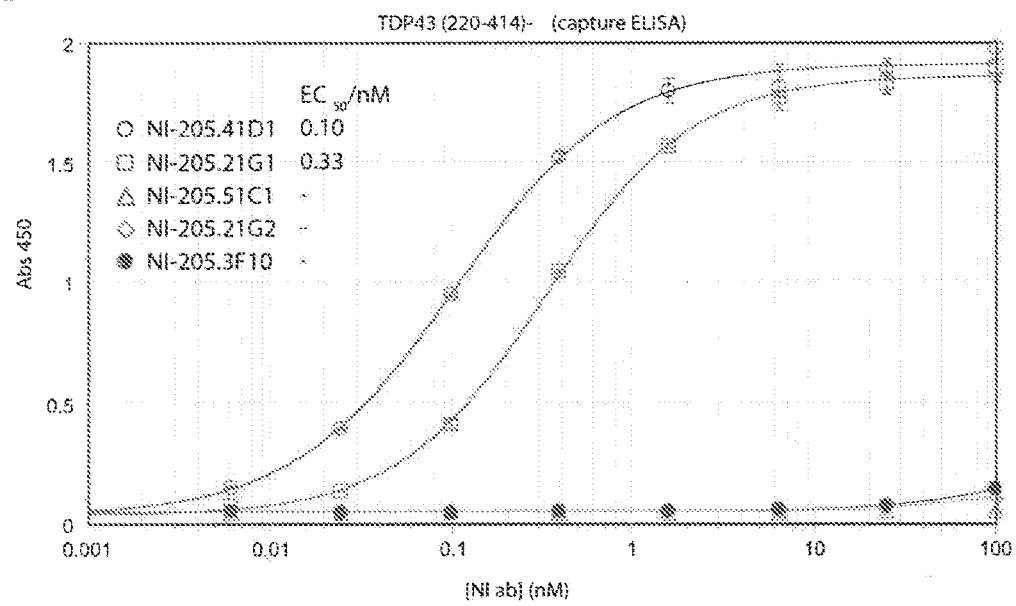

Figure 11A-R
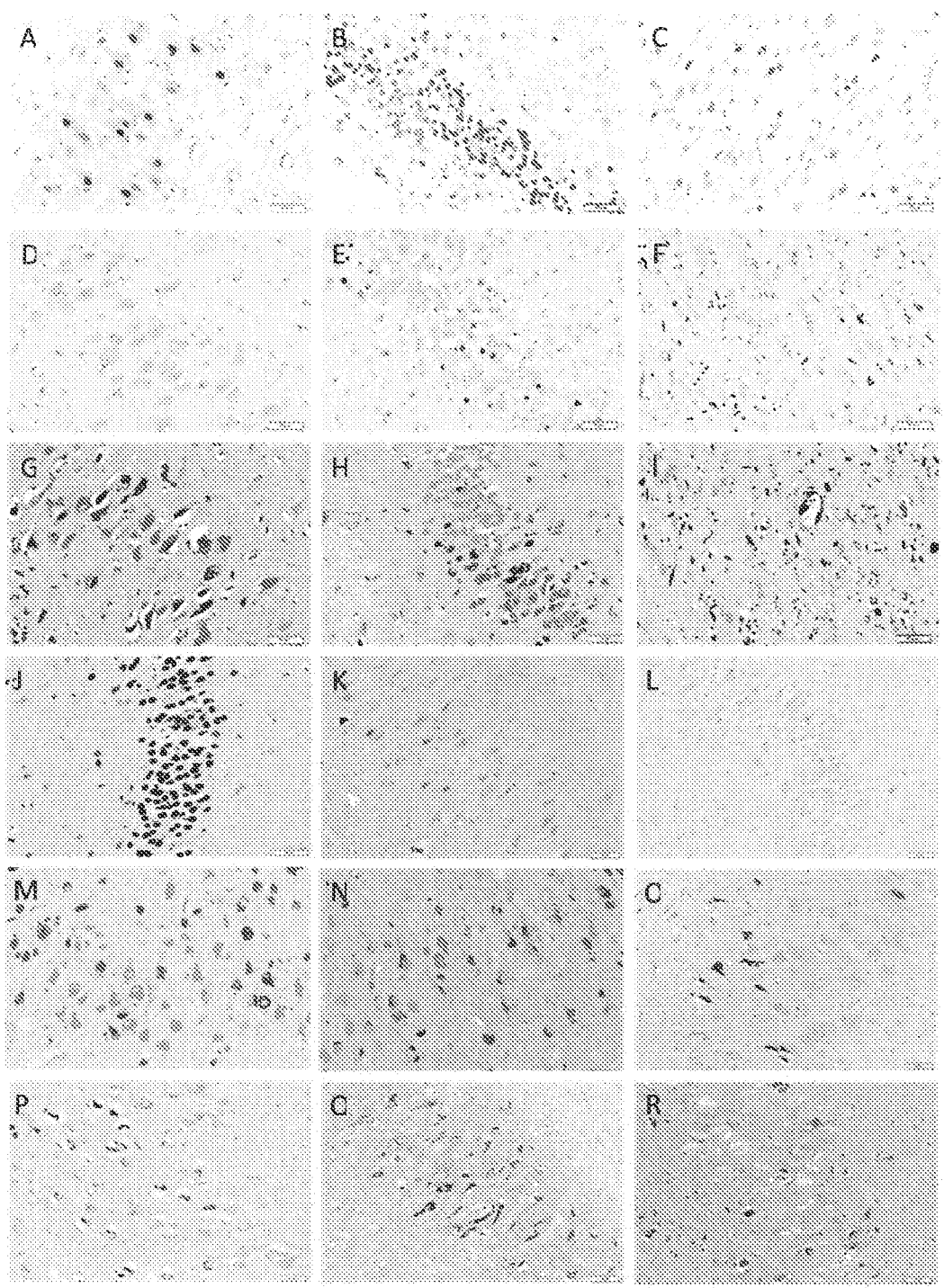

Figure 11S-Z
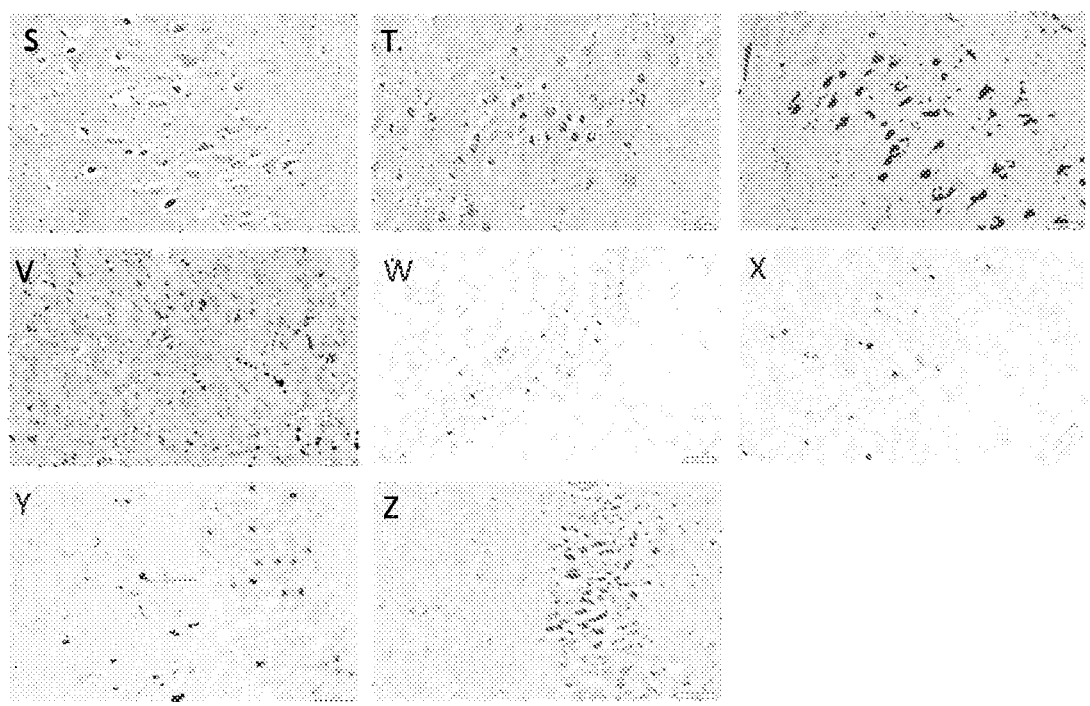

```
                              SEQUENCE LISTING

<160> NUMBER OF SEQ ID NOS: 328

<210> SEQ ID NO 1
<211> LENGTH: 124
<212> TYPE: PRT
<213> ORGANISM: Homo sapiens

<400> SEQUENCE: 1

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Gln
            20                  25                  30

Ala Met Ser Trp Val Arg Gln Ala Pro Gly Lys Gly Leu Glu Trp Val
        35                  40                  45

Ser Ala Leu Ser Arg Thr Gly Asp Tyr Thr Trp Tyr Ala Asp Ser Val
    50                  55                  60

Arg Gly Arg Phe Thr Val Ser Arg Asp Asp Ser Lys Asn Ile Phe Tyr
65                  70                  75                  80

Leu Glu Met Asn Ser Leu Arg Ala Glu Asp Thr Ala Val Tyr Tyr Cys
                85                  90                  95

Ala Lys Asn Tyr Tyr Ser Ser Phe Gly Tyr Asn Trp Ala Ala Phe His
            100                 105                 110

Ile Trp Gly Gln Gly Thr Met Val Thr Val Ser Ser
        115                 120

<210> SEQ ID NO 2
<211> LENGTH: 124
<212> TYPE: PRT
<213> ORGANISM: Homo sapiens

<400> SEQUENCE: 2

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Gln
            20                  25                  30

Ala Met Ser Trp Val Arg Gln Ala Pro Gly Lys Gly Leu Glu Trp Val
        35                  40                  45

Ser Ala Leu Ser Arg Thr Gly Asp Tyr Thr Trp Tyr Ala Asp Ser Val
    50                  55                  60

Arg Gly Arg Phe Thr Val Ser Arg Asp Asp Ser Lys Asn Ile Phe Tyr
65                  70                  75                  80

Leu Glu Met Asn Ser Leu Arg Ala Glu Asp Thr Ala Val Tyr Tyr Cys
```

```
                    85                  90                  95
Ala Lys Asn Tyr Tyr Ser Ser Phe Gly Tyr Asn Trp Ala Ala Phe His
                100                 105                 110

Ile Trp Gly Gln Gly Thr Met Val Thr Val Ser Ser
            115                 120

<210> SEQ ID NO 3
<211> LENGTH: 5
<212> TYPE: PRT
<213> ORGANISM: Homo sapiens

<400> SEQUENCE: 3

Ser Gln Ala Met Ser
1               5

<210> SEQ ID NO 4
<211> LENGTH: 17
<212> TYPE: PRT
<213> ORGANISM: Homo sapiens

<400> SEQUENCE: 4

Ala Leu Ser Arg Thr Gly Asp Tyr Thr Trp Tyr Ala Asp Ser Val Arg
1               5                   10                  15

Gly

<210> SEQ ID NO 5
<211> LENGTH: 15
<212> TYPE: PRT
<213> ORGANISM: Homo sapiens

<400> SEQUENCE: 5

Asn Tyr Tyr Ser Ser Phe Gly Tyr Asn Trp Ala Ala Phe His Ile
1               5                   10                  15

<210> SEQ ID NO 6
<211> LENGTH: 109
<212> TYPE: PRT
<213> ORGANISM: Homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asp Val Asn Asn Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Val Pro Asp Arg Phe Ser
    50                  55                  60

Gly Arg Gly Ser Gly Thr Asp Phe Thr Leu Thr Ile Asn Arg Leu Glu
65                  70                  75                  80

Pro Glu Asp Phe Ala Met Tyr Phe Cys Gln Gln Tyr Gly Gly Ser Pro
                85                  90                  95

Pro Tyr Thr Phe Gly Gln Gly Thr Lys Leu Glu Ile Lys
            100                 105

<210> SEQ ID NO 7
<211> LENGTH: 12
<212> TYPE: PRT
<213> ORGANISM: Homo sapiens

<400> SEQUENCE: 7
```

Arg Ala Ser Gln Asp Val Asn Asn Tyr Leu Ala
1               5                   10

<210> SEQ ID NO 8
<211> LENGTH: 7
<212> TYPE: PRT
<213> ORGANISM: Homo sapiens

<400> SEQUENCE: 8

Gly Ala Ser Arg Arg Ala Thr
1               5

<210> SEQ ID NO 9
<211> LENGTH: 10
<212> TYPE: PRT
<213> ORGANISM: Homo sapiens

<400> SEQUENCE: 9

Gln Gln Tyr Gly Gly Ser Pro Pro Tyr Thr
1               5                   10

<210> SEQ ID NO 10
<211> LENGTH: 114
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Ile Ser Cys Thr Thr Ser Gly Phe Ile Phe Ser Asp Tyr
            20                  25                  30

Trp Met His Trp Val Arg Gln Ala Pro Gly Lys Gly Leu Thr Trp Val
        35                  40                  45

Ser Arg Ile Asn Leu Asp Gly Ser Asp Thr Ile Tyr Ala Asp Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Arg Val Glu Asp Thr Ala Ile Tyr Tyr Cys
                85                  90                  95

Ala Arg Ser Arg Lys Ser Val Trp Gly Gln Gly Thr Met Val Thr Val
            100                 105                 110

Ser Ser

<210> SEQ ID NO 11
<211> LENGTH: 5
<212> TYPE: PRT
<213> ORGANISM: Homo sapiens

<400> SEQUENCE: 11

Asp Tyr Trp Met His
1               5

<210> SEQ ID NO 12
<211> LENGTH: 17
<212> TYPE: PRT
<213> ORGANISM: Homo sapiens

<400> SEQUENCE: 12

Arg Ile Asn Leu Asp Gly Ser Asp Thr Ile Tyr Ala Asp Ser Val Lys
1               5                   10                  15

Gly

<210> SEQ ID NO 13
<211> LENGTH: 5
<212> TYPE: PRT
<213> ORGANISM: Homo sapiens

<400> SEQUENCE: 13

Ser Arg Lys Ser Val
1               5

<210> SEQ ID NO 14
<211> LENGTH: 110
<212> TYPE: PRT
<213> ORGANISM: Homo sapiens

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Ser Asn Thr Asp Val Gly Ala Tyr
            20                  25                  30

Asp Tyr Val Ser Trp Ser Gln Gln Leu Pro Gly Lys Ala Pro Lys Phe
        35                  40                  45

Val Ile Phe Asp Val Asp Val Arg Pro Ser Gly Ile Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Lys Ser
                85                  90                  95

Gly Thr Leu Val Phe Gly Gly Gly Thr Lys Val Thr Val
            100                 105                 110

<210> SEQ ID NO 15
<211> LENGTH: 14
<212> TYPE: PRT
<213> ORGANISM: Homo sapiens

<400> SEQUENCE: 15

Thr Gly Ser Asn Thr Asp Val Gly Ala Tyr Asp Tyr Val Ser
1               5                   10

<210> SEQ ID NO 16
<211> LENGTH: 7
<212> TYPE: PRT
<213> ORGANISM: Homo sapiens

<400> SEQUENCE: 16

Asp Val Asp Val Arg Pro Ser
1               5

<210> SEQ ID NO 17
<211> LENGTH: 10
<212> TYPE: PRT
<213> ORGANISM: Homo sapiens

<400> SEQUENCE: 17

Ser Ser Tyr Thr Lys Ser Gly Thr Leu Val
1               5                   10

<210> SEQ ID NO 18
<211> LENGTH: 119
<212> TYPE: PRT

```
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Thr Ser Tyr
            20                  25                  30

Thr Leu His Trp Val Arg Gln Ala Pro Gly His Arg Pro Glu Trp Met
        35                  40                  45

Gly Trp Ile Asn Ala Ala Phe Ile Asn Thr Lys Tyr Ser Gln Lys Phe
    50                  55                  60

Gln Gly Arg Ile Thr Leu Thr Arg Asp Thr Ser Ala Asn Ile Ala Tyr
65                  70                  75                  80

Leu Glu Leu Arg Ser Leu Thr Thr Glu Asp Thr Ala Val Tyr Tyr Cys
                85                  90                  95

Ala Arg Arg Ala Ser Gly Ser Asn Gly Leu Asp Val Trp Gly Gln Gly
            100                 105                 110

Thr Thr Val Thr Val Ser Ser
        115

<210> SEQ ID NO 19
<211> LENGTH: 5
<212> TYPE: PRT
<213> ORGANISM: Homo sapiens

<400> SEQUENCE: 19

Ser Tyr Thr Leu His
1               5

<210> SEQ ID NO 20
<211> LENGTH: 17
<212> TYPE: PRT
<213> ORGANISM: Homo sapiens

<400> SEQUENCE: 20

Trp Ile Asn Ala Ala Phe Ile Asn Thr Lys Tyr Ser Gln Lys Phe Gln
1               5                   10                  15

Gly

<210> SEQ ID NO 21
<211> LENGTH: 10
<212> TYPE: PRT
<213> ORGANISM: Homo sapiens

<400> SEQUENCE: 21

Arg Ala Ser Gly Ser Asn Gly Leu Asp Val
1               5                   10

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Ile Thr Ile Thr Cys Gln Ala Ser Arg Asp Ile Thr Asn Tyr
            20                  25                  30

Leu Asn Trp Tyr Gln Gln Lys Pro Gly Lys Ala Pro Lys Leu Leu Ile
        35                  40                  45
```

Tyr Asp Ala Ser Tyr Leu Glu Thr Gly Val Pro Ser Thr Phe Ser Gly
        50                  55                  60

Ser Gly Ser Gly Thr His Phe Thr Leu Thr Ile Ser Ser Leu Gln Pro
65                  70                  75                  80

Asp Asp Phe Ala Thr Tyr Tyr Cys Gln Gln Tyr Asp Ser Val Pro Leu
                85                  90                  95

Thr Phe Gly Gly Gly Thr Lys Val Glu Ile Lys
            100                 105

<210> SEQ ID NO 23
<211> LENGTH: 11
<212> TYPE: PRT
<213> ORGANISM: Homo sapiens

<400> SEQUENCE: 23

Gln Ala Ser Arg Asp Ile Thr Asn Tyr Leu Asn
1               5                   10

<210> SEQ ID NO 24
<211> LENGTH: 7
<212> TYPE: PRT
<213> ORGANISM: Homo sapiens

<400> SEQUENCE: 24

Asp Ala Ser Tyr Leu Glu Thr
1               5

<210> SEQ ID NO 25
<211> LENGTH: 9
<212> TYPE: PRT
<213> ORGANISM: Homo sapiens

<400> SEQUENCE: 25

Gln Gln Tyr Asp Ser Val Pro Leu Thr
1               5

<210> SEQ ID NO 26
<211> LENGTH: 121
<212> TYPE: PRT
<213> ORGANISM: Homo sapiens

<400> SEQUENCE: 26

Gln Val Gln Leu Val Glu Ser Gly Gly Val Val Gln Pro Gly Lys
1               5                   10                  15

Ser Leu Arg Leu Ser Cys Ala Ala Ser Gly Phe Thr Phe Arg Asp His
                20                  25                  30

Gly Met His Trp Val Arg Gln Ala Pro Gly Lys Gly Leu Glu Trp Val
            35                  40                  45

Ala Val Ile Trp Leu Asp Gly Ser Ser Arg Phe Tyr Ala Asp Ser Val
        50                  55                  60

Glu Gly Arg Phe Thr Ile Ser Arg Asp Asn Ser Lys Asn Thr Leu Tyr
65                  70                  75                  80

Leu Gln Leu Thr Ser Leu Arg Ala Glu Asp Thr Ala Ile Tyr Tyr Cys
                85                  90                  95

Ala Arg Asp Arg Val Ala Ser Glu Gly Thr Ala Phe Asp Val Trp Gly
                100                 105                 110

Gln Gly Thr Met Val Thr Val Ser Ser
            115                 120

```
<210> SEQ ID NO 27
<211> LENGTH: 121
<212> TYPE: PRT
<213> ORGANISM: Homo sapiens

<400> SEQUENCE: 27

Glu Val Gln Leu Val Glu Ser Gly Gly Val Val Gln Pro Gly Lys
1               5                   10                  15

Ser Leu Arg Leu Ser Cys Ala Ala Ser Gly Phe Thr Phe Arg Asp His
            20                  25                  30

Gly Met His Trp Val Arg Gln Ala Pro Gly Lys Gly Leu Glu Trp Val
        35                  40                  45

Ala Val Ile Trp Leu Asp Gly Ser Ser Arg Phe Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Leu Thr Ser Leu Arg Ala Glu Asp Thr Ala Ile Tyr Tyr Cys
                85                  90                  95

Ala Arg Asp Arg Val Ala Ser Glu Gly Thr Ala Phe Asp Val Trp Gly
            100                 105                 110

Gln Gly Thr Thr Val Thr Val Ser Ser
        115                 120

<210> SEQ ID NO 28
<211> LENGTH: 5
<212> TYPE: PRT
<213> ORGANISM: Homo sapiens

<400> SEQUENCE: 28

Asp His Gly Met His
1               5

<210> SEQ ID NO 29
<211> LENGTH: 17
<212> TYPE: PRT
<213> ORGANISM: Homo sapiens

<400> SEQUENCE: 29

Val Ile Trp Leu Asp Gly Ser Ser Arg Phe Tyr Ala Asp Ser Val Glu
1               5                   10                  15

Gly

<210> SEQ ID NO 30
<211> LENGTH: 12
<212> TYPE: PRT
<213> ORGANISM: Homo sapiens

<400> SEQUENCE: 30

Asp Arg Val Ala Ser Glu Gly Thr Ala Phe Asp Val
1               5                   10

<210> SEQ ID NO 31
<211> LENGTH: 105
<212> TYPE: PRT
<213> ORGANISM: Homo sapiens

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Trp Ala Ser Gln Asn Val Asn His Tyr
            20                  25                  30
```

-continued

Leu Val Trp Tyr Gln Gln Arg Pro Gly Gln Ala Pro Arg Leu Leu Leu
             35                   40                  45

Tyr Asp Thr Ser Val Arg Ala Ala Gly Ile Pro Ala Arg Phe Ile Gly
         50                  55                  60

Ser Gly Ser Gly Thr His Phe Thr Leu Thr Ile Ser Ser Leu Glu Pro
65                  70                  75                  80

Glu Asp Ser Ala Val Tyr Tyr Cys Gln His Arg Ser Asp Trp Thr Phe
                 85                  90                  95

Gly Gln Gly Thr Lys Val Glu Ile Lys
             100                 105

<210> SEQ ID NO 32
<211> LENGTH: 11
<212> TYPE: PRT
<213> ORGANISM: Homo sapiens

<400> SEQUENCE: 32

Trp Ala Ser Gln Asn Val Asn His Tyr Leu Val
1               5                   10

<210> SEQ ID NO 33
<211> LENGTH: 7
<212> TYPE: PRT
<213> ORGANISM: Homo sapiens

<400> SEQUENCE: 33

Asp Thr Ser Val Arg Ala Ala
1               5

<210> SEQ ID NO 34
<211> LENGTH: 7
<212> TYPE: PRT
<213> ORGANISM: Homo sapiens

<400> SEQUENCE: 34

Gln His Arg Ser Asp Trp Thr
1               5

<210> SEQ ID NO 35
<211> LENGTH: 119
<212> TYPE: PRT
<213> ORGANISM: Homo sapiens

<400> SEQUENCE: 35

Gln Val Gln Leu Val Gln Ser Gly Thr Ala Val Lys Lys Pro Gly Ala
1               5                   10                  15

Ser Val Lys Val Ser Cys Lys Ala Ser Gly Phe Ser Phe Asn Gly Tyr
             20                  25                  30

Tyr Met His Trp Val Arg Gln Ala Pro Gly Gln Gly Leu Glu Trp Met
         35                  40                  45

Gly Val Ile Asn Pro Asn Gly Gly Ser Thr Asn Tyr Ala Gln Lys Phe
     50                  55                  60

Lys Gly Arg Ile Thr Met Ser Ala Asp Thr Pro Ala Arg Ser Val Ser
65                  70                  75                  80

Met Glu Leu Gly Ser Leu Arg Ser Asp Asp Thr Ala Met Tyr Tyr Cys
                 85                  90                  95

Ala Arg Leu Pro Val Asn Ile Glu Val Leu Asp Leu Trp Gly Gln Gly
             100                 105                 110

Thr Leu Val Thr Val Ser Ser
         115

<210> SEQ ID NO 36
<211> LENGTH: 119
<212> TYPE: PRT
<213> ORGANISM: Homo sapiens

<400> SEQUENCE: 36

Glu Val Gln Leu Val Glu Ser Gly Thr Ala Val Lys Lys Pro Gly Ala
1               5                   10                  15

Ser Val Lys Val Ser Cys Lys Ala Ser Gly Phe Ser Phe Asn Gly Tyr
            20                  25                  30

Tyr Met His Trp Val Arg Gln Ala Pro Gly Gln Gly Leu Glu Trp Met
        35                  40                  45

Gly Val Ile Asn Pro Asn Gly Gly Ser Thr Asn Tyr Ala Gln Lys Phe
    50                  55                  60

Lys Gly Arg Ile Thr Met Ser Ala Asp Thr Pro Ala Arg Ser Val Ser
65                  70                  75                  80

Met Glu Leu Gly Ser Leu Arg Ser Asp Asp Thr Ala Met Tyr Tyr Cys
                85                  90                  95

Ala Arg Leu Pro Val Asn Ile Glu Val Leu Asp Leu Trp Gly Gln Gly
            100                 105                 110

Thr Leu Val Thr Val Ser Ser
        115

<210> SEQ ID NO 37
<211> LENGTH: 5
<212> TYPE: PRT
<213> ORGANISM: Homo sapiens

<400> SEQUENCE: 37

Gly Tyr Tyr Met His
1               5

<210> SEQ ID NO 38
<211> LENGTH: 17
<212> TYPE: PRT
<213> ORGANISM: Homo sapiens

<400> SEQUENCE: 38

Val Ile Asn Pro Asn Gly Gly Ser Thr Asn Tyr Ala Gln Lys Phe Lys
1               5                   10                  15

Gly

<210> SEQ ID NO 39
<211> LENGTH: 10
<212> TYPE: PRT
<213> ORGANISM: Homo sapiens

<400> SEQUENCE: 39

Leu Pro Val Asn Ile Glu Val Leu Asp Leu
1               5                   10

<210> SEQ ID NO 40
<211> LENGTH: 113
<212> TYPE: PRT
<213> ORGANISM: Homo sapiens

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Thr Val Leu Phe Ser
            20                  25                  30

Ser Asn Asp Lys Asn Tyr Leu Ala Trp Tyr Gln Gln Lys Pro Gly Gln
        35                  40                  45

Pro Pro Lys Leu Leu Ile Tyr Trp Ala Ser Val Arg Ala Ser Gly Val
 50                  55                  60

Pro Asp Arg Phe Ser Gly Ser Gly Ser Gly Thr Asp Phe Ser Leu Thr
65                  70                  75                  80

Ile Asn Gly Leu Gln Ala Glu Asp Val Ala Val Tyr Tyr Cys Gln Gln
                85                  90                  95

Ser Ser Thr Ala Pro Leu Thr Phe Gly Gly Gly Thr Lys Val Glu Ile
                100                 105                 110

Lys

<210> SEQ ID NO 41
<211> LENGTH: 113
<212> TYPE: PRT
<213> ORGANISM: Homo sapiens

<400> SEQUENCE: 41

Glu Ile Val Leu Thr Gln Ser Pro Asp Ser Leu Ala Val Ser Leu Gly
1               5                   10                  15

Glu Arg Ala Thr Ile Asn Cys Arg Ser Ser Gln Thr Val Leu Phe Ser
            20                  25                  30

Ser Asn Asp Lys Asn Tyr Leu Ala Trp Tyr Gln Gln Lys Pro Gly Gln
        35                  40                  45

Pro Pro Lys Leu Leu Ile Tyr Trp Ala Ser Val Arg Ala Ser Gly Val
 50                  55                  60

Pro Asp Arg Phe Ser Gly Ser Gly Ser Gly Thr Asp Phe Ser Leu Thr
65                  70                  75                  80

Ile Asn Gly Leu Gln Ala Glu Asp Val Ala Val Tyr Tyr Cys Gln Gln
                85                  90                  95

Ser Ser Thr Ala Pro Leu Thr Phe Gly Gly Gly Thr Lys Val Glu Ile
                100                 105                 110

Lys

<210> SEQ ID NO 42
<211> LENGTH: 17
<212> TYPE: PRT
<213> ORGANISM: Homo sapiens

<400> SEQUENCE: 42

Arg Ser Ser Gln Thr Val Leu Phe Ser Ser Asn Asp Lys Asn Tyr Leu
1               5                   10                  15

Ala

<210> SEQ ID NO 43
<211> LENGTH: 7
<212> TYPE: PRT
<213> ORGANISM: Homo sapiens

<400> SEQUENCE: 43

Trp Ala Ser Val Arg Ala Ser
1               5

<210> SEQ ID NO 44
<211> LENGTH: 9

```
<212> TYPE: PRT
<213> ORGANISM: Homo sapiens

<400> SEQUENCE: 44

Gln Gln Ser Ser Thr Ala Pro Leu Thr
1               5

<210> SEQ ID NO 45
<211> LENGTH: 134
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Arg Thr Ser Tyr Ala Gln Lys Phe
    50                  55                  60

Gln Gly Arg Ala Ser Met Thr Arg Asp Thr Ser Thr Ser Thr Val Tyr
65                  70                  75                  80

Met Glu Val Ile Ser Leu Arg Ser Glu Asp Thr Ala Val Tyr Tyr Cys
                85                  90                  95

Ala Arg Gln Arg Pro Ser Gly Tyr Ser Gly Tyr Gly Pro Ser Glu Ser
            100                 105                 110

Tyr Gly Asn Pro Thr Asp Asp Ala Phe Asp Val Trp Gly Gln Gly Thr
        115                 120                 125

Thr Val Thr Val Ser Ser
    130

<210> SEQ ID NO 46
<211> LENGTH: 5
<212> TYPE: PRT
<213> ORGANISM: Homo sapiens

<400> SEQUENCE: 46

Asn Tyr Tyr Met His
1               5

<210> SEQ ID NO 47
<211> LENGTH: 17
<212> TYPE: PRT
<213> ORGANISM: Homo sapiens

<400> SEQUENCE: 47

Ile Ile Asn Pro Ser Gly Gly Arg Thr Ser Tyr Ala Gln Lys Phe Gln
1               5                   10                  15

Gly

<210> SEQ ID NO 48
<211> LENGTH: 25
<212> TYPE: PRT
<213> ORGANISM: Homo sapiens

<400> SEQUENCE: 48

Gln Arg Pro Ser Gly Tyr Ser Gly Tyr Gly Pro Ser Glu Ser Tyr Gly
1               5                   10                  15

Asn Pro Thr Asp Asp Ala Phe Asp Val
```

<210> SEQ ID NO 49
<211> LENGTH: 109
<212> TYPE: PRT
<213> ORGANISM: Homo sapiens

<400> SEQUENCE: 49

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Arg Gly Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asp Thr Ala Thr Leu Thr Ile Ser Arg Val Glu Val Gly
65                  70                  75                  80

Asp Glu Ala Asp Tyr Tyr Cys Gln Val Trp Asp Asn Ser Ser Asp His
                85                  90                  95

Leu Val Val Phe Gly Gly Gly Thr Lys Leu Thr Val Leu
            100                 105

<210> SEQ ID NO 50
<211> LENGTH: 11
<212> TYPE: PRT
<213> ORGANISM: Homo sapiens

<400> SEQUENCE: 50

Gly Gly Asn Asn Ile Gly Ser Arg Gly Val His
1               5                   10

<210> SEQ ID NO 51
<211> LENGTH: 7
<212> TYPE: PRT
<213> ORGANISM: Homo sapiens

<400> SEQUENCE: 51

Asp Asp Ser Asp Arg Pro Ser
1               5

<210> SEQ ID NO 52
<211> LENGTH: 12
<212> TYPE: PRT
<213> ORGANISM: Homo sapiens

<400> SEQUENCE: 52

Gln Val Trp Asp Asn Ser Ser Asp His Leu Val Val
1               5                   10

<210> SEQ ID NO 53
<211> LENGTH: 130
<212> TYPE: PRT
<213> ORGANISM: Homo sapiens

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Val Met Tyr Trp Val Arg Gln Ala Pro Gly Lys Gly Leu Glu Trp Val

```
                35                  40                  45
Ala Phe Ile Ser Tyr Asp Gly Ser Asn Lys Tyr Tyr Pro Asp Ser Val
 50                  55                  60

Lys Gly Arg Phe Thr Ile Ser Arg Asp Asn Ser Met Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Asp Thr Tyr Gln Tyr Asp Ser Ser Thr Tyr Tyr Pro Tyr Phe
                100                 105                 110

Tyr Tyr Tyr Gly Met Asp Val Trp Gly Gln Gly Thr Thr Val Thr Val
            115                 120                 125

Ser Ser
130

<210> SEQ ID NO 54
<211> LENGTH: 5
<212> TYPE: PRT
<213> ORGANISM: Homo sapiens

<400> SEQUENCE: 54

Asn Tyr Val Met Tyr
 1               5

<210> SEQ ID NO 55
<211> LENGTH: 17
<212> TYPE: PRT
<213> ORGANISM: Homo sapiens

<400> SEQUENCE: 55

Phe Ile Ser Tyr Asp Gly Ser Asn Lys Tyr Tyr Pro Asp Ser Val Lys
 1               5                  10                  15

Gly

<210> SEQ ID NO 56
<211> LENGTH: 21
<212> TYPE: PRT
<213> ORGANISM: Homo sapiens

<400> SEQUENCE: 56

Asp Thr Tyr Gln Tyr Asp Ser Ser Thr Tyr Tyr Pro Tyr Phe Tyr Tyr
 1               5                  10                  15

Tyr Gly Met Asp Val
            20

<210> SEQ ID NO 57
<211> LENGTH: 111
<212> TYPE: PRT
<213> ORGANISM: Homo sapiens

<400> SEQUENCE: 57

Gln Ser Ala Leu Thr Gln Pro Ala Ser Val Ser Gly Pro Gly Gln
 1               5                  10                  15

Ser Ile Thr Ile Ser Cys Ile Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Glu Val Ser Asn Arg Pro Ser Gly Val Ser Ser Arg Phe
 50                  55                  60

Ser Gly Ser Lys Ser Gly Asn Thr Ala Ser Leu Thr Ile Ser Gly Leu
```

```
                65                  70                  75                  80
Gln Ser Glu Asp Glu Ala Asp Tyr Tyr Cys Ser Ser Phe Ala Ser Ser
                    85                  90                  95

Ser Thr Ser Val Thr Phe Gly Gly Gly Thr Lys Leu Thr Val Leu
                100                 105                 110
```

<210> SEQ ID NO 58
<211> LENGTH: 14
<212> TYPE: PRT
<213> ORGANISM: Homo sapiens

<400> SEQUENCE: 58

```
Ile Gly Thr Ser Ser Asp Val Gly Gly Tyr Asn Tyr Val Ser
1               5                   10
```

<210> SEQ ID NO 59
<211> LENGTH: 7
<212> TYPE: PRT
<213> ORGANISM: Homo sapiens

<400> SEQUENCE: 59

```
Glu Val Ser Asn Arg Pro Ser
1               5
```

<210> SEQ ID NO 60
<211> LENGTH: 11
<212> TYPE: PRT
<213> ORGANISM: Homo sapiens

<400> SEQUENCE: 60

```
Ser Ser Phe Ala Ser Ser Ser Thr Ser Val Thr
1               5                   10
```

<210> SEQ ID NO 61
<211> LENGTH: 129
<212> TYPE: PRT
<213> ORGANISM: Homo sapiens

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Gly Gly Asp Arg Thr Tyr Ser Ala Asp Ser Val
        50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Val Glu Asp Thr Ala Val Tyr Tyr Cys
                85                  90                  95

Ala Gln Gly Gly Gly Gly Glu Met Thr Ala Val Thr Met Asp Gly Thr
                100                 105                 110

Tyr Tyr Gly Met Asp Val Trp Gly Gln Gly Thr Thr Val Thr Val Ser
            115                 120                 125

Ser
```

<210> SEQ ID NO 62
<211> LENGTH: 5
<212> TYPE: PRT

```
<213> ORGANISM: Homo sapiens

<400> SEQUENCE: 62

Ser Tyr Ala Met Ser
1               5

<210> SEQ ID NO 63
<211> LENGTH: 17
<212> TYPE: PRT
<213> ORGANISM: Homo sapiens

<400> SEQUENCE: 63

Ala Ile Ser Gly Gly Gly Asp Arg Thr Tyr Ser Ala Asp Ser Val Lys
1               5                   10                  15

Gly

<210> SEQ ID NO 64
<211> LENGTH: 20
<212> TYPE: PRT
<213> ORGANISM: Homo sapiens

<400> SEQUENCE: 64

Gly Gly Gly Gly Glu Met Thr Ala Val Thr Met Asp Gly Thr Tyr Tyr
1               5                   10                  15

Gly Met Asp Val
            20

<210> SEQ ID NO 65
<211> LENGTH: 110
<212> TYPE: PRT
<213> ORGANISM: Homo sapiens

<400> SEQUENCE: 65

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Ser Asn Val Gly Thr Tyr
                20                  25                  30

Lys Phe Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Tyr Val Phe Gly Ser Gly Thr Lys Val Thr Val Leu
            100                 105                 110

<210> SEQ ID NO 66
<211> LENGTH: 14
<212> TYPE: PRT
<213> ORGANISM: Homo sapiens

<400> SEQUENCE: 66

Thr Gly Thr Ser Ser Asn Val Gly Thr Tyr Lys Phe Val Ser
1               5                   10

<210> SEQ ID NO 67
<211> LENGTH: 7
<212> TYPE: PRT
<213> ORGANISM: Homo sapiens
```

<400> SEQUENCE: 67

Asp Val Thr Lys Arg Pro Ser
1               5

<210> SEQ ID NO 68
<211> LENGTH: 10
<212> TYPE: PRT
<213> ORGANISM: Homo sapiens

<400> SEQUENCE: 68

Cys Ser Tyr Ala Gly Ser Tyr Thr Tyr Val
1               5                   10

<210> SEQ ID NO 69
<211> LENGTH: 119
<212> TYPE: PRT
<213> ORGANISM: Homo sapiens

<400> SEQUENCE: 69

Gln Val Gln Leu Val Glu Ser Gly Gly Val Val Gln Pro Gly Met
1               5                   10                  15

Ser Leu Arg Leu Ser Cys Ala Ala Ser Gly Phe Ser Phe Ser Ser His
                20                  25                  30

Gly Met His Trp Val Arg Gln Thr Pro Gly Lys Gly Leu Glu Trp Leu
            35                  40                  45

Ala Val Ile Ser Tyr Asp Ala Ser Asn Lys Ser Tyr Ala Asp Ser Val
        50                  55                  60

Lys Gly Arg Phe Thr Ile Ser Arg Asp Asn Lys Lys Thr Leu Tyr
65                  70                  75                  80

Leu Gln Met Asp Ser Leu Arg Val Glu Asp Thr Ala Leu Tyr Tyr Cys
                85                  90                  95

Ala Asn Ala Phe Ser Ser Ser Ala Ser Gly Tyr Trp Gly Gln Gly
            100                 105                 110

Thr Leu Val Thr Val Ser Ser
        115

<210> SEQ ID NO 70
<211> LENGTH: 5
<212> TYPE: PRT
<213> ORGANISM: Homo sapiens

<400> SEQUENCE: 70

Ser His Gly Met His
1               5

<210> SEQ ID NO 71
<211> LENGTH: 17
<212> TYPE: PRT
<213> ORGANISM: Homo sapiens

<400> SEQUENCE: 71

Val Ile Ser Tyr Asp Ala Ser Asn Lys Ser Tyr Ala Asp Ser Val Lys
1               5                   10                  15

Gly

<210> SEQ ID NO 72
<211> LENGTH: 10
<212> TYPE: PRT
<213> ORGANISM: Homo sapiens

```
<400> SEQUENCE: 72

Ala Phe Ser Ser Ser Ala Ser Gly Gly Tyr
1               5                   10

<210> SEQ ID NO 73
<211> LENGTH: 113
<212> TYPE: PRT
<213> ORGANISM: Homo sapiens

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Val Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Gly Ile Tyr Tyr Cys Met Gln Gly
                85                  90                  95

Thr His Trp Pro Pro Trp Thr Phe Gly Gln Gly Thr Lys Val Glu Ile
            100                 105                 110

Lys

<210> SEQ ID NO 74
<211> LENGTH: 16
<212> TYPE: PRT
<213> ORGANISM: Homo sapiens

<400> SEQUENCE: 74

Arg Ser Ser Gln Ser Leu Val His Ser Asp Gly Val Thr Tyr Leu Asn
1               5                   10                  15

<210> SEQ ID NO 75
<211> LENGTH: 7
<212> TYPE: PRT
<213> ORGANISM: Homo sapiens

<400> SEQUENCE: 75

Lys Val Ser Asn Arg Asp Ser
1               5

<210> SEQ ID NO 76
<211> LENGTH: 10
<212> TYPE: PRT
<213> ORGANISM: Homo sapiens

<400> SEQUENCE: 76

Met Gln Gly Thr His Trp Pro Pro Trp Thr
1               5                   10

<210> SEQ ID NO 77
<211> LENGTH: 126
<212> TYPE: PRT
<213> ORGANISM: Homo sapiens

<400> SEQUENCE: 77

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Tyr Tyr Asp Ser Ser Gln Arg Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Pro Phe His Tyr His Arg Ser Ala Ser Phe Ala Pro
            100                 105                 110

Ser Asp Thr Trp Gly Gln Gly Thr Leu Val Thr Val Ser Ser
            115                 120                 125
```

<210> SEQ ID NO 78
<211> LENGTH: 126
<212> TYPE: PRT
<213> ORGANISM: Homo sapiens

<400> SEQUENCE: 78

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Tyr Tyr Asp Ser Ser Gln Arg Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Pro Phe His Tyr His Arg Ser Ala Ser Phe Ala Pro
            100                 105                 110

Ser Asp Thr Trp Gly Gln Gly Thr Leu Val Thr Val Ser Ser
            115                 120                 125
```

<210> SEQ ID NO 79
<211> LENGTH: 5
<212> TYPE: PRT
<213> ORGANISM: Homo sapiens

<400> SEQUENCE: 79

```
Ser Tyr Gly Met His
1               5
```

<210> SEQ ID NO 80
<211> LENGTH: 17
<212> TYPE: PRT
<213> ORGANISM: Homo sapiens

<400> SEQUENCE: 80

```
Ile Ile Tyr Tyr Asp Ser Ser Gln Arg Tyr Tyr Ala Asp Ser Val Lys
1               5                   10                  15

Gly
```

<210> SEQ ID NO 81
<211> LENGTH: 17
<212> TYPE: PRT
<213> ORGANISM: Homo sapiens

<400> SEQUENCE: 81

Asp Leu Pro Phe His Tyr His Arg Ser Ala Ser Phe Ala Pro Ser Asp
1               5                   10                  15

Thr

<210> SEQ ID NO 82
<211> LENGTH: 108
<212> TYPE: PRT
<213> ORGANISM: Homo sapiens

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Thr Asn Asn
            20                  25                  30

Tyr Leu Ala Trp Tyr Gln Gln Lys Pro Gly Gln Ala Pro Arg Leu Leu
        35                  40                  45

Val Tyr Ala Ala Ser Ser Arg Ala Thr Gly Ile Pro Asp Arg Phe Tyr
    50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys
            100                 105

<210> SEQ ID NO 83
<211> LENGTH: 108
<212> TYPE: PRT
<213> ORGANISM: Homo sapiens

<400> SEQUENCE: 83

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ala Val Thr Asn Asn
            20                  25                  30

Tyr Leu Ala Trp Tyr Gln Gln Lys Pro Gly Gln Ala Pro Arg Leu Leu
        35                  40                  45

Val Tyr Ala Ala Ser Ser Arg Ala Thr Gly Ile Pro Asp Arg Phe Tyr
    50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys
            100                 105

<210> SEQ ID NO 84
<211> LENGTH: 12
<212> TYPE: PRT
<213> ORGANISM: Homo sapiens

<400> SEQUENCE: 84

Arg Ala Ser Gln Ala Val Thr Asn Asn Tyr Leu Ala

<210> SEQ ID NO 85
<211> LENGTH: 7
<212> TYPE: PRT
<213> ORGANISM: Homo sapiens

<400> SEQUENCE: 85

Ala Ala Ser Ser Arg Ala Thr
1               5

<210> SEQ ID NO 86
<211> LENGTH: 9
<212> TYPE: PRT
<213> ORGANISM: Homo sapiens

<400> SEQUENCE: 86

Gln Gln Tyr Gly Thr Ser Pro Ile Thr
1               5

<210> SEQ ID NO 87
<211> LENGTH: 113
<212> TYPE: PRT
<213> ORGANISM: Homo sapiens

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Tyr Ile Ser Thr Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Asp Tyr Trp Gly Gln Gly Thr Leu Val Thr Val Ser
            100                 105                 110

Ser

<210> SEQ ID NO 88
<211> LENGTH: 5
<212> TYPE: PRT
<213> ORGANISM: Homo sapiens

<400> SEQUENCE: 88

Ser Tyr Arg Met Asn
1               5

<210> SEQ ID NO 89
<211> LENGTH: 17
<212> TYPE: PRT
<213> ORGANISM: Homo sapiens

<400> SEQUENCE: 89

Tyr Ile Ser Thr Ser Ser Ser Thr Ile Tyr Tyr Ala Asp Ser Val Lys
1               5                   10                  15

Gly

<210> SEQ ID NO 90
<211> LENGTH: 4
<212> TYPE: PRT
<213> ORGANISM: Homo sapiens

<400> SEQUENCE: 90

Ala Phe Asp Tyr
1

<210> SEQ ID NO 91
<211> LENGTH: 12
<212> TYPE: PRT
<213> ORGANISM: Homo sapiens

<400> SEQUENCE: 91

Arg Ala Ser Gln Ser Val Ser Ser Ser Tyr Leu Ala
1               5                   10

<210> SEQ ID NO 92
<211> LENGTH: 7
<212> TYPE: PRT
<213> ORGANISM: Homo sapiens

<400> SEQUENCE: 92

Gly Ala Ser Ser Arg Ala Thr
1               5

<210> SEQ ID NO 93
<211> LENGTH: 9
<212> TYPE: PRT
<213> ORGANISM: Homo sapiens

<400> SEQUENCE: 93

Gln Gln Tyr Gly Ser Ser Pro Phe Thr
1               5

<210> SEQ ID NO 94
<211> LENGTH: 414
<212> TYPE: PRT
<213> ORGANISM: Homo sapiens

<400> SEQUENCE: 94

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
                35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Glu Tyr Phe Ser Thr Phe Gly
                115                 120                 125

Glu Val Leu Met Val Gln Val Lys Lys Asp Leu Lys Thr Gly His Ser
        130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
            165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 95
<211> LENGTH: 372
<212> TYPE: DNA
<213> ORGANISM: Homo sapiens

<400> SEQUENCE: 95
gaggtgcagc tgttggagtc tgggggagac ttggtacagc ctgggggggtc cctgagactc      60 tcctgtgcag cctctggatt caccttttagc agccaggcca tgagttgggt ccgccaggct    120
ccagggaagg gctggagtg gtctcggcc cttagtcgca ctggtgatta cacatggtac       180
gcagactccg tgaggggccg gttcaccgtc tccagagacg attccaaaaa catctttttat    240 ctggaaatga acagcctgag agccgaggac acggccgtgt attattgtgc gaaaaactac    300
tatagtagtt ttggttataa ttgggctgct tttcatatct ggggccaagg gacaatggtc    360
accgtctcct cg                                                        372

<210> SEQ ID NO 96
<211> LENGTH: 327
<212> TYPE: DNA
<213> ORGANISM: Homo sapiens

<400> SEQUENCE: 96

```
gaaattgtgt tgacgcagtc tccaggcacc ctgtctttgt ctccagggga aagagccacc    60
ctctcctgca gggccagtca ggatgttaac aacaactact tagcctggta ccagcagaaa   120
cctggccagg ctcccaggct cctcatctat ggtgcatccc gcagggccac tggcgtccca   180
gacaggttca gtggccgtgg gtctgggaca gacttcactc tcaccatcaa cagactggag   240
cctgaagatt ttgcaatgta tttctgtcag cagtatggtg gctcacctcc gtacactttt   300
ggccagggga ccaagctgga gatcaaa                                       327
```

<210> SEQ ID NO 97
<211> LENGTH: 342
<212> TYPE: DNA
<213> ORGANISM: Homo sapiens

<400> SEQUENCE: 97

```
gaggtgcagc tggtggagtc tgggggaggc ttagttcagc ctggggggtc cctgagaatc    60
tcctgcacaa cgtcaggatt catttttcagc gactattgga tgcactgggt ccgccaagct   120
ccagggaagg ggctcacttg gtctcacgt attaatcttg atgggagtga caccatctat   180
gcggactccg tgaagggccg attccaccat tccagagaca cgacaagaa cacactatat   240
ttacaaatga acagtctgag agtcgaggac acggctattt attactgtgc aaggtcaaga   300
aagagtgtct ggggccaagg gacaatggtc accgtctctt cg                      342
```

<210> SEQ ID NO 98
<211> LENGTH: 330
<212> TYPE: DNA
<213> ORGANISM: Homo sapiens

<400> SEQUENCE: 98

```
cagtctgccc tgactcagcc tgcctccgtg tctgggtctc ctggacagtc gatcaccatc    60
tcctgcactg gaagcaacac tgacgttggt gcttatgact atgtctcctg gtcccaacaa   120
ctcccgggca agccccccaa atttgtgatt tttgatgtcg atgttcggcc ctcagggatt   180
tctgatcgct tctctggctc caagtctggc aacacggcct ccctgaccat ctctgggctc   240
caggctgagg acgaggctga ttattattgc agttcatata caaagagcgg cactctggtt   300
ttcggtggag ggaccaaggt gaccgtcgta                                    330
```

<210> SEQ ID NO 99
<211> LENGTH: 357
<212> TYPE: DNA
<213> ORGANISM: Homo sapiens

<400> SEQUENCE: 99

```
caggtgcagc tggtgcaatc tggggctgag gtgaagaagc ctggggcctc agtgaaggtt    60
tcctgcaaga cctctggata ctccttcact agttatactt tacattgggt gcgccaggcc   120
cccggacaca ggcctgagtg gatgggatgg atcaacgctg ccttcattaa cacaaaatat   180
tcacagaagt tccagggcag aatcaccctt accagggaca cgtccgcgaa catagcctac   240
ctggagttga aagcctgac aactgaggac acggctgtgt attactgtgc gagacgggct   300
tcagggagta acggtttgga cgtctggggc caagggacca cggtcaccgt ctcctcg     357
```

<210> SEQ ID NO 100
<211> LENGTH: 321
<212> TYPE: DNA
<213> ORGANISM: Homo sapiens

<400> SEQUENCE: 100

```
gacatccaga tgacccagtc gccatcctcc ctgtctgcat ctgtgggaga cagaatcacc    60
atcacttgcc aggcgagtcg tgacattacc aactatttaa attggtatca gcagaaacca   120
gggaaagccc ctaaactcct gatctacgat gcatcctatt tggaaacagg ggtcccatca   180
acgttcagtg aagtggatc tggcacacat tttactttaa ccatcagcag cctccagcct   240
gacgattttg caacatatta ctgtcaacag tatgattctg tccccctcac tttcggcgga   300
gggaccaagg tggaaatcaa a                                              321
```

<210> SEQ ID NO 101
<211> LENGTH: 363
<212> TYPE: DNA
<213> ORGANISM: Homo sapiens

<400> SEQUENCE: 101

```
caggtgcagc tggtggagtc tgggggaggc gtggtccagc ctgggaagtc cctgagactc    60
tcctgtgcag cgtctgggtt caccttcaga gatcatggca tgcactgggt ccgccaggct   120
ccaggcaaag gctggagtg gtggcagta atatggcttg atggaagtag tcgcttctat   180
gcagactccg tagaaggccg gttcaccatc tccagagaca actccaagaa tacactatat   240
ctacaactga cgagcctgag agccgaggac acggctattt attactgtgc gagagaccgt   300
gtggcatcag aagggactgc ttttgatgtc tggggccaag gacaatggt caccgtctct   360
tcg                                                                  363
```

<210> SEQ ID NO 102
<211> LENGTH: 315
<212> TYPE: DNA
<213> ORGANISM: Homo sapiens

<400> SEQUENCE: 102

```
gaaattgtgc tgactcagtc tccagccacc ctgtccttgt ctccagggga aagagccacc    60
ctctcctgct gggccagtca gaatgttaat cattacttag tctggtatca acagagacct   120
ggccaggctc ccaggctcct cctctatgat acatccgtta gggccgctgg catcccagcc   180
aggttcattg ctctgggtc tgggacacac ttcactctca ccatcagcag cctggagcct   240
gaagattctg cagtttatta ctgtcagcac cgtagcgact ggacgttcgg ccaagggacc   300
aaggtggaga tcaaa                                                     315
```

<210> SEQ ID NO 103
<211> LENGTH: 357
<212> TYPE: DNA
<213> ORGANISM: Homo sapiens

<400> SEQUENCE: 103

```
caggtgcagc tggtgcaatc tggtactgcg gtgaagaagc tggggcctc agtgaaggtt    60
tcctgtaagg catctggatt cagtttcaac ggctattata tgcattgggt gcgacaggcc   120
cctggacagg gcttgagtg gatgggagtc attaaccca atggtggcag tacaaactac   180
gcacaaaaat tcaagggtag aatcaccatg agcgcgaca cgcccgcgag gtcagtctcc   240
atggagttgg gcagtctgag atctgacgac acggccatgt attactgtgc gagacttccc   300
gtgaatatag aagtccttga cctctggggc cagggcaccc tggtcaccgt ctcctcg      357
```

<210> SEQ ID NO 104

```
<211> LENGTH: 339
<212> TYPE: DNA
<213> ORGANISM: Homo sapiens

<400> SEQUENCE: 104
gatattgtga tgacccagag tccagactcc ctggctgtgt ctctgggcga gagggccacc      60
atcaactgca ggtcgagcca gactgttttg ttcagctcca acgataagaa ttacttagca     120
tggtatcagc agaaaccagg acagcctcct aaaattgctca tttactgggc atctgtccgg    180
gcatccgggg tccctgaccg attcagtggc agcgggtctg ggacagattt cagtctcacc     240
atcaacggcc tgcaggctga agatgtggca gtttactatt gtcagcaatc ttctactgct     300
ccgctcacct tcggcggagg gaccaaggtg gaaatcaaa                            339

<210> SEQ ID NO 105
<211> LENGTH: 402
<212> TYPE: DNA
<213> ORGANISM: Homo sapiens

<400> SEQUENCE: 105
caggtgcagc tggtgcaatc tggggctgag gtgaagaagc ctggggcctc agtgaaggtt      60
tcctgcaagg catctggata caccttcacc aactactata tgcactgggt gcgacaggcc     120
cctggacaag gcttgagtg gatgggaata atcaatccta gtggtgggag acaagctac      180 gcacagaagt tccagggcag agcctccatg accaggaca cgtccaccag cacagtctac     240
atggaggtga tcagcctgag atctgaggac acggccgtgt attactgtgc tagacaacgc    300
ccgtcgggat atagtggcta cgggccctca gagtcatacg gtaacccgac agatgatgct    360
tttgatgtct ggggccaagg gaccacggtc accgtctcct cg                       402

<210> SEQ ID NO 106
<211> LENGTH: 327
<212> TYPE: DNA
<213> ORGANISM: Homo sapiens

<400> SEQUENCE: 106
tcctatgtgc tgactcagcc accctcggtg tcagtggccc caggacagac ggccaggatt      60
acgtgtgggg gaaacaacat tggaagtagg ggtgtacact ggtaccagca gaggccaggc     120
caggcccctg tgttggtcgt ctatgatgat agcgaccggc cctcaggat ccctgagcga     180 ttctctggct ccaactctgg ggacacggcc accctgacca tcagcagggt cgaagtcggg     240
gatgaggccg actattactg tcaggtgtgg gataatagta gtgatcatct tgtggttttc     300
ggcggaggga ccaagctgac cgtccta                                         327

<210> SEQ ID NO 107
<211> LENGTH: 390
<212> TYPE: DNA
<213> ORGANISM: Homo sapiens

<400> SEQUENCE: 107
caggtgcagc tggtggagtc tgggggaggc gtggtccagc ctgggaggtc cctgagactc      60
tcctgtgcag cctctggatt cacccttcagt aattatgtta tgtattgggt ccgccaggct    120
ccaggcaagg ggctggagtg ggtggctttt atatcatatg atggaagcaa taaatactac    180
ccagactccg tgaagggccg attcaccatc tccagagaca attccatgaa cacgctgtat    240
ctgcaaatgg acagcctgag agctgaggac acggctgtct attactgtgc gagagacacg    300
tatcaatatg atagtagcac ttattacccg tacttctact actacggtat ggacgtctgg    360
```

```
ggccaaggga ccacggtcac cgtctcctcg                                       390

<210> SEQ ID NO 108
<211> LENGTH: 333
<212> TYPE: DNA
<213> ORGANISM: Homo sapiens

<400> SEQUENCE: 108
cagtctgccc tgactcagcc tgcctccgtg tctgggtctc ctggacagtc gatcaccatc       60
tcctgtattg gaaccagcag tgacgttggt ggttataact atgtctcctg gtaccagcag      120
cacccaggca aagcccccaa actcatgatt tatgaggtca gtaatcggcc ctcagggggtt     180 tctagtcgct tctcaggctc caagtctggc aacacggcct ccctgaccat ctctgggctc      240
cagtctgagg acgaggctga ttattactgc agctcatttg caagcagcag cacttctgtg      300
acgttcggcg agggaccaa gctgaccgtc cta                                    333

<210> SEQ ID NO 109
<211> LENGTH: 387
<212> TYPE: DNA
<213> ORGANISM: Homo sapiens

<400> SEQUENCE: 109
gaggtgcagc tgttggagtc tgggggaggc ttggtacagc ctggggggtc cctgagactc       60
tcctgtgcag cctctggatt cacctttagt agttatgcca tgagttgggt ccgccaggct      120
ccagggaagg ggctggagtg gtctcagct attagcggtg aggtgatag aacttactcc        180 gcagactccg tgaagggccg gttcaccatc tccagagaca attccaagaa caccctgtat      240
ctgcaaataa acagcctgag agttgaggac acggccgtat attactgtgc gcaagggggg      300 ggggggaaa tgaccgcagt aactatggac gggacctact acggtatgga cgtctggggc      360
caagggacca cggtcaccgt ctcctcg                                          387

<210> SEQ ID NO 110
<211> LENGTH: 330
<212> TYPE: DNA
<213> ORGANISM: Homo sapiens

<400> SEQUENCE: 110
cagtctgccc tgactcagcc tcgctcagtg tccgggtctc ctggacagtc aatcaccatc       60
tcctgcactg gaaccagcag taatgttggt acttataagt ttgtctcctg gtaccaacaa      120
cacccccgca aagcccccaa actcatgatt tatgatgtca ctaagcggcc ctcagggggtc     180 cctgatcgct tctctggctc caagtctggc aacacggcct ccctgaccat ctctggactc      240
caggctgaag atgaggctga ttattactgc tgctcatatg caggcagtta cacttatgtc      300
ttcggaagtg ggaccaaggt caccgtccta                                       330

<210> SEQ ID NO 111
<211> LENGTH: 357
<212> TYPE: DNA
<213> ORGANISM: Homo sapiens

<400> SEQUENCE: 111
caggtgcagc tggtggagtc tgggggaggc gtggtccagc ctgggatgtc cctgagactc       60
tcctgtgcag cctctggatt cagcttcagt agtcatggca tgcactgggt ccgccagact      120
ccaggcaagg ggctggagtg gttggcagta atttcatatg atgcaagtaa caaaagttat      180
```

| | |
|---|---|
| gcagactccg tgaagggccg gttcaccatc tccagagaca attccaagaa gacgctgtat | 240 |
| ttgcaaatgg acagcctgag agttgaagac acggctctgt attactgtgc gaatgcgttc | 300 |
| agcagttcgg catctggggg ctactggggc cagggcaccc tggtcaccgt ctcctcg | 357 |

<210> SEQ ID NO 112
<211> LENGTH: 339
<212> TYPE: DNA
<213> ORGANISM: Homo sapiens

<400> SEQUENCE: 112

| | |
|---|---|
| gatgttgtga tgactcagtc tccactctcc ctgcccgtca cccttggaca gccggcctcc | 60 |
| atctcctgca ggtccagtca agcctcgtt cacagtgatg gagtcaccta cttgaattgg | 120 |
| tttcaacaga ggccaggcca atctccaagg cgcctaattt ataaggtttc taatcgggac | 180 |
| tctggggtcc cagacagatt cagcggcagt gggtcaggca ctgatttcac actggaaatc | 240 |
| agcagggtgg aggctgagga tgttggatt tattactgca tgcaaggtac acactggcct | 300 |
| ccctggacgt tcggccaagg gaccaaggtg gaaatcaaa | 339 |

<210> SEQ ID NO 113
<211> LENGTH: 378
<212> TYPE: DNA
<213> ORGANISM: Homo sapiens

<400> SEQUENCE: 113

| | |
|---|---|
| caggtgcagc tggtggagtc tggggagc gtggtccagc ctgggaggtc cctgagactc | 60 |
| tcctgtgcag cgtctggatt caccttcagt agctatggca tgcactgggt ccgccaggct | 120 |
| ccaggcaagg gctggagtg ggtggcgatt atatactatg attcaagtca gagatactat | 180 |
| gcagactccg tgaagggccg attcaccatc tccagagaca attccaagaa cgcgctgtat | 240 |
| ctgcaaatga atagcctgag gccgaggac accgctctgt attactgtgc gagagatctt | 300 |
| ccgtttcact atcatagaag tgcctctttc gcaccttcgg acacctgggg ccagggaacc | 360 |
| ctggtcaccg tctcctcg | 378 |

<210> SEQ ID NO 114
<211> LENGTH: 324
<212> TYPE: DNA
<213> ORGANISM: Homo sapiens

<400> SEQUENCE: 114

| | |
|---|---|
| gaaattgtgc tgactcagtc tccaggcacc ctgtctttgt ctccggggga aagagccacc | 60 |
| ctctcctgca gggccagtca ggctgttacc aacaactact tagcctggta ccagcaaaaa | 120 |
| cctggccagg ctcccagact cctcgtctat gctgcatcca gcagggccac tggcatccca | 180 |
| gacagattct atggcagtgg gtctggggcg gacttcactc tcaccatcag cagactggag | 240 |
| cctgaagatt ttgcagtgta ttactgtcag caatatggta cctcaccgat caccttcggc | 300 |
| caagggacac gactggagat taaa | 324 |

<210> SEQ ID NO 115
<211> LENGTH: 339
<212> TYPE: DNA
<213> ORGANISM: Homo sapiens

<400> SEQUENCE: 115

| | |
|---|---|
| gaggtgcagc tggtggagtc tgggggaggc ttggtacagc ctgggggtc cctgagactc | 60 |
| tcctgtgcag cctctggatt caccttcagt agctatagga tgaactgggt ccgtcaggct | 120 |

```
ccagggaagg ggctggagtg ggtttcatac attagtacta gtagtagtac catatactac    180
gcagactctg tgaagggccg attcaccatc tccagagaca atgccaagaa ctcactgtat    240
ctgcaaatga acagcctgag agccgaggac acggctgtgt attactgtgc gagagcattc    300
gactactggg gccagggaac cctggtcacc gtctcctcg                           339
```

<210> SEQ ID NO 116
<211> LENGTH: 324
<212> TYPE: DNA
<213> ORGANISM: Homo sapiens

<400> SEQUENCE: 116

```
gaaattgtgc tgactcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcat cagactggag    240
cctgaagact ttgcagtgta ttactgtcag cagtatggta gctcaccgtt cacttttggc    300
caggggacca aggtggagat caaa                                           324
```

<210> SEQ ID NO 117
<211> LENGTH: 122
<212> TYPE: PRT
<213> ORGANISM: Artificial
<220> FEATURE:
<223> OTHER INFORMATION: His-huTDP43 domain I

<400> SEQUENCE: 117

```
Met Arg Gly Ser His His His His His His Gly Leu Val Pro Arg Gly
1               5                   10                  15

Ser Ser Glu Tyr Ile Arg Val Thr Glu Asp Glu Asn Asp Glu Pro Ile
            20                  25                  30

Glu Ile Pro Ser Glu Asp Asp Gly Thr Val Leu Leu Ser Thr Val Thr
        35                  40                  45

Ala Gln Phe Pro Gly Ala Cys Gly Leu Arg Tyr Arg Asn Pro Val Ser
    50                  55                  60

Gln Cys Met Arg Gly Val Arg Leu Val Glu Gly Ile Leu His Ala Pro
65                  70                  75                  80

Asp Ala Gly Trp Gly Asn Leu Val Tyr Val Val Asn Tyr Pro Lys Asp
                85                  90                  95

Asn Lys Arg Lys Met Asp Glu Thr Asp Ala Ser Ser Ala Val Lys Val
            100                 105                 110

Lys Arg Ala Val Gln Lys Thr Ser Asp Leu
        115                 120
```

<210> SEQ ID NO 118
<211> LENGTH: 123
<212> TYPE: PRT
<213> ORGANISM: Artificial
<220> FEATURE:
<223> OTHER INFORMATION: His-huTDP43 domain II

<400> SEQUENCE: 118

```
Met Arg Gly Ser His His His His His His Gly Leu Val Pro Arg Gly
1               5                   10                  15

Ser Ala Val Gln Lys Thr Ser Asp Leu Ile Val Leu Gly Leu Pro Trp
            20                  25                  30
```

```
Lys Thr Thr Glu Gln Asp Leu Lys Glu Tyr Phe Ser Thr Phe Gly Glu
            35                  40                  45

Val Leu Met Val Gln Val Lys Lys Asp Leu Lys Thr Gly His Ser Lys
 50                  55                  60

Gly Phe Gly Phe Val Arg Phe Thr Glu Tyr Glu Thr Gln Val Lys Val
 65                  70                  75                  80

Met Ser Gln Arg His Met Ile Asp Gly Arg Trp Cys Asp Cys Lys Leu
                 85                  90                  95

Pro Asn Ser Lys Gln Ser Gln Asp Glu Pro Leu Arg Ser Arg Lys Val
                100                 105                 110

Phe Val Gly Arg Cys Thr Glu Asp Met Thr Glu
                115                 120
```

<210> SEQ ID NO 119
<211> LENGTH: 108
<212> TYPE: PRT
<213> ORGANISM: Artificial
<220> FEATURE:
<223> OTHER INFORMATION: His-huTDP43 domain III

<400> SEQUENCE: 119

```
Met Arg Gly Ser His His His His His His Gly Leu Val Pro Arg Gly
 1               5                  10                  15

Ser Ser Gln Asp Glu Pro Leu Arg Ser Arg Lys Val Phe Val Gly Arg
                 20                  25                  30

Cys Thr Glu Asp Met Thr Glu Asp Glu Leu Arg Glu Phe Phe Ser Gln
             35                  40                  45

Tyr Gly Asp Val Met Asp Val Phe Ile Pro Lys Pro Phe Arg Ala Phe
 50                  55                  60

Ala Phe Val Thr Phe Ala Asp Asp Gln Ile Ala Gln Ser Leu Cys Gly
 65                  70                  75                  80

Glu Asp Leu Ile Ile Lys Gly Ile Ser Val His Ile Ser Asn Ala Glu
                 85                  90                  95

Pro Lys His Asn Ser Asn Arg Gln Leu Glu Arg Ser
                100                 105
```

<210> SEQ ID NO 120
<211> LENGTH: 174
<212> TYPE: PRT
<213> ORGANISM: Artificial
<220> FEATURE:
<223> OTHER INFORMATION: His-huTDP43 domain IV

<400> SEQUENCE: 120

```
Met Arg Gly Ser His His His His His His Gly Leu Val Pro Arg Gly
 1               5                  10                  15

Ser Ser Asn Ala Glu Pro Lys His Asn Ser Asn Arg Gln Leu Glu Arg
                 20                  25                  30

Ser Gly Arg Phe Gly Gly Asn Pro Gly Gly Phe Gly Asn Gln Gly Gly
             35                  40                  45

Phe Gly Asn Ser Arg Gly Gly Gly Ala Gly Leu Gly Asn Asn Gln Gly
 50                  55                  60

Ser Asn Met Gly Gly Gly Met Asn Phe Gly Ala Phe Ser Ile Asn Pro
 65                  70                  75                  80

Ala Met Met Ala Ala Ala Gln Ala Ala Leu Gln Ser Ser Trp Gly Met
                 85                  90                  95

Met Gly Met Leu Ala Ser Gln Gln Asn Gln Ser Gly Pro Ser Gly Asn
                100                 105                 110
```

```
Asn Gln Asn Gln Gly Asn Met Gln Arg Glu Pro Asn Gln Ala Phe Gly
        115                 120                 125
Ser Gly Asn Asn Ser Tyr Ser Gly Ser Asn Ser Gly Ala Ala Ile Gly
        130                 135                 140
Trp Gly Ser Ala Ser Asn Ala Gly Ser Gly Ser Gly Phe Asn Gly Gly
145                 150                 155                 160
Phe Gly Ser Ser Met Asp Ser Lys Ser Ser Gly Trp Gly Met
                165                 170

<210> SEQ ID NO 121
<211> LENGTH: 430
<212> TYPE: PRT
<213> ORGANISM: Artificial
<220> FEATURE:
<223> OTHER INFORMATION: His-huTDP43 full-length

<400> SEQUENCE: 121

Met Arg Gly Ser His His His His His His Gly Leu Val Pro Arg Gly
1               5                   10                  15
Ser Ser Glu Tyr Ile Arg Val Thr Glu Asp Glu Asn Asp Glu Pro Ile
            20                  25                  30
Glu Ile Pro Ser Glu Asp Asp Gly Thr Val Leu Leu Ser Thr Val Thr
        35                  40                  45
Ala Gln Phe Pro Gly Ala Cys Gly Leu Arg Tyr Arg Asn Pro Val Ser
    50                  55                  60
Gln Cys Met Arg Gly Val Arg Leu Val Glu Gly Ile Leu His Ala Pro
65                  70                  75                  80
Asp Ala Gly Trp Gly Asn Leu Val Tyr Val Val Asn Tyr Pro Lys Asp
                85                  90                  95
Asn Lys Arg Lys Met Asp Glu Thr Asp Ala Ser Ser Ala Val Lys Val
            100                 105                 110
Lys Arg Ala Val Gln Lys Thr Ser Asp Leu Ile Val Leu Gly Leu Pro
        115                 120                 125
Trp Lys Thr Thr Glu Gln Asp Leu Lys Glu Tyr Phe Ser Thr Phe Gly
    130                 135                 140
Glu Val Leu Met Val Gln Val Lys Lys Asp Leu Lys Thr Gly His Ser
145                 150                 155                 160
Lys Gly Phe Gly Phe Val Arg Phe Thr Glu Tyr Glu Thr Gln Val Lys
                165                 170                 175
Val Met Ser Gln Arg His Met Ile Asp Gly Arg Trp Cys Asp Cys Lys
            180                 185                 190
Leu Pro Asn Ser Lys Gln Ser Gln Asp Glu Pro Leu Arg Ser Arg Lys
        195                 200                 205
Val Phe Val Gly Arg Cys Thr Glu Asp Met Thr Glu Asp Glu Leu Arg
    210                 215                 220
Glu Phe Phe Ser Gln Tyr Gly Asp Val Met Asp Val Phe Ile Pro Lys
225                 230                 235                 240
Pro Phe Arg Ala Phe Ala Phe Val Thr Phe Ala Asp Asp Gln Ile Ala
                245                 250                 255
Gln Ser Leu Cys Gly Glu Asp Leu Ile Ile Lys Gly Ile Ser Val His
            260                 265                 270
Ile Ser Asn Ala Glu Pro Lys His Asn Ser Asn Arg Gln Leu Glu Arg
        275                 280                 285
Ser Gly Arg Phe Gly Gly Asn Pro Gly Gly Phe Gly Asn Gln Gly Gly
    290                 295                 300
```

-continued

```
Phe Gly Asn Ser Arg Gly Gly Ala Gly Leu Gly Asn Asn Gln Gly
305                 310                 315                 320

Ser Asn Met Gly Gly Met Asn Phe Gly Ala Phe Ser Ile Asn Pro
                325                 330                 335

Ala Met Ala Ala Ala Gln Ala Ala Leu Gln Ser Ser Trp Gly Met
            340                 345                 350

Met Gly Met Leu Ala Ser Gln Gln Asn Gln Ser Gly Pro Ser Gly Asn
        355                 360                 365

Asn Gln Asn Gln Gly Asn Met Gln Arg Glu Pro Asn Gln Ala Phe Gly
        370                 375                 380

Ser Gly Asn Asn Ser Tyr Ser Gly Ser Asn Ser Gly Ala Ala Ile Gly
385                 390                 395                 400

Trp Gly Ser Ala Ser Asn Ala Gly Ser Gly Ser Gly Phe Asn Gly Gly
                405                 410                 415

Phe Gly Ser Ser Met Asp Ser Lys Ser Ser Gly Trp Gly Met
                420                 425                 430

<210> SEQ ID NO 122
<211> LENGTH: 108
<212> TYPE: PRT
<213> ORGANISM: Homo sapiens

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ile Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Gln Gly Thr Lys Val Glu Ile Lys
            100                 105

<210> SEQ ID NO 123
<211> LENGTH: 11
<212> TYPE: PRT
<213> ORGANISM: Homo sapiens

<400> SEQUENCE: 123

Gln Tyr Gly Asp Val Met Asp Val Phe Ile Pro
1               5                   10

<210> SEQ ID NO 124
<211> LENGTH: 11
<212> TYPE: PRT
<213> ORGANISM: Homo sapiens

<400> SEQUENCE: 124

Ala Ala Ile Gly Trp Gly Ser Ala Ser Asn Ala
1               5                   10

<210> SEQ ID NO 125
<211> LENGTH: 11
```

<212> TYPE: PRT
<213> ORGANISM: Homo sapiens

<400> SEQUENCE: 125

Asp Met Thr Glu Asp Glu Leu Arg Glu Phe Phe
1               5                   10

<210> SEQ ID NO 126
<211> LENGTH: 7
<212> TYPE: PRT
<213> ORGANISM: Homo sapiens

<400> SEQUENCE: 126

Glu Asp Glu Asn Asp Glu Pro
1               5

<210> SEQ ID NO 127
<211> LENGTH: 7
<212> TYPE: PRT
<213> ORGANISM: Homo sapiens

<400> SEQUENCE: 127

Val Gln Val Lys Lys Asp Leu
1               5

<210> SEQ ID NO 128
<211> LENGTH: 7
<212> TYPE: PRT
<213> ORGANISM: Homo sapiens

<400> SEQUENCE: 128

Lys Glu Tyr Phe Ser Thr Phe
1               5

<210> SEQ ID NO 129
<211> LENGTH: 130
<212> TYPE: PRT
<213> ORGANISM: Homo sapiens

<400> SEQUENCE: 129

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Val Met Tyr Trp Val Arg Gln Ala Pro Gly Lys Gly Leu Glu Trp Val
            35                  40                  45

Ala Phe Ile Ser Tyr Asp Gly Ser Asn Lys Tyr Tyr Pro Asp Ser Val
        50                  55                  60

Lys Gly Arg Phe Thr Ile Ser Arg Asp Asn Ser Met Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Thr Tyr Gln Tyr Asp Ser Ser Thr Tyr Tyr Pro Tyr Phe
                100                 105                 110

Tyr Tyr Tyr Gly Met Asp Val Trp Gly Gln Gly Thr Thr Val Thr Val
            115                 120                 125

Ser Ser
    130

<210> SEQ ID NO 130
<211> LENGTH: 113

```
<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met His Ser Leu Arg Ala Glu Asp Thr Ala Val Tyr Tyr Cys
                85                  90                  95

Ala Ser Pro Pro Gly Trp Trp Gly Gln Gly Thr Leu Val Thr Val Ser
            100                 105                 110

Ser

<210> SEQ ID NO 131
<211> LENGTH: 10
<212> TYPE: PRT
<213> ORGANISM: Homo sapiens

<400> SEQUENCE: 131

Gly Phe Thr Phe Ser Thr Tyr Tyr Met Ser
1               5                   10

<210> SEQ ID NO 132
<211> LENGTH: 17
<212> TYPE: PRT
<213> ORGANISM: Homo sapiens

<400> SEQUENCE: 132

Asn Ile Lys Gln Asp Gly Ser Glu Lys Tyr Tyr Val Asp Ser Val Lys
1               5                   10                  15

Gly

<210> SEQ ID NO 133
<211> LENGTH: 4
<212> TYPE: PRT
<213> ORGANISM: Homo sapiens

<400> SEQUENCE: 133

Pro Pro Gly Trp
1

<210> SEQ ID NO 134
<211> LENGTH: 112
<212> TYPE: PRT
<213> ORGANISM: Homo sapiens

<400> SEQUENCE: 134

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45
```

```
Pro Gln Leu Leu Ile Tyr Glu Val Ser Asn Arg Phe Ser Gly Val Pro
    50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ser
                 85                  90                  95
Ile Gln Leu Pro Val Thr Phe Gly Gly Gly Thr Lys Val Glu Ile Lys
            100                 105                 110
```

<210> SEQ ID NO 135
<211> LENGTH: 16
<212> TYPE: PRT
<213> ORGANISM: Homo sapiens

<400> SEQUENCE: 135

```
Lys Ser Ser Gln Ser Leu Leu His Ser Asp Gly Lys Thr Tyr Leu Tyr
 1               5                  10                  15
```

<210> SEQ ID NO 136
<211> LENGTH: 7
<212> TYPE: PRT
<213> ORGANISM: Homo sapiens

<400> SEQUENCE: 136

```
Glu Val Ser Asn Arg Phe Ser
 1               5
```

<210> SEQ ID NO 137
<211> LENGTH: 9
<212> TYPE: PRT
<213> ORGANISM: Homo sapiens

<400> SEQUENCE: 137

```
Met Gln Ser Ile Gln Leu Pro Val Thr
 1               5
```

<210> SEQ ID NO 138
<211> LENGTH: 119
<212> TYPE: PRT
<213> ORGANISM: Homo sapiens

<400> SEQUENCE: 138

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Ile Phe Thr Asp Tyr
                 20                  25                  30
Phe Ile His Trp Ile Arg Gln Ala Pro Gly Gln Gly Leu Glu Trp Met
             35                  40                  45
Gly Trp Ile Lys Pro Lys Ser Gly Gly Thr Asp Tyr Ala Glu Lys Phe
 50                  55                  60
Gln Gly Arg Val Thr Leu Thr Arg Asp Thr Ser Ile Thr Thr Val Tyr
 65                  70                  75                  80
Met Glu Leu Ser Arg Leu Asn Ser Asp Thr Ala Val Tyr Tyr Cys
                 85                  90                  95
Ala Arg Leu Lys Tyr Ser Val Pro Asp Ser Asp Tyr Trp Gly Gln Gly
            100                 105                 110
Thr Leu Val Thr Val Ser Ser
            115
```

```
<210> SEQ ID NO 139
<211> LENGTH: 10
<212> TYPE: PRT
<213> ORGANISM: Homo sapiens

<400> SEQUENCE: 139

Gly Tyr Ile Phe Thr Asp Tyr Phe Ile His
1               5                   10

<210> SEQ ID NO 140
<211> LENGTH: 17
<212> TYPE: PRT
<213> ORGANISM: Homo sapiens

<400> SEQUENCE: 140

Trp Ile Lys Pro Lys Ser Gly Gly Thr Asp Tyr Ala Glu Lys Phe Gln
1               5                   10                  15

Gly

<210> SEQ ID NO 141
<211> LENGTH: 10
<212> TYPE: PRT
<213> ORGANISM: Homo sapiens

<400> SEQUENCE: 141

Leu Lys Tyr Ser Val Pro Asp Ser Asp Tyr
1               5                   10

<210> SEQ ID NO 142
<211> LENGTH: 112
<212> TYPE: PRT
<213> ORGANISM: Homo sapiens

<400> SEQUENCE: 142

Asp Val Val Met Thr Gln Ser Pro Leu Ser Leu Pro Val Thr Leu Gly
1               5                   10                  15

Gln Ser Ala Ser Ile Ser Cys Arg Ser Ser Gln Gly Leu Val His Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Phe Asn Arg Asp Ser Gly Val Ser
    50                  55                  60

Asp Arg Phe Ser Gly Ser Gly Ser Gly Ser Asp Phe Thr Leu Met Ile
65                  70                  75                  80

Ser Arg Val Glu Ala Glu Asp Val Gly Ile Tyr Tyr Cys Met Gln Gly
                85                  90                  95

Thr Leu Trp Pro Leu Thr Phe Gly Gln Gly Thr Lys Val Glu Ile Lys
            100                 105                 110

<210> SEQ ID NO 143
<211> LENGTH: 16
<212> TYPE: PRT
<213> ORGANISM: Homo sapiens

<400> SEQUENCE: 143

Arg Ser Ser Gln Gly Leu Val His Ser Asp Gly Asn Thr Tyr Leu Asn
1               5                   10                  15

<210> SEQ ID NO 144
<211> LENGTH: 7
<212> TYPE: PRT
<213> ORGANISM: Homo sapiens
```

```
<400> SEQUENCE: 144

Lys Val Phe Asn Arg Asp Ser
1               5

<210> SEQ ID NO 145
<211> LENGTH: 9
<212> TYPE: PRT
<213> ORGANISM: Homo sapiens

<400> SEQUENCE: 145

Met Gln Gly Thr Leu Trp Pro Leu Thr
1               5

<210> SEQ ID NO 146
<211> LENGTH: 126
<212> TYPE: PRT
<213> ORGANISM: Homo sapiens

<400> SEQUENCE: 146

Glu Val Gln Leu Val Glu Ser Gly Gly Gly Leu Val Lys Pro Gly Gly
1               5                  10                  15

Ser Leu Arg Leu Ser Cys Ala Thr Ser Gly Phe Asn Phe Ser Asn Val
            20                  25                  30

Trp Ile Ser Trp Val Arg Gln Ala Pro Gly Lys Gly Leu Glu Trp Val
        35                  40                  45

Gly Arg Ile Lys Ser Lys Asn Asp Gly Gly Thr Thr Glu Tyr Ala Ala
    50                  55                  60

Pro Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Ala Gly Val Tyr
                85                  90                  95

Tyr Cys Thr Thr Asp Pro Tyr His Tyr Phe Asp Met Gly Gly Pro Gly
                100                 105                 110

Phe Gly Pro Trp Gly Gln Gly Thr Leu Val Thr Val Ser Ser
            115                 120                 125

<210> SEQ ID NO 147
<211> LENGTH: 10
<212> TYPE: PRT
<213> ORGANISM: Homo sapiens

<400> SEQUENCE: 147

Gly Phe Asn Phe Ser Asn Val Trp Ile Ser
1               5                   10

<210> SEQ ID NO 148
<211> LENGTH: 19
<212> TYPE: PRT
<213> ORGANISM: Homo sapiens

<400> SEQUENCE: 148

Arg Ile Lys Ser Lys Asn Asp Gly Gly Thr Thr Glu Tyr Ala Ala Pro
1               5                   10                  15

Val Lys Gly

<210> SEQ ID NO 149
<211> LENGTH: 15
<212> TYPE: PRT
<213> ORGANISM: Homo sapiens
```

-continued

```
<400> SEQUENCE: 149

Asp Pro Tyr His Tyr Phe Asp Met Gly Gly Pro Gly Phe Gly Pro
1               5                   10                  15

<210> SEQ ID NO 150
<211> LENGTH: 113
<212> TYPE: PRT
<213> ORGANISM: Homo sapiens

<400> SEQUENCE: 150

Asp Ile Val Met Thr Gln Ser Pro Asp Ser Leu Ala Val Ser Leu Gly
1               5                   10                  15

Glu Arg Ala Thr Ile Asn Cys Lys Ser Gly Gln Ser Val Leu Tyr Arg
            20                  25                  30

Ser Asn Asn Arg Asn Tyr Ile Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asn Arg Trp Thr Phe Gly Gln Gly Thr Lys Val Glu Ile
            100                 105                 110

Lys

<210> SEQ ID NO 151
<211> LENGTH: 113
<212> TYPE: PRT
<213> ORGANISM: Homo sapiens

<400> SEQUENCE: 151

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Tyr Ser
            20                  25                  30

Ser Asn Asn Lys Asn Phe Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Leu Pro Ile Ser Phe Gly Gln Gly Thr Arg Leu Glu Ile
            100                 105                 110

Lys

<210> SEQ ID NO 152
<211> LENGTH: 17
<212> TYPE: PRT
<213> ORGANISM: Homo sapiens

<400> SEQUENCE: 152

Lys Ser Ser Gln Ser Val Ser Tyr Ser Ser Asn Asn Lys Asn Phe Leu
1               5                   10                  15

Ser
```

<210> SEQ ID NO 153
<211> LENGTH: 7
<212> TYPE: PRT
<213> ORGANISM: Homo sapiens

<400> SEQUENCE: 153

Trp Ala Ser Thr Arg Glu Ser
1               5

<210> SEQ ID NO 154
<211> LENGTH: 9
<212> TYPE: PRT
<213> ORGANISM: Homo sapiens

<400> SEQUENCE: 154

Gln Gln Tyr Ser Ser Leu Pro Ile Ser
1               5

<210> SEQ ID NO 155
<211> LENGTH: 123
<212> TYPE: PRT
<213> ORGANISM: Homo sapiens

<400> SEQUENCE: 155

Glu Val Gln Leu Leu Glu Ser Gly Gly Ala Leu Val Gln Pro Gly Gly
1               5                   10                  15

Ser Leu Arg Leu Ser Cys Ala Ala Ser Gly Leu Thr Phe Ser Arg His
                20                  25                  30

Ala Phe Ser Trp Val Arg Gln Ala Pro Gly Lys Gly Leu Glu Trp Val
            35                  40                  45

Ala Ile Ser Ser Gly Ser Gly Gly Asn Thr Tyr Tyr Ala Ala Ser Val
        50                  55                  60

Lys Gly Arg Phe Thr Ile Ser Arg Asp Glu Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Glu Val Leu Glu Trp Ser Leu Leu Ser Arg Tyr Met Asp Val
            100                 105                 110

Trp Gly Lys Gly Thr Thr Val Thr Val Ser Ser
        115                 120

<210> SEQ ID NO 156
<211> LENGTH: 10
<212> TYPE: PRT
<213> ORGANISM: Homo sapiens

<400> SEQUENCE: 156

Gly Leu Thr Phe Ser Arg His Ala Phe Ser
1               5                   10

<210> SEQ ID NO 157
<211> LENGTH: 17
<212> TYPE: PRT
<213> ORGANISM: Homo sapiens

<400> SEQUENCE: 157

Ile Ser Ser Gly Ser Gly Gly Asn Thr Tyr Tyr Ala Ala Ser Val Lys
1               5                   10                  15

Gly

<210> SEQ ID NO 158
<211> LENGTH: 14
<212> TYPE: PRT
<213> ORGANISM: Homo sapiens

<400> SEQUENCE: 158

Glu Val Leu Glu Trp Ser Leu Leu Ser Arg Tyr Met Asp Val
1               5                   10

<210> SEQ ID NO 159
<211> LENGTH: 110
<212> TYPE: PRT
<213> ORGANISM: Homo sapiens

<400> SEQUENCE: 159

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val Asn Trp Tyr His Gln Leu Pro Gly Thr Ala Pro Lys Leu Leu
        35                  40                  45

Val Tyr Ser Thr Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ala Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
            100                 105                 110

<210> SEQ ID NO 160
<211> LENGTH: 13
<212> TYPE: PRT
<213> ORGANISM: Homo sapiens

<400> SEQUENCE: 160

Ser Gly Ser Ser Ser Asn Ile Gly Gly Asn Thr Val Asn
1               5                   10

<210> SEQ ID NO 161
<211> LENGTH: 7
<212> TYPE: PRT
<213> ORGANISM: Homo sapiens

<400> SEQUENCE: 161

Ser Thr Asn Gln Arg Pro Ser
1               5

<210> SEQ ID NO 162
<211> LENGTH: 11
<212> TYPE: PRT
<213> ORGANISM: Homo sapiens

<400> SEQUENCE: 162

Ala Thr Trp Asp Asp Ser Leu Asn Gly Trp Val
1               5                   10

<210> SEQ ID NO 163
<211> LENGTH: 112
<212> TYPE: PRT
<213> ORGANISM: Homo sapiens -continued

<400> SEQUENCE: 163

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asp Tyr
            20                  25                  30

Tyr Trp Ser Trp Ile Arg Gln Pro Pro Gly Lys Gly Leu Glu Trp Ile
        35                  40                  45

Gly Tyr Ile His Asp Ser Gly Thr Thr Arg Tyr Asn Pro Ser Leu Thr
    50                  55                  60

Ser Arg Leu Ser Met Ser Leu Asp Thr Ser Thr Asn Gln Val Ser Leu
65                  70                  75                  80

Arg Leu Thr Ser Val Thr Ala Ala Asp Thr Ala Val Tyr Tyr Cys Ala
                85                  90                  95

Lys Val Pro Asp Tyr Trp Gly Gln Gly Thr Leu Val Thr Val Ser Ser
            100                 105                 110

<210> SEQ ID NO 164
<211> LENGTH: 10
<212> TYPE: PRT
<213> ORGANISM: Homo sapiens

<400> SEQUENCE: 164

Gly Gly Ser Ile Thr Asp Tyr Tyr Trp Ser
1               5                   10

<210> SEQ ID NO 165
<211> LENGTH: 16
<212> TYPE: PRT
<213> ORGANISM: Homo sapiens

<400> SEQUENCE: 165

Tyr Ile His Asp Ser Gly Thr Thr Arg Tyr Asn Pro Ser Leu Thr Ser
1               5                   10                  15

<210> SEQ ID NO 166
<211> LENGTH: 4
<212> TYPE: PRT
<213> ORGANISM: Homo sapiens

<400> SEQUENCE: 166

Val Pro Asp Tyr
1

<210> SEQ ID NO 167
<211> LENGTH: 113
<212> TYPE: PRT
<213> ORGANISM: Homo sapiens

<400> SEQUENCE: 167

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asp Asn Lys Asn Tyr Leu Ala Trp Leu Gln Gln Lys Pro Gly Gln
        35                  40                  45

Pro Pro Lys Val Leu Ile Tyr Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Val Pro Phe Thr Phe Gly Gly Gly Thr Lys Val Glu Ile
            100                 105                 110
Lys

<210> SEQ ID NO 168
<211> LENGTH: 17
<212> TYPE: PRT
<213> ORGANISM: Homo sapiens

<400> SEQUENCE: 168

Lys Ser Ser Gln Ser Val Leu Tyr Asn Ser Asp Asn Lys Asn Tyr Leu
1               5                   10                  15
Ala

<210> SEQ ID NO 169
<211> LENGTH: 7
<212> TYPE: PRT
<213> ORGANISM: Homo sapiens

<400> SEQUENCE: 169

Trp Ala Ser Thr Arg Glu Phe
1               5

<210> SEQ ID NO 170
<211> LENGTH: 9
<212> TYPE: PRT
<213> ORGANISM: Homo sapiens

<400> SEQUENCE: 170

His Gln Tyr Tyr Ser Val Pro Phe Thr
1               5

<210> SEQ ID NO 171
<211> LENGTH: 116
<212> TYPE: PRT
<213> ORGANISM: Homo sapiens

<400> SEQUENCE: 171

Gln Val Gln Leu Gln Glu Ser Gly Pro Gly Val Val Lys Pro Ser Gln
1               5                   10                  15

Thr Leu Ser Leu Thr Cys Thr Val Ser Gly Val Ser Val Gly Ser Gly
            20                  25                  30

Asp Tyr Tyr Trp Ser Trp Ile Arg His Pro Gly Lys Gly Leu Glu
        35                  40                  45

Trp Ile Gly Tyr Ile Ser Phe Phe Gly Ser Asn Tyr Asn Pro Ser
    50                  55                  60

Leu Lys Gly Arg Val Ser Met Ser Val Asp Thr Ser Asn Asn Gln Phe
65                  70                  75                  80

Ser Leu Asn Leu Lys Ser Val Thr Ala Ala Asp Thr Ala Val Tyr Phe
                85                  90                  95

Cys Ala Thr Gly Asn Ala Tyr Ser Phe Trp Gly Gln Gly Thr Met Val
            100                 105                 110

Thr Val Ser Ser
        115

<210> SEQ ID NO 172
<211> LENGTH: 12
<212> TYPE: PRT

<213> ORGANISM: Homo sapiens

<400> SEQUENCE: 172

Gly Val Ser Val Gly Ser Gly Asp Tyr Tyr Trp Ser
1               5                   10

<210> SEQ ID NO 173
<211> LENGTH: 16
<212> TYPE: PRT
<213> ORGANISM: Homo sapiens

<400> SEQUENCE: 173

Tyr Ile Ser Phe Phe Gly Ser Ser Asn Tyr Asn Pro Ser Leu Lys Gly
1               5                   10                  15

<210> SEQ ID NO 174
<211> LENGTH: 6
<212> TYPE: PRT
<213> ORGANISM: Homo sapiens

<400> SEQUENCE: 174

Gly Asn Ala Tyr Ser Phe
1               5

<210> SEQ ID NO 175
<211> LENGTH: 108
<212> TYPE: PRT
<213> ORGANISM: Homo sapiens

<400> SEQUENCE: 175

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr His
            20                  25                  30

Asn Leu Val Ser Trp Tyr Gln Gln His Pro Gly Lys Ala Pro Lys Leu
        35                  40                  45

Ile Ile Tyr Glu Ile Phe Glu Arg Pro Ser Gly Ile Ser Ser Arg Phe
    50                  55                  60

Thr Gly Ser Lys Ser Gly Asn Thr Ala Ser Leu Thr Ile Ser Gly Leu
65                  70                  75                  80

Gln Ala Glu Asp Glu Ala Asp Tyr Phe Cys Cys Ala Tyr Ser Val Thr
                85                  90                  95

Val Ile Phe Gly Gly Gly Thr Lys Leu Thr Val Leu
            100                 105

<210> SEQ ID NO 176
<211> LENGTH: 14
<212> TYPE: PRT
<213> ORGANISM: Homo sapiens

<400> SEQUENCE: 176

Thr Gly Thr Ser Ser Asp Ile Gly Thr His Asn Leu Val Ser
1               5                   10

<210> SEQ ID NO 177
<211> LENGTH: 7
<212> TYPE: PRT
<213> ORGANISM: Homo sapiens

<400> SEQUENCE: 177

Glu Ile Phe Glu Arg Pro Ser
1               5

<210> SEQ ID NO 178
<211> LENGTH: 8
<212> TYPE: PRT
<213> ORGANISM: Homo sapiens

<400> SEQUENCE: 178

Cys Ala Tyr Ser Val Thr Val Ile
1               5

<210> SEQ ID NO 179
<211> LENGTH: 112
<212> TYPE: PRT
<213> ORGANISM: Homo sapiens

<400> SEQUENCE: 179

Glu Val Gln Leu Val Glu Ser Gly Gly Asp Leu Val Gln Pro Gly Gly
1               5                   10                  15

Ser Leu Arg Leu Ser Cys Thr Ala Ser Gly Phe Asn Leu Gly Asp Tyr
            20                  25                  30

Trp Met His Trp Val Arg Gln Val Pro Gly Lys Gly Leu Val Trp Val
        35                  40                  45

Ser Arg Ile Ser Ser Asp Gly Ala Ser Val Ser Tyr Ala Asp Phe Val
    50                  55                  60

Glu Gly Arg Phe Thr Ile Ser Arg Gly Asn Ala Arg Asn Thr Leu Phe
65                  70                  75                  80

Leu Glu Leu Asn Ser Leu Arg Leu Asp Asp Thr Ala Val Tyr Tyr Cys
                85                  90                  95

Ala Met Gly Val Val Trp Gly Gln Gly Thr Leu Val Thr Val Ser Ser
            100                 105                 110

<210> SEQ ID NO 180
<211> LENGTH: 10
<212> TYPE: PRT
<213> ORGANISM: Homo sapiens

<400> SEQUENCE: 180

Gly Phe Asn Leu Gly Asp Tyr Trp Met His
1               5                   10

<210> SEQ ID NO 181
<211> LENGTH: 17
<212> TYPE: PRT
<213> ORGANISM: Homo sapiens

<400> SEQUENCE: 181

Arg Ile Ser Ser Asp Gly Ala Ser Val Ser Tyr Ala Asp Phe Val Glu
1               5                   10                  15

Gly

<210> SEQ ID NO 182
<211> LENGTH: 3
<212> TYPE: PRT
<213> ORGANISM: Homo sapiens

<400> SEQUENCE: 182

Gly Val Val
1

<210> SEQ ID NO 183
<211> LENGTH: 108

```
<212> TYPE: PRT
<213> ORGANISM: Homo sapiens

<400> SEQUENCE: 183

Ser Tyr Glu Leu Thr Gln Pro Pro Ser Val Ser Val Ser Pro Gly Gln
1               5                   10                  15

Thr Ala Thr Ile Ser Cys Ser Gly Asp Ala Leu Pro Lys Arg Tyr Ala
            20                  25                  30

Tyr Trp Tyr Lys Gln Lys Ser Gly Gln Val Pro Val Leu Ile Ile Tyr
        35                  40                  45

Glu Asp Asn Lys Arg Pro Ser Gly Ile Pro Ala Arg Phe Ser Gly Ser
    50                  55                  60

Ser Ser Gly Thr Met Ala Thr Leu Thr Ile Thr Gly Ala Gln Val Asp
65                  70                  75                  80

Asp Glu Ala Asp Tyr Tyr Cys Tyr Ser Ser Asn Ser Asp Thr Tyr
                85                  90                  95

Ser Val Phe Gly Gly Gly Thr Lys Leu Thr Val Leu
            100                 105

<210> SEQ ID NO 184
<211> LENGTH: 11
<212> TYPE: PRT
<213> ORGANISM: Homo sapiens

<400> SEQUENCE: 184

Ser Gly Asp Ala Leu Pro Lys Arg Tyr Ala Tyr
1               5                   10

<210> SEQ ID NO 185
<211> LENGTH: 7
<212> TYPE: PRT
<213> ORGANISM: Homo sapiens

<400> SEQUENCE: 185

Glu Asp Asn Lys Arg Pro Ser
1               5

<210> SEQ ID NO 186
<211> LENGTH: 11
<212> TYPE: PRT
<213> ORGANISM: Homo sapiens

<400> SEQUENCE: 186

Tyr Ser Ser Asp Asn Ser Asp Thr Tyr Ser Val
1               5                   10

<210> SEQ ID NO 187
<211> LENGTH: 126
<212> TYPE: PRT
<213> ORGANISM: Homo sapiens

<400> SEQUENCE: 187

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Tyr Tyr Asp Ala Thr Gln Lys Tyr Tyr Ala Asp Ser Val
    50                  55                  60
```

-continued

```
Lys Gly Arg Phe Thr Ile Ser Arg Asp Asn Ser Lys Asn Ala Leu Tyr
 65                  70                  75                  80

Leu Gln Met Thr Ser Leu Arg Ala Asp Asp Thr Ala Val Tyr Tyr Cys
                 85                  90                  95

Ala Arg Asp Leu Pro Tyr His Tyr His Arg Ser Ala Ser Phe Ala Pro
            100                 105                 110

Ala Asp Thr Trp Gly Gln Gly Thr Leu Val Thr Val Ser Ser
        115                 120                 125
```

<210> SEQ ID NO 188
<211> LENGTH: 10
<212> TYPE: PRT
<213> ORGANISM: Homo sapiens

<400> SEQUENCE: 188

```
Arg Phe Thr Phe Ser Ser Tyr Gly Met His
 1               5                  10
```

<210> SEQ ID NO 189
<211> LENGTH: 17
<212> TYPE: PRT
<213> ORGANISM: Homo sapiens

<400> SEQUENCE: 189

```
Leu Ile Tyr Tyr Asp Ala Thr Gln Lys Tyr Tyr Ala Asp Ser Val Lys
 1               5                  10                  15

Gly
```

<210> SEQ ID NO 190
<211> LENGTH: 17
<212> TYPE: PRT
<213> ORGANISM: Homo sapiens

<400> SEQUENCE: 190

```
Asp Leu Pro Tyr His Tyr His Arg Ser Ala Ser Phe Ala Pro Ala Asp
 1               5                  10                  15

Thr
```

<210> SEQ ID NO 191
<211> LENGTH: 108
<212> TYPE: PRT
<213> ORGANISM: Homo sapiens

<400> SEQUENCE: 191

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Thr Ile Ser Asn Asn
                20                  25                  30

Tyr Leu Ala Trp Tyr Gln Gln Lys Pro Gly Gln Ala Pro Arg Leu Leu
            35                  40                  45

Val Tyr Ala Ala Ser Ser Arg Ala Thr Gly Ile Pro Asp Arg Phe Tyr
        50                  55                  60

Gly Ser Gly Ser Gly Ala Asp Phe Thr Leu Thr Ile Ser Arg Leu Glu
 65                  70                  75                  80

Pro Glu Asp Phe Val Val Tyr Tyr Cys Gln Gln Tyr Gly Ser Ser Pro
                 85                  90                  95

Ile Thr Phe Gly Gln Gly Thr Arg Leu Glu Ile Lys
            100                 105
```

```
<210> SEQ ID NO 192
<211> LENGTH: 12
<212> TYPE: PRT
<213> ORGANISM: Homo sapiens

<400> SEQUENCE: 192

Arg Ala Ser Gln Thr Ile Ser Asn Asn Tyr Leu Ala
1               5                   10

<210> SEQ ID NO 193
<211> LENGTH: 7
<212> TYPE: PRT
<213> ORGANISM: Homo sapiens

<400> SEQUENCE: 193

Ala Ala Ser Ser Arg Ala Thr
1               5

<210> SEQ ID NO 194
<211> LENGTH: 9
<212> TYPE: PRT
<213> ORGANISM: Homo sapiens

<400> SEQUENCE: 194

Gln Gln Tyr Gly Ser Ser Pro Ile Thr
1               5

<210> SEQ ID NO 195
<211> LENGTH: 120
<212> TYPE: PRT
<213> ORGANISM: Homo sapiens

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ala Thr Val Gly Tyr Gly Gly Thr Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Glu Met Asn Ser Leu Arg Ala Glu Ala Thr Ala Val Tyr Tyr Cys Ala
                85                  90                  95

Lys Ala Asn Tyr Gly Gly Asn Arg Phe Gly Leu Asp Val Trp Gly Gln
            100                 105                 110

Gly Thr Thr Val Thr Val Ser Ser
        115                 120

<210> SEQ ID NO 196
<211> LENGTH: 10
<212> TYPE: PRT
<213> ORGANISM: Homo sapiens

<400> SEQUENCE: 196

Gly Phe Thr Phe Ser Ser Tyr Ser Met Ser
1               5                   10

<210> SEQ ID NO 197
<211> LENGTH: 16
<212> TYPE: PRT
```

```
<213> ORGANISM: Homo sapiens

<400> SEQUENCE: 197

Thr Val Gly Tyr Gly Gly Thr Ile Tyr Tyr Ala Asp Ser Val Lys Gly
 1               5                  10                  15

<210> SEQ ID NO 198
<211> LENGTH: 12
<212> TYPE: PRT
<213> ORGANISM: Homo sapiens

<400> SEQUENCE: 198

Ala Asn Tyr Gly Gly Asn Arg Phe Gly Leu Asp Val
 1               5                  10

<210> SEQ ID NO 199
<211> LENGTH: 111
<212> TYPE: PRT
<213> ORGANISM: Homo sapiens

<400> SEQUENCE: 199

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln His Gln Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
 65                 70                  75                  80

Gln Ala Glu Asp Glu Ala Asp Tyr Tyr Cys Ser Ser Tyr Ala Gly Ser
                85                  90                  95

Asn Asn Leu Gly Val Phe Gly Thr Gly Thr Glu Val Thr Val Leu
            100                 105                 110

<210> SEQ ID NO 200
<211> LENGTH: 14
<212> TYPE: PRT
<213> ORGANISM: Homo sapiens

<400> SEQUENCE: 200

Thr Gly Thr Ser Ser Asp Val Gly Gly Tyr Asn Tyr Val Ser
 1               5                  10

<210> SEQ ID NO 201
<211> LENGTH: 7
<212> TYPE: PRT
<213> ORGANISM: Homo sapiens

<400> SEQUENCE: 201

Glu Val Ser Lys Arg Pro Ser
 1               5

<210> SEQ ID NO 202
<211> LENGTH: 11
<212> TYPE: PRT
<213> ORGANISM: Homo sapiens

<400> SEQUENCE: 202

Ser Ser Tyr Ala Gly Ser Asn Asn Leu Gly Val
 1               5                  10
```

<210> SEQ ID NO 203
<211> LENGTH: 120
<212> TYPE: PRT
<213> ORGANISM: Homo sapiens

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ala Trp Val Arg Gln Ala Pro Gly Lys Gly Leu Glu Trp Val
        35                  40                  45

Ser Ala Ile Pro Ala Arg Gly Asp Lys Thr Tyr Tyr Ala Asp Ser Val
    50                  55                  60

Arg Gly Arg Phe Thr Ile Ser Arg Asp Ile Ser Lys Ser Ala Leu Tyr
65                  70                  75                  80

Leu Gln Met Asn Ser Leu Arg Val Glu Asp Thr Ala Val Tyr Tyr Cys
                85                  90                  95

Ala Lys Ala His His Leu Tyr Asn Lys Asn Phe Asp Tyr Trp Gly Gln
            100                 105                 110

Gly Thr Leu Val Thr Val Ser Ser
        115                 120

<210> SEQ ID NO 204
<211> LENGTH: 10
<212> TYPE: PRT
<213> ORGANISM: Homo sapiens

<400> SEQUENCE: 204

Gly Phe Thr Phe Arg Asn Tyr Ala Met Ala
1               5                   10

<210> SEQ ID NO 205
<211> LENGTH: 17
<212> TYPE: PRT
<213> ORGANISM: Homo sapiens

<400> SEQUENCE: 205

Ala Ile Pro Ala Arg Gly Asp Lys Thr Tyr Tyr Ala Asp Ser Val Arg
1               5                   10                  15

Gly

<210> SEQ ID NO 206
<211> LENGTH: 11
<212> TYPE: PRT
<213> ORGANISM: Homo sapiens

<400> SEQUENCE: 206

Ala His His Leu Tyr Asn Lys Asn Phe Asp Tyr
1               5                   10

<210> SEQ ID NO 207
<211> LENGTH: 104
<212> TYPE: PRT
<213> ORGANISM: Homo sapiens

<400> SEQUENCE: 207

Glu Ile Val Leu Thr Gln Ser Pro Gly Thr Leu Ser Leu Ser Pro Gly
1               5                   10                  15

```
Glu Thr Val Thr Leu Ser Cys Arg Ala Ser Gln Ser Val Ser Ser
                20                  25                  30

Asn Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Arg Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Thr Phe Gly
                 85                  90                  95

Gln Gly Thr Lys Val Asp Ile Lys
                100
```

<210> SEQ ID NO 208
<211> LENGTH: 12
<212> TYPE: PRT
<213> ORGANISM: Homo sapiens

<400> SEQUENCE: 208

```
Arg Ala Ser Gln Ser Val Ser Ser Ser Asn Leu Ala
 1               5                  10
```

<210> SEQ ID NO 209
<211> LENGTH: 7
<212> TYPE: PRT
<213> ORGANISM: Homo sapiens

<400> SEQUENCE: 209

```
Gly Ala Ser Ser Arg Ala Thr
 1               5
```

<210> SEQ ID NO 210
<211> LENGTH: 5
<212> TYPE: PRT
<213> ORGANISM: Homo sapiens

<400> SEQUENCE: 210

```
Gln His Tyr Gly Thr
 1               5
```

<210> SEQ ID NO 211
<211> LENGTH: 123
<212> TYPE: PRT
<213> ORGANISM: Homo sapiens

<400> SEQUENCE: 211

```
Glu Val Gln Leu Leu Glu Ser Gly Gly Gly Val Gln Pro Gly Gly
 1               5                  10                  15

Ser Leu Arg Leu Ser Cys Ala Ala Ser Gly Phe Thr Phe Ser Thr Tyr
                20                  25                  30

Val Met Ser Trp Val Arg Gln Ala Pro Gly Lys Gly Leu Glu Trp Val
             35                  40                  45

Ser Ala Ile Ser Arg Arg Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Trp Leu Thr Gly Arg Thr Gly Gly Val Phe Asp Ile
                100                 105                 110
```

```
Trp Gly Gln Gly Thr Met Val Thr Val Ser Ser
        115                 120

<210> SEQ ID NO 212
<211> LENGTH: 10
<212> TYPE: PRT
<213> ORGANISM: Homo sapiens

<400> SEQUENCE: 212

Gly Phe Thr Phe Ser Thr Tyr Val Met Ser
1               5                   10

<210> SEQ ID NO 213
<211> LENGTH: 17
<212> TYPE: PRT
<213> ORGANISM: Homo sapiens

<400> SEQUENCE: 213

Ala Ile Ser Arg Arg Gly Gly Ser Thr Tyr Tyr Ala Asp Ser Val Lys
1               5                   10                  15

Gly

<210> SEQ ID NO 214
<211> LENGTH: 14
<212> TYPE: PRT
<213> ORGANISM: Homo sapiens

<400> SEQUENCE: 214

Asp Arg Trp Leu Thr Gly Arg Thr Gly Gly Val Phe Asp Ile
1               5                   10

<210> SEQ ID NO 215
<211> LENGTH: 107
<212> TYPE: PRT
<213> ORGANISM: Homo sapiens

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Thr Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 216
<211> LENGTH: 11
<212> TYPE: PRT
<213> ORGANISM: Homo sapiens

<400> SEQUENCE: 216

Gln Ala Ser Gln Asp Ile Ser Asn Tyr Leu Asn
1               5                   10
```

<210> SEQ ID NO 217
<211> LENGTH: 7
<212> TYPE: PRT
<213> ORGANISM: Homo sapiens

<400> SEQUENCE: 217

Asp Ala Ser Asn Leu Glu Thr
1               5

<210> SEQ ID NO 218
<211> LENGTH: 9
<212> TYPE: PRT
<213> ORGANISM: Homo sapiens

<400> SEQUENCE: 218

Gln Gln Tyr Asp Asn Leu Pro Leu Thr
1               5

<210> SEQ ID NO 219
<211> LENGTH: 120
<212> TYPE: PRT
<213> ORGANISM: Homo sapiens

<400> SEQUENCE: 219

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Ser Tyr Tyr
            20                  25                  30

Ala Met Ser Trp Val Arg Gln Ala Pro Gly Lys Gly Leu Glu Trp Val
        35                  40                  45

Ser Thr Ile Gly Asp Ser Gly Ser Thr Thr His Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Gly Pro Val Ala Ala Ile Gly Asp Tyr Trp Gly Gln
            100                 105                 110

Gly Thr Leu Val Thr Val Ser Ser
        115                 120

<210> SEQ ID NO 220
<211> LENGTH: 10
<212> TYPE: PRT
<213> ORGANISM: Homo sapiens

<400> SEQUENCE: 220

Gly Tyr Thr Phe Ser Tyr Tyr Ala Met Ser
1               5                   10

<210> SEQ ID NO 221
<211> LENGTH: 17
<212> TYPE: PRT
<213> ORGANISM: Homo sapiens

<400> SEQUENCE: 221

Thr Ile Gly Asp Ser Gly Ser Thr Thr His Tyr Ala Asp Ser Val Lys
1               5                   10                  15

Gly

<210> SEQ ID NO 222
<211> LENGTH: 11
<212> TYPE: PRT
<213> ORGANISM: Homo sapiens

<400> SEQUENCE: 222

Gly Leu Gly Pro Val Ala Ala Ile Gly Asp Tyr
1               5                   10

<210> SEQ ID NO 223
<211> LENGTH: 110
<212> TYPE: PRT
<213> ORGANISM: Homo sapiens

<400> SEQUENCE: 223

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asn Val Tyr Trp Tyr Gln Gln Leu Pro Gly Thr Ala Pro Lys Leu Leu
        35                  40                  45

Val Tyr Arg Asn Asn Gln Arg Pro Ser Gly Val Pro Asp Arg Val Ser
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Val Thr Val Leu
            100                 105                 110

<210> SEQ ID NO 224
<211> LENGTH: 13
<212> TYPE: PRT
<213> ORGANISM: Homo sapiens

<400> SEQUENCE: 224

Ser Gly Ser Ser Ser Asn Ile Gly Ser Asn Asn Val Tyr
1               5                   10

<210> SEQ ID NO 225
<211> LENGTH: 7
<212> TYPE: PRT
<213> ORGANISM: Homo sapiens

<400> SEQUENCE: 225

Arg Asn Asn Gln Arg Pro Ser
1               5

<210> SEQ ID NO 226
<211> LENGTH: 11
<212> TYPE: PRT
<213> ORGANISM: Homo sapiens

<400> SEQUENCE: 226

Ala Ala Trp Asp Asp Ser Leu Arg Gly Tyr Val
1               5                   10

<210> SEQ ID NO 227
<211> LENGTH: 115
<212> TYPE: PRT
<213> ORGANISM: Homo sapiens

<400> SEQUENCE: 227

-continued

```
Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Asp Asn Tyr
            20                  25                  30

Gly Met His Trp Val Arg Gln Ala Pro Gly Lys Gly Leu Glu Trp Leu
        35                  40                  45

Ala Val Ile Ser Tyr Gly Gly Asp His Gln Phe Tyr Gly Asp Ser Val
    50                  55                  60

Lys Asp Arg Phe Thr Ile Ser Arg Asp Asn Ser Lys Asn Thr Ala Tyr
65                  70                  75                  80

Leu Gln Met His Ser Leu Arg Pro Asp Asp Thr Ala Val Tyr Tyr Cys
                85                  90                  95

Ala Thr Gly Val Thr Pro Asp Phe Trp Gly Gln Gly Thr Leu Val Thr
            100                 105                 110

Val Ser Ser
        115

<210> SEQ ID NO 228
<211> LENGTH: 5
<212> TYPE: PRT
<213> ORGANISM: Homo sapiens

<400> SEQUENCE: 228

Asn Tyr Gly Met His
1               5

<210> SEQ ID NO 229
<211> LENGTH: 17
<212> TYPE: PRT
<213> ORGANISM: Homo sapiens

<400> SEQUENCE: 229

Val Ile Ser Tyr Gly Gly Asp His Gln Phe Tyr Gly Asp Ser Val Lys
1               5                   10                  15

Asp

<210> SEQ ID NO 230
<211> LENGTH: 6
<212> TYPE: PRT
<213> ORGANISM: Homo sapiens

<400> SEQUENCE: 230

Gly Val Thr Pro Asp Phe
1               5

<210> SEQ ID NO 231
<211> LENGTH: 113
<212> TYPE: PRT
<213> ORGANISM: Homo sapiens

<400> SEQUENCE: 231

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser His Arg Asp Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Trp Pro Pro Phe Thr Phe Gly Gln Gly Thr Lys Leu Glu Ile
            100                 105                 110

Lys

<210> SEQ ID NO 232
<211> LENGTH: 16
<212> TYPE: PRT
<213> ORGANISM: Homo sapiens

<400> SEQUENCE: 232

Arg Ser Ser Gln Ser Leu Val His Ser Asp Gly Asn Thr Tyr Leu Asn
1               5                   10                  15

<210> SEQ ID NO 233
<211> LENGTH: 7
<212> TYPE: PRT
<213> ORGANISM: Homo sapiens

<400> SEQUENCE: 233

Lys Val Ser His Arg Asp Ser
1               5

<210> SEQ ID NO 234
<211> LENGTH: 10
<212> TYPE: PRT
<213> ORGANISM: Homo sapiens

<400> SEQUENCE: 234

Leu Gln Gly Thr His Trp Pro Pro Phe Thr
1               5                   10

<210> SEQ ID NO 235
<211> LENGTH: 121
<212> TYPE: PRT
<213> ORGANISM: Homo sapiens

<400> SEQUENCE: 235

Glu Val Gln Leu Val Glu Ser Gly Gly Gly Leu Val Asn Pro Gly Gly
1               5                   10                  15

Ser Leu Arg Leu Ser Cys Thr Ala Ser Gly Phe Ser Phe Ser Thr Tyr
                20                  25                  30

Ser Met Asn Trp Val Arg Gln Ala Pro Gly Lys Gly Leu Glu Trp Val
            35                  40                  45

Ser Leu Ile Thr Ser Ser Gly Ser Tyr Ile Tyr Tyr Ala Asp Ser Val
        50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Asn Met Leu Ala Ala Gly Ser His Tyr Phe His Tyr Trp Gly
            100                 105                 110

Gln Gly Thr Leu Val Thr Val Ser Ser
        115                 120

<210> SEQ ID NO 236
```

```
<211> LENGTH: 5
<212> TYPE: PRT
<213> ORGANISM: Homo sapiens

<400> SEQUENCE: 236

Thr Tyr Ser Met Asn
1               5

<210> SEQ ID NO 237
<211> LENGTH: 17
<212> TYPE: PRT
<213> ORGANISM: Homo sapiens

<400> SEQUENCE: 237

Leu Ile Thr Ser Ser Gly Ser Tyr Ile Tyr Tyr Ala Asp Ser Val Lys
1               5                   10                  15

Gly

<210> SEQ ID NO 238
<211> LENGTH: 12
<212> TYPE: PRT
<213> ORGANISM: Homo sapiens

<400> SEQUENCE: 238

Met Leu Ala Ala Ala Gly Ser His Tyr Phe His Tyr
1               5                   10

<210> SEQ ID NO 239
<211> LENGTH: 112
<212> TYPE: PRT
<213> ORGANISM: Homo sapiens

<400> SEQUENCE: 239

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Glu Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Thr Gln Phe Pro Ile Thr Phe Gly Gly Gly Thr Arg Leu Glu Ile Lys
            100                 105                 110

<210> SEQ ID NO 240
<211> LENGTH: 16
<212> TYPE: PRT
<213> ORGANISM: Homo sapiens

<400> SEQUENCE: 240

Arg Ser Ser Gln Ser Leu Val His Ser Asp Gly Asn Thr Tyr Leu Ser
1               5                   10                  15

<210> SEQ ID NO 241
<211> LENGTH: 7
<212> TYPE: PRT
<213> ORGANISM: Homo sapiens
```

<400> SEQUENCE: 241

Lys Ile Ser Glu Arg Phe Ser
1               5

<210> SEQ ID NO 242
<211> LENGTH: 9
<212> TYPE: PRT
<213> ORGANISM: Homo sapiens

<400> SEQUENCE: 242

Met Gln Val Thr Gln Phe Pro Ile Thr
1               5

<210> SEQ ID NO 243
<211> LENGTH: 114
<212> TYPE: PRT
<213> ORGANISM: Homo sapiens

<400> SEQUENCE: 243

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Lys Lys Tyr Tyr Gly Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Val Glu Asp Thr Ala Ile Tyr Tyr Cys
                85                  90                  95

Val Pro Asp Ala Phe Asp Met Trp Gly Gln Gly Thr Met Val Thr Val
            100                 105                 110

Ser Ser

<210> SEQ ID NO 244
<211> LENGTH: 5
<212> TYPE: PRT
<213> ORGANISM: Homo sapiens

<400> SEQUENCE: 244

Asn Tyr Ala Met His
1               5

<210> SEQ ID NO 245
<211> LENGTH: 17
<212> TYPE: PRT
<213> ORGANISM: Homo sapiens

<400> SEQUENCE: 245

Val Ile Trp Tyr Asp Gly Ser Lys Lys Tyr Tyr Gly Asp Ser Val Lys
1               5                   10                  15

Gly

<210> SEQ ID NO 246
<211> LENGTH: 5
<212> TYPE: PRT
<213> ORGANISM: Homo sapiens

<400> SEQUENCE: 246

```
Asp Ala Phe Asp Met
1               5
```

<210> SEQ ID NO 247
<211> LENGTH: 112
<212> TYPE: PRT
<213> ORGANISM: Homo sapiens

<400> SEQUENCE: 247

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Thr
            20                  25                  30

Asp Gly Lys Thr Tyr Leu Ser Trp Leu His Gln Arg Pro Gly Gln Pro
        35                  40                  45

Pro Arg Pro Leu Ile Tyr Lys Met Ser Lys Arg Phe Ser Gly Val Pro
    50                  55                  60

Asp Arg Phe Ser Gly Ser Gly Ala Glu Thr Glu Phe Thr Leu Lys Ile
65                  70                  75                  80

Ser Arg Val Glu Ala Glu Asp Val Gly Ile Tyr Tyr Cys Leu Gln Leu
                85                  90                  95

Thr Gln Phe Pro Ile Thr Phe Gly Gln Gly Thr Arg Leu Glu Ile Lys
            100                 105                 110
```

<210> SEQ ID NO 248
<211> LENGTH: 16
<212> TYPE: PRT
<213> ORGANISM: Homo sapiens

<400> SEQUENCE: 248

```
Arg Ser Ser Gln Ser Leu Val His Thr Asp Gly Lys Thr Tyr Leu Ser
1               5                   10                  15
```

<210> SEQ ID NO 249
<211> LENGTH: 7
<212> TYPE: PRT
<213> ORGANISM: Homo sapiens

<400> SEQUENCE: 249

```
Lys Met Ser Lys Arg Phe Ser
1               5
```

<210> SEQ ID NO 250
<211> LENGTH: 9
<212> TYPE: PRT
<213> ORGANISM: Homo sapiens

<400> SEQUENCE: 250

```
Leu Gln Leu Thr Gln Phe Pro Ile Thr
1               5
```

<210> SEQ ID NO 251
<211> LENGTH: 123
<212> TYPE: PRT
<213> ORGANISM: Homo sapiens

<400> SEQUENCE: 251

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30
```

```
Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Arg Ile Asp Gly Ser Ser Trp Ser Ser Trp Phe Asp Pro
             100                 105                 110

Trp Gly Gln Gly Thr Leu Val Thr Val Ser Ser
            115                 120
```

<210> SEQ ID NO 252
<211> LENGTH: 4
<212> TYPE: PRT
<213> ORGANISM: Homo sapiens

<400> SEQUENCE: 252

```
Tyr Ala Met Asn
 1
```

<210> SEQ ID NO 253
<211> LENGTH: 17
<212> TYPE: PRT
<213> ORGANISM: Homo sapiens

<400> SEQUENCE: 253

```
Trp Ile Asn Thr Asn Thr Gly Asn Pro Thr Tyr Ala Gln Gly Phe Thr
 1               5                  10                  15

Gly
```

<210> SEQ ID NO 254
<211> LENGTH: 14
<212> TYPE: PRT
<213> ORGANISM: Homo sapiens

<400> SEQUENCE: 254

```
Asp Arg Ile Asp Gly Ser Ser Trp Ser Ser Trp Phe Asp Pro
 1               5                  10
```

<210> SEQ ID NO 255
<211> LENGTH: 111
<212> TYPE: PRT
<213> ORGANISM: Homo sapiens

<400> SEQUENCE: 255

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Phe Asp Ser Ser
                 85                  90                  95
```

Leu Ser Ser Ser Val Phe Gly Gly Gly Thr Lys Leu Thr Val Leu
            100                 105                 110

<210> SEQ ID NO 256
<211> LENGTH: 14
<212> TYPE: PRT
<213> ORGANISM: Homo sapiens

<400> SEQUENCE: 256

Thr Gly Ser Ser Ser Asn Ile Gly Ala Gly Tyr Asp Val His
1               5                   10

<210> SEQ ID NO 257
<211> LENGTH: 7
<212> TYPE: PRT
<213> ORGANISM: Homo sapiens

<400> SEQUENCE: 257

Gly Asn Ser Asn Arg Pro Ser
1               5

<210> SEQ ID NO 258
<211> LENGTH: 11
<212> TYPE: PRT
<213> ORGANISM: Homo sapiens

<400> SEQUENCE: 258

Gln Ser Phe Asp Ser Ser Leu Ser Ser Val
1               5                   10

<210> SEQ ID NO 259
<211> LENGTH: 120
<212> TYPE: PRT
<213> ORGANISM: Homo sapiens

<400> SEQUENCE: 259

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Pro Val Asn Asn Tyr
            20                  25                  30

Ala Ile Asn Trp Val Arg Gln Ala Pro Gly Gln Gly Leu Glu Trp Met
        35                  40                  45

Gly Phe Ile Asn Thr Asn Thr Gly Ile Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Gly Leu Lys Ala Asp Asp Thr Ala Val Tyr Tyr Cys
                85                  90                  95

Ala Arg Val Gly Ile Val Gly Val Ile Val Phe Asp Tyr Trp Gly Gln
            100                 105                 110

Gly Thr Leu Val Thr Val Ser Ser
        115                 120

<210> SEQ ID NO 260
<211> LENGTH: 5
<212> TYPE: PRT
<213> ORGANISM: Homo sapiens

<400> SEQUENCE: 260

Asn Tyr Ala Ile Asn
1               5

<210> SEQ ID NO 261
<211> LENGTH: 17
<212> TYPE: PRT
<213> ORGANISM: Homo sapiens

<400> SEQUENCE: 261

Phe Ile Asn Thr Asn Thr Gly Ile Pro Thr Tyr Ala Gln Gly Phe Thr
1               5                   10                  15
Gly

<210> SEQ ID NO 262
<211> LENGTH: 11
<212> TYPE: PRT
<213> ORGANISM: Homo sapiens

<400> SEQUENCE: 262

Val Gly Ile Val Gly Val Ile Val Phe Asp Tyr
1               5                   10

<210> SEQ ID NO 263
<211> LENGTH: 122
<212> TYPE: PRT
<213> ORGANISM: Homo sapiens

<400> SEQUENCE: 263

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Ser Lys Asn Lys Asn His Leu Ala Trp Tyr Gln Gln Lys Pro Gly Gln
        35                  40                  45

Pro Pro Lys Leu Leu Ile Tyr Trp Ala Ser Thr Arg Glu Ser Gly Tyr
    50                  55                  60

Trp Ala Ser Thr Arg Glu Ser Gly Val Pro Asp Arg Phe Ser Gly Ser
65                  70                  75                  80

Gly Ser Gly Thr Asp Phe Thr Leu Thr Ile Ser Ser Leu Gln Ala Glu
                85                  90                  95

Asp Val Ala Val Tyr Tyr Cys Gln Gln Tyr Tyr Ser Pro Ser Val Thr
            100                 105                 110

Phe Gly Gly Gly Thr Lys Val Glu Ile Lys
        115                 120

<210> SEQ ID NO 264
<211> LENGTH: 17
<212> TYPE: PRT
<213> ORGANISM: Homo sapiens

<400> SEQUENCE: 264

Lys Ser Ser Gln Ser Val Leu Ser Ser Ser Lys Asn Lys Asn His Leu
1               5                   10                  15
Ala

<210> SEQ ID NO 265
<211> LENGTH: 7
<212> TYPE: PRT
<213> ORGANISM: Homo sapiens

<400> SEQUENCE: 265

Trp Ala Ser Thr Arg Glu Ser
1               5

```
<210> SEQ ID NO 266
<211> LENGTH: 9
<212> TYPE: PRT
<213> ORGANISM: Homo sapiens

<400> SEQUENCE: 266

Gln Gln Tyr Tyr Ser Pro Ser Val Thr
1               5

<210> SEQ ID NO 267
<211> LENGTH: 126
<212> TYPE: PRT
<213> ORGANISM: Homo sapiens

<400> SEQUENCE: 267

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Tyr Tyr Asp Ser Ser Gln Arg Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Pro Phe His Tyr His Arg Ser Ala Ser Phe Ala Pro
            100                 105                 110

Ser Asp Thr Trp Gly Gln Gly Thr Leu Val Thr Val Ser Ser
        115                 120                 125

<210> SEQ ID NO 268
<211> LENGTH: 5
<212> TYPE: PRT
<213> ORGANISM: Homo sapiens

<400> SEQUENCE: 268

Ser Tyr Gly Met His
1               5

<210> SEQ ID NO 269
<211> LENGTH: 17
<212> TYPE: PRT
<213> ORGANISM: Homo sapiens

<400> SEQUENCE: 269

Ile Ile Tyr Tyr Asp Ser Ser Gln Arg Tyr Tyr Ala Asp Ser Val Lys
1               5                   10                  15

Gly

<210> SEQ ID NO 270
<211> LENGTH: 17
<212> TYPE: PRT
<213> ORGANISM: Homo sapiens

<400> SEQUENCE: 270

Asp Leu Pro Phe His Tyr His Arg Ser Ala Ser Phe Ala Pro Ser Asp
1               5                   10                  15
```

Thr

<210> SEQ ID NO 271
<211> LENGTH: 108
<212> TYPE: PRT
<213> ORGANISM: Homo sapiens

<400> SEQUENCE: 271

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Thr Asn Asn
            20                  25                  30

Tyr Leu Ala Trp Tyr Gln Gln Lys Pro Gly Gln Ala Pro Arg Leu Leu
        35                  40                  45

Val Tyr Ala Ala Ser Ser Arg Ala Thr Gly Ile Pro Asp Arg Phe Tyr
    50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys
            100                 105

<210> SEQ ID NO 272
<211> LENGTH: 12
<212> TYPE: PRT
<213> ORGANISM: Homo sapiens

<400> SEQUENCE: 272

Arg Ala Ser Gln Ala Val Thr Asn Asn Tyr Leu Ala
1               5                   10

<210> SEQ ID NO 273
<211> LENGTH: 7
<212> TYPE: PRT
<213> ORGANISM: Homo sapiens

<400> SEQUENCE: 273

Ala Ala Ser Ser Arg Ala Thr
1               5

<210> SEQ ID NO 274
<211> LENGTH: 9
<212> TYPE: PRT
<213> ORGANISM: Homo sapiens

<400> SEQUENCE: 274

Gln Gln Tyr Gly Thr Ser Pro Ile Thr
1               5

<210> SEQ ID NO 275
<211> LENGTH: 339
<212> TYPE: DNA
<213> ORGANISM: Homo sapiens

<400> SEQUENCE: 275
gaggtgcagc tggtggagtc tgggggaggc ttggtccagc ctggggggtc cctgagactc      60
tcctgtgcag cctctggatt cacctttagt acctattata tgagctgggt ccgccaggct     120
ccaggaaagg ggctggagtg ggtggccaac ataaagcaag atggaagtga aaatactat      180 gtggactctg tgaagggccg attcaccatc tccagagaca acgccaggaa ctcactgtat     240

```
ctgcagatgc acagcctgag agccgaggac acggctgtgt attactgtgc gagtcccct      300 gggtggtggg gccagggcac cctggtcacc gtctcctcg                             339
```

<210> SEQ ID NO 276
<211> LENGTH: 336
<212> TYPE: DNA
<213> ORGANISM: Homo sapiens

<400> SEQUENCE: 276

```
gatattgtga tgacccagac tccactctct ctgtccgtca cccctggaca gccggcctcc      60
atctcctgta agtctagtca gagcctcctg catagtgatg aaagaccta tttgtattgg      120 tacctgcaga agccaggcca gcctccacag ctcctgatct atgaagtttc aaccggttc      180 tctggagtgc cagataggtt cagtggcagc gggtcaggga cagattcac actgaaaatc      240 agccgggtgg aggctgagga tgttggggtt tattactgca tgcaaagtat acagcttccc      300
gtgactttcg gcggagggac caaggtggag atcaaa                                336
```

<210> SEQ ID NO 277
<211> LENGTH: 357
<212> TYPE: DNA
<213> ORGANISM: Homo sapiens

<400> SEQUENCE: 277

```
caggtgcagc tggtgcagtc tggggctgag gtgaagaagc ctggggcctc agtgaaggtc      60
tcctgcaagg cttccggata catcttcacc gactatttta tacactggat aagacaggcc      120
cctggacaag gcttgagtg gatggggtgg atcaagccta aaagtggtgg cacagactat      180
gcagagaaat ttcagggcag ggtcaccctg actagggaca cgtccatcac cacagtttat      240
atggaattga gcaggctgaa ttctgacgac acggccgtgt attactgtgc gagacttaag      300
tactcagtgc ctgattcaga ttattggggc cagggaaccc tggtcaccgt ctcctcg        357
```

<210> SEQ ID NO 278
<211> LENGTH: 336
<212> TYPE: DNA
<213> ORGANISM: Homo sapiens

<400> SEQUENCE: 278

```
gatattgtga tgacccagac tccactctct ctgtccgtca cccctggaca gccggcctcc      60
atctcctgta agtctagtca gagcctcctg catagtgatg aaagaccta tttgtattgg      120 tacctgcaga agccaggcca gcctccacag ctcctgatct atgaagtttc aaccggttc      180 tctggagtgc cagataggtt cagtggcagc gggtcaggga cagattcac actgaaaatc      240 agccgggtgg aggctgagga tgttggggtt tattactgca tgcaaagtat acagcttccc      300
gtgactttcg gcggagggac caaggtggag atcaaa                                336
```

<210> SEQ ID NO 279
<211> LENGTH: 378
<212> TYPE: DNA
<213> ORGANISM: Homo sapiens

<400> SEQUENCE: 279

```
gaggtgcagc tggtggagtc tgggggaggc ttggtaaagc ctgggggggtc ccttagactc      60 tcctgtgcaa cctctggatt caatttcagt aacgtctgga taagctgggt ccgccaggct      120
ccaggaaagg ggctggagtg ggttggccgt attaaaagca aaaatgatgg tgggacaaca      180
```

```
gaatatgctg cacccgtgaa aggcagattc accatctcaa gagatgattc aaaaaatacg        240
gtgtatctcc aaatgaacag cctgaaaacc gaagacgcag gcgttttacta ctgtaccaca       300 gacccgtatc attactttga tatggggggg cctgggttcg gcccctgggg ccagggcacc        360
ctggtcaccg tctcctcg                                                     378

<210> SEQ ID NO 280
<211> LENGTH: 339
<212> TYPE: DNA
<213> ORGANISM: Homo sapiens

<400> SEQUENCE: 280
gatattgtga tgactcaatc accagactcc ctggctgtgt ctctgggcga gagggccacc        60
atcaactgca gtccggcca gagtgtttta tacaggtcca ataataggaa ctatatagct        120
tggtatcagc agaaaccagg acagcctcct aagttgctca tttactgggc atctacccgg        180
gaatccgggg tccctgaccg attcagtggc agcgggtctg ggacagattt cactctcacc        240
atcagcagcc tgcaggctga agatgtgca gtttattact gtcaacaata ttatagtaat         300
cgttggacgt tcggccaagg gaccaaggtg gagatcaaa                              339

<210> SEQ ID NO 281
<211> LENGTH: 339
<212> TYPE: DNA
<213> ORGANISM: Homo sapiens

<400> SEQUENCE: 281
gatattgtga tgactcaatc accagactcc ctggctgtgt ctctgggcga gagggccacc        60
atcaactgca gtccagcca gagtgttttcg tacagctcca acaataagaa cttcttatct        120
tggtaccagc agaaaccagg acagcctcct aagctgctca tttactgggc atctacccgg        180
gaatccgggg tccctgaccg attcagtggc agcgggtctg ggacagattt cactctcacc        240
atcagcagcc tgcaggctga agatgtgca gtttattact gtcagcaata ttctagtctc         300
ccgatctcct tcggccaagg gacacgactg gagattaaa                              339

<210> SEQ ID NO 282
<211> LENGTH: 369
<212> TYPE: DNA
<213> ORGANISM: Homo sapiens

<400> SEQUENCE: 282
gaggtgcagc tgttggagtc tgggggagcc ttggtacagc ctggggggtc cctgagactc        60
tcctgtgcag cctctggact cactttagc aggcatgcct ttagttgggt ccgccaggct         120
ccagggaagg ggctggagtg ggtcgcaatt agtagtggta gtgggggtaa cacatactac        180
gcagcctccg tgaagggccg gttcaccatc tccagagacg aatcaaagaa cacgctgtat        240
ctgcaaatga acagtctgag agtcgaggac acggccctgt attactgtgc gaaagaggtc        300
ttggagtggt cattattgag tcgatacatg gacgtctggg gcaaagggac cacggtcacc        360
gtctcctcg                                                               369

<210> SEQ ID NO 283
<211> LENGTH: 330
<212> TYPE: DNA
<213> ORGANISM: Homo sapiens

<400> SEQUENCE: 283
cagtctgtgc tgactcagcc accctcagcg tctgggaccc ccgggcagag ggtcaccatc        60
```

```
tcttgttctg gaagcagctc aacatcgga ggtaatactg tgaactggta ccaccagctc    120
ccaggaacgg cccccaaact cctcgtctat agtactaatc agcggccctc aggggtccct    180
gaccgattct ctggctccaa gtctggcacc tcagcctccc tggccatcag tgggctccag    240
gctgaggatg aggctgatta ttactgtgca acatgggatg acagcctgaa tggttgggtg    300
ttcggcggag ggaccaagct gaccgtcctg                                     330
```

<210> SEQ ID NO 284
<211> LENGTH: 336
<212> TYPE: DNA
<213> ORGANISM: Homo sapiens

<400> SEQUENCE: 284

```
caggtgcagc tgcaggagtc gggcccaggg ctggtgaagc cttcggagac cctgtccctc     60
acctgcactg tctctggtgg ctccatcact gattactact ggagttggat ccggcagccc    120
ccagggaagg gactggagtg gattggctat atccatgaca gtgggaccac caggtacaac    180
ccctccctca cgagtcgact cagcatgtca ttagacacgt ccacgaacca ggtctccctg    240
aggttgacct ctgtgaccgc tgcggacacg gccgtgtatt actgtgcgaa agttcctgac    300
tactggggcc agggcaccct ggtcaccgtc tcctcg                              336
```

<210> SEQ ID NO 285
<211> LENGTH: 339
<212> TYPE: DNA
<213> ORGANISM: Homo sapiens

<400> SEQUENCE: 285

```
gatattgtga tgactcaatc accagactcc ctggctgtgt ctctgggcga gagggccacc     60
atcaactgca gtccagtca gagtgttttg tacaactccg acaataagaa ctacttagct    120
tggttgcagc agaagccagg acagcctcct aaggtcctca tttactgggc atctacccgg    180
gaattcgggg tccctgaccg attcagtggc agcgggtctg ggacagattt cactctcacc    240
atcagcagcc tgcaggctga agatgtggca gtttattact gtcatcaata ttatagtgtt    300
cccttcactt tcggcggagg gaccaaggtg gagatcaaa                           339
```

<210> SEQ ID NO 286
<211> LENGTH: 348
<212> TYPE: DNA
<213> ORGANISM: Homo sapiens

<400> SEQUENCE: 286

```
caggtgcagc tgcaggagtc gggcccagga gtggtgaagc ttcacagac cctgtccctc      60 acctgcactg tctctggtgt ctccgtcggt agtggtgatt actactggag ttggatccgc    120
caccacccag ggaagggcct ggagtggatt ggatacatct cttttttttgg gagttccaat   180 tacaacccgt ccctcaaggg tcgagtttcc atgtcagtag acacgtctaa caaccagttc    240
tccctgaatt tgaagtctgt gactgccgcg gacacggccg tctatttctg tgccacggga    300
aatgcctatt ctttctgggg ccaggggaca atggtcaccg tctcttcg                 348
```

<210> SEQ ID NO 287
<211> LENGTH: 324
<212> TYPE: DNA
<213> ORGANISM: Homo sapiens

<400> SEQUENCE: 287

```
cagtctgccc tgactcagcc tgcctccgtg tcggggtctc ctggacagtc gatcaccatc    60
tcctgcactg gaaccagcag tgatattggg acccataacc ttgtctcctg gtaccaacaa   120
caccccggca aagcccccaa actcatcatt tatgagatct ttgagcggcc ttcagggatt   180
tcttctcgct tcactggctc caagtctggc aacacggcct ccctgacaat ctctgggctc   240
caggctgagg acgaggctga ttatttctgc tgcgcatatt cagttactgt tatattcggc   300
ggagggacca aattgaccgt cctt                                          324
```

<210> SEQ ID NO 288
<211> LENGTH: 336
<212> TYPE: DNA
<213> ORGANISM: Homo sapiens

<400> SEQUENCE: 288

```
gaggtgcagc tggtggagtc cggggggagac ctagttcagc ctggggggtc cctgagactc    60
tcctgtacag cctctggatt caacttaggt gactactgga tgcactgggt ccgccaagtt   120
ccagggaagg ggctggtgtg gtctcacgt attagtagta tggagcttc tgtaagttac    180 gcggacttcg tggagggccg attcaccatc tccagaggca acgccaggaa tacactttt    240 ctggaactga acagtctgag actcgacgac acggctgtgt attattgtgc catgggggtg   300
gtctggggcc agggcaccct ggtcaccgtc tcctcg                             336
```

<210> SEQ ID NO 289
<211> LENGTH: 324
<212> TYPE: DNA
<213> ORGANISM: Homo sapiens

<400> SEQUENCE: 289

```
tcctatgagc tgactcagcc accctcggtg tcagtgtccc caggacaaac ggccacgatc    60
tcctgctctg gagatgcatt gccaaaaaga tatgcttatt ggtataagca gaagtcaggc   120
caggtccctt ttctgatcat ctatgaggac aacaaacgac cctccgggat ccctgcgaga   180
ttctctggct ccagctccgg gacaatggcc acattgacta tcactggggc ccaggtggac   240
gatgaagctg actactactg ttactcatca gacaatagtg atacttacag tgtgttcggc   300
ggagggacca agctgaccgt ccta                                          324
```

<210> SEQ ID NO 290
<211> LENGTH: 378
<212> TYPE: DNA
<213> ORGANISM: Homo sapiens

<400> SEQUENCE: 290

```
caggtgcagc tggtggagtc tgggggaggc gtggtccagc ctggggaggtc cctgagactc    60 tcctgtgcag cgtccagatt caccttcagt agctatggca tgcactgggt ccgccaggcg   120
ccaggcaagg ggctggagtg gtggcactt atatactatg atcgactca aaaatattat    180 gcagactccg tgaagggccg attcaccatc tccagagaca attccaagaa cacgctgtat   240
ctgcaaatga ctagcctgag ggccgacgac accgctgtct attactgtgc gagagatctt   300
ccgtatcact atcatagaag tgcctctttc gcacctgcgg cacctggggg ccagggaacc   360
ctggtcaccg tctcctcg                                                 378
```

<210> SEQ ID NO 291
<211> LENGTH: 324
<212> TYPE: DNA
<213> ORGANISM: Homo sapiens

<400> SEQUENCE: 291

| | | | | | |
|---|---|---|---|---|---|
| gaaattgtgt | tgacgcagtc | tccaggcacc | ctgtctttgt | ctccagggga | aagagccacc | 60
| ctctcctgca | gggccagtca | gaccattagc | aacaactact | tagcctggta | ccagcaaaaa | 120
| cctggccagg | ctcccagact | cctcgtctat | gctgcatcca | gcagggccac | aggcatccca | 180
| gacagatttt | atggcagtgg | gtctgggcg | gacttcactc | tcaccatcag | cagactggag | 240
| cctgaagatt | ttgtagtcta | ttactgtcag | caatacggta | gctcaccgat | caccttcggc | 300
| caagggacac | gactggagat | taaa | | | | 324

<210> SEQ ID NO 292
<211> LENGTH: 360
<212> TYPE: DNA
<213> ORGANISM: Homo sapiens

<400> SEQUENCE: 292

| | | | | | |
|---|---|---|---|---|---|
| gaggtgcagc | tgttggagtc | tgggggaggc | ctggtacagc | ctgggggtc | cctgagactc | 60
| tcctgtgcag | cctctggatt | cacctttagc | agctattcca | tgagctgggt | ccgccaggct | 120
| cctgggaagg | ggctggagtg | ggtcgcaact | gttggttatg | gtggtactat | ctactacgcc | 180
| gactccgtga | agggccggtt | caccatctcc | agagacaatt | ccaagaacac | gctgtatctg | 240
| gaaatgaaca | gcctgagagc | cgaggccacg | gccgtatatt | actgtgcgaa | agcgaactac | 300
| ggtggtaacc | gcttcggttt | ggacgtctgg | ggccagggga | ccacggtcac | cgtctcctcg | 360

<210> SEQ ID NO 293
<211> LENGTH: 333
<212> TYPE: DNA
<213> ORGANISM: Homo sapiens

<400> SEQUENCE: 293

| | | | | | |
|---|---|---|---|---|---|
| cagtctgccc | tgactcagcc | tccctccgcg | tccgggtctc | ctggacagtc | agtcaccatc | 60
| tcctgcactg | gaaccagcag | tgacgttggt | ggttataact | atgtctcctg | gtaccaacac | 120
| cagccaggca | agcccccaa | actcatgatt | tatgaggtca | gtaagcgcc | ctcaggggtc | 180
| cctgatcgct | tctctggctc | caagtctggc | aacacggcct | ccctgaccgt | tctctgggctc | 240
| caggctgagg | atgaggctga | ttactattgc | agctcatatg | caggcagtaa | caatttggga | 300
| gtcttcggaa | ctgggaccga | ggtcaccgtc | cta | | | 333

<210> SEQ ID NO 294
<211> LENGTH: 360
<212> TYPE: DNA
<213> ORGANISM: Homo sapiens

<400> SEQUENCE: 294

| | | | | | |
|---|---|---|---|---|---|
| gaggtgcagc | tgttggagtc | tgggggaggc | ttggtacagc | ctgggggtc | cctgagactc | 60
| tcctgtgcag | cctctggatt | cacctttaga | aactatgcca | tggcctgggt | ccgccaggct | 120
| ccagggaagg | ggctggagtg | gtctcagcc | attcctgcta | ggggtgataa | gacatactac | 180
| gcagactccg | tgaggggccg | gttcaccatc | tccagagaca | tttccaagag | cgcactgtat | 240
| ttgcaaatga | acagcctgag | agtcgaggac | acggccgtat | actactgtgc | gaaagcccac | 300
| cacctgtaca | acaaaaactt | tgactactgg | ggccagggaa | ccctggtcac | cgtctcctcg | 360

<210> SEQ ID NO 295
<211> LENGTH: 312
<212> TYPE: DNA

```
<213> ORGANISM: Homo sapiens

<400> SEQUENCE: 295
gaaattgtgc tgactcagtc tccaggcacc ctgtctttgt ctccagggga gacagtcacc      60
ctctcctgta gggccagtca gagtgttagc agcagcaact tagcctgta ccagcagaaa      120 cctggccagg ctcccaggct cctcatctat ggtgcatcca gcagggccac tggcatccca     180
gacaggttca gtggccgtgg gtctgggaca gacttcactc tcaccatcag cagactggag      240
cctgaagatt ttgcagtgta ttactgtcag cactatggca cttttggcca ggggaccaaa     300
gtggatatca aa                                                           312

<210> SEQ ID NO 296
<211> LENGTH: 369
<212> TYPE: DNA
<213> ORGANISM: Homo sapiens

<400> SEQUENCE: 296
gaggtgcagc tgttggagtc tgggggaggc tcggtacagc ctggggggtc cctgagactc      60
tcctgtgcag cctccggatt cacctttagc acctatgtca tgagctgggt ccgccaggct     120
ccagggaagg ggctggagtg ggtctcagct attagtcgtc gtggtggtag cacatactac     180
gcagactccg tgaagggccg gttcaccatc tccagagaca attccaagaa cacactgtat     240
ctgcaaatga acagcctgag agccgaggac acggccgtat attactgtgc gaaagatcgt     300
tggctaactg gaaggacggg gggtgttttt gatatctggg gccaagggac aatggtcacc     360
gtctcttcg                                                             369

<210> SEQ ID NO 297
<211> LENGTH: 321
<212> TYPE: DNA
<213> ORGANISM: Homo sapiens

<400> SEQUENCE: 297
gacatccaga tgacccagtc tccatcctcc ctgtctgcat ctgtaggaga cagagtcacc      60
atcacttgcc aggcgagtca ggacattagc aactatttaa attggtatca gcagaagcca     120
gggaaagccc ctaagctcct gatctacgat gcatccaatt tggaaacagg ggtcccatca     180
aggttcagtg gaagtggatc tgggacagat tttactttca ccatcagtag cctgcagcct     240
gaagatactg caacatatta ctgtcaacag tatgataatc tcccgctcac tttcggcgga     300
gggaccaagg tggaaatcaa a                                                321

<210> SEQ ID NO 298
<211> LENGTH: 360
<212> TYPE: DNA
<213> ORGANISM: Homo sapiens

<400> SEQUENCE: 298
gaggtgcagc tgttggagtc tgggggaggc ttggtacagc ctggggggtc cctgagactc      60
tcctgtgcag cctctggata cacctttagc tactatgcca tgagctgggt ccgccaggct     120
ccagggaagg ggctggagtg ggtctcaacc attggtgata gtggttctac cacacactac     180
gcagactccg tgaagggccg gttcaccatc tccagagaca attccaagag cacgctgtat     240
ctgcaaatga acagcctgag agccgaggac acggccgtat attactgtgc gaagggactt     300
ggaccagtgg ctgctattgg tgactactgg ggccaggga ccctggtcac cgtctcctcg     360
```

```
<210> SEQ ID NO 299
<211> LENGTH: 330
<212> TYPE: DNA
<213> ORGANISM: Homo sapiens

<400> SEQUENCE: 299
cagtctgtgc tgactcagcc accctcagcg tctgggaccc ccgggcagag ggtcaccatc    60
tcttgttctg gaagcagctc caacatcgga agtaataatg tatactggta ccagcagctc   120
ccaggaacgg cccccaaact cctcgtctat aggaataatc agcggccctc agggtccct    180 gaccgagtct ctggctccaa gtctggctcc tcagcctccc tggccatcag tgggctccgg   240
tccgaggatg aggctgatta ttactgtgca gcatgggatg acagcctgcg tggttatgtc   300
ttcggaactg ggaccaaggt caccgtccta                                    330

<210> SEQ ID NO 300
<211> LENGTH: 345
<212> TYPE: DNA
<213> ORGANISM: Homo sapiens

<400> SEQUENCE: 300
caggtgcagc tggtggagtc tgggggaggc gtggtccagc ctgggaggtc cctgagactc    60
tcctgtgtag cctctggatt caccttcgat aactatggca tgcactgggt acgccaggct   120
ccaggcaagg ggctggagtg gctggcagtt atatcatatg gtggagatca tcaattctat   180
ggagactccg tgaaggaccg attcaccatc tccagagaca attccaagaa cacagcgtat   240
ctgcaaatgc acagcctgag acctgacgac acggctgtct actactgtgc gacggggtg    300 accctgatt tttggggcca gggcaccctg gtcaccgtct cctcg                    345

<210> SEQ ID NO 301
<211> LENGTH: 339
<212> TYPE: DNA
<213> ORGANISM: Homo sapiens

<400> SEQUENCE: 301
gatgttgtga tgactcagtc tccactctcc ctgcccgtca cccttggaca gccggcctcc    60
atctcctgca ggtctagtca aagcctcgta cacagtgatg gaataccta cttgaattgg    120 tttcagcaga ggccaggcca atctccaagg cgcctaattt ataaggtttc tcaccgggac   180
tctggggtcc cagatagatt cagcggcagt gggtcaggca ctgatttcac actgaaaatc   240
agcagggtgg aggctgagga tgttggggtt tattactgcc tgcaaggaac acactggcct   300
ccgttcactt ttggccaggg gaccaagctg gagatcaaa                          339

<210> SEQ ID NO 302
<211> LENGTH: 363
<212> TYPE: DNA
<213> ORGANISM: Homo sapiens

<400> SEQUENCE: 302
gaggtgcagc tggtggagtc tgggggaggc ctggtcaacc ctgggggtc cctgagactc     60 tcctgtacag cctctggatt cagcttcagt acctatagca tgaactgggt ccgccaggct   120
ccagggaagg ggctggagtg gtctcattg attactagta gtggtagtta catatactac   180
gcagactcag tgaagggccg attcaccatc tccagagacg acgccaagaa ctcactctat   240
ctgcaaatga acagcctgag agccgaggac acggctgtgt attactgtgc gaatatgttg   300
gcagcagctg gtagtcacta ctttcactac tggggccagg gaaccctggt caccgtctcc   360
```

```
tcg                                                                  363

<210> SEQ ID NO 303
<211> LENGTH: 336
<212> TYPE: DNA
<213> ORGANISM: Homo sapiens

<400> SEQUENCE: 303
gatattgtga tgacccagac tccactctcc tcacctgtca cccttggaca gccggcctct       60
atctcctgca ggtccagtca aagcctcgta cacagtgatg gaaacaccta cttgagttgg      120
cttcagcaga ggccaggcca gcctccaaga ctcctaattt ataagatttc tgaacggttc      180
tctggggtcc cagacagatt cagtggcagt ggggcaggga cagatttcac actgaaaatc      240
agcagggtgg aagctgagga tgtcggggtt tattactgca tgcaagttac acaatttcct      300
atcaccttcg gccaagggac acgactggag attaaa                                336

<210> SEQ ID NO 304
<211> LENGTH: 342
<212> TYPE: DNA
<213> ORGANISM: Homo sapiens

<400> SEQUENCE: 304
caggtgcagc tggtggagtc tgggggaggc gtggtccagc ctgggaggtc cctgagactc       60
tcctgtgcag cgtctggatt caccttcagt aattatgcca tgcactgggt ccgccaggct      120
ccaggcaagg ggctggagtg ggtggcagtt atttggtatg atggaagtaa aaatattat      180 ggcgactccg tgaagggccg attcaccatc tccagagaca atcccaagaa cacgttgtat      240
ctacagatga acagtctgag agtcgaagac acggctatat attactgtgt ccccgacgct      300
tttgatatgt ggggccaagg gacaatggtc accgtctctt cg                        342

<210> SEQ ID NO 305
<211> LENGTH: 337
<212> TYPE: DNA
<213> ORGANISM: Homo sapiens

<400> SEQUENCE: 305
ggatattgtg atgacccaga ctcctctctc ctcacctgtc acccttgggc agccggcctc       60
catctcctgc aggtctagtc aaagcctcgt acacactgat ggaaagacct acttgagttg      120
gcttcatcag aggccaggcc agcctccaag acccctaatt tataagatgt ctaagcggtt      180
ctctggggtc ccagacagat tcagtggcag tggggcagag acagagttca cactgaaaat      240
cagcagggtg gaagctgagg atgtcggaat ttattactgc ttgcaactta cacaatttcc      300
gatcaccttc ggccaaggga cacgactgga gattaaa                              337

<210> SEQ ID NO 306
<211> LENGTH: 369
<212> TYPE: DNA
<213> ORGANISM: Homo sapiens

<400> SEQUENCE: 306
caggtgcagc tggtgcagtc tgggtctgag ttgaagaagc tggggcctc agtgaaggtt        60 tcctgcaagg cttctggata caccttcact agctatgcta tgaattgggt gcgacaggcc      120
cctggacaag gcttgagtg gatgggatgg atcaacacca acactgggaa cccaacgtat      180
gcccagggct tcacaggacg gtttgtcttc tccttggaca cctctgtcag cacggcatat      240
ctgcagatca gcagcctaaa ggctgaggac actgccgtgt attactgtgc gagagatcgg      300
```

```
attgatggca gcagctggtc gtcctggttc gaccoctggg gccagggaac cctggtcacc    360
gtctcctcg                                                            369

<210> SEQ ID NO 307
<211> LENGTH: 334
<212> TYPE: DNA
<213> ORGANISM: Homo sapiens

<400> SEQUENCE: 307
ccagtctgtg ctgacgcagc cgccctcagt gtctggggcc ccagggcaga gggtcaccat     60
ctcctgcact gggagcagct ccaacatcgg ggcaggttat gatgtacact ggtaccagca    120
acttccagga acagccccca aactcctcat ctatggtaac agcaatcggc cctcaggggt    180
ccctgaccga ttctctggct ccaagtctgg cacctcagcc tccctggcca tcactgggct    240
ccaggctgag gatgaggctg attattactg ccagtccttt gacagtagcc tgagtagttc    300
ggtattcggc ggagggacca agctgaccgt ccta                                334

<210> SEQ ID NO 308
<211> LENGTH: 361
<212> TYPE: DNA
<213> ORGANISM: Homo sapiens

<400> SEQUENCE: 308
ccaggtgcag ctggtgcaat ctgggtctga gttgaagaag cctggggcct cagtgaaggt     60
ttcctgcaag gcttctggat accccgtcaa caactatgcc attaattggg tgcgacaggc    120
ccctggacaa gggcttgagt ggatgggctt catcaacacc aacactggga tccccacgta    180
tgcccagggc ttcacaggac ggtttgtctt ctccttagac acctctgtca acacggcata    240
tctgcagatc agtggcctaa aggctgacga cactgccgtg tattactgtg cgagagtcgg    300
tatagtggga gttattgttt ttgactactg gggccaggga accctggtca ccgtctcctc    360
g                                                                    361

<210> SEQ ID NO 309
<211> LENGTH: 366
<212> TYPE: DNA
<213> ORGANISM: Homo sapiens

<400> SEQUENCE: 309
gatgttgtga tgactcagtc tccagactcc ctggctgtgt ctctgggcga gagggccacc     60
atcaactgca gtccagcca gagtgtttta tccagctcca agaataagaa ccacttagcc     120
tggtaccagc agaaaccagg acagcctcct aagctgctca tctactgggc atctacccgg    180
gaatccggct actgggcatc tacccgggaa tccggggtcc ctgaccgatt cagtggcagc    240
gggtctggga cagattttac tctcaccatc agcagcctgc aggctgaaga tgtggcagtt    300
tattactgtc agcaatatta tagtccttcg gtcactttcg gcggagggac caaggtggaa    360
atcaaa                                                               366

<210> SEQ ID NO 310
<211> LENGTH: 378
<212> TYPE: DNA
<213> ORGANISM: Homo sapiens

<400> SEQUENCE: 310
caggtgcagc tggtggagtc tgggggaggc gtggtccagc ctgggaggtc cctgagactc     60
```

```
tcctgtgcag cgtctggatt caccttcagt agctatggca tgcactgggt ccgccaggct    120
ccaggcaagg ggctggagtg ggtggcgatt atatactatg attcaagtca gagatactat    180
gcagactccg tgaagggccg attcaccatc tccagagaca attccaagaa cgcgctgtat    240
ctgcaaatga atagcctgag ggccgaggac accgctctgt attactgtgc gagagatctt    300
ccgtttcact atcatagaag tgcctctttc gcaccttcgg acacctgggg ccagggaacc    360
ctggtcaccg tctcctcg                                                  378
```

\<210\> SEQ ID NO 311
\<211\> LENGTH: 324
\<212\> TYPE: DNA
\<213\> ORGANISM: Homo sapiens

\<400\> SEQUENCE: 311

```
gaaattgtgt tgacgcagtc tccaggcacc ctgtctttgt ctccggggga aagagccacc     60
ctctcctgca gggccagtca ggctgttacc aacaactact tagcctggta ccagcaaaaa    120
cctggccagg ctcccagact cctcgtctat gctgcatcca gcagggccac tggcatccca    180
gacagattct atggcagtgg gtctgggcg gacttcactc tcaccatcag cagactggag    240
cctgaagatt ttgcagtgta ttactgtcag caatatggta cctcaccgat caccttcggc    300
caagggacac gactggagat taaa                                           324
```

\<210\> SEQ ID NO 312
\<211\> LENGTH: 12
\<212\> TYPE: RNA
\<213\> ORGANISM: Homo sapiens

\<400\> SEQUENCE: 312

```
ugugugugug ug                                                         12
```

\<210\> SEQ ID NO 313
\<211\> LENGTH: 12
\<212\> TYPE: RNA
\<213\> ORGANISM: Homo sapiens

\<400\> SEQUENCE: 313

```
uuuuuuuuuu uu                                                         12
```

\<210\> SEQ ID NO 314
\<211\> LENGTH: 27
\<212\> TYPE: PRT
\<213\> ORGANISM: Homo sapiens

\<400\> SEQUENCE: 314

Ser Ile Asn Pro Gly Gly Gly Ala Ala Ala Gln Ala Ala Leu Gln Ser
1               5                   10                  15

Ser Trp Gly Met Met Gly Met Leu Ala Ser Gln
            20                  25

\<210\> SEQ ID NO 315
\<211\> LENGTH: 7
\<212\> TYPE: PRT
\<213\> ORGANISM: Homo sapiens

\<400\> SEQUENCE: 315

Ile Ile Lys Gly Ile Ser Val
1               5

\<210\> SEQ ID NO 316

```
<211> LENGTH: 7
<212> TYPE: PRT
<213> ORGANISM: Homo sapiens

<400> SEQUENCE: 316

Asn Gln Ser Gly Pro Ser Gly
1               5

<210> SEQ ID NO 317
<211> LENGTH: 7
<212> TYPE: PRT
<213> ORGANISM: Homo sapiens

<400> SEQUENCE: 317

Phe Asn Gly Gly Phe Gly Ser
1               5

<210> SEQ ID NO 318
<211> LENGTH: 11
<212> TYPE: PRT
<213> ORGANISM: Homo sapiens

<400> SEQUENCE: 318

Phe Gly Asn Ser Arg Gly Gly Ala Gly Leu
1               5                   10

<210> SEQ ID NO 319
<211> LENGTH: 11
<212> TYPE: PRT
<213> ORGANISM: Homo sapiens

<400> SEQUENCE: 319

Ser Asn Ala Gly Ser Gly Ser Gly Phe Asn Gly
1               5                   10

<210> SEQ ID NO 320
<211> LENGTH: 11
<212> TYPE: PRT
<213> ORGANISM: Homo sapiens

<400> SEQUENCE: 320

Gln Leu Glu Arg Ser Gly Arg Phe Gly Gly Asn
1               5                   10

<210> SEQ ID NO 321
<211> LENGTH: 7
<212> TYPE: PRT
<213> ORGANISM: Homo sapiens

<400> SEQUENCE: 321

Glu Ile Pro Ser Glu Asp Asp
1               5

<210> SEQ ID NO 322
<211> LENGTH: 11
<212> TYPE: PRT
<213> ORGANISM: Homo sapiens

<400> SEQUENCE: 322

Phe Asn Gly Gly Phe Gly Ser Ser Met Asp Ser
1               5                   10

<210> SEQ ID NO 323
<211> LENGTH: 27
<212> TYPE: PRT
```

```
<213> ORGANISM: Homo sapiens

<400> SEQUENCE: 323

Ser Ile Asn Pro Ala Met Met Ala Ala Ala Gln Ala Ala Leu Gln Ser
1               5                   10                  15

Ser Trp Gly Met Met Gly Met Leu Ala Ser Gln
            20                  25

<210> SEQ ID NO 324
<211> LENGTH: 12
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: PHOSPHORYLATION

<400> SEQUENCE: 324

Cys Asn Gly Gly Phe Gly Ser Ser Met Asp Ser Lys
1               5                   10

<210> SEQ ID NO 325
<211> LENGTH: 11
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: PHOSPHORYLATION

<400> SEQUENCE: 325

Cys Met Asp Ser Lys Ser Ser Gly Trp Gly Met
1               5                   10

<210> SEQ ID NO 326
<211> LENGTH: 17
<212> TYPE: PRT
<213> ORGANISM: Homo sapiens

<400> SEQUENCE: 326

Lys Ser Gly Gln Ser Val Leu Tyr Arg Ser Asn Asn Arg Asn Tyr Ile
1               5                   10                  15

Ala

<210> SEQ ID NO 327
<211> LENGTH: 7
<212> TYPE: PRT
<213> ORGANISM: Homo sapiens

<400> SEQUENCE: 327

Trp Ala Ser Thr Arg Glu Ser
1               5

<210> SEQ ID NO 328
<211> LENGTH: 9
<212> TYPE: PRT
<213> ORGANISM: Homo sapiens

<400> SEQUENCE: 328

Gln Gln Tyr Tyr Ser Asn Arg Trp Thr
1               5
```

TDP-43 SPECIFIC BINDING MOLECULES

FIELD OF THE INVENTION

The invention generally relates to novel TDP-43 (TAR DNA-binding protein of 43 kDa)-specific binding molecules, such as antibodies, including fragments, derivatives and variants thereof, that specifically recognize TDP-43. In addition, the invention relates to pharmaceutical and diagnostic compositions comprising such antibodies and other TDP-43-specific binding molecules and their use to detect and identify TDP-43 in plasma, cerebrospinal fluid, brain, and other samples, as well as in therapeutic applications including for example, passive vaccination strategies for treating disorders related to aggregates or other aberrations in TDP-43 expression, such as, frontotemporal lobar degeneration and/or, amyotrophic lateral sclerosis, Alzheimer's disease, Parkinson's disease and other TDP-43 proteinopathies.

BACKGROUND OF THE INVENTION

Frontotemporal lobar degeneration (FTLD) is the second most common cause of dementia affecting individuals younger than 65 years; see, e.g., McKhann et al., Arch. Neurol. 58 (2001), 1803; Forman et al., Ann. Neurol. 59 (2006), 952-62. On a cellular pathologic level, the characteristic lesions in the majority of FTLD brains are abnormal ubiquitinated protein inclusions. The biochemical composition of the ubiquitinated inclusions in the most common pathological form of FTLD, namely FTLD-U, remained unknown until 2006, when the TAR-DNA binding protein 43 (TDP-43) was identified as the major disease protein in the majority of sporadic and familial FTLD-U cases. Subsequently, the ubiquitinated compact inclusions, characteristic for amyotrophic lateral sclerosis (ALS) were also found to be composed of TDP-43, thereby providing evidence that both conditions are mechanistically linked and part of spectrum of diseases which can be classified as TDP-43 proteinopathies, see, e.g., Neumann et al., Science 314 (2006), 130-133.

Other than FTLD and ALS, TDP-43 is also known to accumulate in the nerve cells and glial cells of ALS-Parkinsonism dementia complex of Guam, corticobasal degeneration, Dementia with Lewy bodies, Huntington's disease, Lewy body disease, motor neuron disease, frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula and Pick's disease and the like; see e.g., Lagier-Tourenne et al., Hum. Mol. Gen. 19 (2010), R46-64, which is herein incorporated by reference in its entirety. These diseases are collectively referred to as TDP-43 proteinopathies. Abnormal accumulation of TDP-43 is observed at the site of lesions of each disease which appears to imply involvement in the cause of nerve degeneration in these diseases. Increased cytoplasmic localization of TDP-43 in brains and spinal cords of patients termed as "pre-inclusions" has been proposed to be an early event in TDP-43 proteinopathies, with the implication of a possible pathogenic role in these diseases; see, e.g. Giordano et al., Brain Pathol, 20 (2010), 351-60, Consistently, increased cytoplasmic TDP-43 localization at presymptomatic stages has been reported to be found in mice overexpressing wild type TDP-43; see e.g., Wils et al., Proc. Natl Acad. Sci. USA 107 (2010), 3858-63 as well as in an acute rat model with adenovirus-mediated wild-type TDP-43 expression; see, e.g., Tatom et al., Mol. Ther. 17 (2009), 607-613. Commercially available monoclonal murine antibodies are primarily used in the studies on TDP-43 and to conduct pathological diagnosis of TDP-43 proteinopathies. A monoclonal murine anti-TDP-43 antibody, which recognizes the phosphorylated form of TDP-43 is disclosed in European Patent Application No. 2 189 526 A1. Additional anti-TDP-43 antibodies are disclosed in Mang et al., Proc Natl Acad Sci USA, 106(18): 7607-12 (2009) and U.S. Patent Application Pub. No. 20100136573.

The success in generating monoclonal antibodies rests among other things, on the efficient and selective fusion of antigen-stimulated B cells with a murine myeloma cell line followed by selection of stable antibody producing hybrids as originally described by Köhler and Milstein, Nature 256 (1975), 495-497. However, the therapeutic utility of murine based antibodies in human is hampered by the human anti-mouse antibody (HAMA) response as a consequence of their non-human origin. Approaches for making human or human-like monoclonal antibodies became available through genetic engineering. However, these methods typically suffer from the drawback that they are not suitable for producing antibodies displaying many of the characteristics of antibodies that are endogenously produced by the human immune system during the course of a physiological human immune response. Furthermore these genetically engineered antibodies may show undesired cross-reactivity with other proteins and/or the target protein in the context of the biologically relevant native conformation and normal physiological function of the target antigen. The resulting side effects upon systemic administration of the exogenous antibodies may range from for example, undesired autoimmune disease to anaphylactic reactions. These side effects have been reported in so-called "humanized antibodies," which originally stem from non-human organisms, such as mice, as well as so called "fully human antibodies," in vitro or in xenogeneic mice genetically engineered to express a repertoire of human antibodies. On the other hand, active immunization with pathologically relevant antigens bears the considerable risk of patients developing uncontrollable immune responses against these antigens and cross-reactivity with endogenous antigens that may consequently lead to dangerous autoimmune responses.

Furthermore, the development of assays to detect and monitor levels of normal and pathological TDP-43 in plasma, cerebrospinal fluid, and other samples as biomarkers of FTLD and ALS will provide the ability to diagnose and distinguish TDP-43 proteinopathies from other clinically similar neurodegenerative disorders, such as tauopathies or related proteinopathies. In addition, the development of imaging ligands that enable the detection and/or quantification of TDP-43 neuropathology in living patients will provide a powerful tool not only for diagnosis, but also for monitoring the response of patients having a neurodegenerative TDP-43 proteinopathy to disease-modifying therapies when they become available.

Thus, there is a need to overcome the above-described limitations and to provide therapeutic and diagnostic antibodies and other binding molecules that specifically recognizes biologically relevant conformations of TDP-43.

SUMMARY OF THE INVENTION

The invention relates to TDP-43 (TAR DNA-binding protein of 43 kDa)-specific binding molecules, such as antibodies, including fragments, derivatives and variants of antibodies that are capable of specifically recognizing TDP-43. By "specifically recognizing TDP-43", "antibody specific to/for TDP-43" and "anti-TDP-43 antibody" is meant specifically, generally, and collectively, antibodies to TDP-43, or misfolded or oligomeric or aggregated or posttranslationally modified TDP-43. According to one embodiment, antibodies of the invention (including antigen-binding antibody fragments and derivatives) specifically recognize full-length, truncated, or aggregated human TDP-43. In an additional embodiment, the antibodies recognize full-length human TDP-43 having the sequence of SEQ ID NO:94 or a peptide consisting of residues 390-414 of the C-terminal sequence of SEQ ID NO:94 phosphorylated at residues 409 and 410.

In one embodiment, the TDP-43 specific binding molecule is an antibody (including antigen-binding fragments or derivatives thereof) having an immunological binding characteristic of an antibody described herein, such as, an antibody having the variable regions $V_H$ and/or $V_L$ of the amino acid sequence set forth in (SEQ ID NO:1) and (SEQ ID NO:6), (SEQ ID NO:10) and (SEQ ID NO:14), (SEQ ID NO:18) and (SEQ ID NO:22), (SEQ ID NO:26) and (SEQ ID NO:31), (SEQ ID NO:35) and (SEQ ID NO:40), (SEQ ID NO:45) and (SEQ ID NO:49), (SEQ ID NO:53) and (SEQ ID NO:57), (SEQ ID NO:61) and (SEQ ID NO:65), (SEQ NO:69) and (SEQ ID NO:73), (SEQ ID NO:77) and (SEQ ID NO:82), (SEQ ID NO:87) and (SEQ ID NO:122), (SEQ ID NO:130) and (SEQ ID NO:134), (SEQ ID NO:138) and (SEQ ID NO:142), (SEQ ID NO:146) and (SEQ ID NO:150), (SEQ ID NO:146) and (SEQ ID NO:151), (SEQ ID NO:155) and (SEQ ID NO:159), (SEQ ID NO:163) and (SEQ ID NO:167), (SEQ ID NO:171) and (SEQ ID NO:175), (SEQ ID NO:179) and (SEQ ID NO:183) (SEQ ID NO:187) and (SEQ ID NO:191), (SEQ ID NO:195) and (SEQ ID NO:199), (SEQ NO:203) and (SEQ ID NO:207), (SEQ ID NO:211) and (SEQ ID NO:215), (SEQ NO:219) and (SEQ ID NO:223), (SEQ ID NO:227) and (SEQ ID NO:213), (SEQ ID NO:235) and (SEQ ID NO:239), (SEQ ID NO:243) and (SEQ ID NO:247), (SEQ ID NO:251) and (SEQ ID NO:255), (SEQ ID NO:259) and (SEQ ID NO:263), or (SEQ ID NO:267) and (SEQ ID NO:271), respectively.

The invention also relates to compositions comprising an antibody of the invention (including TDP-43-binding antibody fragments and derivatives) or TDP-43 agonists and cognate molecules, or alternately, antagonists of the same and to immunotherapeutic and immunodiagnostic methods using such compositions in the prevention, diagnosis or treatment of a TDP-43 proteinopathy, wherein an effective amount of the composition is administered to a patient in need thereof.

Polynucleotides encoding TDP-43-binding molecules such as, antibodies (including TDP-43 binding antibody fragments or variants), are also encompassed by the invention. In some embodiments, the polynucleotide encodes at least a variable region of an immunoglobulin chain of an antibody of the invention. In an additional embodiment, the polynucleotide encodes at least one complementarity determining region (CDR) of a $V_H$ and/or $V_L$ variable region as depicted in FIGS. 1 and 3. In an additional embodiment, the polynucleotide encodes at least one complementarity determining region (CDR) of a $V_H$ and/or $V_L$ variable region encoded by a polynucleotide sequence as set forth in Table 3. Polynucleotides encoding derivatives or analogs of the above-encoded TDP-43 binding peptides and the polypeptides encoded by these polynucleotides are also encompassed by the invention.

Vectors containing polynucleotides encoding TDP-43-binding molecules (e.g., antibodies) of the invention and host cells transformed with these vectors and/or polynucleotides are also encompassed by the invention, as are their use for the production of an antibody and equivalent binding molecules which are specific for TDP-43. Means and methods for the recombinant production of antibodies and other binding polypeptides and mimics thereof as well as methods of screening for molecules, e.g., antibodies, that compete with these antibodies or other binding proteins for binding with TDP-43 are known in the art. As described herein, in some embodiments, for example those relating to therapeutic applications in human, the TDP-43 specific binding antibody of the invention is a human antibody in the sense that application of said antibody is substantially free of a HAMA response otherwise observed for chimeric and even humanized antibodies.

In one embodiment, the invention encompasses molecules that specifically bind TDP-43 and the use of these molecules to detect the presence of TDP-43 in a sample. Accordingly, TDP-43 binding molecules of the invention, such as, anti-TDP-43 antibodies, can be used to screen human blood, CSF, and urine for the presence of TDP-43 in samples, for example, by using ELISA-based or surface adapted assay. The methods and compositions disclosed herein have applications in diagnosing TDP-43 proteinopathies such as, amyotrophic lateral sclerosis (ALS) or frontotemporal lobar degeneration (FTLD). The methods and compositions of the invention also have applications in diagnosing presymptomatic disease and in monitoring disease progression and therapeutic efficacy. According to some embodiments, an antibody specific for TDP-43 (e.g., a full-length antibody or a TDP-43 binding fragment or derivative of an antibody) is contacted with a sample (e.g., blood, cerebrospinal fluid, or brain tissue) to detect, diagnose or monitor frontotemporal lobar degeneration (FTLD) or Amyotrophic lateral sclerosis (ALS). In another embodiment, an antibody specific for TDP-43 is contacted with a sample to detect, diagnose or monitor a disease selected from Alzheimer's disease, Parkinson's disease, and Lewy Body disease: In another embodiment, an antibody specific for TDP-43 is contacted with a sample to detect, diagnose or monitor a disease selected from: argyrophilic grain disease, ALS Parkinsonism dementia complex of Guam, corticobasal degeneration. Dementia with Lewy bodies, Huntington's disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease dementia, Parkinson-dementia complex in Kii peninsula, Pick's disease, and Machado-Joseph disease or dementia.

In additional embodiments, the invention provides methods for treating or preventing a TDP-43 neurologic proteinopathy. According to one embodiment, the methods of the invention comprise administering an effective concentration of an antibody specific for TDP-43 (e.g., a full-length antibody or a TDP-43 binding fragment or derivative of an antibody) to a subject. In an additional embodiment, the invention provides a method for treating or preventing TDP-43 neurologic proteinopathies. According to some embodiments, an antibody specific for TDP-43 is administered to treat or prevent frontotemporal lobar degeneration (FTLD) or Amyotrophic lateral sclerosis (ALS). In another embodiment, an antibody specific for TDP-43 is administered to treat or prevent a neurodegenerative disease selected from Alzheimer's disease, Parkinson's disease, and Lewy Body disease. In another embodiment, an antibody specific for TDP-43 is administered to treat or prevent a disease selected from: argyrophilic grain disease, ALS-Parkinsonism dementia complex of Guam, corticobasal, degeneration, Dementia with Lewy bodies, Huntington's disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease dementia, Parkinson-dementia complex in Kii peninsula, Pick's disease, and Machado-Joseph disease or dementia.

Further embodiments of the invention are apparent from the description and Examples that follow.

BRIEF DESCRIPTION OF THE DRAWINGS

FIGS. 1A-1K: Amino acid sequences of the variable region, i.e. heavy chain and kappa/lambda light chain of human antibodies NI-205.3F10 (FIG. 1A), NI-205.51C1 (FIG. 1B), NI-205.21G2 (FIG. 1C), NI-205.8A2 (FIG. 1D), NI-205.15F12 (FIG. 1E), NI-205.113C4 (FIG. 1T), NI-205.25F3 (FIG. 1O), NI-205.87E7 (FIG. 1H), NI-205.21O1 (FIG. 1I), NI-205.68G5 (FIG. 1J), and NI-205.20A1 (FIG. 1K). Framework (FR), complementarity determining regions (CDRs; underlined), heavy chain joining region (JH), and light chain joining region (JK) or (JL) are indicated. Amino acid positions modified to account for potential PCR-primer induced cloning artifacts and that have been modified to match the corresponding human germ line variable region sequences are provided in bold.

FIGS. 3A-3R: Amino acid sequences of the variable region, i.e. heavy chain (VH) and kappa (VK)/lambda (VL) light chain of human antibodies NI205.41D1 (FIG. 3A), NI205.29E11 (FIG. 3B), NI205.9E12 (FIG. 3C), NI205.98H6 (FIG. 3D), NI205.10D3 (FIG. 3E), NI205.44B2 (FIG. 3F), NI205.38H2 (FIG. 3G), NI205.36D5 (FIG. 3H), NI205.58E11 (FIG. 3I), NI205.14H5 (FIG. 3J), NI205.31D2 (FIG. 3K), NI205.8F8 (FIG. 3L), NI205.31C11 (FIG. 3M), NI205.8C10 (FIG. 3N), NI205.10H7 (FIG. 3O), NI205.1A9 (FIG. 3P), NI205.14W3 (FIG. 3Q), and NI205.19G5 (FIG. 3R). Complementarity determining regions (CDRs) are underlined.

FIGS. 4A-4H: Determination of the half maximal effective concentration (EC$_{50}$) of human-derived TDP-43 antibodies by direct ELISA to (A-D) recombinant full length TDP-43 (●), *Escherichia coli* extract (▲) and BSA (■), or (E-H) a synthetic peptide covering residues 390 to 414 of the C-terminal domain of TDP-43 with phosphorylation modification at residues 409/410 (●) and BSA (■).

FIGS. 5A-5M: Binding specificity of the human-derived antibodies to TDP-43 domains comprising amino acids 2-106 (domain I), 99-204 (domain II), 183-273 (domain III), 258-414 (domain IV) and 2-414 (full length) of TDP-43 as determined by direct ELISA.

FIGS. 6A-6Q: Binding of the human-derived antibodies to TDP-43 domains comprising amino acids 2-414 (full length), 2-106 (domain I), 99-204 (domain II), 183-273 (domain III), and 258-414 (domain IV) of TDP-43 as determined by Western Blot analysis.

FIGS. 7A-7C: (A) NI-205.41D1 antibody binding to full length TDP-43 and TDP-43 fragments comprising amino acid residues 258-414, 258-384, 258-375, 258-362, 258-353, 258-319, 317-414 and 340-414. (B) NI-205.41D1 and 12892-1-AP antibody binding to full length TDP-43, TDP-43 fragment comprising amino acid residues 258-414, and to a mutant TDP-43 polypeptide fragment comprising amino acid residues 258-414 and the A to G substitution at residue 321, M to G substitution at residue 322, and M to substitution at residue 323 (TDP-43 258-414 AMM321GGG). (C) NI-205.41D1 antibody binding to TDP-43 fragments comprising amino acid residues 316-353, 316-343, and 316-333.

FIGS. 8A-8C: Purification of monomeric forms of TDP-43 using mild chaotropic conditions. A) Coomassie stained SDS-PAGE gel of purified TDP-43 forms in the presence or absence of chaotrope KSCN. Lane 1 to 4, respectively: Molecular Weight standards, 6×His-TDP-43 (1-414), 6×His-SUMO-TDP-43 (1-414), 6×His-SUMO-TDP-43 (220-414), all purified in the presence of 1.5M KSCN, and lane 5 and 6: 6×His-SUMO-TDP-43 (101-265) purified in the presence of KCl (lane 5) or KSCN (lane 6) B) Domain arrangement of purified proteins illustrating location of RNA binding domains (RRM1 and RRM2) as well as tags (6His and SUMO), C) Analytical ultracentrifugation sedimentation coefficient distributions for purified 6His-SUMO and 6H is tagged full-length TDP-43. Sedimentation coefficients and calculated molecular weights are shown above peaks.

FIG. 10: Titration curves for human NI-205.41D1, NI-205.21G1, NI-205.51C1, NI-205.21G2 and NI-205.3F10 antibody binding to A) folded full-length TDP-43, and B) TDP-43 fragment comprising residues 220-414 in a capture ELISA assay.

FIG. 11: Immunohistochemical staining of human FTLD-U hippocampus tissue with antibodies (A-C) 2E2-D3, (D-F) control antibody p403/p404, (G-I) control antibody p409/p410, (J) NI-205.10D3, (K) NI-205.8C10, (L) NI-205.15F12, (M) NI-205.8A2, (N) NI-205.3F10, (O) NI-205.21G2, (P) NI-205.8F8, (Q) NI-205.31C11, (R) NI-205.36D5, (S) NI-205.31D2, (T) NI-205.10H7, (U) NI-205.14H5, (V) NI-205.68G5, (W) NI-205.14W3, (X) NI-205.21G1, and (Y) NI-205.41D1. (Z) Immunohistochemical staining of control hippocampus tissue with NI-205.41D1.

DETAILED DESCRIPTION OF THE INVENTION

I. Definitions

Figure 2A:
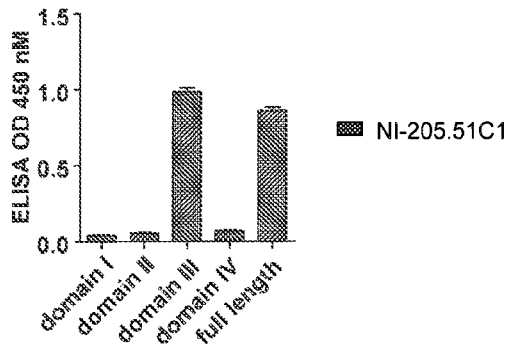
FIGS. 2A-2J: Binding of human TDP-43 antibodies to amino terminal His-tagged fragments of TDP-43 consisting of amino acid residues 2-106 (domain I (SEQ ID NO:117)), 99-204 (domain II (SEQ NO:118)), 183-273 (domain 111 (SEQ ID NO:119)), 258-414 (domain IV (SEQ ID NO:120)), or 2-414 (full length (SEQ ID NO:121)).
Figure 2B:
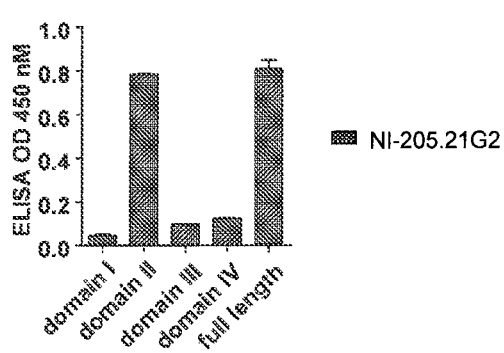
Figure 2C:
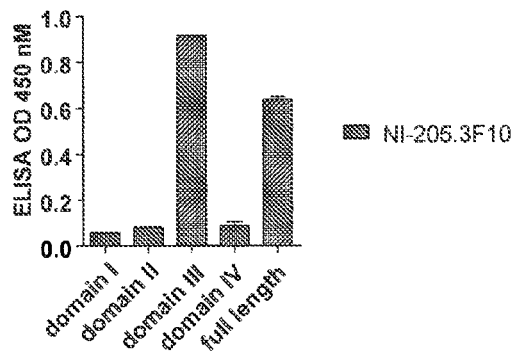
Figure 2D:
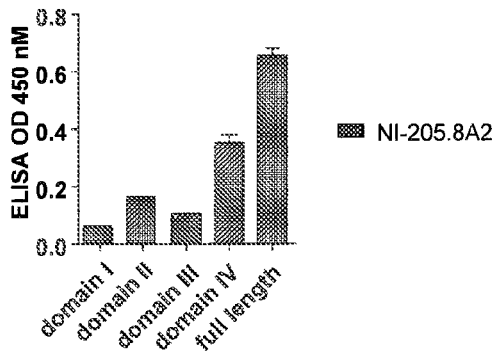
Figure 2E:
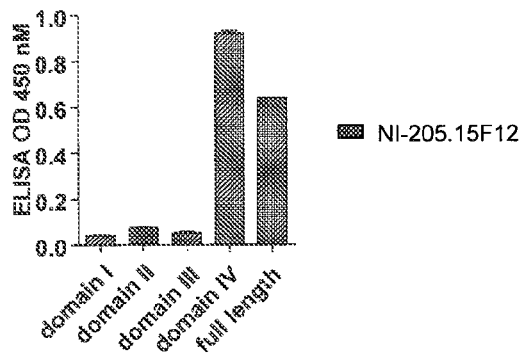
Figure 2F:
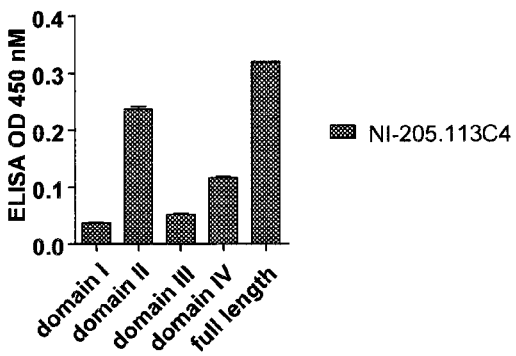
Figure 2G:
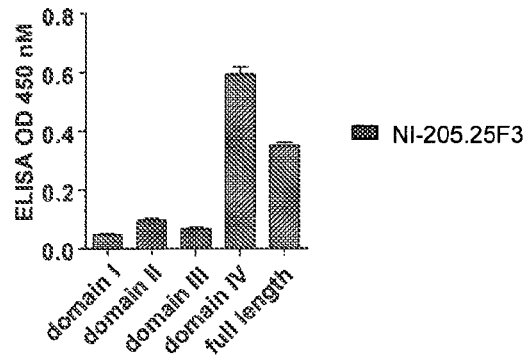
Figure 2H:
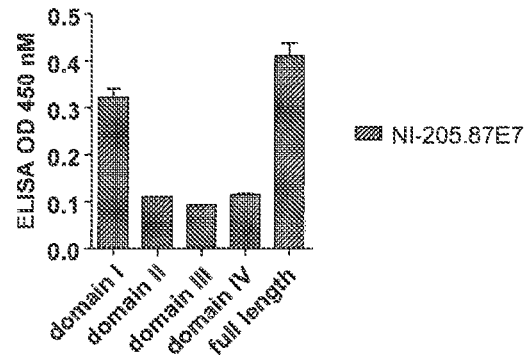
Figure 2I:
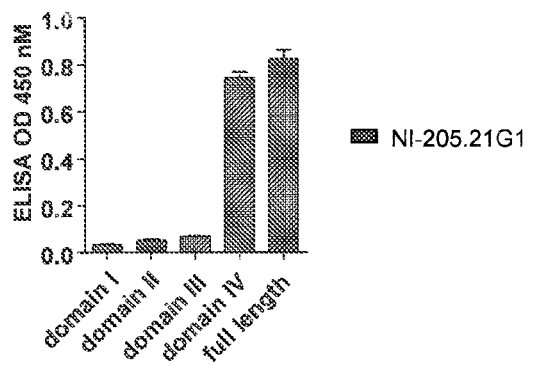
Figure 2J:
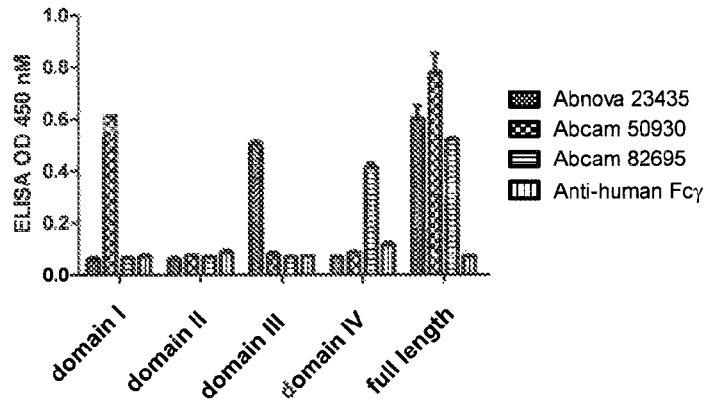

As used herein, the phrase "neurodegenerative diseases" refers to presence of abnormal protein accumulation, cellular localization, or protein folding in the brain, spinal cord, or other neural tissue and are caused by the death or functional impairment of neurons. In some cases of neurodegenerative diseases, genetically defined abnormalities contribute to the development of the disease. Neurodegenerative diseases include for example, cerebral degenerative disease (e.g., Alzheimer's disease, Parkinson's disease, progressive supranuclear palsy, and Huntington's disease) and spinal degenerative diseases/motor neuron degenerative diseases e.g., amyotrophic lateral sclerosis and spinal muscular atrophy; see, e.g., Forman et al. Nat. Med. 10 (2004), 1055-63.

"TDP-43 proteinopathy" relates to the nervous system diseases, in particular to neurodegenerative diseases and are known as a heterologous group of disorders linked by the TAR (Transactivation responsive)-DNA-binding protein of 43 kDa. TDP-43 proteinopathies are characterized by the fact that TDP-43 is a disease protein that mechanistically links frontotemporal lobar degeneration with ubiquitin-positive inclusions (FTLD-U) with and without motor neuron disease to amyotrophic lateral sclerosis (ALS) argyrophilic grain disease, Alzheimer's disease, amyotrophic lateral sclerosis (ALS), ALS-Parkinsonism dementia complex of Guam, corticobasal degeneration. Dementia with Lewy bodies, Huntington's disease, Lewy body disease, motor neuron disease, frontotemporal lobar degeneration (FILM, frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula, Pick's disease, Machado-Joseph disease and the like; see e.g., Lagier-Tourenne et al., Hum. Mol. Gen. 19 (2010), R46-64, which is herein incorporated by reference in its entirety.

Under normal physiological conditions, TDP-43 predominantly localizes to the nucleus. However, a substantial loss of nuclear TDP-43 is observed in neurons bearing aberrant cytoplasmic TDP-43 inclusions. TDP-43 exhibits a disease-specific biochemical signature; pathologically altered TDP-43. TDP-43 proteinopathies are distinct from most other neurodegenerative disorders in which protein misfolding leads to brain amyloidosis, as pathologic TDP-43 forms neuronal and glial inclusions lacking the features of brain amyloid deposits; see e.g., Neumann et al., Arch Neurol. 64 (2007), 1388-1394, herein incorporated by reference in its entirety.

As used herein, the term "pathologic TDP-43" refers to extracellular, cytoplasmic, neuritic, and nuclear inclusions, is also referred to as a "TDP-43 inclusion body" wherein the protein forms fibril-like clumps. Specifically, pathologic TDP-43 has been found to be hyperphosphorylated, ubiquitinated, and N-terminally truncated, thereby generating abnormal species of TDP-43 that migrate with a higher molecular mass at approximately 45 kDa, as well as a smear of high-molecular-mass proteins and C-terminal fragments of approximately 25 kDa; see, e.g., Neumann et al., Science 314 (2006), 130-133 and Arai et al., Biochem. Biophys. Res. Commun. 351 (2006), 602-611, each of which is herein incorporated by reference in its entirety. Additionally, TDP-43 has been found to exhibit multiple phosphorylation sites in carboxy-terminal regions of deposited TDP-43 and it is suggested that phosphorylation leads to increased oligomerization and fibrillization of TDP-43; see, for example, Hasegawa et al., Annals of Neurology 64 (2008), 60-70.

TDP-43 inclusion body formation is accompanied by change in the subcellular distribution of TDP-43 with complete lack of normal diffuse nuclear TDP-43 staining in inclusion-bearing cells. The presence and extent of this pathologic signature in affected cortical gray and white matter, as well as the spinal cord, roughly correspond with the density of TDP-43-positive inclusions; see, e.g., Neumann et al., J. Neuropath. Exp. Neurol. 66 (2007), 177-183. The composition of the ubiquitinated inclusions (UBIs) in FTLD-U is characterized by a relative low abundance, uneven distribution of UBIs among different FTLD-U cases, and the non-amyloidogenic nature of them. Thus, TDP-43 is a specific and sensitive marker to detect the characteristic ubiquitin-immunoreactive lesions in FTLD-U, including neuronal cytoplasmic inclusions (NCIs), dystrophic neurites, and neuronal intranuclear inclusions (NIIs).

As used herein, the terms "TARDBP," "Transactivation responsive-DNA binding protein of 43 kDa", "Transactive responsive-DNA binding protein of 43 kDa", "TAR-DNA binding protein of 43 kDA" and "TDP-43" are used interchangeably to refer to the native form of TDP-43. The term "TDP-43" is also used to refer collectively to all types and forms of TDP-43. "TDP-43" is also used to generally identify other conformers of TDP-43, including for example, phosphorylated forms of TDP-43 and ubiquitin-associated aggregates or aggregates of TDP-43.

The amino acid sequence of human TDP-43 is known in the art; see, e.g., Strausberg et al., TARDBP protein (*Homo sapiens*) GenBank Pubmed: AAH71657 version GI:47939520 herein incorporated by reference in its entirety. According to one embodiment, the amino acid sequence of native human TDP-43 is:

(SEQ ID NO: 94)
MSEYIRVTEDENDEPIEIPSEDDGTVLLSTVTAQFPGACGLRYRNPVSQC

MRGVRLVEGILHAPDAGWGNLVYVVNYPKDNKRKMDETDASSAVKVKR

AVQKTSDLIVLGLPWKTTEQDLKEYFSTFGEVLMVQVKKDLKTGHSKGF

GFVRFTEYETQVKVMSQRHMIDGRWCDCKLPNSKQSQDEPLRSRKVFVG

RCTEDMTEDELREFFSQYGDVMDVFIPKPFRAFAFVTFADDQIAQSLCGE

DLIIKGISVHISNAEPKHNSNRQLERSGRFGGNPGGFGNQGGFGNSRGGG

AGLGNNQGSNMGGGMNFGAFSINPAMMAAAQAALQSSWGMMGMLAS

QQNQSGPSGNNQNQGNMQREPNQAFGSGNNSYSGSNSGAAIGWGSASN

AGSGSGFNGGFGSSMDSKSSGWGM

As used herein, the term "antibody" or "antibodies" is meant to refer to complete, intact antibodies, and Fab, Fab', F(ab)2, and other antibody fragments. Complete, intact antibodies include, but are not limited to, monoclonal antibodies such as murine monoclonal antibodies, polyclonal antibodies, chimeric antibodies, human antibodies, and humanized antibodies. Various forms of antibodies can be produced using standard recombinant DNA techniques (Winter and Milstein, Nature 349 (1991), 293-99. For example, "chimeric" antibodies can be constructed, in which the antigen binding domain from an animal antibody is linked to a human constant domain (an antibody derived initially from a nonhuman mammal in which recombinant DNA technology has been used to replace all or part of the hinge and constant regions of the heavy chain and/or the constant region of the light chain, with corresponding regions from a human immunoglobulin light chain or heavy chain) (see, e.g., U.S. Pat. No. 4,816,567; Morrison et al., Proc. Natl. Acad. Sci. 81 (1984), 6851-6855. Chimeric antibodies reduce the immunogenic responses elicited by animal antibodies when used in human clinical treatments.

In addition, recombinant "humanized" antibodies can be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., International Patent Application Publication No. WO 94/04679). Animals are immunized with the desired antigen, the corresponding antibodies are isolated and the portions of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Additional embodiments of the invention relate to human antibodies as well as the uses of these human antibodies. In one embodiment, the human antibodies are derived from human B cells or other immune cells and are generally referred to herein as "completely human antibodies." Thus, the invention encompasses the immortalized human B memory lymphocyte and B cell, respectively, that produces the antibody having the distinct and unique characteristics as defined below. Alternatively, human antibodies can be produced in nonhuman animals, such as transgenic animals harboring one or more human immunoglobulin transgenes. Such animals can be used as a source for splenocytes for producing hybridomas, as is described in U.S. Pat. No. 5,569,825.

The antigen-binding fragments of antibodies of the invention can be a single chain Fv fragment, an F(ab') fragment, an F(ab) fragment, and an F(ab')$_2$ fragment. In additional embodiments, the antigen-binding fragment is a TDP-43-binding fragment that recognizes TDP-43 by one or more antibody variable domains, or fragments or variants thereto, such as, one or more CDRs or a derivative) of one or more CDS. In a specific embodiment, infra, the antibody or fragment thereof is a human IgG isotype antibody. Alternatively, the antibody is a chimeric human-murine or murinized antibody, the latter being particularly useful for diagnostic methods and studies in animals.

Antibody fragments, univalent antibodies, and single domain antibodies can also be used in the methods and compositions of the invention. Univalent antibodies comprise a heavy chain/light chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as F(ab)2), whether any of the above are covalently or non-covalently aggregated, so long as the aggregation is capable of specifically reacting with a particular antigen or antigen family.

The TDP-43 antibodies of the invention specifically bind TDP-43, epitopes of TDP-43, and to various conformations of TDP-43 and epitopes thereof. For example, disclosed herein are antibodies that specifically bind native TDP-43, full-length and truncated TDP-43, and pathologic TDP-43. As used herein, reference to an antibody that "specifically binds", "selectively binds", or "preferentially binds" or even more generally "binds TDP-43" or "TDP-43 binding", refers to an antibody that binds TDP-43 preferentially over other distinct proteins. As used herein, an antibody that "specifically binds" or "selectively binds" an TDP-43 conformer does not bind at least one other TOP-43 conformer. For example, disclosed herein are antibodies that selectively bind full-length TDP-43 as well as those that selectively bind cytoplasmic TDP-43 over nuclear TDP-43.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is used interchangeably with the term "polypeptide" and encompasses a singular polypeptide/protein as well as plural polypeptides/proteins and refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the terms "polypeptide" is used instead of or interchangeably with any of these terms.

As used herein, the terms "polypeptide" and "protein" also refer to products of post-expression modifications of the polypeptide, including without limitation glycosylation, acetylation, phosphorylation, amidation, derivatization by known protecting/blocking groups, proteolytic cleavage, or modification by non-naturally occurring amino acids or other chemical moieties. A polypeptide can be derived from a natural biological source or produced by recombinant technology, but need not necessarily be translated from a particular nucleic acid sequence. Polypeptides of the invention can be generated in any manner, including by chemical synthesis.

A polypeptide of the invention can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure can be referred to herein as folded, and polypeptides which do not possess a defined three-dimensional structure, but rather can adopt a large number of different conformations, and may be referred to herein as unfolded. As used herein, the term glycoprotein refers to a polypeptide coupled to at least one carbohydrate moiety that is attached to the protein via an oxygen-containing or a nitrogen-containing side chain of an amino acid residue, e.g., a serine residue or an asparagine residue.

As used herein, an "isolated" polypeptide or a fragment, variant, or derivative thereof, refers to a polypeptide that is not in its natural milieu. No particular level of purification is required. For example, an isolated polypeptide can be removed from its native or natural environment. Recombinantly produced polypeptides and proteins expressed in host cells can be considered isolated for the purposes of the invention, as are native or recombinant polypeptides which have been separated, fractionated, or partially or substantially purified by any suitable technique.

Also included as polypeptides of the invention are fragments, derivatives, analogs, or variants of the foregoing polypeptides, and any combination thereof. The terms "fragment," "variant," "derivative" and "analog" when referring to antibodies or TDP-43 binding polypeptides of the invention include any polypeptides which retain at least some of the antigen-binding properties of the corresponding reference antibody or TDP-43 binding molecule. Fragments of TDP-43 binding polypeptides such as antigen binding antibody fragments, include proteolytic fragments, as well as deletion fragments, in addition to additional antibody fragments discussed herein. Variants of TDP-43 binding molecule, such as antibodies (including antigen binding antibody fragments) and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of TDP-43 specific binding molecules, e.g., antibodies and other TDP-43 specific binding molecules, are polypeptides which have been altered so as to exhibit altered or additional features not found on a reference polypeptide. Examples of derivatives of TDP-43 specific binding molecules include fusion proteins. Variant polypeptides can also be referred to herein as "polypeptide analogs". As used herein, a "derivative" of a of TDP-43 specific binding molecules or fragment thereof, refers to a subject polypeptide having one or more residues chemically derivatized by reaction of a functional side group. Also included as "derivatives" are those peptides which contain one or more naturally occurring amino acid derivatives of the twenty standard amino acids. For example, according to some embodiments, 4-hydroxyproline can be substituted for proline; 5-hydroxylysine can be substituted for lysine; 3-methylhistidine can be substituted for histidine; homoserine can be substituted for serine; or ornithine can be substituted for lysine.

As used herein, the term "polynucleotide" or "nucleic acid" encompasses a singular nucleic acid as well as plural nucleic acids, and includes an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)).

The term "polynucleotide acid" can also refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody heavy or light chain variable domain contained in a vector is considered isolated for the purposes of the invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the invention. Isolated polynucleotides or nucleic acids according to the invention further include such molecules produced synthetically. In addition, polynucleotide or a nucleic acid can be or can include a regulatory element such as a promoter, ribosome binding site, or a transcription terminator operably associated with a sequence encoding a TDP-43 specific binding polypeptide of the invention.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions of the invention can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector including a nucleic acid of the invention can optionally encode one or more heterologous coding regions, either fused or unfused to a nucleic acid encoding a TDP-43 binding polypeptide, including for example, an antibody or a fragment, variant, or derivative thereof. Heterologous coding regions include without limitation specialized elements or motifs, such as a secretory signal peptide or a heterologous functional domain.

In certain embodiments, the polynucleotide or nucleic acid of the invention is DNA. A polynucleotide comprising a nucleic acid which encodes a polypeptide optionally includes a promoter and/or other transcription or translation control elements operably associated with one or more coding regions. An operable association is present when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the linkage between the two DNA fragments does not interfere with the ability of the expression regulatory sequences to direct the expression of the gene product or prevent with the ability of the DNA template to be transcribed. Thus, a promoter region can be operably associated with a nucleic acid encoding a polypeptide if the promoter is capable of effecting transcription of that nucleic acid. The promoter can be a cell-specific promoter that directs substantial transcription of the DNA only in predetermined cells. The promoter can also be constitutive or regulatable. Other transcription control elements that are optionally operably linked with the nucleic acids of the invention include for example, enhancers, operators, repressors, and transcription termination signals, can be operably associated with the polynucleotide to direct cell-specific transcription. Examples of suitable promoters and other transcription control regions are disclosed herein or otherwise known in the art.

A variety of transcription control regions that can be used to control the expression of the polynucleotides of the invention are known in the art. These include, without limitation, transcription control regions which function in vertebrate cells, including but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include but are not limed to, those derived from vertebrate genes such as, actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of suitable translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide or nucleic acid of the invention is RNA, for example, in the form of messenger RNA (mRNA).

Polynucleotide and nucleic acid coding sequences of the invention can be associated with additional heterologous coding sequences which encode for example, secretory or signal peptides, which direct the secretion of a polypeptide encoded by a polynucleotide of the invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of a polypeptide to which it is operably associated. Alternatively, a heterologous mammalian signal peptide, or a functional derivative thereof, can be used. For example, the native signal peptide sequence can be substituted with the signal peptide sequence of human tissue plasminogen activator (TPA), mouse β-glucuronidase, or a signal sequence derived from a secreted protein of a preferred host cell.

Unless stated otherwise, the terms "disorder" and "disease" are used interchangeably herein.

A "binding molecule" as used herein relates primarily to antibodies (including TDP-43 binding antibody fragments or derivatives), but can also refer to other proteins and polypeptides that specifically recognize TDP-43 including, but not limited to, hormones, receptors, ligands, major histocompatibility complex (MHC) molecules, chaperones such as heat shock proteins (HSPs), and cell-cell adhesion molecules such as, members of the cadherin, intergrin, C-type lectin and immunoglobulin (Ig) superfamilies. Fragments, variants, and derivatives of these polypeptides that specifically recognize TDP-43 are also encompassed by the invention. For the sake of clarity only and without restricting the scope of the invention most of the following embodiments are discussed with respect to antibodies (including antibody fragments and derivatives) which represent one embodiment of the molecules and compositions of the invention that specifically recognize TDP-43.

The terms "antibody" and "immunoglobulin" are used interchangeably herein. An antibody or immunoglobulin is an TDP-43-binding molecule which comprises at least the variable domain of a heavy chain, and normally comprises at least the variable domains of a heavy chain and a light chain. Basic immunoglobulin structures in vertebrate systems are well understood; see, e.g., Harlow et al., Antibodies: A Laboratory Manual, (Cold Spring Harbor Laboratory Press, 2nd ed. 1988). As will be discussed in more detail below, the term "immunoglobulin" comprises various broad classes of polypeptides that can be distinguished biochemically. As generally understood in the art, heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgG, or IgE, respectively. The immunoglobulin subclasses (isotypes) e.g., IgG1, IgG2, IgG3, IgG4, IgA1, etc. are well characterized and are known to confer functional specialization that can be incorporated or modified in the antibodies of the invention to modify functional or other properties of these antibodies. Modified versions of antibody classes and isotypes of the invention are readily discernible to person of ordinary skill in the art in view of the disclosure and are within the scope of the invention. Additionally while all immunoglobulin classes are encompassed by the scope of the invention, for brevity and exemplary purposes, the following discussion is generally directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000 Daltons. The four chains are typically joined by disulfide bonds in a "Y" configuration wherein the light chains bracket the heavy chains starting at the mouth of the "Y" and continuing through the variable region.

Light chain polypeptides are classified as either kappa or lambda (κ, λ). Each heavy chain polypeptide class can be bound with either a kappa or lambda light chain. In general, the light and heavy chain polypeptides are covalently bonded to each other, and the "tail" portions of the two heavy chain polypeptides are bonded to each other by covalent disulfide linkages or non-covalent linkages when the immunoglobulins are generated either by hybridomas, B cells or genetically engineered host cells. In the heavy chain polypeptide, the amino acid sequences run from the N-terminus at the forked ends of the Y configuration to the C-terminus at the bottom of each heavy chain polypeptide.

Both the light and heavy chain polypeptides contain regions of structural and functional homology. The terms "constant" and "variable" are used functionally. In this regard, it will be appreciated that the variable domains of both the light ($V_L$) and heavy ($V_H$) chain regions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or aminoterminus of the antibody. The N-terminal portion of the heavy and light chain polypeptides is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y structure of the antibody. The antigen-binding site of a complete antibody is defined by three CDRs on each of the $V_H$ and $V_L$ chains, Any antibody (including antibody fragments, derivatives, and variants) which contains sufficient immunoglobulin related structure so as to allow it to specifically bind to TDP-43 is referred to herein interchangeably as a "binding fragment" or "immunospecific fragment," and can generally be referred to as antibody that specifically recognizes TDP-43.

In naturally occurring antibodies, an antibody comprises six hyper-variable regions that are often referred to as "complementarity determining regions" or "CDRs" present in each antigen-binding domain. CDRs are short, non-contiguous sequences of amino acids that form the antigen-binding domain as the antibody assumes its three dimensional configuration in an aqueous environment. The "CDRs" are flanked by four relatively conserved "framework" regions or "FRs" which show less inter-molecular sequence variability than the CDRs. The framework regions largely adopt a β-sheet conformation and the CDRs form loops which connect, and in some cases form part of the β-sheet structure. Thus, the framework regions act to form a scaffold that provides for positioning the CDRs in correct orientation by inter-chain, non-covalent interactions. The antigen-binding domain formed by the collectively positioned heavy and light chain CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified and defined for any given heavy or light chain variable region using methods known in the art; see, "Sequences of Proteins of Immunological Interest," Kabat, E., et al., U.S. Department of Health and Human Services, (1983); and Chothia and Lesk, J. Mol. Biol., 196 (1987), 901-917, which are herein incorporated by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are herein incorporated by reference in their entireties, where the definitions include overlapping or subsets of amino acid residues when compared against each other. Nevertheless, application of either definition to refer to a CDR of an antibody or variants thereof is intended to be within the scope of the term CDR as used herein. The appropriate amino acid residues which encompass the CDRs as defined in each of the above cited references are set forth in FIG. 1. The exact residue numbers which encompass a particular CDR will vary depending on the sequence and size of the CDR. A person of ordinary skill in the art provided with the variable region sequence of an antibody can routinely determine which residues comprise a particular hypervariable region or CDR of a human IgG antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 2 is according to the numbering conventions set forth by Kabat et al., (see below).

Kabat et al., also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human. Services, "Sequence of Proteins of Immunological Interest" (1983). Unless otherwise specified, references to the numbering of specific amino acid residue positions in an antibody or antigen-binding fragment, variant, or derivative thereof of the invention are according to the Kabat numbering system, which, however, is theoretical and may not equally apply to every antibody of the invention. For example, depending on the position of the first CDR (i.e., CDR1), the following CDRs might be shifted in either direction.

In some embodiments, an antibody of the invention is a monoclonal antibody. In additional embodiments, an antibody of the invention is not a polyclonal antibody. According to some embodiments, an antibody of the invention is a bivalent, or multispecific antibody. In other embodiments, an antibody of the invention is a polyclonal antibody. In further embodiments, the compositions of the invention contain monoclonal antibodies. In additional embodiments, the compositions of the invention do not contain a polyclonal antibody.

In additional embodiments, the antibody is human (e.g., a fully human and/or completely human antibody), humanized, primatized, murinized or a chimeric antibody. In further embodiments, an antibody of the invention is a single chain antibody, epitope binding fragment, e.g., Fab, Fab' and F(ab')$_2$, Fd, Fv single-chain Fv (scFv), single-chain antibody, disulfide-linked Fv (sdFv), a fragment comprising either a $V_L$ or $V_H$ domain, a fragment produced by a Fab expression library, or an anti-idiotypic (anti-Id) antibodies (including, e.g., anti-Id antibodies to antibodies containing a variable domain sequence provided in FIG. 1, and other antibodies disclosed herein). ScFv molecules are known in the art and are described, e.g., in U.S. Pat. No. 5,892,019. Antibodies of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In some embodiments, antibodies of the invention are IgG1. In other embodiments, antibodies of the invention are IgG3. In a further embodiment, the antibody of the invention is not IgM or a derivative thereof that contains a pentavalent structure. More particularly, in certain applications of the invention, especially those relating to therapeutic use, IgMs are less desirable than IgG and other bivalent antibodies or corresponding binding molecules since IgMs often show unspecific cross-reactivities and very low affinity as a consequence of their pentavalent structure and lack of affinity maturation.

In a particular embodiment, the antibody of the invention is not a polyclonal antibody, i.e., it substantially consists of one particular antibody species rather than being a mixture obtained from a plasma immunoglobulin sample.

According to one embodiment, an antibody of the invention is a "completely" human" monoclonal antibody that specifically recognizes human TDP-43 and that is isolated from a human. Compared to other human monoclonal antibodies, such as those derived from single chain antibody fragments (scFvs) identified using a phage display library or xenogeneic mice, completely human monoclonal antibodies of the invention are characterized by (i) being obtained using the human immune response rather than from animal surrogates, i.e. the antibody has been generated in response to native endogenous TDP-43 in its relevant conformation in the human body, (ii) having protected the individual or is at least significant for the presence of TDP-43 and (iii) having a reduced risks of self-reactivity against self-antigens due to the fact that the antibody is of human origin.

Thus, while the terms "completely human antibody," or "human monoclonal autoantibody" encompasses the terms "human antibody," "human monoclonal antibody," and the like, these terms are used herein to denote a TDP-43 binding molecule which is of human origin, i.e. which has been derived from a human antibody producing cell such as a B cell or hybridoma thereof or a cell containing nucleic acids such as cDNA that is the cDNA of which has been directly cloned from or derived from a human antibody producing cell such as, a human memory B cell. An antibody is considered "completely human" for the purposes of this disclosure when the antibody contains one or more amino acid substitutions or other alterations of a completely human antibody, e.g., to improve binding characteristics. Optionally, the framework regions of the completely human antibody or other antibodies of the invention are or have been modified to conform with a human germ line variable region sequence or to conform with a portion of a human germ line variable region sequence, such as a sequence obtained from a publically available data base such as, for example, in Vbase hosted by the MRC Centre for Protein Engineering (Cambridge, UK). Such modifications can be useful, inter alia, to reduce or eliminate germ line sequence deviations resulting from cloning artifacts, such as those that may result from PCR primers.

Antibodies derived from human immunoglobulin libraries or from animals transgenic for one or more human are generally referred to herein as human antibodies, or "human-like antibodies." Such immunoglobulins do not correspond to endogenous human immunoglobulins, as described infra. See, e.g., U.S. Pat. No. 5,939,598). For example, the pairing of heavy and light chains of human-like antibodies such as synthetic and semi-synthetic antibodies typically isolated from phage display do not necessarily reflect the original pairing as it occurred in the original human B cell. Accordingly, Fab and scFv fragments obtained from recombinant expression libraries can be considered to be artificial and may display immunogenicity and stability effects as a result of their artificial composition. By contrast, completely human antibodies of the invention are isolated, affinity-matured antibodies from selected human subjects and the antibodies have been characterized by their tolerance in man.

As used herein, the term "murinized antibody" or "murinized immunoglobulin" refers to an antibody comprising one or more CDRs from a human antibody or other antibody of the invention; and for example a human framework region that contains amino acid substitutions and/or deletions and/or insertions that are based on a mouse antibody sequence. In this case, the human or other immunoglobulin providing the CDRs is called the "parent" or "acceptor" and the mouse antibody providing the framework changes is called the "donor." Constant regions need not be present, but if they are, they are usually substantially identical to mouse antibody constant regions, i.e. at least about 85-90%, or at least about 95%, about 97%, about 98%, or about 99% or more identical to corresponding sequence of the mouse constant region. Hence, in some embodiments, a complete murinized human heavy or light chain immunoglobulin contains a mouse constant region, one or more human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide of the invention can comprise a polypeptide containing a variable region(s) or portions of a variable region (e.g., one or more CDRs, such as the $V_H$ CDR3), alone or in combination with a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a variable region(s) or portions of a variable region (e.g., one or more CDRs, such as, $V_H$ CDR3) and a polypeptide chain comprising a CH3 domain. In a further embodiment, a polypeptide of the invention lacks at least a portion of a CH2 domain (e.g., all or part of a CH2 domain). As set forth herein, and as would be appreciated by one of ordinary skill in the art, the above heavy chain polypeptide domains (e.g., the heavy chain portions) can be modified such that they vary in amino acid sequence from the naturally occurring immunoglobulin molecule. Accordingly, the invention encompasses polypeptides comprising fragments, variants, and derivatives of the heavy chain portions of the invention.

According to some embodiments, the heavy chain portions of one polypeptide chain of an antibody (including antigen-binding fragments, variants, or derivatives thereof) are identical to those on a second polypeptide chain of the antibody. In alternative embodiments, the heavy chain portions of one polypeptide chain of an antibody (including antigen-binding fragments, variants, or derivatives thereof) are different from that on a second polypeptide chain of the antibody. Thus, each monomer component of an antibody of the invention can comprise a different target binding site, forming, for example, a bispecific antibody or diabody.

Antibody fragments of the invention, including single-chain antibodies, can comprise variable region(s) or portions of variable regions (e.g., one or more CDRs, such as, VH CDR3 or VL CDR3) alone or in combination with the entirety or a portion of the following: hinge region, CH1, CH2, and CH3 domains. Also encompassed by the invention are TDP-43-binding fragments that comprise any combination of variable region(s) with a hinge region, CH1, CH2, and CH3 domains. Antibodies (including immunospecific fragments thereof) of the invention can be derived from any animal origin including birds and mammals. In one embodiment, the antibodies are human, murine, donkey, rabbit, goat, guinea pig, camel, llama, horse, or chicken antibodies. In another embodiment, the variable region can be condricthoid in origin (e.g., from sharks).

In another embodiment, the antibodies disclosed herein are composed of a single polypeptide chain such as says and are to be expressed intracellularly (intrabodies) for potential in vivo therapeutic and diagnostic applications.

The heavy chain portions or light chain portions of a binding polypeptide for use in the diagnostic and treatment methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In one embodiment, the light chain portion comprises at least one $V_L$ or CL domain. As used herein, the term "light chain portion" includes amino acid sequences derived from an immunoglobulin light chain. A polypeptide comprising a light chain portion comprises at least a light chain variable region(s) or portions of a variable region (e.g., one or more CDRs, such as the $V_L$ CDR3). In some embodiments, the light chain portion includes a CH1 domain. In another embodiment, the light chain portion comprises at least one of a or CL domain. Polypeptides comprising fragments, variants, and derivatives of these light chain portions are also encompassed by the invention.

The minimum size of a peptide or polypeptide epitope for an antibody is thought to be about four to five amino acids. Peptide or polypeptide epitopes can contain at least seven, at least nine, or between at least about 15 to about 30 amino acids. Since a CDR can recognize an antigenic peptide or polypeptide in its tertiary form, the amino acids comprising an epitope need not be contiguous, and in some cases, may not even be on the same peptide chain. According to one embodiment, a peptide or polypeptide epitope recognized by an antibody of the invention contains a sequence of at least 4, at least 5, at least 6, at least 7, at least 8, at least 9, at least 10, at least 15, at least 20, at least 25 contiguous or non-contiguous amino acids of TDP-43. In an additional embodiment, a peptide or polypeptide epitope recognized by an antibody of the invention contains between about 5 to about 30, about 10 to about 30, or 15 to about 30 contiguous or non-contiguous amino acids of TDP-43.

The terms "specifically binding" and "specifically recognizing" are used interchangeably herein and generally refer to a binding molecule (e.g., a polypeptide such as an antibody) that binds to an epitope or antigen more readily than it would bind to a random, unrelated epitope or antigen. As understood in the art, an antibody can specifically bind to or specifically recognize an isolated polypeptide comprising, or consisting of, amino acid residues corresponding to a linear portion of a non-contiguous epitope. The term "specificity" is used herein to qualify the relative affinity by which a certain antibody binds to a certain epitope or antigen. For example, antibody "A" can be deemed to have a higher specificity for a given epitope than antibody "B," or antibody "A" can be said to bind to epitope "C" with a higher specificity than it has for related epitope "D". For example, antibody "A" can be deemed to have a higher specificity for a given epitope than antibody "B," or antibody "A" can be said to bind to epitope "C" with a higher specificity than it has for related epitope "D." Likewise, an antibody "A" can be deemed to have a higher specificity for a given antigen than antibody "B," or antibody "A" can be said to bind to antigen "C" with a higher specificity than it has for related antigen "D."

Where present, the term "immunological binding characteristics," or other binding characteristics of an antibody with an antigen, in all of its grammatical forms, refers to the specificity, affinity, cross-reactivity, or other binding characteristics of an antibody.

By "preferentially binding", it is meant that the binding molecule, e.g., antibody specifically binds to an epitope or antigen more readily than it would bind to a related, similar, homologous, or analogous epitope or antigen. Thus, an antibody which "preferentially binds" to a given epitope or antigen would more likely bind to that epitope or antigen than to a related epitope or antigen, even though such an antibody can cross-react with the related epitope or antigen.

By way of a non-limiting example, a binding molecule, e.g., an antibody can be considered to bind a first epitope or antigen preferentially if it binds said first epitope or antigen with a dissociation constant ($K_D$) that is less than the antibody's $K_D$ for the second epitope or antigen. In another non-limiting example, an antibody can be considered to bind a first antigen preferentially if it binds the first epitope or antigen with an affinity that is at least one order of magnitude less than the antibody's $K_D$ for the second epitope or antigen. In another non-limiting example, an antibody can be considered to bind a first epitope or antigen preferentially if it binds the first epitope or antigen with an affinity that is at least two orders of magnitude less than the antibody's $K_D$ for the second epitope or antigen.

In another non-limiting example; a binding molecule, e.g., an antibody can be considered to bind a first epitope or antigen preferentially if it binds the first epitope or antigen with an off rate (k(off)) that is less than the antibody's k(off) for the second epitope or antigen. In another non-limiting example, an antibody can be considered to bind a first epitope or antigen preferentially if it binds the first epitope with an affinity that is at least one order of magnitude less than the antibody's k(off) for the second epitope or antigen. In another non-limiting example, an antibody can be considered to bind a first epitope or antigen preferentially if it binds the first epitope or antigen with an affinity that is at least two orders of magnitude less than the antibody's k(off) for the second epitope or antigen.

According to one embodiment, a TDP-43 binding molecule (e.g., an antibody, including an antigen-binding fragment or variant of an antibody or derivative thereof) binds TDP-43 or a fragment or variant thereof, with an off rate (k(off)) of less than or equal to $5 \times 10^{-2}$ $sec^{-1}$, $10^{-2}$ $sec^{-1}$, $5 \times 10^{-3}$ $sec^{-1}$ or $10^{-3}$ $sec^{-1}$. In another embodiment, a TDP-43 binding molecule binds TDP-43 or a fragment or variant thereof, with an off rate (k(off)) less than or equal to $5 \times 10^{-4}$ $sec^{-1}$, $10$ $sec^{-1}$, $5 \times 10^{-5}$ $sec^{-1}$, or $10^{-5}$ $sec^{-1}$ $5 \times 10^{-6}$ $sec^{-1}$, $10^{-6}$ $sec^{-1}$, $5 \times 10^{-7}$ $sec^{-1}$ or $10^{-7}$ $sec^{-1}$.

According to another embodiment, a TDP-43 binding molecule an antibody, including an antigen-binding fragment or variant of an antibody or derivative thereof) binds TDP-43 or a fragment or variant thereof, with an on rate (k(on)) of greater than or equal to $10^3$ $M^{-1}$ $sec^{-1}$, $5 \times 10^3$ $M^{-1}$ $sec^{-1}$, $10^4$ $M^4$ $sec^{-1}$ or $5 \times 10^4$ $M^{-1}$ $sec^{-1}$. In an additional embodiment, a TDP-43 binding molecule of the invention binds TDP-43 or a fragment or variant thereof with an on rate (k(on)) greater than or equal to $10^5$ $M^{-1}$ $sec^{-1}$, $5 \times 10^5$ $M^{-1}$ $sec^{-1}$, $10^6$ $M^{-1}$ $sec^{-1}$, or $5 \times 10^6$ $M^{-1}$ $sec^{-1}$ or $10^7$ $M^{-1}$ $sec^{-1}$.

The invention also encompasses a TDP-43 binding molecule that competes with one or more of the TDP-43 binding molecules of the invention for binding with TDP-43. For the purposes of this invention, a TDP-43 binding molecule (e.g., an antibody) is said to competitively inhibit binding of a reference TDP-43 binding molecule (e.g., antibody) to a given epitope or antigen if it preferentially binds to that epitope or antigen to the extent that it blocks, to some degree, binding of the reference anti hod to the epitope or antigen. Competitive inhibition, can be determined by any method known in the art, for example, competition ELISA assays. According to one embodiment, an a TDP-43 binding molecule (e.g., an antibody) competitively inhibits binding of a reference TDP-43 binding molecule (e.g., an antibody) to a given epitope or antigen by at least 90%, at least 80%, at least 70%, at least 60%, or at least 50%.

As used herein, the term "affinity" refers to a measure of the strength of the binding of an individual epitope or antigen with a TDP-43 binding molecule (e.g., an antibody, including fragments, variants, and derivatives thereof. See, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes or antigens, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen interactions" In *Fundamental Immunology*, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction, can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

TDP-43 binding molecules (e.g., antibodies including antigen-binding fragments of antibodies and variants or derivatives thereof) of the invention are also described or specified in terms of their cross-reactivity. As used herein, the term "cross-reactivity" refers to the ability of an TDP-43 binding molecule (e.g., an antibody) specific for one antigen, to react with a second distinct antigen; a measure often reflective of the degree of relatedness between two different antigenic substances.

For example, certain antibodies have some degree of cross-reactivity, in that they bind related, but non-identical epitopes or antigens, e.g., epitopes with at least 95%, at least 90%, at least 85%, at least 80%, at least 75%, at least 70%, at least 65%, at least 60%, at least 55%, and at least 50% identity (as calculated using methods described herein or otherwise known in the art) to a reference epitope or antigen. An antibody can be deemed "highly specific" for a certain epitope, if it does not bind any other analog, ortholog, or homolog of that epitope or antigen. According to one embodiment TDP-43 binding molecules (e.g., antibodies including antigen-binding fragments of antibodies, and variants or derivatives thereof) do not bind epitopes with less than 95%, less than 90%, less than 85%, less than 80%, less than 75%, less than 70%, less than 65%, less than 60%, less than 55%, and less than 50% identity (as calculated using methods described herein or otherwise known in the art) to a reference epitope or antigen under physiological conditions.

TDP-43 binding molecules such as antibodies (including antigen-binding fragments of an antibody and variants or derivatives thereof) of the invention can also be described in terms of their binding affinity to TDP-43. According to one embodiment TDP-43 binding molecules (e.g., antibodies including antigen-binding fragments, variants or derivatives thereof) binding affinities include those with a dissociation constant or Kd of less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E. A. et al., op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al. J. Immunol, 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original. ORFs (which segments are not normally so joined in nature). Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptides). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one embodiment, a sample comprises blood, cerebrospinal fluid ("CSF"), or urine. In another embodiment a sample comprises whole blood, plasma, B cells enriched from blood samples, or cultured cells (e.g., B cells from a subject). In another embodiment a sample of the invention contains a biopsy or tissue sample including neural tissue. In a further embodiment, a sample of the invention comprises whole cells or a lysate of the cells. Samples of the invention, including blood samples and CSF samples can be collected using by methods known in the art.

As used herein, the terms "treat" or "treatment" refer to therapeutic treatment and prophylactic or preventative measures, wherein the object is to prevent or slow down (lessen) an undesired physiological Change or disorder, such as the development of dementia. Beneficial or desired clinical results include, but are not limited to, alleviation of symptoms, diminishment of extent of disease, stabilized not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Antibodies

Antibodies that selectively bind TDP-43 are encompassed by the invention. As used herein, the term antibody or antibodies encompasses complete antibodies, as well as TDP-43-binding antibody fragments and variants and derivatives of these complete antibodies or antibody fragments that bind TDP-43. In one embodiment, an antibody of the invention demonstrates at least one, two, three, four, five or more of the structural characteristics (e.g., sequence), immunological binding characteristics (e.g., $IC_{50}$, or epitope binding), and/or biological properties of the antibodies disclosed in the Examples and elsewhere in the specification.

According to some embodiments, the antibody of the invention is a completely human antibody. The invention also encompasses fragments, variants and derivatives of a completely human antibody. As disclosed in the Examples, the completely human antibodies disclosed herein were derived from a pool of samples from healthy subjects. Antibodies of potential interest were analyzed for class and light chain subclass determination, message from selected memory B cell cultures were transcribed by RT PCR, cloned and combined into expression vectors for recombinant production; see the appended Examples. The completely human antibodies were then recombinantly expressed in HEK293 cells and subsequently characterized based on their binding specificities towards full-length TDP-43, truncated TDP-43 and a modified form of TDP-43 (FIGS. 2, 4-7, 10, and 11). This characterization confirmed that for the first time, human antibodies have been cloned that are highly specific for TDP-43 and recognize different epitopes within the TDP-43 protein.

Thus, according to one embodiment, the invention generally relates to an antibody that specifically recognizes TDP-43. In a further embodiment, the invention is directed to a human antibody that specifically recognizes TDP-43. In yet a further embodiment, the invention is directed to a total human antibody that specifically recognizes TDP-43. In additional embodiments, the invention encompasses a TDP-43 binding fragment, variant or derivative of a TDP-43 binding intact human (including completely human) antibody of the invention. In another embodiment, the antibodies of the invention specifically recognize full length, truncated, or pathologic human TDP-43 in a Western Blot. In a further embodiment, the antibodies of the invention selectively bind full length or pathologic TDP-43 in a Western Blot, in another embodiment, the antibodies of the invention specifically recognize full length, truncated, or pathologic human TDP-43 in an ELISA. In a further embodiment, the antibodies of the invention selectively bind full length or pathologic TDP-43 in an ELISA. In another embodiment, the antibodies of the invention specifically recognize any combination of full length, truncated, or pathologic human TDP-43 in an immunohistochemistry. In a further embodiment, the antibodies of the invention selectively bind full length or pathologic TDP-43 in an immunohistochemistry. In another embodiment, the antibodies of the invention specifically recognize any combination of full length, truncated, or pathologic human TDP-43 in an immunohistochemistry of the hippocampus. In a further embodiment, the antibodies of the invention selectively bind full length or pathologic TDP-43 in an immunohistochemistry of the hippocampus. In a further embodiment, the antibodies of the invention selectively bind to one or more of nuclear TDP-43, cytoplasmic TDP-43, axonal TDP-43, or neuritic TDP-43 in an immunohistochemistry of human FTLD-U hippocampus. In another embodiment, the antibodies of the invention selectively bind to one or more of cytoplasmic TDP-43 and neuritic TDP-43 in hippocampal granule cells in an immunohistochemistry of human FTLD-U hippocampus. According to one embodiment, the antibodies of the invention specifically recognize pathologic human-TDP-43.

In another embodiment, the invention encompasses an antibody (including an antigen-binding fragment, variant or derivatives thereof), that specifically binds to the same epitope of TDP-43 as a reference antibody having the heavy and light chain variable domain of an antibody selected from the group consisting of: NI-205.3F10, NI-205.51C1, NI-205.21G2, NI-205.8A2, NI-205.15F12, NI-205.113C4, NI-205.25E3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5. In a further embodiment, the antibody (including an antigen-binding fragment, variant or derivatives thereof), specifically binds to the same epitope of TDP-43 as a reference antibody selected from the group consisting of: NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5.

In another embodiment, the invention encompasses an antibody (including an antigen-binding fragment, variant or derivatives thereof), that specifically binds to a TDP-43 polypeptide sequence selected from: QYGDVMDVFIP (SEQ ID NO: 123); AAIGWGSASNA (SEQ ID NO: 124); DMTEDELREFF (SEQ ID NO: 125), EDENDEP (SEQ ID NO: 126), VQVKKDL (SEQ ID NO: 127), KEYFSTF (SEQ ID NO: 128), IIKGISV (SEQ ID NO:315), NQSGPSG (SEQ ID NO:316), FNGGFGS (SEQ ID NO:317), FGNSRGGGAGL (SEQ ID NO:31.8), SNAGSGSGFNG (SEQ ID NO:319), QLERSGRFGGN (SEQ ID NO:320), EIPSEDD (SEQ ID NO:321), FNGGFGSSMDS (SEQ ID NO:322) and SINPAMMAAAQAALQSSWGMMGMLASQ (SEQ ID NO:323). In another embodiment, the invention encompasses an antibody (including an antigen-binding fragment, variant or derivatives thereof), that specifically binds to TDP-43 polypeptides FGNSRGGGAGL (SEQ ID NO:318) and SNAGSGSGFNG (SEQ ID NO:319). In another embodiment, the invention encompasses an antibody (including an antigen, binding fragment, variant or derivatives thereof), that specifically binds to TDP-43 polypeptide SINPAMMAAAQAALQSSWGMMGMLASQ (SEQ ID NO:323), but does not specifically bind to SINPGGGAAAQAALQSSWGMMGMLASQ (SEQ ID NO:314).

In a further embodiment, the invention encompasses an antibody (including an antigen-binding fragment, variant or derivatives thereof), that competitively inhibits the binding to TDP-43 by a reference antibody having the heavy and light chain variable domain of an antibody selected from the group consisting of: NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H15, NI205.31D2, NI205.8F8, NI205.31C11, NI205.8C10, NI205.10H7, NI205.1A9, NI205.14W3, and NI205.19G5.

In a further embodiment, the antibody (including an antigen-binding fragment, variant or derivatives thereof), competitively inhibits the binding to TDP-43 by a reference antibody selected from the group consisting of: NI-205.31'10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5.

As illustrated in the Examples, the invention encompasses antibodies that bind to different portions and epitopes of TDP-43. According to some embodiments, an antibody of the invention binds a linear epitope of TDP-43. According to other embodiments, an antibody of the invention binds to a conformational epitope of TDP-43. In an additional embodiment an antibody of the invention selectively binds a TDP-43 domain selected from the group consisting of TDP-43 domain I (amino acid residues 2-106 of SEQ ID NO:94), TDP-43 domain II (amino acid residues 99-204 of SEQ ID NO:94), TDP-43 domain III (amino acid residues 183-273 of SEQ ID NO:94), and TDP-43 domain IV (amino acid residues 258-414 of SEQ ID NO:94). In another embodiment, the anti-TDP-43 antibody does not recognize a truncated form of TDP-43. In an additional embodiment, the invention provides an anti-TDP-43 antibody which recognizes an N-terminal$_{1-259}$ fragment of TDP-43. In a further embodiment, the anti-TDP-43 antibody selectively binds pathologic TDP-43. In a further embodiment, an anti-TDP-43 antibody specifically binds TDP-43 domain IV (amino acid residues 258-414 of SEQ ID NO:94), but does not specifically binds TDP-43 domain IV comprising the A321G, M322G, and M323G substitutions.

The invention encompasses human anti-TDP-43 antibodies having different TDP-43 specificities, which are thus particularly useful for diagnostic and therapeutic purposes. The invention is also drawn to an antibody comprising an antigen-binding domain having an amino acid sequence selected from that present in a reference antibody selected from the group consisting of: NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5.

The examples and Figures disclose TDP-43 binding molecules that are characterized by containing in their binding domain at least one complementarity determining region (CDR) of the $V_H$ and/or $V_L$ variable region comprising any one of the amino acid sequences depicted in FIGS. 1A-1K and 3A-3R and listed in Table 2. The corresponding nucleotide sequences encoding these variable regions are set forth in Table 3. An exemplary set of CDRs of the above amino acid sequences of the $V_H$ and/or $V_L$ region is depicted in FIGS. 1A-1K and 3A-3R. However, as would be understood by a person of ordinary skill in the art, additional or alternative CDRs can be used, which specifically bind. TDP-43, but which differ in their amino acid sequence from those set forth in FIGS. 1A-1K and 3A-3R by one, two, three or even more amino acids in case of CDR2 and CDR3.

TABLE 2

SEQ ID NOs of the V$_H$ region, V$_H$ CDR1, V$_H$ CDR2, V$_H$ CDR2, V$_L$ region, V$_L$ CDR2, V$_L$ CDR2, and V$_L$ CDR3 of TDP-43 specific antibodies.

| Antibody | V$_H$/V$_L$ | CDR1 | CDR2 | CDR3 |
|---|---|---|---|---|
| NI-205.3F10 | V$_H$ | SEQ ID NO: 1 | SEQ ID NO: 3 | SEQ ID NO: 4 | SEQ ID NO: 5 |
|  | V$_L$ | SEQ ID NO: 6 | SEQ ID NO: 7 | SEQ ID NO: 8 | SEQ ID NO: 9 |
| NI-205.51C1 | V$_H$ | SEQ ID NO: 10 | SEQ ID NO: 11 | SEQ ID NO: 12 | SEQ ID NO: 13 |
|  | V$_L$ | SEQ ID NO: 14 | SEQ ID NO: 15 | SEQ ID NO: 16 | SEQ ID NO: 17 |
| NI-205.21G2 | V$_H$ | SEQ ID NO: 18 | SEQ ID NO: 19 | SEQ ID NO: 20 | SEQ ID NO: 21 |
|  | V$_L$ | SEQ ID NO: 22 | SEQ ID NO: 23 | SEQ ID NO: 24 | SEQ ID NO: 25 |
| NI-205.8A2 | V$_H$ | SEQ ID NO: 26 | SEQ ID NO: 28 | SEQ ID NO: 29 | SEQ ID NO: 30 |
|  | V$_L$ | SEQ ID NO: 31 | SEQ ID NO: 32 | SEQ ID NO: 33 | SEQ ID NO: 34 |
| NI-205.15F12 | V$_H$ | SEQ ID NO: 35 | SEQ ID NO: 37 | SEQ ID NO: 38 | SEQ ID NO: 39 |
|  | V$_L$ | SEQ ID NO: 40 | SEQ ID NO: 42 | SEQ ID NO: 43 | SEQ ID NO: 44 |
| NI-205.113C4 | V$_H$ | SEQ ID NO: 45 | SEQ ID NO: 46 | SEQ ID NO: 47 | SEQ ID NO: 48 |
|  | V$_L$ | SEQ ID NO: 49 | SEQ ID NO: 50 | SEQ ID NO: 51 | SEQ ID NO: 52 |
| NI-205.25F3 | V$_H$ | SEQ ID NO: 53 | SEQ ID NO: 54 | SEQ ID NO: 55 | SEQ ID NO: 56 |
|  | V$_L$ | SEQ ID NO: 57 | SEQ ID NO: 58 | SEQ ID NO: 59 | SEQ ID NO: 60 |
| NI-205.87E7 | V$_H$ | SEQ ID NO: 61 | SEQ ID NO: 62 | SEQ ID NO: 63 | SEQ ID NO: 64 |
|  | V$_L$ | SEQ ID NO: 65 | SEQ ID NO: 66 | SEQ ID NO: 67 | SEQ ID NO: 68 |
| NI-205.21G1 | V$_H$ | SEQ ID NO: 69 | SEQ ID NO: 70 | SEQ ID NO: 71 | SEQ ID NO: 72 |
|  | V$_L$ | SEQ ID NO: 73 | SEQ ID NO: 74 | SEQ ID NO: 75 | SEQ ID NO: 76 |
| NI-205.68G5 | V$_H$ | SEQ ID NO: 77 | SEQ ID NO: 79 | SEQ ID NO: 80 | SEQ ID NO: 81 |
|  | V$_L$ | SEQ ID NO: 82 | SEQ ID NO: 84 | SEQ ID NO: 85 | SEQ ID NO: 86 |
| NI-205.20A1 | V$_H$ | SEQ ID NO: 87 | SEQ ID NO: 88 | SEQ ID NO: 89 | SEQ ID NO: 90 |
|  | V$_L$ | SEQ ID NO: 122 | SEQ ID NO: 91 | SEQ ID NO: 92 | SEQ ID NO: 93 |
| NI205.41D1 | V$_H$ | SEQ ID NO: 130 | SEQ ID NO: 131 | SEQ ID NO: 132 | SEQ ID NO: 133 |
|  | V$_L$ | SEQ ID NO: 134 | SEQ ID NO: 135 | SEQ ID NO: 136 | SEQ ID NO: 137 |
| NI205.29E11 | V$_H$ | SEQ ID NO: 138 | SEQ ID NO: 139 | SEQ ID NO: 140 | SEQ ID NO: 141 |
|  | V$_L$ | SEQ ID NO: 142 | SEQ ID NO: 143 | SEQ ID NO: 144 | SEQ ID NO: 145 |
| NI205.9E12 | V$_H$ | SEQ ID NO: 146 | SEQ ID NO: 147 | SEQ ID NO: 148 | SEQ ID NO: 149 |
|  | V$_L$ | SEQ ID NO: 150 | SEQ ID NO: 326 | SEQ ID NO: 327 | SEQ ID NO: 328 |
|  | V$_L$ | SEQ ID NO: 151 | SEQ ID NO: 152 | SEQ ID NO: 153 | SEQ ID NO: 154 |
| NI205.98H6 | V$_H$ | SEQ ID NO: 155 | SEQ ID NO: 156 | SEQ ID NO: 157 | SEQ ID NO: 158 |
|  | V$_L$ | SEQ ID NO: 159 | SEQ ID NO: 160 | SEQ ID NO: 161 | SEQ ID NO: 162 |
| NI205.10D3 | V$_H$ | SEQ ID NO: 163 | SEQ ID NO: 164 | SEQ ID NO: 165 | SEQ ID NO: 166 |
|  | V$_L$ | SEQ ID NO: 167 | SEQ ID NO: 168 | SEQ ID NO: 169 | SEQ ID NO: 170 |
| NI205.44B22 | V$_H$ | SEQ ID NO: 171 | SEQ ID NO: 172 | SEQ ID NO: 173 | SEQ ID NO: 174 |
|  | V$_L$ | SEQ ID NO: 175 | SEQ ID NO: 176 | SEQ ID NO: 177 | SEQ ID NO: 178 |
| NI205.38H2 | V$_H$ | SEQ ID NO: 179 | SEQ ID NO: 180 | SEQ ID NO: 181 | SEQ ID NO: 182 |
|  | V$_L$ | SEQ ID NO: 183 | SEQ ID NO: 184 | SEQ ID NO: 185 | SEQ ID NO: 186 |
| NI205.36D5 | V$_H$ | SEQ ID NO: 187 | SEQ ID NO: 188 | SEQ ID NO: 189 | SEQ ID NO: 190 |
|  | V$_L$ | SEQ ID NO: 191 | SEQ ID NO: 192 | SEQ ID NO: 193 | SEQ ID NO: 194 |
| NI205.58E11 | V$_H$ | SEQ ID NO: 195 | SEQ ID NO: 196 | SEQ ID NO: 197 | SEQ ID NO: 198 |
|  | V$_L$ | SEQ ID NO: 199 | SEQ ID NO: 200 | SEQ ID NO: 201 | SEQ ID NO: 202 |
| NI205.14H5 | V$_H$ | SEQ ID NO: 203 | SEQ ID NO: 204 | SEQ ID NO: 205 | SEQ ID NO: 206 |
|  | V$_L$ | SEQ ID NO: 207 | SEQ ID NO: 208 | SEQ ID NO: 209 | SEQ ID NO: 210 |
| NI205.31D2 | V$_H$ | SEQ ID NO: 211 | SEQ ID NO: 212 | SEQ ID NO: 213 | SEQ ID NO: 214 |
|  | V$_L$ | SEQ ID NO: 215 | SEQ ID NO: 216 | SEQ ID NO: 217 | SEQ ID NO: 218 |
| NI205.8F8 | V$_H$ | SEQ ID NO: 219 | SEQ ID NO: 220 | SEQ ID NO: 221 | SEQ ID NO: 222 |
|  | V$_L$ | SEQ ID NO: 223 | SEQ ID NO: 224 | SEQ ID NO: 225 | SEQ ID NO: 226 |
| NI205.31C11 | V$_H$ | SEQ ID NO: 227 | SEQ ID NO: 228 | SEQ ID NO: 229 | SEQ ID NO: 230 |
|  | V$_L$ | SEQ ID NO: 231 | SEQ ID NO: 232 | SEQ ID NO: 233 | SEQ ID NO: 234 |
| NI205.8C10 | V$_H$ | SEQ ID NO: 235 | SEQ ID NO: 236 | SEQ ID NO: 237 | SEQ ID NO: 238 |
|  | V$_L$ | SEQ ID NO: 239 | SEQ ID NO: 240 | SEQ ID NO: 241 | SEQ ID NO: 242 |
| NI205.10H7 | V$_H$ | SEQ ID NO: 243 | SEQ ID NO: 244 | SEQ ID NO: 245 | SEQ ID NO: 246 |
|  | V$_L$ | SEQ ID NO: 247 | SEQ ID NO: 248 | SEQ ID NO: 249 | SEQ ID NO: 250 |
| NI205.1A9 | V$_H$ | SEQ ID NO: 251 | SEQ ID NO: 252 | SEQ ID NO: 253 | SEQ ID NO: 254 |
|  | V$_L$ | SEQ ID NO: 255 | SEQ ID NO: 256 | SEQ ID NO: 257 | SEQ ID NO: 258 |
| NI205.14W3 | V$_H$ | SEQ ID NO: 259 | SEQ ID NO: 260 | SEQ ID NO: 261 | SEQ ID NO: 262 |
|  | V$_L$ | SEQ ID NO: 263 | SEQ ID NO: 264 | SEQ ID NO: 265 | SEQ ID NO: 266 |
| NI205.19G5 | V$_H$ | SEQ ID NO: 267 | SEQ ID NO: 268 | SEQ ID NO: 269 | SEQ ID NO: 270 |
|  | V$_L$ | SEQ ID NO: 271 | SEQ ID NO: 272 | SEQ ID NO: 273 | SEQ ID NO: 274 |

In one embodiment, an antibody of the invention comprises at least one CDR comprising, or consisting of an amino acid sequence selected from the group consisting of SEQ ID NO: 3-5, 7-9, 11-13, 15-17, 19-21, 23-25, 28-30, 32-34, 37-39, 42-44, 46-48, 50-52, 54-56, 58-60, 62-64, 66-68, 70-72, 74-76, 79-81, 84-86, 88-93, 131-133, 135-137, 139-141, 143-145, 147-149, 152-154, 156-158, 160-162, 164-166, 168-170, 172-174, 176-178, 180-182, 184-186, 188-190, 192-194, 196-198, 200-202, 204-206, 208-210, 212-214, 216-218, 220-222, 224-226, 228-230, 232-234, 236-238, 240-242, 244-246, 248-250, 252-254, 256-258, 260-262, 264-266, 268-270, 272-274 and 326-328.

In one embodiment, an antibody of the invention comprises one, two, three, four, five or six CDRs comprising, or consisting of an amino acid sequence selected from the group consisting of SEQ ID NO: 3-5, 7-9, 11-13, 15-1.7, 19-21, 23-25, 28-30, 32-34, 37-39, 42-44, 46-48, 50-52, 54-56, 58-60, 62-64, 66-68, 70-72, 74-76, 79-81, 84-86, 88-93, 131-133, 135-137, 139-141, 143-145, 147-149, 152-154, 156-158, 160-162, 164-166, 168-170, 172-174, 176-178, 180-182, 184-186, 188-190, 192-194, 196-198, 200-202, 204-206, 208-210, 212-214, 216-218, 220-222, 224-226, 228-230, 232-234, 236-238, 240-242, 244-246, 248-

250, 252-254, 256-25, 260-262, 264-266, 268-270, 272-274 and 326-328.

In one embodiment, an antibody of the invention comprises one, two, three, four, five or six CDRs comprising, or consisting of an amino acid sequence selected from the group consisting of SEQ ID NO: 3-5 and 7-9, 11-13 and 15-17, 19-21 and 23-25, 28-30 and 32-34, 37-39 and 42-44, 46-48 and 50-52, 54-56 and 58-60, 62-64 and 66-68, 70-72 and 74-76, 79-81 and 84-86, 88-93, 131-133 and 135-137, 139-141 and 143-145, 147-149 and 152-154, 156-158 and 160-162, 164-166 and 168-170, 172-174 and 176-178, 180-182 and 184-186, 188-190 and 192-194, 196-198 and 200-202, 204-206 and 208-210, 212-214 and 216-218, 220-222 and 224-226, 228-230 and 232-234, 236-238 and 240-242, 244-246 and 248-250, 252-254 and 256-258, 260-262 and 2.64-266, 268-270 and 272-274, and 147-149 and 326-328.

In one embodiment, an antibody of the invention comprises one, two, or three VH CDRs comprising, or consisting of an amino acid sequence selected from the group consisting of SEQ ID NO: 3-5, 11-13, 19-21, 28-30, 37-39, 46-48, 54-56, 62-64, 70-72, 79-81, 88-90, 131-133, 139-141, 147-149, 156-158, 164-166, 172-174, 18-182, 188-190, 196-198, 204-206, 212-214, 220-222, 228-230, 236-238, 244-246, 252-254, 260-262, and 268-270.

In one embodiment, an antibody of the invention comprises one, two, or three VL CDRs comprising, or consisting of an amino acid sequence selected from the group consisting of SEQ ID NO: 7-9, 15-17, 23-25, 32-34, 42-44, 50-52, 58-60, 66-68, 74-76, 84-86, 91-93, 135-137, 143-145, 152-154, 160-162, 168-170, 176-178, 184-186, 192-194, 200-202, 208-210, 216-218, 224-226, 232-234, 240-242, 248-250, 256-258, 264-266, 272-274 and 326-328.

According to one embodiment, an antibody of the invention comprises a heavy chain variable region comprising a VH CDR1 of SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; a NTH CDR2 of SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; or a VH CDR3 of SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270. According to another embodiment, an antibody comprises a light chain, variable region comprising a VL CDR1 of SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; a VL CDR2 of SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; or a VL CDR3 of SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328. In another embodiment, the antibody comprises a heavy Chain variable region comprising a VH CDR1 of SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; a VH CDR2 of SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; or a VH CDR3 of SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270, and further comprises a light chain variable region comprising a VL CDR1 of SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; a VL CDR2 of SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; a VL CDR3 of SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

According to one embodiment, an antibody of the invention comprises a heavy chain variable region comprising a VH CDR1 of SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; a VH CDR2 of SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and a VH CDR3 of SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270. According to another embodiment, an antibody comprises a light chain variable region comprising a VL CDR1 of SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; a VL CDR2 of SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and a VL CDR3 of SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328. In another embodiment, the antibody comprises a heavy chain variable region comprising a VH CDR1 of SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; a VH CDR2 of SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and a VH CDR3 of SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270, and further comprises a light chain variable region comprising a VL CDR1 of SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; a VL CDR2 of SEQ 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and a VL CDR3 of SW ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

In one embodiment, an antibody of the invention can comprise a heavy chain variable region comprising a VH CDR1 of SEQ ID NO: 3, a VH CDR2 of SEQ ID NO: 4, and VH CDR3 of SEQ ID NO: 5, and can further comprise a light chain variable region comprising a VL CDR1 of SEQ ID NO:7, a VL CDR2 of SEQ ID NO: 8, and a VL CDR3 of SEQ ID NO: 9.

In one embodiment, an antibody of the invention can comprise a heavy chain variable region comprising a VH CDR1 of SEQ ID NO: 11, a VH CDR2 of SEQ ID NO: 12, and VH CDR3 of SEQ ID NO: 13, and can further comprise a light chain variable region comprising a VL CDR1 of SEQ ID NO:15, a VL CDR2 of SEQ ID NO: 16, and a VL CDR3 of SEQ ID NO: 17.

In one embodiment, an antibody of the invention can comprise a heavy chain variable region comprising a VH CDR1 of SEQ ID NO: 19, a VH CDR2 of SEQ ID NO; 20, and VH CDR3 of SEQ ID NO: 21, and can further comprise a light chain variable region comprising a VL CDR1 of SEQ ID NO:23, a VL CDR2 of SEQ ID NO: 24, and a VL CDR3 of SEQ ID NO: 25.

In one embodiment, an antibody of the invention can comprise a heavy chain variable region comprising a VH CDR1 of SEQ ID NO: 28, a VH CDR2 of SEQ ID NO 29, and VH CDR3 of SEQ ID NO: 30, and can further comprise a light chain variable region comprising a VL CDR1 of SEQ ID NO:32, a VL CDR2 of SEQ ID NO: 33, and a VL CDR3 of SEQ ID NO: 34.

In one embodiment, an antibody of the invention can comprise a heavy chain variable region comprising a VH CDR1 of SEQ ID NO 37, a VH CDR2 of SEQ ID NO: 38, and VH CDR3 of SEQ ID NO: 39, and can further comprise a light chain variable region comprising a VL CDR1 of SEQ ID NO:42, a VL CDR2 of SEQ ID NO: 43, and a VL CDR3 of SEQ ID NO: 44.

In one embodiment, an antibody of the invention can comprise a heavy chain variable region comprising a VH CDR1 of SEQ ID NO: 46, a VH CDR2 of SEQ ID NO: 47, and VH CDR3 of SEQ ID NO: 48, and can further comprise a light chain variable region comprising a VL CDR1 of SEQ ID NO:50, a VL CDR2 of SEQ ID NO: 51, and a VL CDR3 of SEQ ID NO: 52.

In one embodiment, an antibody of the invention can comprise a heavy chain variable region comprising a VH CDR1 of SEQ ID NO: 54, a VH CDR2 of SEQ ID NO: 55, and VH CDR3 of SEQ ID NO: 56, and can further comprise a light chain variable region comprising a VL CDR1 of SEQ. ID NO: 58, a VL CDR2 of SEQ ID NO: 59, and a VL CDR3 of SEQ ID NO: 60.

In one embodiment, an antibody of the invention can comprise a heavy chain variable region comprising a VH CDR1 of SEQ ID NO: 62, a VH CDR2 of SEQ NO: 63, and VH CDR3 of SEQ ID NO: 64, and can further comprise a light chain variable region comprising a VL CDR1 of SEQ ID NO:66, a VL CDR2 of SEQ ID NO: 67, and a VL CDR3 of SEQ ID NO: 68.

In one embodiment, an antibody of the invention can comprise a heavy chain variable region comprising a VH CDR1 of SEQ ID NO: 70, a VH CDR2 of SEQ NO: 71, and VH CDR3 of SEQ ID NO: 72, and can further comprise a light chain variable region comprising a VL CDR1 of SEQ ID NO:74, a VL CDR2 of SEQ ID NO: 75, and a VL CDR3 of SEQ ID NO: 76.

In one embodiment, an antibody of the invention can comprise a heavy chain variable region comprising a VH CDR1 of SEQ ID NO: 79, a VH CDR2 of SEQ ID NO: 80, and VH CDR3 of SEQ ID NO: 81, and can further comprise a light chain variable region comprising a VL CDR1 of SEQ ID NO:84, a VL CDR2 of SEQ ID NO: 85, and a VL CDR3 of SEQ ID NO: 86.

In one embodiment, an antibody of the invention can comprise a heavy chain variable region comprising a VH CDR1 of SEQ ID NO: 88, a VH CDR2 of SEQ ID NO: 89, and VH CDR3 of SEQ ID NO: 90, and can further comprise a light chain variable region comprising a VL CDR1 of SEQ ID NO:91, a VL CDR2 of SEQ. ID NO: 92, and a VL CDR3 of SEQ ID NO: 93.

In one embodiment, an antibody of the invention can comprise a heavy chain variable region comprising a VH CDR1 of SEQ ID NO: 131, a VH CDR2 of SEQ ID NO: 132, and VH CDR3 of SEQ ID NO: 133, and can further comprise a light chain variable region comprising a VL CDR1 of SEQ ID NO:135, a VL CDR2 of SEQ ID NO: 136, and a VL CDR3 of SEQ ID NO: 137.

In one embodiment, an antibody of the invention can comprise a heavy chain variable region comprising a VH CDR1 of SEQ ID NO: 147, a VH CDR2 of SEQ ID NO: 148, and VH CDR3 of SEQ ID NO: 149, and can further comprise a light chain variable region comprising a VL CDR1 of SEQ ID NO:152, a VL CDR2 of SEQ ID NO: 153, and a NT CDR3 of SEQ ID NO: 154.

In one embodiment, an antibody of the invention can comprise a heavy chain variable region comprising a VH CDR1 of SEQ ID NO: 147, a VH CDR2 of SEQ ID NO: 148, and VH CDR3 of SEQ ID NO: 149, and can further comprise a light chain variable region comprising a VL CDR1 of SEQ ID NO:326, a VL CDR2 of SEQ ID NO: 327, and a VL CDR3 of SEQ ID NO: 328.

In one embodiment, an antibody of the invention can comprise a heavy chain variable region comprising a VH CDR1 of SEQ ID NO: 156, a VH CDR2 of SEQ NO: 157, and VH CDR3 of SEQ ID NO: 158, and can further comprise a light chain variable region comprising a VH CDR1 of SEQ ID NO:160, a VL CDR2 of SEQ ID NO: 161, and a VL CDR3 of SEQ ID NO: 162.

In one embodiment, an antibody of the invention can comprise a heavy chain variable region comprising a VH CDR1 of SEQ ID NO: 164, a VH CDR2 of SEQ ID NO: 165, and VH CDR3 of SEQ ID NO: 166, and can further comprise a light chain variable region comprising a VL CDR1 of SEQ ID NO:168, a VL CDR2 of SEQ ID NO: 169, and a VL CDR3 of SEQ ID NO: 170.

In one embodiment, an antibody of the invention can comprise a heavy chain variable region comprising a VH CDR1 of SEQ ID NO: 172, a VH CDR2 of SEQ NO: 173, and VH CDR3 of SEQ ID NO: 174, and can further comprise a light chain variable region comprising a VL CDR1 of SEQ ID NO:176, a VL CDR2 of SEQ ID NO: 177, and a VL CDR3 of SEQ ID NO: 178.

In one embodiment, an antibody of the invention can comprise a heavy chain variable region comprising a VH CDR1 of SEQ ID NO: 180, a VH CDR2 of SEQ ID NO: 181, and VH CDR3 of SEQ ID NO: 182, and can further comprise a light chain variable region comprising a VL CDR1 of SEQ ID NO:184, a VL CDR2 of SEQ NO: 185, and a VL CDR3 of SEQ ID NO: 186.

In one embodiment, an antibody of the invention can comprise a heavy chain variable region comprising a VH CDR1 of SEQ ID NO: 188, a VH CDR2 of SEQ. ID NO: 189, and VH CDR3 of SEQ ID NO: 190, and can further comprise a light chain variable region comprising a VL CDR1 of SEQ ID NO:192, a VL CDR2 of SEQ NO: 193, and a VL CDR3 of SEQ ID NO: 194.

In one embodiment, an antibody of the invention can comprise a heavy chain variable region comprising a VH CDR1 of SEQ ID NO: 196, a VH CDR2 of SEQ ID NO: 197, and VH CDR3 of SEQ ID NO: 198, and can further comprise a light chain variable region comprising a VL CDR1 of SEQ ID NO:200, a VL CDR2 of SEQ ID NO: 201, and a VL CDR3 of SEQ ID NO: 202.

In one embodiment, an antibody of the invention can comprise a heavy chain variable region comprising a VH CDR1 of SEQ ID NO: 204, a VH CDR2 of SEQ NO: 205, and VH CDR3 of SEQ ID NO: 206, and can further comprise a light chain variable region comprising a VL CDR1 of SEQ ID NO:208, a VL CDR2 of SEQ ID NO: 209, and a VL CDR3 of SEQ ID NO: 210.

In one embodiment, an antibody of the invention can comprise a heavy chain variable region comprising a VH CDR1 of SEQ ID NO: 212, a VH CDR2 of SEQ ID NO: 213, and VH CDR3 of SEQ ID NO: 214, and can further comprise a light chain variable region comprising a VL CDR1 of SEQ ID NO:216, a VL CDR2 of SEQ ID NO: 217, and a VL CDR3 of SEQ ID NO: 218.

In one embodiment, an antibody of the invention can comprise a heavy chain variable region comprising a VH CDR1 of SEQ ID NO: 220, a VH CDR2 of SEQ ID NO: 221, and VH CDR3 of SEQ ID NO: 222, and can further comprise a light chain variable region comprising a VL CDR1 of SEQ NO:224, a VL CDR2 of SEQ ID NO: 225, and a VL CDR3 of SEQ ID NO: 226.

In one embodiment, an antibody of the invention can comprise a heavy chain variable region comprising a VH CDR1 of SEQ ID NO: 228, a VH CDR2 of SEQ ID NO: 229, and VH CDR3 of SEQ ID NO: 230, and can further comprise a light chain variable region comprising a VL CDR1 of SEQ ID NO:232, a VL CDR2 of SEQ ID NO: 233, and a VL CDR3 of SEQ ID NO: 234.

In one embodiment, an antibody of the invention can comprise a heavy chain variable region comprising a VH CDR1 of SEQ ID NO: 236, a VH CDR2 of SEQ ID NO: 237, and VH CDR3 of SEQ ID NO: 238, and can further comprise a light chain variable region comprising a VL CDR1 of SEQ ID NO:240, a VL CDR2 of SEQ ID NO: 241, and a VL CDR3 of SEQ ID NO: 242.

In one embodiment, an antibody of the invention can comprise a heavy chain variable region comprising a VH CDR1 of SEQ ID NO: 244, a VH CDR2 of SEQ ID NO: 245, and VH CDR3 of SEQ ID NO: 246, and can further comprise a light chain variable region comprising a VL CDR1 of SEQ ID NO:248, a VL CDR2 of SEQ ID NO: 249, and a VL CDR3 of SEQ ID NO: 250.

In one embodiment, an antibody of the invention can comprise a heavy chain variable region comprising a VH CDR1 of SEQ ID NO: 252, a VH CDR2 of SEQ ID NO: 253, and VH CDR3 of SEQ ID NO: 254, and can further comprise a light chain variable region comprising a VL CDR1 of SEQ ID NO:256, a VL CDR2 of SEQ ID NO: 257, and a VL CDR3 of SEQ ID NO: 258.

In one embodiment, an antibody of the invention can comprise a heavy chain variable region comprising a VH CDR1 of SEQ ID NO: 260, a VH CDR2 of SEQ ID NO: 261, and VH CDR3 of SEQ ID NO: 262, and can further comprise a light chain variable region comprising a VL CDR1 of SEQ ID NO:264, a VL CDR2 of SEQ ID NO: 265, and a VL CDR3 of SEQ ID NO: 266.

In one embodiment, an antibody of the invention can comprise a heavy chain variable region comprising a VH CDR1 of SEQ ID NO: 268, a VH CDR2 of SEQ ID NO: 269, and VH CDR3 of SEQ ID NO: 270, and can further comprise a light chain variable region comprising a VL CDR1 of SEQ ID NO:272, a VL CDR2 of SEQ ID NO: 273, and a VL CDR3 of SEQ ID NO: 274.

In one embodiment, an antibody of the invention is an antibody comprising an amino acid sequence of the $V_H$ and/or $V_L$ region as depicted in FIGS. 1A-1K and 3A-3R.

In another embodiment, an antibody of the invention is characterized by the preservation of the cognate pairing of the heavy and light chain that is present in a human B-cell.

In one embodiment, an antibody of the invention comprises a heavy chain variable region (VH) comprising, or consisting of an amino acid sequence selected from the group consisting of SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, and 267. In one embodiment, an antibody of the invention comprises a light chain variable region (VL) comprising, or consisting of an amino acid sequence selected from the group consisting of SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, and 271. In one embodiment, an antibody of the invention comprises a heavy chain variable region. (VH) comprising, or consisting of an amino acid sequence selected from the group consisting of SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, and 267, and further comprises a light chain variable region (VL) comprising, or consisting of an amino acid sequence selected from the group consisting of SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, and 271. In a specific embodiment, the antibody comprises a VH of SEQ ID NO: 1 and a VL of SEQ ID NO: 6; or a VH of SEQ ID NO: 10 and a VL of SEQ ID NO: 14; or a VH of SEQ ID NO: 18 and a VL of SEQ ID NO: 22; or a VH of SEQ NO: 26 and a VL of SEQ ID NO: 31; or a VH of SEQ ID NO: 35 and a VL of SEQ ID NO: 40, or a VH of SEQ ID NO:45 and a VL of SEQ ID NO: 49; or a VH of SEQ ID NO: 53 and a VL of SEQ ID NO: 57; or a VH of SEQ ID NO: 61 and a VL of SEQ ID NO: 65; or a VH of SEQ ID NO: 69 and a VL of SEQ ID NO: 73; or a VH of SEQ ID NO: 77 and a VL of SEQ ID NO: 82, or a VH of SEQ ID NO:87 and a VL of SEQ ID NO: 122, or a VH of SEQ ID NO:130 and a VL of SEQ ID NO: 134, or a VH of SEQ ID NO:138 and a VL of SEQ ID NO: 142, or a VH of SEQ ID NO:146 and a VL of SEQ ID NO: 150, or a VH of SEQ ID NO:146 and a VL of SEQ ID NO: 151, or a VH of SEQ ID NO:155 and a VL of SEQ ID NO: 159, or a VH of SEQ ID NO:163 and a VL of SEQ ID NO: 1.67, or a VH of SEQ ID NO:171 and a VL of SEQ ID NO: 175, or a VH of SEQ ID NO:179 and a VL of SEQ ID NO: 183, or a VH of SEQ ID NO:187 and a VL of SEQ ID NO: 191, or a VH of SEQ ID NO:195 and a VL of SEQ ID NO: 199, or a VH of SEQ ID NO:203 and a VL of SEQ ID NO: 207, or a VH of SEQ ID NO:211 and a VL of SEQ ID NO: 215, or a VH of SEQ NO:219 and a VL of SEQ ID NO: 223, or a VH of SEQ ID NO:227 and a AIL of SEQ ID NO: 231, or a VH of SEQ ID NO:235 and a VL of SEQ ID NO: 239, or a VH of SEQ ID NO:243 and a VL of SEQ ID NO: 247, or a VH of SEQ. ID NO:251 and a VL of SEQ ID NO: 255, or a VH of SEQ ID NO:259 and a VL of SEQ ID NO: 263, or a VH of SEQ ID NO:267 and a VL of SEQ ID NO: 271.

Alternatively, the TDP-binding molecule of the invention is a polypeptide such as an antibody (including an antigen-binding fragment of an antibody, or a derivative or variant thereof), which competes for binding to TDP-43, with at least one antibody having a $V_H$ and/or $V_L$ region as depicted in FIGS. 1A-1K and 3A-3R. Those antibodies can be human as well, in particular for therapeutic applications. Alternatively, the antibody is a murine, murinized or chimeric murine-human antibody, which is particularly useful for diagnostic methods and efficacy and safety studies in animals.

As discussed herein, the TDP-43 epitope of a completely human antibody is particularly relevant for diagnostic and therapeutic applications due to the fact that the antibody was initially generation as a result of a human immune response. Therefore, human completely human monoclonal antibodies of the invention recognize epitopes which are of particular physiological relevance and which might not be accessible or less immunogenic using conventional immunization and other antibody screening processes for the generation of for example, mouse monoclonal antibodies and antibodies derived from in vitro screening of phage display libraries. Therefore, the invention also extends generally to anti-TDP-43 antibodies and other TDP-43 binding molecules which compete with a human monoclonal antibody of the invention for specific binding to TDP-43. According to one embodiment, the antibody, or other TDP-43 binding molecule, competes with an antibody containing the variable domains disclosed in FIGS. 1A-1K and 3A-3R for binding with TDP-43. In another embodiment, the antibody or other TDP-43 binding molecule competes with a reference antibody selected from the group consisting of: NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5, for binding with TDP-43.

The invention also encompasses anti-TDP-43 antibodies and other TDP-43 binding molecules which hind to the same epitope of TDP-43 as a human monoclonal antibody of the invention. According to one embodiment, the antibody (including TDP-43 binding antibody fragments and variant or derivative thereof) or other TDP-43 binding molecule binds to the same epitope of TDP-43 as an antibody containing the variable domains disclosed in FIGS. 1A-1K and 3A-3R. In another embodiment, the antibody (including TDP-43 binding antibody fragments and variant or derivative thereof) or other TDP-43 binding molecule binds to the same epitope of TDP-43 as a reference antibody selected from the group consisting of: NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10H7, NI205.1A9, NI205.14W3, and NI205.19G5.

In another embodiment, the invention encompasses an antibody (including an antigen-binding fragment, variant or derivatives thereof), that specifically binds to a TDP-43 polypeptide sequence selected from: QYGDVMDVFIP (SEQ ID NO: 123); AAIGWGSASNA (SEQ ID NO: 124); DMTEDELREFF (SEQ ID NO: 125), EDENDEP (SEQ ID NO: 126), VQVKKDL (SEQ ID NO: 127), KEYFSTF (SEQ ID NO: 128), IIKGISV (SEQ ID NO:315), NQSGPSG (SEQ ID NO:316), FNGGFGS (SEQ ID NO:317), FGNSRGGGAGL (SEQ ID NO:318), SNAGSGSGFNG (SEQ ID NO:319), QLERSGRFGGN (SEQ ID NO:320), EIPSEDD (SEQ ID NO:321), FNGGFGSSMDS (SEQ ID NO:322) and SINPAMMAAAQAALQSSWGMMGMLASQ (SEQ ID NO:323). In another embodiment, the invention encompasses an antibody (including an antigen-binding fragment, variant or derivatives thereof), that specifically binds to TDP-43 polypeptides FGNSRGGGAGL (SEQ ID NO:31.8) and SNAGSGSGFNG (SEQ ID NO:319). In another embodiment, the invention encompasses an antibody (including an antigen-binding fragment, variant or derivatives thereof), that specifically binds to TDP-43 polypeptide SINPAMMAAAQAALQSSWGMMGMLASQ (SEQ ID NO:323), but does not specifically bind to SINPGGGAAAQAALQSSWGMMGMLASQ (SEQ ID NO:314).

Competition between antibodies is determined by an assay in which the immunoglobulin under test inhibits specific binding of a reference antibody to a common antigen, such as TDP-43. Numerous types of competitive binding assays are known in the art and can routinely be applied or modified to test the ability of two compounds to compete for binding to an antigen, such as, solid phase direct or indirect radioimmunoassay (MA), solid phase direct or indirect enzyme immunoassay (EIA), sandwich competition assay: see Stahli et al., Methods in Enzymology 9 (1983), 242-253; solid phase direct biotin-avidin EIA; see Kirkland et al., J. Immunol. 137 (1986), 3614-3619, and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al, Molec. Immunol. 25 (1988), 7-15 and Moldenhauer et al., Scand. J. Immunol. 32 (1990), 77-82. Typically, such an assay involves the use of purified TDP-43 or aggregates thereof bound to a solid surface or cells bearing either of these, an unlabeled test immunoglobulin and a labeled reference immunoglobulin, e.g., a human monoclonal antibody of the invention. Competitive inhibition is measured by determining the amount of label bound to the solid surface or cells in the presence of the test immunoglobulin. Usually the test immunoglobulin is present in excess. In one embodiment, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the invention is further drawn to an antibody (e.g., an antigen-binding fragment of an antibody), where the antibody competitively inhibits binding to TDP-43 by a reference antibody selected from the group consisting of NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38H2, NI205.36D5, NI205.58E11, NI205.14H5, NI205.31D2, NI205.8F8, NI205.31C11, NI205.8C10, NI205.10F17, NI205.1A9, NI205.14W3, and NI205.19G5.

The invention also provides antibodies that comprise, consist essentially of, or consist of, variants (including derivatives) of the antibody molecules (e.g., the $V_H$ regions and/or $V_L$ regions) described herein, which antibodies immunospecifically bind to a TDP-43 polypeptide or fragment or variant thereof. Standard techniques known in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3.

According to one embodiment, the invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90%, 95%, 96%, 97%, 98% or 99% identical to reference heavy chain V$_H$-CDR1, V$_H$-CDR2 or V$_H$-CDR3 amino acid sequences from the antibodies disclosed herein. Alternatively, the V$_H$-CDR1, V$_H$-CDR2 and V$_H$-CDR3 regions of the V$_H$ are at least 80%, 85%, 90%, 95%, 96%, 97%, 98% or 99% identical to reference heavy chain V$_H$ CDR1, V$_H$-CDR2 and V$_H$-CDR3 amino acid sequences from the antibodies disclosed herein. Thus, according to this embodiment a heavy chain variable region of the invention has V$_H$-CDR1, V$_H$-CDR2 and V$_H$-CDR3 polypeptide sequences related to the groups shown in FIGS. 1A-1K and 3A-3R. While FIGS. 1A-1K and 3A-3R shows V$_H$-CDRs defined by the Kabat system, other CDR definitions, e.g., V$_H$-CDRs defined by the Chothia system, are also included in the invention, and can be easily identified by a person of ordinary skill in the art using the data presented in FIGS. 1A-1K and 3A-3R. In one embodiment, the amino acid sequence of the reference VH CDR1 is SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; the amino acid sequence of the reference VH CDR2 is SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and the amino acid sequence of the reference VH CDR3 is SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270.

In another embodiment, the invention provides an isolated polypeptide comprising, consisting essentially of, or consisting of an immunoglobulin heavy chain variable region (V$_H$) in which the V$_H$-CDR1, V$_H$-CDR2 and V$_H$-CDR3 regions have polypeptide sequences which are identical to the V$_H$-CDR1, V$_H$-CDR2 and V$_H$-CDR3 groups shown in FIGS. 1A-1K and 3A-3R. In one embodiment, the amino acid sequence of the VH CDR1 is SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; the amino acid sequence of the reference VH CDR2 is SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and the amino acid sequence of the reference VH CDR3 is SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270.

In another embodiment, the invention provides an isolated polypeptide comprising, consisting essentially of, or consisting of an immunoglobulin heavy chain variable region (V$_H$) in which the V$_H$-CDR1, V$_H$-CDR2 and V$_H$-CDR3 regions have polypeptide sequences which are identical to the V$_H$-CDR1, V$_H$-CDR2 and V$_H$-CDR3 groups shown in FIGS. 1A-1K and 3A-3R, except for one, two, three, four, five, six, seven, eight, nine, or ten amino acid substitutions in any one V$_H$-CDR. In certain embodiments the amino acid substitutions are conservative. In one embodiment, the amino acid sequence of the VH CDR1 is SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; the amino acid sequence of the reference VH CDR2 is SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and the amino acid sequence of the reference VH CDR3 is SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270.

In another embodiment, the invention provides an isolated polypeptide comprising, consisting essentially of, or consisting of an immunoglobulin light chain variable region (V$_L$), where at least one of the V$_L$-CDRs of the light chain variable region or at least two of the V$_L$-CDRs of the light chain variable region are at least 80%, 85%, 90%, 95%, 96%, 97%, 98% or 99% identical to reference light chain V$_L$-CDR1, V$_L$-CDR2 or V$_L$-CDR3 amino acid sequences from antibodies disclosed herein. Alternatively, the V$_L$-CDR1, V$_L$-CDR2 and V$_L$-CDR3 regions of the V$_L$ are at least 80%, 85%, 90%, 95%, 96%, 97%, 98% or 99% identical to reference light chain V$_L$-CDR1, V$_L$-CDR2 and V$_L$-CDR3 amino acid sequences from antibodies disclosed herein. Thus, according to this embodiment a light chain variable region of the invention has V$_L$-CDR1, V$_L$-CDR2 and V$_L$-CDR3 polypeptide sequences related to the polypeptides shown in FIGS. 1A-1K and 3A-3R. While FIGS. 1A-1K and 3A-3R show V$_L$-CDRs defined by the Kabat system, other CDR definitions, e.g., V$_L$-CDRs defined by the Chothia system, are also included in the invention. In one embodiment, the amino acid sequence of the reference VL CDR1 is SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; the amino acid sequence of the reference VL CDR2 is SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and the amino acid sequence of the reference VL CDR3 is SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

In another embodiment, the invention provides an isolated polypeptide comprising, consisting essentially of, or consisting of an immunoglobulin light chain variable region (V$_L$) in which the V$_L$-CDR1, V$_L$-CDR2 and V$_L$-CDR3 regions have polypeptide sequences which are identical to the V$_L$-CDR1, V$_L$-CDR2 and V$_L$-CDR3 groups shown in FIGS. 1A-1K and 3A-3R. In one embodiment, the amino acid sequence of the VL CDR1 is SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; the amino acid sequence of the VL CDR2 is SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and the amino acid sequence of the VL CDR3 is SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

In another embodiment, the invention provides an isolated polypeptide comprising, consisting essentially of, or consisting of an immunoglobulin heavy chain variable region (V$_H$) in which the V$_H$-CDR1, V$_H$-CDR2 and V$_H$-CDR3 regions have polypeptide sequences which are identical to the V$_H$-CDR1, V$_H$-CDR2 and V$_H$-CDR3 groups shown in FIGS. 1A-1K and 3A-3R, except for one, two, three, four, five, six, seven, eight, nine, or ten amino acid substitutions in any one V$_L$-CDR. In certain embodiments the amino acid substitutions are conservative. In one embodiment, the amino acid sequence of the VL CDR1 is SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; the amino acid sequence of the VL CDR2 is SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and the amino acid sequence of the VL CDR3 is SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

According to one embodiment, the invention provides an isolated polypeptide comprising, consisting essentially of or consisting of an immunoglobulin heavy chain variable region ($V_H$) at least 80%, 85%, 90%, 95%, 96%, 97%, 98% or 99% identical to a reference heavy chain variable region ($V_H$) amino acid sequence from the antibodies disclosed herein. Thus, according to this embodiment a heavy chain variable region of the invention has a polypeptide sequence related to the heavy chain variable regions shown in FIGS. 1A-1K and 3A-3R. In one embodiment, the amino acid sequence of the reference heavy chain variable region ($V_H$) is SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, or 267.

In another embodiment, the invention provides an isolated polypeptide comprising, consisting essentially of, or consisting of an immunoglobulin heavy chain variable region ($V_H$) which is identical to a reference heavy chain variable region shown in FIGS. 1A-1K and 3A-3R. In one embodiment, the amino acid sequence of the reference heavy chain variable region is SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, and 267.

In another embodiment, the invention provides an isolated polypeptide comprising, consisting essentially of or consisting of an immunoglobulin heavy chain variable region ($V_H$) having a polypeptide sequence which is identical to a reference heavy chain variable region ($V_H$) sequence shown in FIGS. 1A-1K and 3A-3R, except for one, two, three, four, five, six, seven, eight, nine, or ten amino acid substitutions. In certain embodiments the amino acid substitutions are conservative. In one embodiment, the amino acid sequence of the reference heavy chain variable region sequence is SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, or 267.

According to one embodiment, the invention provides an isolated polypeptide comprising, consisting essentially of, or consisting of an immunoglobulin light chain variable region ($V_L$) at least 80%, 85%, 90%, 95%, 96%, 97%, 98% or 99% identical to a reference light chain variable region ($V_L$) amino acid sequence from the antibodies disclosed herein. Thus, according to this embodiment a light chain variable region of the invention has a polypeptide sequence related to the light chain variable regions shown in FIGS. 1A-1K and 3A-3R. In one embodiment, the amino acid sequence of the reference light chain variable region ($V_L$) is SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, and 271.

In another embodiment, the invention provides an isolated polypeptide comprising, consisting essentially of or consisting of an immunoglobulin light chain variable region ($V_L$) which is identical to a reference light chain variable region shown in FIGS. 1A-1K and 3A-3R. In one embodiment, the amino acid sequence of the reference light chain variable region is SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, and 271.

In another embodiment, the invention provides an isolated polypeptide comprising, consisting essentially of, or consisting of an immunoglobulin light chain variable region ($V_L$) having a polypeptide sequence which is identical to a reference light chain variable region ($V_L$) sequence shown in FIGS. 1A-1K and 3A-3R, except for one, two, three, four, five, six, seven, eight, nine, or ten amino acid substitutions. In certain embodiments the amino acid substitutions are conservative. In one embodiment, the amino acid sequence of the reference light chain variable region sequence is SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, and 271.

An immunoglobulin or its encoding nucleic acid (e.g., a cDNA) can be further modified. Thus, in a further embodiment the method of the invention comprises any one of the step(s) of producing a chimeric antibody, murinized antibody, single-chain antibody, Fab-fragment, bi-specific antibody, fusion antibody, labeled antibody or an analog of any one of those. Corresponding methods are known in the art and are described, e.g., in Harlow and Lane "Antibodies, A Laboratory Manual", CSH Press, Cold Spring Harbor (1988). When derivatives of said antibodies are obtained by for example, the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Mahnborg, J. Immunol. Methods 183 (1995), 7-13). The production of chimeric antibodies is described, for example, in International Application Publication No. WO89/09622. Methods for the production of humanized antibodies are described in, e.g., European application EP-A1 0 239 400 and International Application WO90/07861. A further source of antibodies to be utilized in accordance with the invention is so-called xenogeneic antibodies. The general principle for the production of xenogeneic antibodies such as human-like antibodies in mice is described in, e.g., International Application Publication Nos. WO91/10741, WO94/02602, WO96/34096 and WO 96/33735. As discussed above, the antibody of the invention can exist in a variety of forms besides complete antibodies; including, for example, Fv, Fab and F(ab)$_2$, as well as in single chains; see, e.g., international Application Publication. No. WO88/09344.

The antibodies of the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the nucleic acid sequence encoding the amino acid sequence of an immunoglobulin chain are well known to a person of ordinary skill in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the invention encompasses the production of chimeric proteins (i.e., fusion proteins) which comprise the TDP-43 binding polypeptides of the invention such as antibodies, at the amino terminus fused to heterologous molecule such as an immunostimulatory ligand at the carboxyl terminus; see, e.g., International Application Publication No. WO00/30680 for corresponding technical details.

Additionally, the invention encompasses peptides and polypeptides that specifically bind TDP-43. For example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides and polypeptides can readily be synthesized or produced by recombinant means to produce a TDP-43 binding molecule of the invention. Such methods are known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Accordingly, the invention relates to TDP-43 binding molecules such antibodies (e.g., a TDP-43 binding fragment of an antibody) that display one or more properties of the TDP-43 binding molecules described herein. For example, such antibodies and binding molecules can be tested for their binding specificity and affinity by for example, ELISA or Western Blot and immunohistochemistry as described herein; see, e.g., the Examples. As disclosed in Example 2, the half maximal effective concentration ($EC_{50}$) of NI-205.3F10, NI-205.51C1, NI-205.21G2, NI-205.8A2, NI-205.15F12, NI-205.113C4, NI-205.25F3, NI-205.87E7, NI-205.21G1, NI-205.68G5, NI-205.20A1, NI205.41D1, NI205.29E11, NI205.9E12, NI205.98H6, NI205.10D3, NI205.44B2, NI205.38142, NI205.36D5, NI205.58E11, NI205.14E15, NI205.3D2, NI205.8F8, NI205.31C11, NI205.8C10, NI205.10H7, NI205.1A9, NI205.14W3, and NI205.19G5, was determined for human TDP-43 by direct ELISA to bind human TDP-43 with high affinity at a sub-mid nanomolar $EC_{50}$ (0.18-17.2 nM).

As an alternative to obtaining immunoglobulins directly from the culture of immortalized B cells or B memory cells, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs which retain the ability to bind a desired target is straightforward. Methods for cloning antibody variable regions and generation of recombinant antibodies are known in the art and are described, for example, in Gilliland et Tissue Antigens 47 (1996), 1-20; Doenecke et al., Leukemia 11 (1997), 1787-4792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells can be used; for efficient processing, however, mammalian cells can be considered. Mammalian cell lines useful for this purpose include, but are not limited to CHO cells, HEK 293 cells, or NSO The production of the antibody or analog is then undertaken by culturing the modified recombinant host under culture conditions appropriate for the growth of the host cells and the expression of the coding sequences. The antibodies are then recovered by isolating them from the culture. The expression systems are designed to include signal peptides so that the resulting antibodies are secreted into the medium; however, intracellular production is also possible.

In accordance with the above, the invention also relates to a polynucleotide encoding the antibody or equivalent binding molecule of the invention. In one embodiment, the polynucleotide encodes at least a variable region of an immunoglobulin chain of the antibody described above. Typically, said variable region encoded by the polynucleotide comprises at least one complementarity determining region (CDR) of the $V_H$ and/or $V_L$ of the variable region of said antibody.

The person of ordinary skill in the art will readily appreciate that the variable domain of the antibody having the above-described variable domain Can be used for the construction of other polypeptides or antibodies of desired specificity and biological function. Thus, the invention also encompasses polypeptides and antibodies comprising at least one CDR of the above-described variable domain and which advantageously have substantially the same or similar binding properties as the antibody described in the appended examples. As generally understood in the art, binding affinity can be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the invention also relates to antibodies wherein one or more of the mentioned CDRs comprise one or more, or not more than two amino acid substitutions. In one embodiment, the antibody of the invention comprises in one or both of its immunoglobulin chains two or all three CDRs of the variable regions as set forth in FIGS. 1A-1K and 3A-3R.

Binding molecules such as antibodies (including antigen-binding fragments, variants, or derivatives thereof) of the invention, can comprise a constant region which mediates one or more effector functions. For example, binding of the C1 component of complement to an antibody constant region can activate the complement system. Activation of complement is important in the opsonization and lysis of cell pathogens. The activation of complement also stimulates the inflammatory response and can also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include an antibody (including an antibody antigen-binding fragment, variant, or derivative thereof), in which at least a fraction of one or more of the constant region domains has been substituted, deleted or otherwise altered so as to provide desired biochemical characteristics such as reduced effector functions, the ability to non-covalently dimerize, increased ability to localize at the site of TDP-43 aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain embodiments an antibody of the invention is missing an entire domain of the constant region of the modified antibody, such as, all or part of the CH2 domain. In other embodiments, antibodies of the invention useful for example in diagnostic or therapeutic methods have a constant region, e.g., an IgG heavy chain constant region, which is altered to eliminate glycosylation, referred to elsewhere herein as aglycosylated or "agly" antibodies. Such "agly" antibodies can be prepared enzymatically or by other techniques known in the art including for example, by engineering the consensus glycosylation site(s) in the constant region. While not being bound by theory, it is believed that "agly" antibodies can have an improved safety and stability profile in vivo. Methods of producing aglycosylated antibodies, having desired effector function are found for example in International Application Publication No. WO2005/018572, which is herein incorporated by reference in its entirety, In certain antibodies, including antigen-binding antibody fragments and variants described herein, the Fc portion can be mutated to decrease effector function using techniques known in the art. For example, the deletion or inactivation (through point mutations or other means) of a constant region domain can reduce Fc receptor binding of the circulating modified antibody thereby increasing TDP-43 localization. In other cases it can be that constant region modifications consistent with the instant invention moderate complement binding and thus reduce the serum half-life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as TDP-43 localization, biodistribution and serum half-life, can routinely be measured using techniques known in the art.

In certain embodiments, the Fc portion of antibodies of the invention are mutated or exchanged for alternative protein sequences to increase the cellular uptake of antibodies by way of example, by enhancing receptor-mediated endocytosis of antibodies via Fcγ receptors, LRP, or Thy1 receptors or by 'SuperAntibody Technology', which is said to enable antibodies to be shuttled into living cells without harming them (Muller, S., et al., Expert Opin. Biol. Then (2005), 237-241). For example, the generation of fusion proteins of the antibody binding region and the cognate protein ligands of cell surface receptors or bispecific or multi-specific antibodies with a specific sequences binding to TDP-43 as well as a cell surface receptor can be engineered using techniques known in the art.

In certain antibodies, including antigen-binding antibody fragments and variants described herein, the Fc portion can be mutated or exchanged for alternative protein sequences or the antibody can be chemically modified to increase its blood brain barrier penetration.

Modified forms of antibodies (e.g., antigen-binding fragments of antibodies and variants, or derivatives thereof) of the invention can be made from whole precursor or parent antibodies using techniques known in the art. Exemplary techniques are discussed in more detail herein. Antibodies of the invention, including antigen-binding antibody fragments and variants described herein, can routinely be made or manufactured using techniques known in the art. In certain embodiments, antibodies (including antibody fragments and derivatives) are "recombinantly produced," i.e., are produced using recombinant DNA technology. Exemplary techniques for making antibodies are discussed in more detail elsewhere herein.

Antibodies (including antigen-binding fragments of antibodies and variants, and derivatives thereof) of the invention also include derivatives that are modified, e.g., by the covalent attachment of any type of molecule to the antibody such that the covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids.

In particular embodiments the TDP-43 binding molecules of the invention, are polypeptides such as antibodies (including antigen-binding fragments, variants, or derivatives thereof) do not elicit a deleterious immune response in the animal to be treated, e.g., in a human. In certain embodiments, binding molecules, e.g., antibodies (including antigen-binding fragments of antibodies) of the invention are derived from a patient, e.g., a human patient, and are subsequently used in the same species from which they are derived, e.g., human, thus, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., International Application Publication Nos. WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, TDP-43-specific antibodies, including immunospecific fragments thereof, for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al. A Laboratory Manual, Cold Spring Harbor Laboratory Press, 2nd ed. (1988); Hammerling et al., in; *Monoclonal Antibodies and T-Cell Hybridomas* Elsevier, N.Y., 563-681 (1981), each of which references are herein incorporated by reference in their entireties. The term "monoclonal antibody" as used herein is not limited to antibodies produced through hybridoma technology. The term "monoclonal antibody" refers to an antibody that is derived from a single isolated clone, including any eukaryotic, prokaryotic, or phage clone, and not the method by which it is produced. Thus, the term "monoclonal antibody" is not limited to antibodies produced through hybridoma technology. In certain embodiments, antibodies of the invention are derived from human B cells which have been immortalized via transformation with Epstein-Barr virus, as described herein. For clarity, the term "monoclonal antibody" as used herein, does not encompass an endogenous antibody that can be isolated from the plasma of a host organism.

In the well known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. The selected hybridomas produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Reagents, cell lines and methods for forming, selecting and growing of hybridomas are known in the art. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELBA) as described herein. After hybridoma cells are identified that produce antibodies of the desired specificity, affinity and/or activity, the clones can be subcloned by limiting dilution procedures and grown by standard methods; see, e.g., Goding, *Monoclonal Antibodies: Principles and Practice*, Academic Press, pp. 59-103 (1986). It will further be appreciated that the monoclonal antibodies secreted by the hybridoma subclones can be separated from culture medium, ascites fluid or serum by conventional purification procedures such as, for example, protein-A, hydroxylapatite chromatography, gel electrophoresis, dialysis or affinity chromatography.

In another embodiment, lymphocytes are selected by micromanipulation and the variable genes isolated. For example, peripheral blood mononuclear cells can be isolated from an immunized or naturally immune mammal, e.g., a human, and cultured for about 7 days in vitro. The PBMC cultures are then screened for specific IgGs that meet the screening criteria and the cells from positive wells are isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines can be selected and cultured using or routinely modifying techniques known in the art. Such techniques are described in a variety of laboratory manuals and primary publications. In this respect, techniques suitable for use in the invention as described below are described in *Current Protocols in Immunology*, Coligan et al., Eds., Green Publishing Associates and Wiley-interscience, John Wiley and Sons, New York (1991) which is herein incorporated by reference in its entirety, including supplements.

Antibody fragments that recognize specific antigens and/or epitopes can be generated using techniques known in the art. For example, Fab and F(ab')$_2$ fragments can be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Completely human antibodies, such as those described herein, are particularly desirable for therapeutic treatment of human patients. Human antibodies of the invention are isolated, e.g., from elderly healthy subjects who because of their age can be suspected to be at risk of developing a disorder, e.g., amyotrophic lateral sclerosis and/or frontotemporal lobar degeneration, or a patient with the disorder but with an unusually stable disease course. However, though it is prudent to expect that elderly healthy and symptom-free subjects, respectively, more regularly will have developed protective anti-TDP-43 antibodies than younger subjects, the latter can be used as well as a source for obtaining a human antibody of the invention. This is particularly true for younger patients who are predisposed to develop a familial form of a TDP-43 proteinopathies but remain symptom-free since their immune system and immune response functions more efficiently than that in older adults.

Antibodies of the invention can be produced by any method known in the art for synthesis of antibodies, including in particular, chemical synthesis or recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide can be substituted for the deleted domain to provide flexibility and freedom of movement for the variable region. Those of ordinary skill in the art will appreciate that such constructs can be desirable due to the regulatory properties of the CH2 domain on the catabolic rate of the antibody. Domain deleted constructs can be derived using a vector encoding an IgG$_1$ human constant domain; see, e.g., International Applications WO02/060955 and WO02/096948A2. This vector is engineered to delete the CH2 domain and provide a synthetic vector expressing a domain deleted IgG$_1$ constant region.

In certain embodiments the antibodies (including antigen-binding fragments, variants, or derivatives thereof) of the invention are minibodies. Minibodies can be made using methods known in the art; see, e.g., U.S. Pat. No. 5,837,821 or International Application Publication No. WO 94/09817.

In one embodiment, an antibody (e.g., antigen-binding fragment, variant, or derivative thereof of an antibody) of the invention comprises an immunoglobulin heavy chain having deletion or substitution of a few or even a single amino acid as long as it permits association between the monomeric subunits. For example, the mutation of a single amino acid in selected areas of the CH2 domain can be enough to substantially reduce Fc binding and thereby increase TDP-43 localization. Similarly, it can be desirable to simply delete that part of one or more constant region domains that control the effector function (e.g., complement binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be synthetic through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The invention also provides antibodies that comprise, consist essentially of or consist of, variants (including derivatives) of antibodies (e.g., the $V_H$ regions and/or $V_L$ regions) described herein, which antibodies (inducing antibody fragments), immunospecifically bind to TDP-43. Standard techniques known to those of skill in the art can be used to introduce mutations in the nucleotide sequence encoding an antibody, including, but not limited to, site-directed mutagenesis and PCR-mediated mutagenesis which result in amino acid substitutions. In one embodiment, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind TDP-43).

For example, it is possible to introduce mutations only in framework regions or only in CDR regions of an antibody. Introduced mutations can be silent or neutral missense mutations, e.g., have no, or little, effect on an antibody's ability to bind antigen, indeed some such mutations do not alter the amino acid sequence whatsoever. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in a CDR, though this is not an absolute requirement. A person of ordinary skill in the art is able to design and test altered molecules for desired properties including for example, improvements in antigen-binding activity or change in antibody specificity. Following mutagenesis, proteins displaying the desired properties can routinely be expressed and the functional and/or biological activity of the encoded protein, (e.g., ability to immunospecifically bind at least one epitope of TDP-43) can be determined using or routinely modifying techniques known in the art.

Anti-TDP-43 antibodies of the present invention can be characterized using any in vivo or in vitro models of TDP-43 proteinopathies. A skilled artisan readily understands that an anti-TDP-43 antibody of the invention can be characterized in a mouse model for TDP-43 proteinopathies, for example, but not limited to, any one of the animal models for TDP-43 proteinopathies described in Example 5. Wegorzewska et al., Proc. Natl. Acad. Sci. U.S.A. 106 (2009), 18809-14; Gurney et al., Science 264 (1994), 1772-75; Shan et al., Neuropharmacol. Letters 458 (2009), 70-74; Wils et al., Proc. Natl, Acad. Sci, USA. 106 (2010), 3858-63; Duchen and Strich, J. Neurol. Neurosurg. Psychiatry 31 (1968), 535-42; Dennis and Citron, Neuroscience 185 (2009), 745-50; Swarup et al., Brain 134 (2011), 2610-2626; Igaz et al., J. Clin Invest. 121(2):726-38 (2011); Caccamo et al., Am Pathol. 180(1): 293-302 (2012), Cannon et al., Acta Neuropathol. 123(6): 807-23 (2012), Custer et al., Hum Mol Genet. 19(9):1741-55 (2010); and Tatom et al., Mol. Ther. 17 (2009), 607-613.

A skilled artisan understands that an experimental model of TDP-43 proteinopathy can be used in a preventative setting or it can be used in a therapeutic setting. In a preventative setting, the dosing of animals starts prior to the onset of the TDP-43 proteinopathy or symptoms thereof. In preventative settings, an anti-TDP-43 antibody of the invention is evaluated for its ability to prevent, reduce or delay the onset of TDP-43 proteinopathy or symptoms thereof. In a therapeutic setting, the dosing of animals start after the onset of TDP-43 proteinopathy or a symptom thereof. In a therapeutic setting, an anti-TDP-43 antibody of the invention is evaluated for its ability to treat, reduce or alleviate the TDP-43 proteinopathy or a symptom thereof. Symptoms of the TDP-43 proteinopathies include, but are not limited to, accumulation of pathological TDP-43 deposits, pathological TDP-43 distribution, phosphorylated TDP-43, or insoluble TDP-43 fractions in the neurons, brain, spinal cord, cerebrospinal fluid or serum of the experimental object. A skilled artisan understands that a positive preventative or therapeutic outcome in any animal model of TDP-43 proteinopathies indicates that the particular anti-TDP-43 antibody can be used for preventative or therapeutic purposes in a subject other than the experimental model organism, for example, it can be used to treat TDP-43 proteinopathies in a human subject in need thereof.

In one embodiment, an anti-TDP-43 antibody of the invention can be administered to a TDP-43 proteinopathy mouse model and corresponding control wild type mice. The antibody administered can be a murinized antibody of the present invention or a human-murine chimera of an antibody of the present invention. The anti-TDP-43 antibody can be administered by any means known in the art, for example, by intraperitoneal, intracranial, intramuscular, intravenous, subcutaneous, oral, and aerosol administration. Experimental animals can be given one, two, three, four, five or more doses of the anti-TDP-43 antibody or a control composition, such as PBS. In one embodiment, experimental animals will be administered one or two doses of an anti-TDP-43 antibody. In another embodiment, the animals are chronically dosed with the anti-TDP 43 antibody over several weeks or months. A skilled, artisan can readily design a dosing regimen that fits the experimental purpose, for example, dosing regimen for acute studies, dosing regimen for chronic studies, dosing regimen for toxicity studies, dosing regimen for preventative or therapeutic studies. The presence of the anti-TDP-43 antibody in a particular tissue compartment of the experimental, animals, for example, but not limited to, serum, blood, cerebrospinal fluid, brain tissue, can be established using well know methods of the art. In one embodiment, an anti-TDP-43 antibody of the invention is capable to penetrate the blood brain barrier. In another embodiment, an anti-TDP-43 antibody of the invention is capable to enter neurons. A skilled artisan understands that by adjusting the anti-TDP-43 antibody dose and the dosing frequency, a desired anti-TDP-43 antibody concentration can be maintained in the experimental animals. Any effect of an anti-TDP-43 antibody of the present invention in the TDP-43 proteinopathy models can be assessed by comparing the level, biochemical characteristics or distribution of TDP-43 in the treated and control animals. In one embodiment, an antibody of present invention is capable of reducing the level, amount or concentration of TDP-43 inclusions in the brain or spinal cord in an animal model. The antibody can reduce the level, amount or concentration of TDP-43 inclusions by at least about 5%, 10%, 20%, 30%, 50%, 70%, 90% or more. In another embodiment, an antibody of the present invention is capable of reducing the number or frequency of TDP-43 inclusion-positive neurons in the brain or spinal cord in an animal model, for example, by at least about 5%, 10%, 20%, 30%, 50%, 70%, 90% or more. The effect of an antibody of the present invention can also be assessed by examining the distribution and biochemical properties of TDP-43 following antibody administration. In one embodiment, an antibody of the present invention is capable of reducing the amount or concentration of cytoplasmic TDP-43 protein in the brain or spinal cord of an animal model, for example, by at least about 5%, 10%, 20%, 30%, 50%, 70%, 90% or more. In another embodiment, an antibody of the present invention is capable of reducing the amount or concentration of neuritic TDP-43 protein in the brain or spinal cord of an animal model, for example, by at least about 5%, 10%, 20%, 30%, 50%, 70%, 90% or more. In a further embodiment, an antibody of the present invention can reduce the amount or concentration of phosphorylated TDP-43 protein in the brain or spinal cord in an animal model, for example, by at least about 5%, 10%, 20%, 30%, 50%, 70%, 90% or more. Phosphorylated TDP-43 can be detected using antibodies specific for pathologically phosphorylated forms of TDP-43, such as p403/p404 and p409/p410. Hasegawa et al., Ann Neurol, 64(1):60-70 (2008) An antibody of the present invention can also alter, for example, reduce or increase TDP-43 concentration in the blood, serum or cerebrospinal fluid of an animal model, for example, by at least about 5%, 10%, 20%, 30%, 50%, 70%, 90% or more. In one embodiment, the % reduction or increase is relative compared to the level, number, frequency, amount or concentration that existed before treatment, or to the level, number, frequency, amount or concentration that exist in an untreated/control treated subject.

In one embodiment, an antibody of the present invention can prevent or delay the onset of at least one symptom of a TDP-43 proteinopathy in a subject. In one embodiment, an antibody of the present invention can reduce or eliminate at least one symptom of a TDP-43 proteinopathy in a subject. The symptom can be the formation of pathological TDP-43 deposits, phosphorylated TDP-43 deposits, or insoluble TDP-43 deposits. The symptom can also be the presence, or elevated concentration or amount, of TDP-43 in the serum, blood, urine or cerebrospinal fluid, wherein elevated concentration amount is compared to a healthy subject. The symptom can be a neurological symptom, for example, altered conditioned taste aversion, altered contextual fear conditioning, memory impairment, loss of motor function. In one embodiment, memory impairment is assessed using a two-trial Y-maze task. In one embodiment, the at least one symptom is reduced by at least about 5%, 10%, 15%, 20%, 30%, 50%, 70%, or 90%. In another embodiment, the two-trial Y-maze task ratio is significantly higher in an antibody treated subject than in a control subject. In a specific embodiment, the two-trial Y-maze task ratio is increased by at least about 5%, 10%, 20%, 30%, 40%, 50%, 60%, 70%, 80%, or 90%. In another embodiment, the two-trial Y-maze task ratio is at least about two times, three times, four times, five times, ten times, or twenty times higher. The present invention also provides a method of preventing or delaying the onset of at least one symptom of a TDP-43 proteinopathy in a subject in need thereof, comprising administering a therapeutically effective amount of an anti-TDP-43 antibody described herein. The present invention further provides a method of reducing or eliminating least one symptom of a TDP-43 proteinopathy in a subject in need thereof, comprising administering a therapeutically effective amount of an anti-TDP-43 antibody described herein. In one embodiment, the subject is an experimental organism, such as, but not limited to, transgenic mouse. In one embodiment, the subject is a human.

III. Polynucleotides Encoding Antibodies

A polynucleotide encoding an antibody, or antigen-binding fragment, variant, or derivative thereof can be composed of any polyribonucleotide or polydeoxyribonucleotide, which can be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody (including an antigen-binding fragment of an antibody, or a variant, or derivative thereof) can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence encoding the immunoglobulin such that one or more amino acid substitutions, additions or deletions are introduced into the encoded protein. Mutations can be introduced by standard techniques, such as site-directed mutagenesis and PCR-mediated mutagenesis. In one embodiment, conservative amino acid substitutions are made at one or more amino acid residue positions that are non-essential.

RNA can be isolated from the original B cells, hybridoma cells or from other transformed cells by standard techniques, such as guanidinium isothiocyanate extraction and precipitation followed by centrifugation or chromatography. Where desirable, mRNA can be isolated from total RNA using standard techniques such as, chromatography on oligo dT cellulose. Suitable techniques are familiar in the art. In one embodiment, cDNAs that encode the light and the heavy chains of the antibody can be made, either simultaneously or separately, using reverse transcriptase and DNA polymerase in accordance with known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as human constant region probes.

DNA, typically plasmid DNA, can be isolated from the cells using techniques known in the art, restriction mapped and sequenced in accordance with standard, known techniques set forth in detail, e.g., in the foregoing references relating to recombinant DNA techniques. Of course, the DNA can be synthetic according to the invention at any point during the isolation process or subsequent analysis.

In one embodiment, the invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90%, 95%, 96%, 98%, or 99% identical to reference heavy chain $V_H$-CDR1 $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90%, 95%, 96%, 98%, or 99% identical to reference heavy chain $V_H$CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIGS. 1A-1K and 3A-3R. In one embodiment, the amino acid sequence of the reference VH CDR1 is SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; the amino acid sequence of the reference VH CDR2 is SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and the amino acid sequence of the reference VH CDR3 is SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270. In one embodiment, the invention provides an isolated polynucleotide comprising, consisting essentially of, or consisting of a nucleic acid encoding an immunoglobulin heavy chain variable region ($V_H$), in which the $V_H$-CDR1, $V_H$-CDR2 and $V_H$-CDR3 regions have the polypeptide sequences of the $V_H$-CDR1, $V_H$CDR2 and $V_H$-CDR3 groups shown in FIGS. 1A-1K and 3A-3R, except for one, two, three, four, five, six, seven, eight, nine, or ten amino acid substitutions in any one $V_H$-CDR. In certain embodiments the amino acid substitutions are conservative. In one embodiment, the amino acid sequence of the VH CDR1 is SEQ ID NO: 3, 11, 19, 28, 37, 46, 54, 62, 70, 79, 88, 131, 139, 147, 156, 164, 172, 180, 188, 196, 204, 212, 220, 228, 236, 244, 252, 260, or 268; the amino acid sequence of the VH CDR2 is SEQ ID NO: 4, 12, 20, 29, 38, 47, 55, 63, 71, 80, 89, 132, 140, 148, 157, 165, 173, 181, 189, 197, 205, 213, 221, 229, 237, 245, 253, 261, or 269; and the amino acid sequence of the VH CDR3 is SEQ ID NO: SEQ ID NO: 5, 13, 21, 30, 39, 48, 56, 64, 72, 81, 90, 133, 141, 149, 158, 166, 174, 182, 190, 198, 206, 214, 222, 230, 238, 246, 254, 262, or 270.

In another embodiment, the invention provides an isolated polynucleotide comprising, consisting essentially of or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90%, 95%, 96%, 98%, or 99% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90%, 95%, 96%, 98%, or 99% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIGS. 1A-1K and 3A-3R. In one embodiment, the amino acid sequence of the reference VL CDR1 is SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; the amino acid sequence of the reference VL CDR2 is SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and the amino acid sequence of the reference VL CDR3 is SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

In another embodiment, the invention provides an isolated polynucleotide comprising, consisting essentially of or consisting of a nucleic acid encoding an immunoglobulin light chain variable region ($V_L$) in which the $V_L$-CDR1, $V_L$-CDR2 and $V_L$-CDR3 regions have the polypeptide sequences of the $V_L$-CDR1, $V_L$-CDR2 and $V_L$-CDR3 groups shown in FIGS. 1A-1K and 3A-3R, except for one, two, three, four, five, six, seven, eight, nine, or ten amino acid substitutions in any one $V_L$-CDR. In certain embodiments the amino acid substitutions are conservative. In one embodiment, the amino acid sequence of the VL CDR1 is SEQ ID NO: 7, 15, 23, 32, 42, 50, 58, 66, 74, 84, 91, 135, 143, 152, 160, 168, 176, 184, 192, 200, 208, 216, 224, 232, 240, 248, 256, 264, 272 or 326; the amino acid sequence of the VL CDR2 is SEQ ID NO: 8, 16, 24, 33, 43, 51, 59, 67, 75, 85, 92, 136, 144, 153, 161, 169, 177, 185, 193, 201, 209, 217, 225, 233, 241, 249, 257, 265, 273 or 327; and the amino acid sequence of the VL CDR3 is SEQ ID NO: 9, 17, 25, 34, 44, 52, 60, 68, 76, 86, 93, 137, 145, 154, 162, 170, 178, 186, 194, 202, 210, 218, 226, 234, 242, 250, 258, 266, 274 or 328.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the invention, the parameters are set, of course, such that the percentage of identity is calculated over the full length of the reference polypeptide sequence and that gaps in homology of up to 5% of the total number of amino acids in the reference sequence are allowed.

In one embodiment of the invention, the polynucleotide comprises, consists essentially of, or consists of a nucleic acid having a polynucleotide sequence of the $V_H$ or $V_L$ region of an TDP-43 binding antibody as listed in Table 3. In this respect, a person of ordinary skill in the art will readily appreciate that the polynucleotides encoding at least the variable domain of the light and/or heavy chain can encode the variable domain of both immunoglobulin chains or only one.

TABLE 3

Nucleotide sequences of the $V_H$ and $V_L$ region of TDP-43 specific antibodies.

| Antibody | | Nucleotide sequences of variable heavy (VH) and variable light (VL) chains |
|---|---|---|
| NI-205.3F10 | $V_H$ | SEQ ID NO: 95 |
| | $V_L$ | SEQ ID NO: 96 |
| NI-205.51C1 | $V_H$ | SEQ ID NO: 97 |
| | $V_L$ | SEQ ID NO: 98 |
| NI-205.21G2 | $V_H$ | SEQ ID NO: 99 |
| | $V_L$ | SEQ ID NO: 100 |
| NI-205.8A2 | $V_H$ | SEQ ID NO: 101 |
| | $V_L$ | SEQ ID NO: 102 |
| NI-205.15F12 | $V_H$ | SEQ ID NO: 103 |
| | $V_L$ | SEQ ID NO: 104 |
| NI-205.113C4 | $V_H$ | SEQ ID NO: 105 |
| | $V_L$ | SEQ ID NO: 106 |
| NI-205.25F3 | $V_H$ | SEQ ID NO: 107 |
| | $V_L$ | SEQ ID NO: 108 |
| NI-205.87E7 | $V_H$ | SEQ ID NO: 109 |
| | $V_L$ | SEQ ID NO: 110 |
| NI-205.21G1 | $V_H$ | SEQ ID NO: 111 |
| | $V_L$ | SEQ ID NO: 112 |
| NI-205.68G5 | $V_H$ | SEQ ID NO: 113 |
| | $V_L$ | SEQ ID NO: 114 |

TABLE 3-continued

Nucleotide sequences of the $V_H$ and $V_L$ region of TDP-43 specific antibodies.

| Antibody | | Nucleotide sequences of variable heavy (VH) and variable light (VL) chains |
|---|---|---|
| NI-205.20A1 | $V_H$ | SEQ ID NO: 115 |
| | $V_L$ | SEQ ID NO: 116 |
| NI205.41D1 | $V_H$ | SEQ. ID. NO: 275 |
| | $V_L$ | SEQ. ID. NO: 276 |
| NI205.29E11 | $V_H$ | SEQ. ID. NO: 277 |
| | $V_L$ | SEQ. ID. NO: 278 |
| NI205.9E12 | $V_H$ | SEQ. ID. NO: 279 |
| | $V_L$ | SEQ. ID. NO: 280 |
| | $V_L$ | SEQ. ID. NO: 281 |
| NI205.98H6 | $V_H$ | SEQ. ID. NO: 282 |
| | $V_L$ | SEQ. ID. NO: 283 |
| NI205.10D3 | $V_H$ | SEQ. ID. NO: 284 |
| | $V_L$ | SEQ. ID. NO: 285 |
| NI205.44B22 | $V_H$ | SEQ. ID. NO: 286 |
| | $V_L$ | SEQ. ID. NO: 287 |
| NI205.38H2 | $V_H$ | SEQ. ID. NO: 288 |
| | $V_L$ | SEQ. ID. NO: 289 |
| NI205.36D5 | $V_H$ | SEQ. ID. NO: 290 |
| | $V_L$ | SEQ. ID. NO: 291 |
| NI205.58E11 | $V_H$ | SEQ. ID. NO: 292 |
| | $V_L$ | SEQ. ID. NO: 293 |
| NI205.14H5 | $V_H$ | SEQ. ID. NO: 294 |
| | $V_L$ | SEQ. ID. NO: 295 |
| NI205.31D2 | $V_H$ | SEQ. ID. NO: 296 |
| | $V_L$ | SEQ. ID. NO: 297 |
| NI205.8F8 | $V_H$ | SEQ. ID. NO: 298 |
| | $V_L$ | SEQ. ID. NO: 299 |
| NI205.31C11 | $V_H$ | SEQ. ID. NO: 300 |
| | $V_L$ | SEQ. ID. NO: 301 |
| NI205.8C10 | $V_H$ | SEQ. ID. NO: 302 |
| | $V_L$ | SEQ. ID. NO: 303 |
| NI205.10H7 | $V_H$ | SEQ. ID. NO: 304 |
| | $V_L$ | SEQ. ID. NO: 305 |
| NI205.1A9 | $V_H$ | SEQ. ID. NO: 306 |
| | $V_L$ | SEQ. ID. NO: 307 |
| NI205.14W3 | $V_H$ | SEQ. ID. NO: 308 |
| | $V_L$ | SEQ. ID. NO: 309 |
| NI205.19G5 | $V_H$ | SEQ. ID. NO: 310 |
| | $V_L$ | SEQ. ID. NO: 310 |

In one embodiment, the invention provides an isolated polynucleotide comprising, consisting essentially of or consisting of a nucleic acid encoding an immunoglobulin heavy chain variable region at least 80%, 85%, 90%, 95%, 96%, 98%, or 99% or 95% identical to reference heavy chain VH. In one embodiment, the amino acid sequence of the reference heavy chain variable region is SEQ ID NO: 1, 10, 18, 26, 35, 45, 53, 61, 69, 77, 87, 130, 138, 146, 155, 163, 171, 179, 187, 195, 203, 211, 219, 227, 235, 243, 251, 259, or 267.

In one embodiment, the invention provides an isolated polynucleotide comprising, consisting essentially of or consisting of a nucleic acid encoding an immunoglobulin light chain variable region at least 80%, 85%, 90%, 95%, 96%, 98%, or 99% or 95% identical to reference light chain VL. In one embodiment, the amino acid sequence of the reference light chain variable region is SEQ ID NO: 6, 14, 22, 31, 40, 49, 57, 65, 73, 82, 122, 134, 142, 150, 151, 159, 167, 175, 183, 191, 199, 207, 215, 223, 231, 239, 247, 255, 263, or 271.

The invention also includes fragments of the polynucleotides of the invention. Preferably the polynucleotides encode a polypeptide that binds TDP-43. Additionally polynucleotides which encode fusion polynucleotides, Fab fragments, and other derivatives, as described herein, are also contemplated by the invention.

The polynucleotides can be produced or manufactured by any appropriate method known in the art. For example, if the nucleotide sequence of the antibody is known, a polynucleotide encoding the antibody can be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including an antigen, binding fragment of an antibody, or variant or derivative thereof) can be generated from nucleic acid from a suitable source. If a clone containing a nucleic acid encoding a particular antibody is not available, but the sequence of the antibody is known, a nucleic acid encoding the antibody can be chemically synthesized or obtained from a suitable source (e.g., an antibody cDNA library, or a cDNA library generated from, or nucleic acid, preferably polyA+ RNA, isolated from, any tissue or cells expressing the TDP-43-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method known in the art.

Once the nucleotide sequence and corresponding amino acid sequence of the antibody, or antigen-binding fragment, variant, or derivative thereof is determined, its nucleotide sequence can be manipulated using methods known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), the contents of both of which are herein incorporated by reference in their entireties), to generate antibodies having a different amino acid sequence, for example to create amino acid substitutions, deletions, and/or insertions.

IV. Expression of Antibody Polypeptides

Following manipulation of the isolated genetic material to provide an antibody (including an antigen-binding fragment of an antibody, or variant or derivative thereof) of the invention, the polynucleotide encoding the antibody is typically inserted in an expression vector for introduction into host cells that can be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody or a heavy or light chain of an antibody, or portion thereof (preferably containing the heavy or light chain variable domain), of the invention has been obtained, the vector for the production of the antibody can be produced by recombinant DNA technology using techniques known in the art. Thus, methods for preparing a protein by expressing a polynucleotide containing an antibody encoding nucleotide sequence are described herein. Methods which are known to those of ordinary skill in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody of the invention, or a heavy or light chain thereof, or a heavy or light chain variable domain, operably linked to a promoter. Such vectors can include the nucleotide sequence encoding the constant region of the antibody (see, e.g., International Application Publication No. WO 86/05807 and U.S. Pat. No. 5,122,464) and the variable domain of the antibody can be cloned into such a vector for expression of the entire heavy or light chain.

The term "vector" or "expression vector" is used herein to mean vectors used in accordance with the invention as a vehicle for introducing into and expressing a desired gene in a host cell. As known in the art, such vectors can readily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. Numerous expression vector systems can be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g. antibiotics) or resistance to heavy metals such as copper. The selectable marker gene can either be directly linked to the DNA sequences to be expressed, or introduced into the same cell by co-transformation. Additional elements can also be needed for optimal synthesis of mRNA. These elements can include signal sequences, splice signals, as well as transcriptional promoters, enhancers, and termination signals.

In particular embodiments the cloned variable region genes are inserted into an expression vector along with the heavy and light chain constant region coding sequences (e.g., human heavy or light chain constant region genes) as discussed above. In one embodiment, this is effected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells can be used in the invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is herein incorporated by reference in its entirety. This system provides for high expression levels, e.g., >30 pg/cell/day. Other exemplary vector systems are disclosed e.g., in U.S. Pat. No. 6,413,777.

In other embodiments the antibodies (e.g., antigen-binding fragments of antibodies and variants or derivatives thereof) of the invention can be expressed using polycistronic constructs such as those disclosed in U.S. Patent Application Publication No. 2003-0157641 A1 and herein incorporated by reference in its entirety. In these expression systems, multiple gene products of interest such as heavy and light chains of antibodies can be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those ordinary skill in the art will appreciate that such expression systems can be used to effectively produce the full range of antibodies disclosed in the application.

More generally, once the vector or DNA sequence encoding a monomeric subunit of the antibody has been prepared, the expression vector can be introduced into an appropriate host cell. Introduction of the plasmid into the host cell can be accomplished by various techniques known to those in the art. These include, but are not limited to, transfection including lipotransfection using, e.g., Fugene or lipofectamine, protoplast fusion, calcium phosphate precipitation, cell fusion with enveloped DNA, microinjection, and infection with intact virus. Typically, plasmid introduction into the host is via standard methods known in the art, such as, calcium phosphate co-precipitation method. The host cells harboring the expression construct are grown under conditions appropriate to the production of the light chains and heavy chains, and assayed for heavy and/or light chain protein synthesis. Non-limiting exemplary assay techniques include enzyme-linked immunosorbent assay (ELISA), radioimmunoassay (RIA), or fluorescence-activated cell sorter analysis (FACS), and immunohistochemistry.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In particular embodiments for the expression of double-chained antibodies, vectors encoding both the heavy and light chains can be co-expressed in the host cell for expression of the entire immunoglobulin molecule, as detailed below.

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci, USA 77 (1980), 2197. The coding sequences for the heavy and light chains can comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of an antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibodies for use in methods described herein. Such host-expression systems represent vehicles by which the coding sequences of interest can be produced and subsequently purified, but also represent cells which can, when transformed or transfected with the appropriate nucleotide coding sequences, express an antibody of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In one embodiment, bacterial cells such as *Escherichia coli*, and eukaryotic cells, especially for the expression of whole recombinant antibody, are used for the expression of a recombinant antibody. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell lines used for protein expression of the TDP-43 binding molecules of the invention include, for example cells of mammalian origin; those of ordinary skill in the art are credited with ability to determine particular host cell lines which are best suited for the desired gene product to be expressed therein. Exemplary host cell lines include, but are not limited to, CHO (Chinese Hamster Ovary), DG44 and DUXB11. (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610. (Chinese hamster fibroblast) BALB/C3T3 (mouse fibroblast), HAK (hamster kidney line), SPIT. (mouse myeloma), P3x63-Ag3.653 (mouse myeloma), BFA-1c1BPT (bovine endothelial cells), RAJI (human lymphocyte) and 293 (human kidney). In a specific embodiment, host cell lines are CHO or 293 cells. Host cell lines are readily available and are typically available from commercial services, including for example, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the antibody can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody.

A number of selection systems can be used according to the present invention, including but not limited to, the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods known in the art of recombinant DNA technology which can be used are described in Ausubel et al., (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al., (eds), *Current Protocols in Human Genetics*, John Wiley & Sons, NY (1994); Colberre-Garapin et al., J. Mol. Biol. 150:1 (1981), each of which are herein incorporated by reference in their entireties.

The expression levels of an antibody can be increased using techniques known in the art, including for example, by vector amplification, see e.g. Bebbington and Hentschel, *The use of vectors based on gene amplification for the expression of cloned genes in mammalian cells in DNA cloning*, Academic Press, New York, Vol. 3. (1987). When a marker in the vector system expressing an antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, after preferential biosynthesis of a synthetic hinge region polypeptide or prior to or subsequent to the HIC chromatography step described herein.

Genes encoding antibodies (including for example, antigen-binding fragments of antibodies and variants, or derivatives thereof) of the invention can also be expressed in non-mammalian cells such as bacteria or insect or yeast or plant cells. Bacteria which readily take up nucleic acids include members of the enterobacteriaceae, such as strains of *Escherichia coli* of *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., International Application Publication No. WO02/096948.

In bacterial systems, a number of expression vectors can be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified can be desirable. Such vectors include, but are not limited, to the *E. coli* expression vector pUR278 (Rather et al., EMBO J. 2 (1983), 1791), in which the antibody coding sequence can be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once an antibody of the invention has been recombinantly expressed, the whole antibodies, their dimers, individual light and heavy chains, or other immunoglobulin forms of the invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, another method for increasing the affinity of antibodies of the invention is disclosed in U.S. Patent Publication No. 2002-0123057 A1.

V. Fusion Proteins and Conjugates

In certain embodiments, the antibody polypeptide comprises an amino acid sequence or one or more moieties not normally associated with an antibody. Exemplary modifications are described in more detail below. For example, a single-chain fv antibody fragment of the invention can comprise a flexible linker sequence, or can be modified to add a functional moiety (e.g., PEG, a drug, a toxin, or a label such as a fluorescent, radioactive, enzyme, nuclear magnetic, heavy metal and the like)

An antibody polypeptide of the invention can comprise, consist essentially of or consist of a fusion protein. Fusion proteins are chimeric molecules which comprise, for example, an immunoglobulin TDP-43-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, (e.g., antigen-binding fragments of antibodies and variants or derivatives thereof) or antigen-binding fragments, variants, or derivatives thereof of the invention can further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins; see, e.g., international Application Publication Nos, WO92/08495; WO91/14438; WO89/12624; U.S. Pat. No. 5,314,995; and European Patent Application No. EP 0 396 387.

Antibodies (e.g., antigen-binding fragments of antibodies and variants, or derivatives thereof) of the invention, can be composed of amino acids joined to each other by peptide bonds or modified peptide bonds, i.e., peptide isosteres, and can contain amino acids other than the 20 gene-encoded amino acids. Antibodies can be modified by natural processes, such as posttranslational processing, or by chemical modification techniques which are known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification can be present in the same or varying degrees at several sites in a given antibody. Also, a given antibody can contain many types of modifications. Antibodies can be branched, for example, as a result of ubiquitination, and they can be cyclic, with or without branching. Cyclic, branched, and branched cyclic antibodies can result from posttranslation natural processes or can be made by synthetic methods. Modifications include acetylation, acylation, ADP-ribosylation amidation, covalent attachment of flavin, covalent attachment of a lime moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs, 1-12 (1983); Seifter et al., Meth. Enzymol. 182 (1990), 626-646; Rattan et al. Ann. NY Acad. Sci. 663 (1992), 48-62).

The invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the invention, or fragment, derivative, or variant thereof, and a heterologous polypeptide sequence, which fusion protein specifically binds to TDP-43. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. In one embodiment, the $V_H$ and $V_L$ regions of the fusion protein correspond to a single source antibody (or scFv or Fab fragment) which specifically binds TDP-43. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. In one embodiment, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell. Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al. Nature 349 (1991), 164-167); CD44 (Aruffo et al., Cell 61 (1990). 1303-1313); CD28 and B7 (Linsley et al., J. Exp. Med. 173 (1991), 721-730); CTLA-4 (Usley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol, 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, (e.g., intact antibodies, and antigen-binding fragments of antibodies and variants, or derivatives thereof) of the invention can be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies (e.g., intact antibodies, and antigen-binding fragments of antibodies and variants, or derivatives thereof) of the invention can be fused to marker sequences, such as a peptide to facilitate their purification or detection. In particular embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made can be selected empirically to optimize the secretion or binding characteristics of the fusion protein. DNA encoding the fusion protein is then transfected into a host cell for expression.

Antibodies of the invention can be used in non-conjugated form or can be conjugated to at least one of a variety of molecules, e.g., to improve the therapeutic properties of the molecule, to facilitate target detection, or for imaging or therapy of the patient. Antibodies (e.g., intact antibodies, and antigen-binding fragments of antibodies and variants, or derivatives thereof) of the invention can be labeled or conjugated either before or after purification, when purification is performed, in particular, antibodies of the invention can be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins can be coupled to the antibodies by conventional coupling techniques or immunotoxins containing protein toxin portions can be produced as fusion proteins. The antibodies of the invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those of ordinary skill in the art will appreciate that conjugates can also be assembled using a variety of techniques depending on the selected agent to be conjugated. For example, conjugates with biotin are prepared e.g. by reacting an TDP-43 binding polypeptide with an activated ester of biotin such as the biotin N-hydroxysuccinimide ester. Similarly, conjugates with a fluorescent marker can be prepared in the presence of a coupling agent, e.g. those listed herein, or by reaction with an isothiocyanate or fluorescein-isothiocyanate, Conjugates of the of the invention are prepared in an analogous manner.

The invention further encompasses antibodies (e.g., intact antibodies, and antigen-binding fragments of antibodies and variants, or derivatives thereof) of the invention conjugated to a diagnostic or therapeutic agent. The antibodies can be used diagnostically to, for example, demonstrate presence of a neurological disease, to indicate the risk of getting a neurological disease, to monitor the development or progression of a neurological disease, i.e. TDP-43 proteinopathy as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is herein incorporated by reference in its entirety). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are known; see, e.g., Arnon et al., "Monoclonal Antibodies For Immunotargeting Of Drugs In Cancer Therapy", in *Monoclonal Antibodies And Cancer Therapy*, Reisfeld et al., (eds.), pp. 243-56 (Alan R. Liss, Inc. (1985); Hellstrom et al., "Antibodies For Drug Delivery", in *Controlled Drug Delivery* (2nd Ed.), Robinson et al., (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al., (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al., (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv, Rev. 54 (2002), 531; or Weir et al., Biochem. Soc. Transactions 30 (2002), 512.

VI. Compositions and Methods of Use

The invention relates to compositions comprising the aforementioned TDP-43 binding molecule, e.g., antibody or antigen-binding fragment thereof of the invention or derivative or variant thereof, or the polynucleotide, vector or cell of the invention. The composition of the invention can further comprise a pharmaceutically acceptable carrier. Furthermore, the pharmaceutical composition of the invention can comprise further agents such as interleukins or interferons depending on the intended use of the pharmaceutical composition. For example, for use in the treatment of TDP-43 proteinopathy the additional agent can be selected from the group consisting of small organic molecules, anti-TDP-43 antibodies, and combinations thereof. Hence, in a particular embodiment the invention relates to the use of the TDP-43 binding molecule, e.g., antibody or antigen-binding fragment thereof of the invention or of a binding molecule having substantially the same binding specificities of any one thereof the polynucleotide, the vector or the cell of the invention for the preparation of a pharmaceutical or diagnostic composition for prophylactic and therapeutic treatment of a TDP-43 proteinopathy, monitoring the progression of a TDP-43 proteinopathy or a response to a TDP-43 proteinopathy treatment in a subject or for determining a subject's risk for developing a TDP-43 proteinopathy.

Hence, in one embodiment the invention relates to a method of treating neurological disorder characterized by abnormal accumulation and/or deposition of TDP-43 in the brain and the central nervous system, respectively, which method comprises administering to a subject in need thereof a therapeutically effective amount of any one of the aforedescribed TDP-43 binding molecules, antibodies, polynucleotides, vectors or cells of the instant invention. The term "TDP-43 proteinopathy" includes but is not limited to TDP-43 proteinopathies such as argyrophilic grain disease, Alzheimer's disease, Amyotrophic lateral sclerosis (ALS), ALS-Parkinsonism dementia complex of Guam, corticobasal degeneration. Dementia with Lewy bodies, Huntington's disease, Lewy body disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula and Pick's disease as well as other movement disorders, neurodegenerative diseases and disease of the central nervous system (CNS) in general. Unless stated otherwise, the terms neurodegenerative, neurological or neuropsychiatric are used interchangeably herein.

A particular advantage of the therapeutic approach of the invention lies in the fact that the antibodies of the invention are derived from B cells or B memory cells from healthy human subjects with no signs of ALS and/or FTLD and thus are, with a certain probability, capable of preventing a clinically manifest TDP-43 proteinopathies, or of diminishing the risk of the occurrence of the clinically manifest disease, or of delaying the onset of the clinically manifest disease. Typically, the antibodies of the invention also have already successfully gone through somatic maturation, i.e. the optimization with respect to target selectivity and effectiveness in the high affinity binding to the target TDP-43 molecule by means of somatic variation of the variable regions of the antibody.

The knowledge that such cells in vivo, e.g., in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-TDP-43 antibodies of the invention, both its target structure-specific efficiency as therapeutic agent and its decreased probability of side effects significantly increase its clinical probability of success.

The invention also provides a pharmaceutical and diagnostic, respectively, pack or kit comprising one or more containers filled with one or more of the above described ingredients, e.g. anti-TDP-43 antibody, binding fragment, derivative or variant thereof, polynucleotide, vector or cell of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the invention is of course particularly suitable for the risk assessment, diagnosis, prevention and treatment of a disorder which is accompanied with the presence of TDP-43, and in particular applicable for the treatment of neurodegenerative diseases, TDP-43 proteinopathies, argyrophilic grain disease, Alzheimer's disease, Amyotrophic lateral sclerosis (ALS), ALS-Parkinsonism dementia complex of Guam, corticobasal degeneration, Dementia with Lewy bodies, Huntington's disease, Lewy body disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula and Pick's disease.

In a specific embodiment, the composition of invention is in a sterile aqueous solution. In another embodiment, one or more of the components of a composition of the invention have been lyophilized. In an additional embodiment, the composition of the invention does not contain serum. In a further embodiment, one or more antibodies contained in a composition of the invention are recombinantly produced. In another embodiment, the population of antibodies of the invention in the composition constitutes at least 10% of the immunoglobulin population in the composition.

The pharmaceutical compositions of the invention can be formulated according to methods known in the art; see for example Remington: The Science and Practice of Pharmacy (2000) by the University of Sciences in Philadelphia, ISBN 0-683-306472. Examples of suitable pharmaceutical carriers are known in the art and include phosphate buffered saline solutions, water, emulsions, such as oil/water emulsions, various types of wetting agents, sterile solutions etc. Compositions comprising such carriers can be formulated by known conventional methods. These pharmaceutical compositions can be administered to the subject at a suitable dose. Administration of the suitable compositions can be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are adjusted to a pH and isotonic state compatible with the nasal mucous membranes. Formulations for rectal or vaginal ad-ministration can be presented as a suppository with a suitable carrier.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Furthermore, whereas the invention includes the now standard (though fortunately infrequent) procedure of drilling a small hole in the skull to administer a drug of the invention, in one aspect, the binding molecule, especially antibody or antibody based drug of the invention can cross the blood-brain barrier, which allows for intravenous or oral administration.

The dosage regimen will be determined by the attending physician and clinical factors. As is known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 025 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the invention can comprise further agents such as dopamine or psychopharmacologic drugs, depending on the intended use of the pharmaceutical composition.

Furthermore, in a particular embodiment of the invention the pharmaceutical composition can be formulated as a vaccine, for example, if the pharmaceutical composition of the invention comprises an anti-TDP-43 antibody or binding fragment, derivative or variant thereof for passive immunization. It is prudent to expect that the human anti TDP-43 antibodies and equivalent TDP-43 binding molecules of the invention are particularly useful as a vaccine for the prevention or amelioration of TDP-43 proteinopathies such as amyotrophic lateral sclerosis (ALS) argyrophilic grain disease, Alzheimer's disease, ALS-Parkinsonism dementia complex of Guam, corticobasal degeneration. Dementia with Lewy bodies, Huntington's disease, Lewy body disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula, Pick's disease, Machado-Joseph disease and the like.

In one embodiment, it can be beneficial to use recombinant Fab (rFab) and single chain fragments (scFvs) of the antibody of the invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (says) of monoclonal antibody WO-2 which recognizes an epitope in the N-terminal region of Aβ. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and say engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other neuroprotective agents useful for treating a TDP-43 proteinopathy can be desirable. In one embodiment, the additional agent is comprised in the pharmaceutical composition of the invention. Examples of neuroprotective agents which can be used to treat a subject include, but are not limited to, an acetylcholinesterase inhibitor, a glutamatergic receptor antagonist, kinase inhibitors, HDAC inhibitors, anti-inflammatory agents, divalproex sodium, or any combination thereof. Examples of other neuroprotective agents that can be used concomitant with pharmaceutical composition of the invention are described in the art; see, e.g. International Application Publication No. WO2007/011907. In one embodiment, the additional agent is dopamine or a dopamine receptor agonist.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In one embodiment, the therapeutic agent in the composition is present in an amount sufficient to restore or preserve normal behavior and/or cognitive properties in case of ALS and/or FTLD or other TDP-43 proteinopathies.

From the foregoing, it is evident that the invention encompasses any use of an TDP-43 binding molecule comprising at least one CDR of the above described antibody, in particular for diagnosing and/or treatment of a TDP-43 proteinopathies as mentioned above, particularly amyotrophic lateral sclerosis and/or frontotemporal lobar degeneration. In one embodiment, said binding molecule is an antibody of the invention or an immunoglobulin chain thereof. In addition, the invention relates to anti-idiotypic antibodies of any one of the mentioned antibodies described hereinbefore. Anti-idiotypic antibodies are antibodies or other binding molecules which bind to the unique antigenic peptide sequence located on an antibody's variable region near the antigen-binding site and are useful, e.g., for the detection of anti-TDP-43 antibodies in sample of a subject.

In another embodiment the invention relates to a diagnostic composition comprising any one of the above described TDP-43 binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the invention include enzymes, radioisotopes, colloidal metals, fluorescent compounds, chemiluminescent compounds, and bioluminescent compounds; see also the embodiments discussed hereinabove.

By a further embodiment, the TDP-43 binding molecules, in particular antibodies of the invention can also be used in a method for the diagnosis of a disorder in an individual by obtaining a body fluid sample from the tested individual which can be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention can also be used. Thus, the invention relates to an in vitro immunoassay comprising the binding molecule, e.g., antibody or antigen-binding fragment thereof of the invention.

In this context, the invention also relates to means specifically designed for this purpose. For example, an antibody-based array can be used, which is for example loaded with antibodies or equivalent antigen-binding molecules of the invention which specifically recognize TDP-43. Design of microarray immunoassays is summarized in Kusnezow et al., Mol. Cell. Proteomics 5 (2006), 1681-1696. Accordingly, the invention also relates to microarrays loaded with TDP-43 binding molecules identified in accordance with the invention.

In one embodiment, the invention relates to a method of diagnosing a TDP-43 proteinopathy in a subject, the method comprising:

(a) assessing the level of TDP-43 in a sample front the subject to be diagnosed with an antibody of the invention, an TDP-43 binding fragment thereof or an TDP-43 binding molecule having substantially the same binding specificities of any one thereof; and (b) Comparing the level of the TDP-43 to a reference standard that indicates the level of the TDP-43 in one or more control subjects, Wherein a difference or similarity between the level of the TDP-43 and the reference standard indicates that the subject suffers from a TDP-43 proteinopathy.

The subject to be diagnosed can be asymptomatic or preclinical for the disease. In one embodiment, the control subject has a TDP-43 proteinopathy, for example ALS or FTLD, wherein a similarity between the level of TDP-43 and the reference standard indicates that the subject to be diagnosed has a TDP-43 proteinopathy. Alternatively, or in addition as a second control the control subject does not have a TDP-43 proteinopathy, wherein a difference between the level of TDP-43 and the reference standard indicates that the subject to be diagnosed has a TDP-43 proteinopathy. I, the subject to be diagnosed and the control subject(s) are age-matched. The sample to be analyzed can be any body fluid suspected to contain TDP-43, for example a blood, CSF, or urine sample.

The level of TDP-43 can be assessed by any suitable method known in the art comprising, analyzing TDP-43 by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In one embodiment, said in vivo imaging of TDP-43 comprises positron emission tomography (PET), single photon emission tomography (SPECT), near infrared (NIR) optical imaging or magnetic resonance imaging (MRI).

Methods of diagnosing a neurodegenerative disease such as AD, Parkinson's disease, ALS, Huntington's disease, Dementia with Lewy bodies or FTLD for monitoring a TDP-43 proteinopathy progression, and monitoring a TDP-43 proteinopathy treatment using antibodies and related means which can be adapted in accordance with the invention are also described in International Application Publication Nos. WO 2010/111587 and WO2007/011907, which is herein incorporated by reference in its entirety. Those methods can be applied as described but with an TDP-43 specific antibody, binding fragment, derivative or variant of the invention.

These and other embodiments are disclosed and encompassed by the description and examples of the invention. Further literature concerning any one of the materials, methods, uses and compounds to be employed in accordance with the invention can be retrieved from public libraries and databases, using for example electronic devices. For example the public database "Medline" can be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person of ordinary skill in the art and can also be obtained using internet search engines. An overview of patent information in biotechnology and a survey of relevant sources of patent information useful for retrospective searching and for current awareness are given in Berks, TIBTECH 12 (1994), 352-364.

The above disclosure generally describes the invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations can be found at the end of the specification immediately preceding the claims. The contents of all cited references (including literature references, issued patents, published patent applications as cited throughout this application and manufacturer's specifications, instructions, etc.) are hereby incorporated by reference in their entireties; however, there is no admission that any document cited is indeed prior art as to the invention.

A more complete understanding can be obtained by reference to the following specific examples which are provided herein for purposes of illustration only and are not intended to limit the scope of the invention.

EXAMPLES

Material and Methods

Detailed descriptions of conventional methods, such as those employed herein can be found in the cited literature. Unless indicated otherwise below, identification of TDP-43-specific B cells and molecular cloning of TDP-43 antibodies displaying specificity of interest as well as their recombinant expression and functional characterization has been or can be performed as described in the Examples and Supplementary Methods section of International Application PCT/EP2008/000053 published as WO2008/081008, each of which are herein incorporated by reference in its entirety.

Human TDP43 Antibody Screening

ELISA 96 well half area microplates (Corning) were coated with either:
(a) recombinant full-length His-tagged human TDP-43 (Biogen Idec, USA); or
(b) a synthetic peptide consisting of residues 390-414 of the C-terminal domain of TDP-43 with phosphorylation modification at residues 409 and 410 (Shafer-N, DK)

at a concentration of 5 µg/ml and 3.3 µg/ml, respectively, in carbonate ELISA coating buffer (pH 9.6) overnight at 4° C.

Plates were washed in PBS-TWEEN (polysorbate surfactant) (pH 7.6) and non-specific binding sites were blocked for 1 hr. at room temperature with PBS-T containing 2% BSA (Sigma, Buchs, Switzerland). B cell conditioned medium was transferred from memory B cell culture plates to ELISA plates and incubated for 1 hr. at room temperature. ELISA plates were washed in PBS-T and then incubated with horse radish peroxidase (HRP)-conjugated anti-human immunoglobulins polyclonal antibodies (Jackson ImmunoResearch, USA). After washing with PBS-T, binding of human antibodies was determined by measurement of HRP activity in a standard colorimetric assay.

MSD

Standard 96 well 10-Spot MULTI-SPOT plates (Meso Scale Discovery, USA) were coated with a mixture of TDP-43 protein fragments corresponding to amino acids 1-259, 260 to 277 and 350-366 (Abeam plc, UK), respectively. 10 µg/ml of each peptide was used and formulated in PBS. Non-specific binding sites were blocked for 1 hr. at room temperature with PBS-T containing 3% BSA followed by incubation with B cell conditioned medium for 1 hr. at room temperature. Plates were washed in PBS-T and then incubated with SULFO-Tag conjugated anti-human polyclonal antibody (Mesoscale Discovery, USA). After washing with PBS-T, bound antibody was detected by electrochemiluminescence measurement using a SECTOR Imager 6000 (Meso Scale Discovery, USA).

Molecular Cloning of Human TDP-43 Antibodies

Samples containing memory B cells were obtained from healthy human subjects. Living B cells of selected memory B cell cultures were harvested, mRNA was isolated and cDNA was prepared by Reverse Transcriptase (Clontech, USA). Immunoglobulin heavy and light chain sequences were then obtained using a nested PCR approach.

A combination of primers representing all sequence families of the human immunoglobulin germline repertoire are used for the amplifications of leader peptides V-segments and J-segments. The first round amplification is performed using leader peptide-specific primers in 5'-end and constant region-specific primers in 3'-end (Smith et al., Nat. Protoc. 4 (2009), 372-384). For heavy chains and kappa light chains, the second round amplification is performed using V-segment-specific primers at the 5'-end and J-segment-specific primers at the 3' end. For lambda light chains, the second round amplification is performed using V-segment-specific primers at the 5'-end and a C-region-specific primer at the 3' end (Marks et al., Mol. Biol. 222 (1991), 581-597: de Haard et al., J. Biol. Chem. 26 (1999), 18218-18230).

Identification of the antibody clone with the desired specificity is performed by re-screening on ELISA upon recombinant expression of complete antibodies. Recombinant expression of complete human IgG1 antibodies or chimeric IgG2a antibodies is achieved upon insertion of the variable heavy and light chain sequences "in the correct reading frame" into expression vectors that complement the variable region sequence with a sequence encoding a leader peptide at the 5'-end and with a sequence encoding the appropriate constant domain(s) at the 3'-end. To that end the primers contained restriction sites designed to facilitate cloning of the variable heavy and light chain sequences into antibody expression vectors. Heavy chain immunoglobulins are expressed by inserting the immunoglobulin heavy chain RT-PCR product in frame into a heavy chain expression vector bearing a signal peptide and the constant domains of human immunoglobulin gamma 1 or mouse immunoglobulin gamma 2a. Kappa light chain immunoglobulins are expressed by inserting the kappa light chain RT-PCR-product in frame into a light chain expression vector providing a signal peptide and the constant domain of human kappa light chain immunoglobulin. Lambda light chain immunoglobulins are expressed by inserting the lambda light chain RT-PCR-product in frame into a lambda light chain expression vector providing a signal peptide and the constant domain of human or mouse lambda light chain immunoglobulin.

Functional recombinant monoclonal antibodies are obtained upon co-transfection into HEK293 or CHO cells (or any other appropriate recipient cell line of human or mouse origin) of an heavy-chain expression vector and a kappa or lambda Ig-light-chain expression vector. Recombinant human monoclonal antibody is subsequently purified from the conditioned medium using a standard Protein A column purification. Recombinant human monoclonal antibody can be produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)$_2$ and scFv can also be generated from these Ig-variable regions.

Purification and Characterization of His-Tagged TDP-43

An expression vector for 6×His-tagged TDP-43 (pCGB026) was generated by cloning the TDP-43 sequence into the pRSET A expression vector (Invitrogen). BL21 STAR (DE3)pLysS *E. coli* cells (Invitrogen) were transformed with pCGB026. Following growth at 37° C. to approximately 1 OD in a 1 L shake flask containing LB broth, IPTG was added to 0.5 mM and the cells were grown overnight at 18° C. Cells were pelleted by low-speed centrifugation, the supernatant was decanted and the cell pellets were frozen for storage at −20° C.

Cell pellets were equilibrated to room temperature and resuspended in 50 mL of 50 mM Tris-HCl pH 7.5, 20 mM imidazole, 150 mM NaCl, containing protease inhibitors (PI) (final concentration PI: 1 mM PMSF, 5 µM pepstatin A, 1 mM benzamide, 10 µM bestatin, 10 µM E64, 20 µM leupeptin, 1.5 µM aprotinin). Following homogenization for 5 min. to break up large particles, the cells were disrupted under high pressure using a Microfluidizer (Microfluidics, Inc.). The cell lysate was centrifuged for 30 min. at 10,000 rpm at 4° C. The pellet, containing insoluble his-tagged TDP-43, was resuspended in 5 mL B-PER solution (Thermo Scientific) containing 2 mM MgCl$_2$, COMPLETE EDTA-free protease inhibitor tablets (Roche), 100 µg/mL lysozyme, 5 U/mL DNase (Thermo Scientific) and incubated for 15 min, at room temperature. Additional B-PER/2 mM MgCl$_2$/PI tablet solution was added to a final volume of 50 mL and the mixture was centrifuged for 10 min. at 10,000 rpm. The isolated pellet was washed twice in 20 mL of 50 mM Tris-HCl pH 7.5, 20 mM imidazole, 150 mM NaCl, PI buffer, followed by centrifugation for 10 min, at 10,000 rpm. The isolated pellet was then resuspended in 8 M urea, 20 mM sodium phosphate pH 7.8 containing PI, mixed for 5 min. by homogenization and centrifuged at 10,000 rpm for 10 min.

The supernatant was isolated, filtered through a 0.45 µm filter, combined with 4 mL of Ni-NTA resin (Invitrogen) equilibrated in 8 M urea, 20 mM sodium phosphate pH 7.8, 0.5 M NaCl, with PI, and incubated while rocking overnight at 4° C. The flow-through was collected and the resin was washed with 10 column volumes of 8 M urea, 20 mM sodium phosphate pH 5.3, 0.5 M NaCl. His-tagged TDP-43 was eluted in 0.5 column volume fractions with 8 M urea, 20 mM sodium phosphate pH 4, 0.5 M sodium chloride. Peak fractions were pooled, and protein concentration was determined using UV spectrometry. The total purified yield was ~8 mg/L culture.

SDS-PAGE analysis of the purified protein showed a major band at ~47 kDa (data not provided), consistent with the predicted molecular mass of 46.5 kDa. Intact mass spectrometry on the purified protein indicated a major peak at 46538 Da, consistent with the predicted mass of 46529.9 Da. The ability of known commercially available antibodies against TDP-43 to bind the purified protein was determined by ELISA. Mouse monoclonal antibody 2E2-D3, recognizing amino acids 205-222 (Zhang, H.-X. et al., 2008, Neuroscience Lett., 434, 170-74), and rabbit polyclonal antibodies A260 and G400, recognizing sequences around amino acids Ala-260 and Gly-400, respectively, all bound to the purified His-tagged TDP-43 (data not provided).

Recombinant Expression of Human TDP-43 Domains

The human TDP-43 domain coding sequences were amplified by PCR from the full length cDNA sequence (Q13148, TARDBP_HUMAN) and cloned into the expression vector pRSET-A (Invitrogen, USA), The four expression vectors (His-huTDP-43 domain I, His-huTDP-43 domain II, His-huTDP-43 domain III and His-huTDP-43 domain IV) are coding for the four TDP-43 domains: the N-terminal domain (amino acid residues 2-106 of SEQ ID NO:94), the RNA binding domain 1 (amino acid residues 99-204 of SEQ ID NO:94), the RNA binding domain 2 (amino acid residues 183-273 of SEQ ID NO:94) and the Glycine-rich domain (amino acid residues 258-414 of SEQ ID NO:94), respectively. DNA constructs comprising the cDNA encoding the TDP-43 domains under the control of the T7 promoter were used to transform an appropriate *Escherichia coli* strain such as BL21(DE3) (New England Biolabs, USA) and expression of 15 ml cell culture was induced by the addition of 0.5 mM isopropyl β-D-thiogalactopyranoside (IPTG). Cells were harvested after 4 hrs. induction at 37° C. and then resuspended in 1 ml 100 mM KCl, 50 mM HEPES, 2 mM EGTA, 1 mM MgCl$_2$, 1 mM Dithiothreitol, 0.1 mM PMSF, 10% glycerol and 0.1 mg/ml lysozyme, pH 7.5, followed by sonification. Soluble and insoluble fractions were collected after centrifugation at 9000 rpm at 4° C. for 45 min. Similarly, 9000 g supernatant from mock *Escherichia coli* was collected. When required (TDP-43 domain IV), insoluble fraction was solubilized in 1 ml 8M Urea, 20 mM Tris, 200 mM KCl and 1 mM β-Mercaptoethanol. Soluble and solubilized fractions were loaded onto Ni-NTA SUPERFLOW Columns (Qiagen, USA) and His-TDP-43 domains were purified according to manufacturer's protocol. Purity grade of recombinant proteins was estimated by SDS-PAGE and Coomassie staining. Concentration of purified proteins was determined by 280 nM absorbance measurement.

96 well microplates (Corning) were coated with human full length TDP-43, TDP-43 domain I (amino acid residues 2-106 of SEQ ID NO:94), TDP-43 domain II (amino acid residues 99-204 of SEQ ID NO:94), TDP-43 domain III (amino acid residues 183-273 of SEQ ID NO:94), TDP-43 domain IV (amino acid residues 258-414 of SEQ ID NO:94) or with a synthetic peptide covering residues 390 to 414 of the C-terminal domain of TDP-43 (see, SEQ ID NO:94) with phosphorylation modification at residues 409/410 (Schafer-N, DK) diluted to a concentration of 6.6 µg/ml or 3.3 µg/ml, respectively, in carbonate ELISA coating buffer (pH 9.6) overnight at 4° C. Non-specific binding sites were blocked for 1 hr. at room temperature with PBST (Phosphate Buffered Saline TWEEN) containing 2% BSA (Sigma, Buchs, Switzerland). Antibodies were incubated 1 hr. at room temperature. Binding was determined using either a donkey anti-human IgGγ-specific antibody conjugated with HRP (Jackson ImmunoResearch, USA) or a goat-anti mouse IgG (H+L)-specific secondary antibody conjugated with HRP (Jackson ImmunoResearch, USA), followed by measurement of HRP activity in a standard colorimetric assay.

Western Blot Analysis

Recombinant full length TDP-43, TDP-43 domain I (amino acid residues 2-106 of SEQ ID NO:94), TDP-43 domain II (amino acid residues 99-204 of SEQ ID NO:94), TDP-43 domain III (amino acid residues 183-273 of SEQ ID NO:94), TDP-43 domain IV (amino acid residues 258-414 of SEQ ID NO:94), 300 ng of each, were resolved by SDS-PAGE (NUPAGE 12% Bis-Tris Gel; Invitrogen, Basel, Switzerland) followed by electroblotting on nitrocellulose membranes. Non-specific binding sites were blocked for 1 hr. at room temperature with phosphate buffered saline TWEEN containing 2% BSA (Sigma, Buchs, Switzerland). Blots were incubated overnight with primary antibodies (10 nM) followed by either a donkey anti-human IgGγ-specific secondary antibody conjugated with HRP (Jackson ImmunoResearch, USA) or a goat-anti mouse IgG (H+L)-specific secondary antibody conjugated with HRP (Jackson ImmunoResearch, USA). Blots were developed using ECL and ImageQuant 350 detection (GE Healthcare, Otelfingen, Switzerland).

Two-Trial Y-Maze Task

Improvement of working memory in antibody treated TDP-43 proteinopathy mouse model can be tested using a two-trial Y-maze task (e.g., Pennanen, Genes Brain Behav. 5 (2006), 369-79, which is herein incorporated by reference in its entirety). The three arms of the maze are 22 cm long, 5 cm wide and 15 cm deep. Black and white abstractive clues are placed on a black curtain surrounding the maze. Experiments are conducted with an ambient light level of 6 lux during the dark phase. Each experiment comprises a training session and an observation session. During the training session, a mouse is assigned to two of the three arms (the start arm and the second arm), which can be freely explored during 4 min, with no access to the third arm (the novel arm). The mouse is then removed from the maze and kept in a holding cage for 1.5-5 min, while the maze is thoroughly cleaned with 70% ethanol to remove any olfactory clues. The mouse is then put back again in the maze for observation with all three arms accessible for 4 min. The sequence of entries, the number of entry to each arm and the time spent in each arm is recorded. From that the ratio of time spent in the novel third arm over the average of time spent in the other two arms (start arm and second arm) is calculated and compared among different treatment groups in tauopathy mouse model and corresponding control wild type mice. Rodents typically prefer to investigate a new arm of the maze rather than returning to one that was previously visited. Effects of the antibodies can be monitored in regard of regaining this preference by treated TDP-43 proteinopathy model mice in comparison to non-discriminative behavior of untreated mice due to their disorder-related working memory impairment. Therefore, a ratio close to 1 indicates impaired working memory. A higher ratio indicates better working memory. Impaired working memory in a TDP-43 proteinopathy model mice is considered to be due to TDP-43 pathology resulting from the overexpression of human TDP-43. Therefore a significantly higher ratio observed in anti-TDP-43 antibody treated mice than in the control mice will indicate that the anti-TDP-43 antibody has therapeutic effect on TDP-43 pathology.

Pole Test

Mice are tested at the beginning of the dark phase when they are most active. The pole is made of a wooden stick with 50 cm length and 1 cm width covered with cloth to facilitate climbing. The base of the pole is placed in the home cage of the mouse. The mouse is placed on the top of the pole and the time to orient downwards and time to climb down to the home cage is recorded over 5 trials with 30 min intertrial intervals. The best performance trial is analyzed.

Elevated Plus Maze Test

Mice are tested at the beginning of the dark phase when they are most active. Testing is performed in dim light (40 lux). The elevated plus maze consists of two open and two closed arms (arm length: 30 cm; width: 5 cm). Open arms have a small 1 cm edge and the closed arms are bordered by a 15 cm wall. At the beginning of the task, mice are placed in the center of the elevated plus maze facing an open arm. Mice are video-tracked while exploring the maze for 5 min. The time spent in the open and closed arms and the distance covered are measured and analyzed.

Example 1

Human TDP-43 Antibody Binding Analysis by ELISA and Western Blotting

Direct ELISAs 96 well microplates (Corning) were coated with polypeptides comprising TDP-43 amino acid residues 2-106 of SEQ ID NO:94 (TDP-43 domain I), residues 99-204 of SEQ ID NO:94 (TDP-43 domain 11), residues 183-273 of SEQ ID NO:94 (TDP-43 domain III), residues 258-414 of SEQ ID NO:94 (TDP-43 domain IV), residues 2-414 of SEQ ID NO:94 (full-length TDP-43) and a synthetic polypeptide containing residues 390-414 with phosphorylation modification at residues 409/410 of SEQ ID NO:94. The polypeptides were coated onto ELISA plates at equal coating concentration of 6.6 µg/ml (recombinant TDP-43 and TDP-43 fragments) or 3.3 ml (synthetic peptides). Binding of the human-derived antibodies was determined by direct ELISA.

Antibodies NI-205.51C1 (FIG. 2A) and NI-205.3F10 (FIG. 2C) bound specifically to TDP-43 domain III (amino Kid residues 183-273 of SEQ ID NO:94). Antibodies NI-205.8A2 (FIG. 2D), NI-205.15F12 (FIG. 2E), NI-205.25F3 (FIG. 2G) and NI-205.21G1 (FIG. 2I) bound specifically to TDP-43 domain IV (amino acid residues 258-414 of SEQ ID NO:94). Antibody NI-205.87E7 (FIG. 2H) bound specifically to TDP-43 domain I (amino acid residues 2-106 of SEQ ID NO:94). Antibodies NI-205.21G2 (FIG. 2B) and NI-205.113C4 (FIG. 2F) bound specifically to TDP-43 domain II (amino acid residues 99-204 of SEQ ID NO:94). All human derived TDP-43 specific antibodies specifically recognized full-length TDP-43. To control for coating efficiency, of the different TDP-43 domains, commercially available antibodies binding to full-length TDP-43 and a specific TDP-43 domain were used: Ab50930 (Abeam, UK). TDP-43 domain-1; TARDBP monoclonal antibody (M01), clone 2E2-D3 (Abnova, Taiwan), TDP-43 domain III, and Ab82695 (Abeam, US), TDP-43 domain IV. Control antibodies bound to full-length TDP-43 and their specific TDP-43 domain.

Binding to Distinct TDP-43 Domains by Western Blot

Recombinant full length TDP-43, TDP-43 domain I (amino acid residues 2-106 of SEQ ID NO:94), TDP-43 domain II (amino acid residues 99-204 of SEQ ID NO:94), TDP-43 domain III (amino acid residues 183-273 of SEQ ID NO:94), and TDP-43 domain IV (amino acid residues 258-414 of SEQ ID NO:94) were resolved by SDS-PAGE. Commercially available TDP-43 specific antibody TARDBP (M01), clone 2E2-D3 (Abnova, Taiwan) was used as positive control for human TDP-43 detection whereas, an anti-human IgG Fcγ-specific antibody was used as a negative control. Binding of the human-derived antibodies to specific TDP-43 domains was determined by Western Blot analysis.

Western blotting indicated that antibodies: (a) NI-205.51C1 and NI-205.3F10 antibodies bound specifically to TDP-43 domain III (amino acid residues 183-273 of SEQ ID NO:94); (b) NI-205.8A2 and NI-205.21G1 bound specifically to TDP-43 domain IV (amino acid residues 258-414 of SEQ ID NO:94); (c) NI-205.21G2 specifically recognized TDP-43 domain II (amino acid residues 99-204 of SEQ ID NO:94); (d) NI-205.51C1, NI-205.3F10, NI-205.8A2, NI-205.21G1, NI-205.21G2, recognized full length human TDP-43 in addition to a domain of TDP-43; and (e) human-derived antibodies NI-205.25F3, NI-205.15F12 and NI-205.87E7 recognized full length TDP-43 but did not appear to bind a specific TDP-43 domain (data not provided). Additionally, the antibodies NI-205.68G5 and NI-205.20A1, that preferentially or exclusively bound the phospho-TDP-43 C-terminal peptide (see Example 2), did not appear to recognize recombinant full length TDP-43 or any of its fragments (data not provided).

Example 2

$EC_{50}$ Determination for Human TDP-43 Binding Antibodies

Determination of Half Maximal Effective Concentration ($EC_{50}$)

To determine the half maximal effective concentration ($EC_{50}$) of the human-derived TDP-43-specific antibodies for human TDP-43 and to evaluate target-specificity, 96 well microplates (Corning) were coated with recombinant full length TDP-43 (Biogen Idec, USA), *Escherichia coli* extract and BSA (Sigma, Buchs, Switzerland), diluted to a concentration of 5 µg/ml in carbonate ELISA coating buffer (pH 9.6) overnight at 4° C. Alternatively, 96 well half area microplates (Corning) were coated with a synthetic peptide covering residues 390 to 414 of the C-terminal domain of TDP-43 with phosphorylation modification at residues 409/410 (Schafer-N, DK) and BSA (Sigma, Buchs, Switzerland), diluted to a concentration of 3.3 µg/ml in carbonate ELISA coating buffer (pH 9.6) overnight at 4° C. Non-specific binding sites were blocked for 1 hr. at room temperature with PBS containing 2% BSA (Sigma, Buchs, Switzerland), Human TDP-43-specific antibodies were diluted to the indicated concentrations and incubated 1 hr. at room temperature. Binding was determined using a donkey anti-human IgGγ-specific secondary antibody conjugated with HRP (Jackson ImmunoResearch, USA), followed by measurement of HRP activity in a standard colorimetric assay. $EC_{50}$ values were estimated by a non-linear regression using GraphPad Prism software (San Diego, USA).

As disclosed in Table 4, antibodies NI-205.51C1 and NI-205.21G2 bind to human TDP-43 with high affinity at subnanomolar $EC_{50}$ of 180 pM and 240 pM, respectively. No binding was observed to the phospho-TDP-43 C-terminal peptide for these antibodies, Antibodies NI-205.3F10, NI-205.8A2, NI-205.15F12, NI-205.113C4, NI-205.25F3, and NI-205.87E7 bound to human TDP-43, but not to the phospho-TDP-43 C-terminal peptide. The EC values of these antibodies for human TDP-43 proteins ranged from 1 to 18 nM. NI-205.21G1 bound to full-length TDP-43 at 4.1 nM $EC_{50}$ and recognized phosphor-TDP-43 C-terminal peptide with lower affinity at 49.5 nM $EC_{50}$. Antibodies NI-205.68G5 and NI-205.20A1 showed preferential or exclusive binding to the phosphor-TDP-43 C-terminal peptide at 16.9 and 15.8 nM $EC_{50}$, respectively, suggesting that phosphorylation of serine at position 409 and/or serine at position 410 of TDP-43 is required thr the binding by NI-205.68G5 and NI-205.20A1.

TABLE 4

Antibody Affinity for TDP-43 and phosphorylated TDP-43

| Antibody | Full-length TDP-43 $EC_{50}$ (nM)] | Phospho-TDP-43 Peptide $EC_{50}$ (nM) |
|---|---|---|
| NI-205.51Cl | 0.18 | N.A. |
| NI-205.21G2 | 0.24 | N.A. |

TABLE 4-continued

Antibody Affinity for TDP-43 and phosphorylated TDP-43

| Antibody | Full-length TDP-43 $EC_{50}$ (nM)] | Phospho-TDP-43 Peptide $EC_{50}$ (nM) |
|---|---|---|
| NI-205.3F10 | 1.4-2.8 | N.A. |
| NI-205.8A2 | 7.2 | N.A. |
| NI-205.15F12 | 7.2 | N.A. |
| NI-205.113C4 | 13.2 | N.A. |
| NI-205.25F3 | 13.3 | N.A. |
| NI-205.87E7 | 17.2 | N.A. |
| NI-205.21G1 | 4.1 | 49.5 |
| NI-205.68G5 | >100 | 16.9 |
| NI-205.20A1 | N.A. | 15.8 |

$EC_{50}$ binding of human derived TDP-43 binding antibodies to recombinant TDP-43 and phosphor-TDP-43 peptide.

Example 3

Epitope Mapping with Synthetic Peptides

Scans of overlapping peptides were used to map the epitopes within the human TDP-43 protein that are recognized by the human-derived TDP-43 specific antibodies. Pepscan membranes (PEPSPOT, JPT Peptide Technologies, Berlin, Germany) with 101 linear 15mer peptides of 11 amino acid overlapping sequences that collectively represent the entire sequence of human TDP-43 (Q13148, TAR-DBP_HUMAN), The peptides were spotted onto nitrocellulose membranes that were then activated for 5 min. in methanol and subsequently washed at room temperature in TBS for 10 min. Non-specific binding sites were blocked for 2 hours at room temperature with ROTI-Block (Carl Roth GmbH Co. KG, Karlsruhe, Germany). Human-derived TDP-43 specific antibodies (1 µg/ml) were incubated for 3 hours at room temperature in ROTI-Block. Binding of primary antibody was determined using HRP conjugated donkey-anti human IgGγ-specific secondary antibody (Jackson ImmunoResearch, USA). Blots were developed using ECL and ImageQuant 350 detection (GE Healthcare, Otelfingen, Switzerland). Table 4 summarizes the identified binding epitopes for the different human-derived TDP-43-specific antibodies identified using PEPSPOT.

TABLE 5

Identified binding epitopes within the human TDP-43 protein sequence

| Antibody | Binding epitope | |
|---|---|---|
| NI-205.3F10 | 213-QYGDVMDVFIP-223 | (SEQ ID NO: 123) |
| NI-205.8A2 | 381-AAIGWGSASNA-391 | (SEQ ID NO: 124) |
| NI-205.51C1 | 201-DMTEDELREFF-211 | (SEQ ID NO: 125) |
| NI-205.87E7 | 9-EDENDEP-15 | (SEQ ID NO: 126) |
| NI-205.113C4 | 133-VQVKKDL-139 | (SEQ ID NO: 127) |
| NI-205.21G2 | 121-KEYFSTF-127 | (SEQ ID NO: 128) |

Example 4

Binding of Human Recombinant TDP-43 Antibodies to Pathologic Forms of TDP-43 in Human Spinal Cord and Brain Tissue For validation of TDP-43 antibody-binding capacity, spinal cord and brain sections derived from human ALS patients or patients with FTLD were used. Antibody binding to TDP-43 pathology was assessed by immunohistochemical staining. Binding of human recombinant TDP-43 antibodies was characterized on human FTLD-TDP-43 case tissue (10 patient cases, 7 control cases). Immunohistochemistry was performed on 5 um thick paraffin embedded sections, and included the use of EDTA-based epitope retrieval prior to conducting otherwise standard immunoperoxidase procedures with Elite ABC kits (Vector Laboratories) with DAB (Pierce). The following primary antibodies were used: mouse monoclonal antibody 2E2-D3 raised against human TDP-43 (Abnova) as a positive control; recombinant human TDP-43 antibodies described here/above NI205.3F10, NI205.51C1, NI205.21G2, NI205.8A2, NI205.15F12, NI205.25F3, NI205.87E7, NI205.21G1, NI205.68G5, NI205.20A1. Sections were counterstained with Haematoxylin to reveal cell nuclei.

The antibodies NI205.8A2, NI205.3F10, NI205.21G2, and NI205.21G1 preferentially bound to cytoplasmic TDP-43 (i.e., pathologic forms of TDP-43) over nuclear TDP-43. By contrast, the commercially available positive control antibody, 2E2 (Abnova, Taiwan) was observed to bind both nuclear and cytoplasmic TDP-43. Interestingly, the binding of the antibody NI205.21G1 demonstrated very specific binding that appears to be comparable to the binding observed for control antibodies that recognize phosphorylated TDP-43 (FIGS. 11E and H).

Example 5

In Vivo Validation of TDP-43 Antibody

Experiments for preclinical validation of the TDP-43 antibodies are performed in mouse models of TDP-43 proteinopathy, Human TDP-43 antibodies are administered by peripheral injection or intraventricular brain infusion via osmotic minipumps. Treatment effects are monitored by analysis of blood and CSF samples, and analysis of body weight, general clinical impression and signs of motor or cognitive impairment as seen through for example, though behavioral tests including open field, Y-maze, elevated plus maze, novel, object recognition, grip strength, paw grip strength endurance, pole test, challenging beam walk, rotarod, or otherwise known in the art.

Upon completion of the treatment studies, changes in TDP-43 levels in collected blood and CSF are measured and brain and spinal cord tissues are evaluated by quantitative immunohistochemical and biochemical techniques for brain and spinal cord content of physiological and pathological TDP-43 and general neuropathology.

Preclinical models useful for validating the antibodies and other TDP-43 binding molecules of the invention include the TDP-43-A315T mouse model system as described by Wegorzewska et al., Proc. Natl. Acad. Sci. U.S.A. 106 (2009), 18809-14. The A315T mouse is a transgenic model of TDP-43 proteinopathy, wherein the phenotype of the mice shows features of both ALS and frontotemporal lobar degeneration with ubiquitin aggregates (FTLD-U).

Further suitable models include the B6.Cg-Tg (SOD1*G93A)1Gur/J mouse model system as described by Gurney et al., Science 264 (1994), 1772-75. This mouse line expresses the G93A mutant form of the human superoxide dismutase 1 and develops signs of motor neuron disease followed by progression to death within 6 to 8 months. These mice show a characteristic redistribution of TDP-43 to the cytoplasm of motor neurons and the occurrence of TDP-43 immunoreactive inclusions and are therefore a suitable model to study pharmacological interventions targeting TDP-43; see e.g., Shan et al., Neuropharmacol. Letters 458 (2009), 70-74.

Further experiments for validating the TDP-43 antibodies are performed in the TDP43WT mouse model system as described by Wils et al., Proc. Natl. Acad. Sci. USA. 106 (2010), 3858-63. This mouse line expresses wild type human TDP-43 and develops degeneration of cortical and spinal motor neurons and development of spastic quadriplegia reminiscent of ALS. A dose-dependent degeneration of nonmotor cortical and subcortical neurons characteristic of PIED is also observed in this mouse line. Neurons in the affected spinal cord and brain regions show accumulation of TDP-43 nuclear and cytoplasmic aggregates that are both ubiquitinated and phosphorylated as observed in ALS/FTLD patients.

Further experiments for validating the TDP-43 antibodies are performed in an independent model of motor neuron disease, the Wobbler mouse model (B6.B-Vps54wr/J, available from the Jackson Laboratories) as described by Duchen and Strict, J. Neurol. Neurosurg. Psychiatry 31 (1968), 535-42. This mouse model was reported to display extensive intracellular ubiquitin inclusions and abnormal cytoplasmic distribution of TDP-43 reminiscent to sporadic ALS, see e.g., Dennis and Citron, Neuroscience 185 (2009), 745-50.

Further experiments for validating the TDP-43 antibodies are performed in recently characterized TDP-43_G348C transgenic mice overexpressing human genomic TDP-43_G348C under the control of the endogenous promoter. Swamp et al. Brain 134 (2011), 2610-2626.

Further experiments for validating the TDP-43 antibodies are performed in model systems, including transgenic cell lines and transgenic animals, that express or overexpress TDP-43, TDP-43 mutants, such as C-terminal truncations of TDP-43, TDP-43 mutations seen in a patient population, or Mutants that effect cellular localization, e.g. nuclear localization of TDP-43. TDP-43 model systems, e.g., cell lines and animal models, for validating the TDP-43 antibodies further include systems with demonstrated TDP-43 upregulation or accumulation resulting from the changes in the expression of a different gene, e.g. the Wobbler mouse and models with down-regulation of progranulin. In one embodiment, experiments for validating the TDP-43 antibodies are performed in mice expressing human TDP-43 with a defective nuclear localization signal in the forebrain (Igaz et al., J Clin Invest, 121(2):726-38 (2011)); transgenic mice that selectively express 25-kDa C-terminal fragment of TDP-43 in neurons Caccamo et al., Am J Pathol, 180(1): 293-302 (2012)), transgenic mice that conditionally express wild-type human TDP-43 (hTDP-43) in the forebrain (Cannon et al., Acta Neuropathol. 123(6):807-23 (2012)), and transgenic mice with ubiquitous expression of wild-type and disease-causing versions of human VCP/p97 (Custer et al., Hum Mol Genet. 19(9):1741-55 (2010)). In another embodiment, experiments for validating the TDP-43 antibodies are performed in mice transfected with an AAV vector encoding wild type TDP-43, nuclear localization signal defective TDP-43, or a truncated C-terminal fragment of TDP-43 comprising residues 220-414 of SEQ ID NO: 94, Tatom et al., Mol. Ther. 17 (2009), 607-613.

Chronic Efficacy Study:

To assess the pharmacological effects of the human anti-TDP-43 antibodies disclosed herein, TDP-43_G348C transgenic mice (Swarup et al., Brain 134 (2011), 2610-2626) are treated weekly with 10 mg/kg i.p. injection of a human anti-TDP-43 antibody or vehicle control for a period of 16-24 weeks. After 12 weeks of treatment, blood samples are collected by tail vein bleeding. The serum anti-TDP-43 antibody levels are determined by ELISA. After 12 weeks and 22 weeks of treatment, neurological and cognitive/motor behavior is evaluated using open field test, Y-maze test, elevated plus maze test, novel object recognition test, grip strength test, paw grip strength endurance (PAGE) test, pole test, challenging beam walk test, or rotarod test. The neurological and cognitive/motor behavior test results for antibody treated and control animals are compared. Improved performance of antibody treated animals indicates therapeutic efficacy of the anti-TDP-43 antibody.

Acute Efficacy Study:

TDP-43_G348C transgenic mice (Swarup et al., Brain 134 (2011), 2610-2626) are treated with 1-4 i.p. injections of up to 50 mg/kg anti-TDP-43 antibody or vehicle control within a period of one week. At the end of the treatment period, blood samples are collected by tail vein bleeding. The serum anti-TDP-43 antibody levels are determined by ELISA. At the end of the 1-week treatment period, neurological and cognitive/motor behavior is evaluated using open field test, Y-maze test, elevated plus maze test, novel object recognition test, grip strength test, paw grip strength endurance (PAGE) test, pole test, challenging beam walk test, or rotarod test. The neurological and cognitive/motor behavior test results for antibody treated and control animals are compared. Improved performance of antibody treated animals indicates therapeutic efficacy of the anti-TDP-43 antibody.

Example 6

Determination of Binding Affinity ($EC_{50}$) for Human TDP-43 Antibodies by Direct ELISA The half maximal effective concentration ($EC_{50}$) of the human-derived TDP-43-specific antibodies for human TDP-43 and their target target-specificity was determined substantially as described in Example 2 above. Briefly, 96 well microplates (Corning) were coated with recombinant full length TDP-43 (Biogen Idec, USA), *Escherichia coli* extract and BSA (Sigma, Buchs, Switzerland), diluted to a concentration of 5 µg/ml in carbonate ELISA coating buffer (pH 9.6) overnight at 4° C. Alternatively, 96 well half area microplates (Corning) were coated with a synthetic peptide covering residues 390 to 414 of the C-terminal domain of TDP-43 with phosphorylation modification at residues 409/410 (Schafer-N, DK) and BSA (Sigma, Buchs, Switzerland), diluted to a concentration of 3.3 µg/ml in carbonate ELISA coating buffer (pH 9.6) overnight at 4° C. Non-specific binding sites were blocked for 1 hr, at room temperature with PBS containing 2% BSA (Sigma, Buchs, Switzerland). Human TDP-43-specific antibodies were diluted to the indicated concentrations and incubated 1 hr. at room temperature. Binding was determined using a donkey anti-human IgGγ-specific secondary antibody conjugated with HRP (Jackson ImmunoResearch, USA), followed by measurement of HRP activity in a standard colorimetric assay. $EC_{50}$ values were estimated by a non-linear regression using GraphPad Prism software (San Diego, USA). Exemplary titration curves obtained with the 41D1, 21G1, 31D2, and 8F8 antibodies are shown in FIG. 4.

As disclosed in Table 6, antibodies NI-205.41D1 (FIGS. 4A and E), NI-205.51C1 and NI.205-2102 bound to human TDP-43 with high affinity at subnanomolar $EC_{50}$ of 60 pM, 180 pM and 240 pM, respectively. No binding was observed to the phospho-TDP-43 C-terminal peptide. Antibodies NI-205.1A9, NI-205.3F10, NI-205.14W3, NI-205.98H6, NI-205.44B2, NI-205.9E12A, NI-205.8A2, NI-205.15F12, NI-205.10D3, NI-205.38H2, NI-205.29E11, NI-205.9E12D, NI-205.31C11, NI-205.113C4, NI-205.25.25F3, NI-205.10H7, NI-205.8C10, and NI-205.87E7 bound to human TDP-43 but not to the phospho-TDP-43 C-terminal peptide with nanomolar $EC_{50}$. For these antibodies $EC_{50}$ values ranged from 1 to 18 nM (see Table 6), Antibody NI-205.2101 (FIGS. 4B and F) bound to full length TDP-43 at 4.1 nM $EC_{50}$ and recognized phospho-TDP-43 C-terminal peptide with lower affinity at 49.5 nM $EC_{50}$. Antibodies NI-205.31D2 (FIGS. 4C and G), NI-205.14H5, NI-205.36D5, NI-205.19G5 and NI-205.68G5 showed preferential binding to the phospho-TDP-43 C-terminal peptide with $EC_{50}$ values that ranged from 0.7 to 17 nM (see Table 6). In contrast, antibodies NI-205.8F8, NI-205.8F8 (FIGS. 4D and H) and NI-205.20A1 bound exclusively to the human phospho-TDP-43 C-terminal peptide with high affinity at nanomolar $EC_{50}$ of 5 nM, nM and 16 nM, respectively (see Table 6) consistent with the idea that phosphorylation of serine 409 and/or serine 410 was required for binding.

TABLE 6

$EC_{50}$ binding of human-derived TDP-43 antibodies to recombinant human TDP-43 and phospho TDP-43 C-terminal peptide.

| Antibody | $EC_{50}$ [nM] | |
|---|---|---|
| | full length TDP-43 | phospho-TDP-43 peptide |
| NI-205.41D1 | 0.06 | no binding |
| NI-205.51C1 | 0.18 | no binding |
| NI-205.21G2 | 0.24 | no binding |
| NI-205.1A9 | 1.0 | no binding |
| NI-205.3F10 | 1.4 | no binding |
| NI-205.14W3 | 1.5 | no binding |
| NI-205.98H6 | 2.6 | no binding |
| NI-205.44B2 | 2.8 | no binding |
| NI-205.9E12A | 3.7 | no binding |
| NI-205.8A2 | 7.2 | no binding |
| NI-205.15F12 | 7.2 | no binding |
| NI-205.10D3 | 7.3 | no binding |
| NI-205.38H2 | 8.2 | no binding |
| NI-205.29E11 | 10.4 | no binding |
| NI-205.9E12D | 11.2 | no binding |
| NI-205.31C11 | 11.0 | no binding |
| NI-205.113C4 | 13.2 | no binding |
| NI-205.25F3 | 13.3 | no binding |
| NI-205.10H7 | 15.3 | no binding |
| NI-205.8C10 | 15.6 | no binding |
| NI-205.87E7 | 17.2 | no binding |
| NI-205.21G1 | 4.1 | 49.5 |
| NI-205.31D2 | >41.0 | 0.69 |
| NI-205.14H5 | >100 | 0.90 |
| NI-205.36D5 | >72.0 | 4.3 |
| NI-205.19G5 | >200 | 13.6 |
| NI-205.68G5 | >100 | 16.9 |
| NI-205.8F8 | no binding | 5.1 |
| NI-205.58E11 | no binding | 6.9 |
| NI-205.20A1 | no binding | 15.8 |

Example 7

Human TDP-43 Antibody Binding Analysis by ELISA and Western Blotting

Direct ELISAs

Direct ELISA assays were performed substantially as described in Example 1. Briefly; fragments of TDP-43 (SEQ ID NO:94) comprising amino acids 2-106 (domain I), 99-204 (domain II), 183-273 (domain III), 258-414 (domain IV) and full length TDP-43 (2-414) were coated onto ELISA plates at equal coating concentration of 6.6 µg/ml. Binding of the human-derived antibodies was determined by direct ELISA. Examples of the obtained results are shown in FIG. 5. Antibodies NI-205.41D1 (FIG. 5A), NI-205.14W3 (FIG. 5C), NI-205.44B2 (FIG. 5E), NI-205.10D3 (FIG. 5G), and NI-205.10H7 (FIG. 5L) bound specifically to TDP-43 domain IV (aa 258-414). Antibody NI-NI-205.98H6 (FIG. 5D) bound specifically to TDP-43 domain III (aa 183-273). Antibodies NI-205.1A9 (FIG. 5B), NI-205.38H2 (FIG. 5H), and NI-205.31C11 (FIG. 5K) specifically recognized TDP-43 domain II (aa 99-204) whereas antibodies NI-205.9E12A (FIG. 5F), NI-205.29E11 (FIG. 5I), NI-205.9E12D (FIG. 5J), and NI-205.8C10 (FIG. 5M) bound to TDP-43 domain I (aa 2-106). All the human-derived TDP-43 specific antibodies also recognized full length human TDP-43. To control for coating efficiency of the different recombinant TDP-43 domains, commercially available antibodies binding to full length TDP-43 and a specific TDP-43 domain were used (FIG. 5W): i) Ab50930 (Abcam, UK), TDP-43 domain I; ii) TARDBP monoclonal antibody (M01), clone 2E2-D3 (Abnova 23435, Abnova, Taiwan), TDP-43 domain III and iii) Ab82695 (Abcam, UK), TDP-43 domain IV. Control antibodies bound to length TDP-43 and their specific TDP-43 domain.

Binding to Distinct TDP-43 Domains by Western Blot

Recombinant full length TDP-43, TDP-43 domain I (amino acid residues 2-106 of SEQ ID NO:94), TDP-43 domain II (amino acid residues 99-204 of SEQ ID NO:94), TDP-43 domain III (amino acid residues 183-273 of SEQ ID NO:94), and TDP-43 domain IV (amino acid residues 258-414 of SEQ ID NO:94) were resolved by SDS-PAGE. Binding to specific TDP-43 domains of the human-derived antibodies was determined by Western Blot analysis.

Examples of the obtained results are shown in FIG. 6. Antibodies NI-205.41D1 (FIG. 6A), NI-205.14W3 (FIG. 6F), NI-205.8A2 (FIG. 6H), NI-205.15F12 (FIG. 6I), NI-205.10D3 (FIG. 6J), NI-205.10H7 (FIG. 6L) and NI-205.21G1 (FIG. 6M) bound specifically to TDP-43 domain IV (aa 258-414). Antibodies NI-205.51C1 (FIG. 6B), NI-205.3E10 (FIG. 6E) and NI-205.98H6 bound specifically to TDP-43 domain III (aa 183-273) whereas antibodies NI-205.21G2 (FIG. 6C), NI-205.1A9 (FIG. 6D) and NI-205.31C11 (FIG. 6K) specifically recognized TDP-43 domain II (99-204 aa). These thirteen human-derived TDP-43 specific antibodies also recognized full length human TDP-43. Only antibody NI-205.10D3 (FIG. 6J) recognized an additional unspecific signal, most probably an E. coli-derived protein contaminant. NI-205.68G5 (FIG. 6N) and NI-205.20A1 (FIG. 6O), two antibodies showing preferential or exclusive binding to the phospho-TDP-43 C-terminal peptide, did not recognize recombinant full length TDP-43 or any of its fragments. Commercially available TDP-43 specific antibody 2E2-D3 (Abnova 23435, Abnova, Taiwan) (FIG. 6P) was used as positive control for human TDP-43 detection whereas the anti-human IgG Fcγ-specific antibody (FIG. 6Q) was used as a negative control.

Human-derived antibodies NI-205.44B2, NI-205.9E1.2A, NI-205.38H2, NI-205.29E11, NI-205.9E12D, NI-205.113C4, NI-205.25F3, NI-205.8C10 and NI-205.87E7 recognized full length TDP-43 but did not identify a specific TDP-43 fragment (data not shown).

Example 8

Epitope Mapping with Synthetic Peptides

The epitopes recognized by the human-derived TDP-43 specific antibodies within the human TDP-43 protein were mapped using pepscan membranes (PEPSPOT, JDT Peptide Technologies, Berlin, Germany) with 101 linear 15-meric peptides with 11 as overlap between individual peptides covering the entire human TDP-43 protein sequence. The pepscan mapping was performed substantially as described in Example 3. Briefly, the peptides were spotted onto nitrocellulose membranes that were then activated for 5 min, in methanol and subsequently washed at room temperature in TBS for 10 min, Table 7 summarizes binding epitopes for the different human-derived TDP-43-specific antibodies identified using PEPSPOT.

TABLE 7

Binding epitopes within the human TDP-43 protein sequence for the different human-derived TDP-43-specific antibodies identified using PEPSPOT.

| Antibody | Binding epitope | Effect of phosphorylation at Ser409 and/or Ser410 residues |
| --- | --- | --- |
| NI-205.41D1 | 317-SINPAMMAAAQAAL QSSWGMMGMLASQ-343 (SEQ ID NO: 323) | NA |
| NI-205.51C1 | 201-DMTEDELREFF-211 (SEQ ID NO: 125) | NA |
| NI-205.21G2 | 121-KEYFSTF-127 (SEQ ID NO: 128) | NA |
| NI-205.3F10 | 213-QYGDVMDVFIP-223 (SEQ ID NO: 123) | NA |
| NI-205.98H6 | 249-IIKGISV-255 (SEQ ID NO: 315) | NA |
| NI-205.44B2 | 345-NQSGPSG-351 (SEQ ID NO: 316) | NA |
| NI-205.8A2 | 381-AAIGWGSASNA-391 (SEQ ID NO: 124) | NA |

TABLE 7-continued

Binding epitopes within the human TDP-43 protein sequence for the different human-derived TDP-43-specific antibodies identified using PEPSPOT.

| Antibody | Binding epitope | Effect of phosphorylation at Ser409 and/or Ser410 residues |
|---|---|---|
| NI-205.15F12 | 397-FNGGFGS-403 (SEQ ID NO: 317) | NA |
| NI-205.10D3 | 289-FGNSRGGGAGL-299 (SEQ ID NO: 318) 389-SNAGSGSGFNG-399 (SEQ ID NO: 319) | NA |
| NI-205.113C4 | 133-VQVKKDL-139 (SEQ ID NO: 127) | NA |
| NI-205.10H7 | 269-QLERSGRFGGN-279 (SEQ ID NO: 320) | NA |
| NI-205.8C10 | 17-EIPSEDD-23 (SEQ ID NO: 321) | NA |
| NI-205.87E7 | 9-EDENDEP-15 (SEQ ID NO: 126) | NA |
| NI-205.21G1 | 390-414 | Ser409/Ser410 phosphorylation partially inhibited binding |
| NI-205.31D2 | 390-414 | Bound to peptide phosphorylated at Ser409 and Ser410 |
| NI-205.14H5 | 390-414 | Bound to peptide phosphorylated at Ser409 and/or Ser410; weak binding also observed independent of phosphorylation |
| NI-205.36D5 | 390-414 | Bound to peptide phosphorylated at Ser409; simultaneous Ser410 phosphorylation abrogates binding |
| NI-205.19G5 | 390-414 | Bound to peptide phosphorylated at Ser409; simultaneous Ser410 phosphorylation abrogates binding |
| NI-205.68G5 | 390-414 | Bound to peptide phosphorylated at Ser409 and/or Ser410 |
| NI-205.8F8 | 390-414 | not determined |
| NI-205.58E11 | 390-414 | not determined |
| NI-205.20A1 | 390-414 | Bound to peptide phosphorylated at Ser409 and Ser410 |

NA - not applicable.

Determination of NI-205.41D1 Binding Epitope by ELISA Assays.

Full length TDP-43 (2-414) and TDP-43 C terminal fragments comprising amino acids 258-414 (domain IV), 258-384, 258-375, 258-362, 258-353, 258-319, 317-414 and 340-414 were coated onto ELISA plates at equal coating concentration of 10 μg/ml. Binding of NI-205.41D1 antibody to specific TDP-43 fragments was determined by direct ELISA. Examples of the data obtained are provided in FIG. 7A. NI-205.41D1 bound to all recombinant fragments except fragments 258-319 and 340-414, indicating that NI-205.41D1 binding epitope was in the C-terminal TDP-43 region 317-353. NI-205.41D1 antibody bound to full length TDP-43.

Full length TDP-43 (2-414), wild-type TDP-43 domain IV comprising residues 258-414 of SEQ ID NO:94 (TDP-43 258-414) and a mutant TDP-43 domain IV (TDP-43 258-414 AMM321GGG) carrying the A to G substitution at residue 321, M to G substitution at residue 322, and M to G substitution at residue 323 were coated onto ELISA plates at equal coating concentration of 10 μg/ml. Binding of NI-205.41D1 antibody to specific TDP-43 domain IV variants was determined by direct ELISA (FIG. 7B).

NI-205.41D1 specifically bound to full length TDP-43 and to wild type TDP-43 domain IV, but not to the mutant TDP-43 domain IV, indicating that one or more of the mutated residues was essential for NI-205.41D1 binding to human TDP-43. To control for coating efficiency of the different recombinant TDP-43 species, commercially available antibody 12892-1-AP binding to full length TDP-43 was used.

Figure 7C:
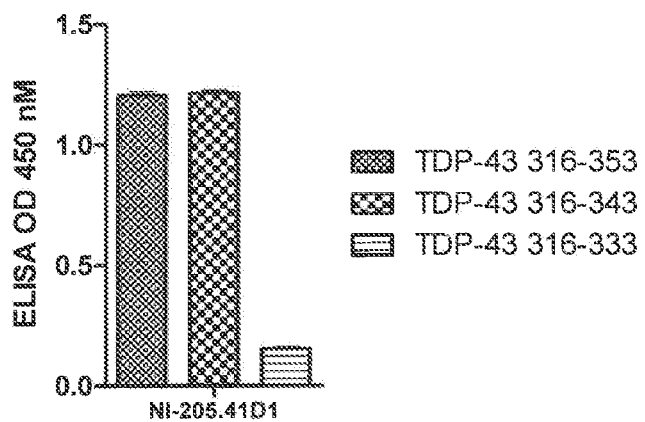

Synthetic biotinylated peptides comprising residues 316-353 (TDP-43 316-353), 316-343 (TDP-43 316-343) and 316-333 (TDP-43 316-333) of SEQ ID NO:94 were coated on streptavidin-coated plates at equal coating concentration of 10 µg/ml, Binding of NI-205.41D1 antibody to specific TDP-43 C-terminal peptides was determined by direct ELISA (FIG. 7C). NI-205.41D1 specifically bound to peptides TDP-43 316-353 and TDP-43 316-343 but not to peptide TDP-43 316-333. This result is consistent with the idea that residues 334-343 of SEQ ID NO:94 at the TDP-43 C-terminal region are involved in NI-205.41D1 antibody binding to human TDP-43. Our results are consistent with an understanding that the binding epitope of antibody NI-205.41 is discontinuous between residues 317-343 of SEQ ID NO:94 and is formed by two independent binding regions: the first one comprising residues 321-323 of SEQ ID NO:94 and the second one comprising residues 334-343 of SEQ ID NO:94.

Example 9

The Human-Derived TDP-43 Specific Antibodies Interact with Native TDP-43

Pure full-length TDP-43 protein has a natural propensity to aggregate. Therefore, only very small quantities of soluble, full-length TDP-43 were recovered under standard purification conditions. We thus developed a recombinant expression and purification strategy for isolating large quantities of functional 6xHis-SUMO-tagged full-length human TDP-43 from *Escherichia coli* using KSCN and arginine, mild chaotropic agents known to preserve native protein structure while preventing protein aggregation.

Figure 8C:
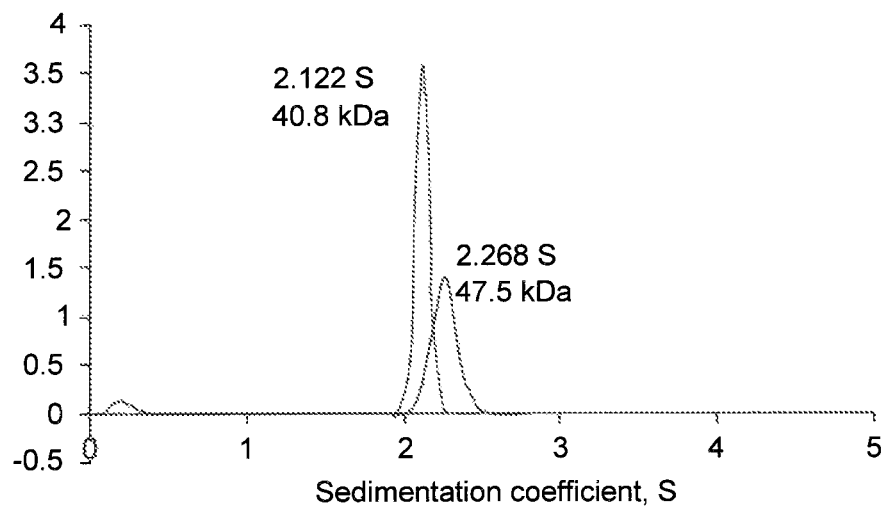
Figure 9A:
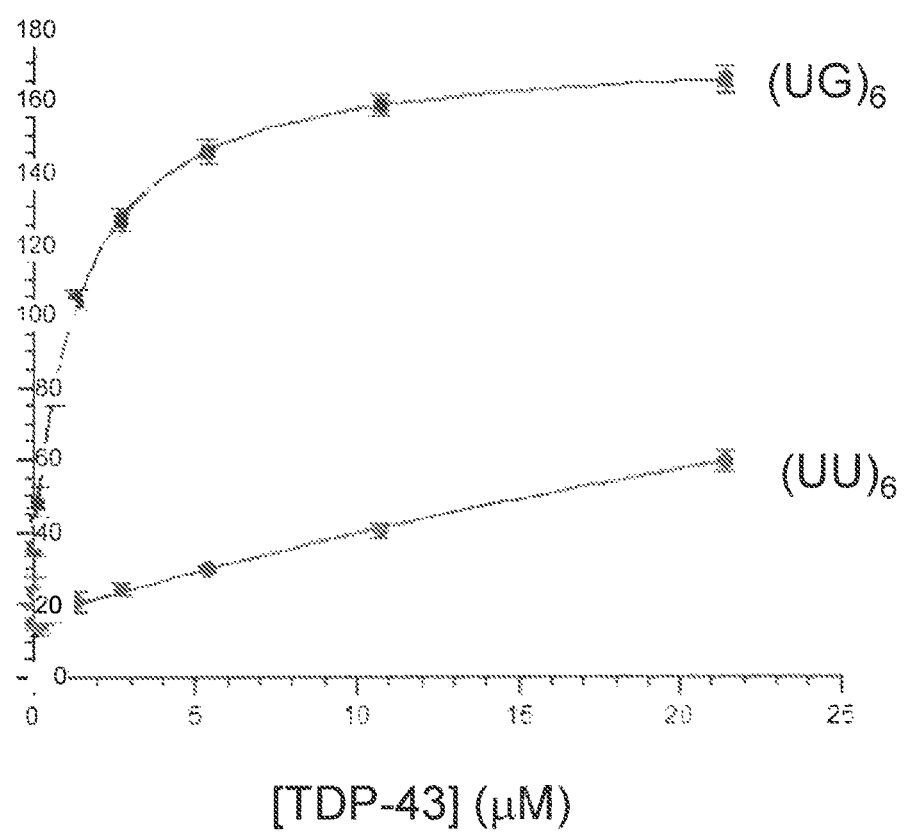
FIG. 9: A) Full-length TDP-43 binding to specific ((UG)$_6$) or control ((UU)$_6$) RNA in buffer containing 40 mM HEPES, 0.5 M KCl, 0.4 M Arginine, pH 7.4 B), C) and D) RNA binding by TDP-43 (101-265) in the presence of a physiological buffer containing 20 mM HEPES, 80 mM potassium glutamate, 4 mM magnesium acetate, 5% glycerol, pH 7.5, 2 mM DTT, to determine B) K$_d$, and stoichiometry purified in C) non-chaotropic conditions or D) mild chaotropic conditions.
Figure 9B:
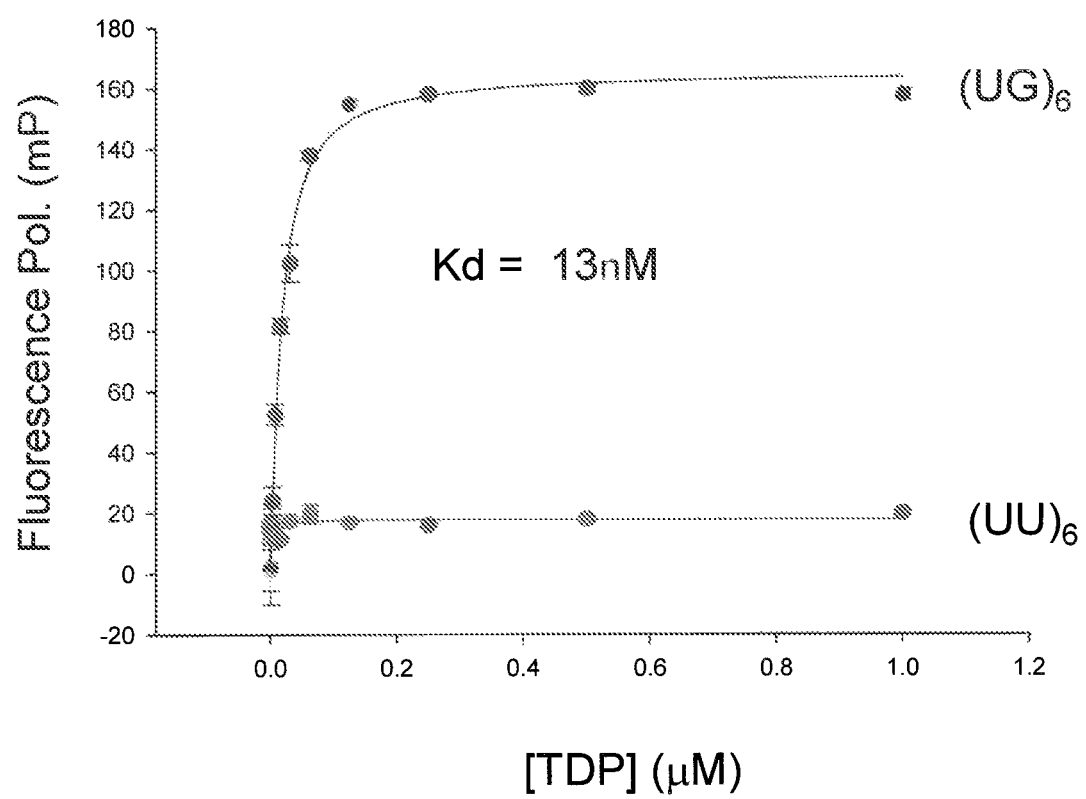
Figure 9C:
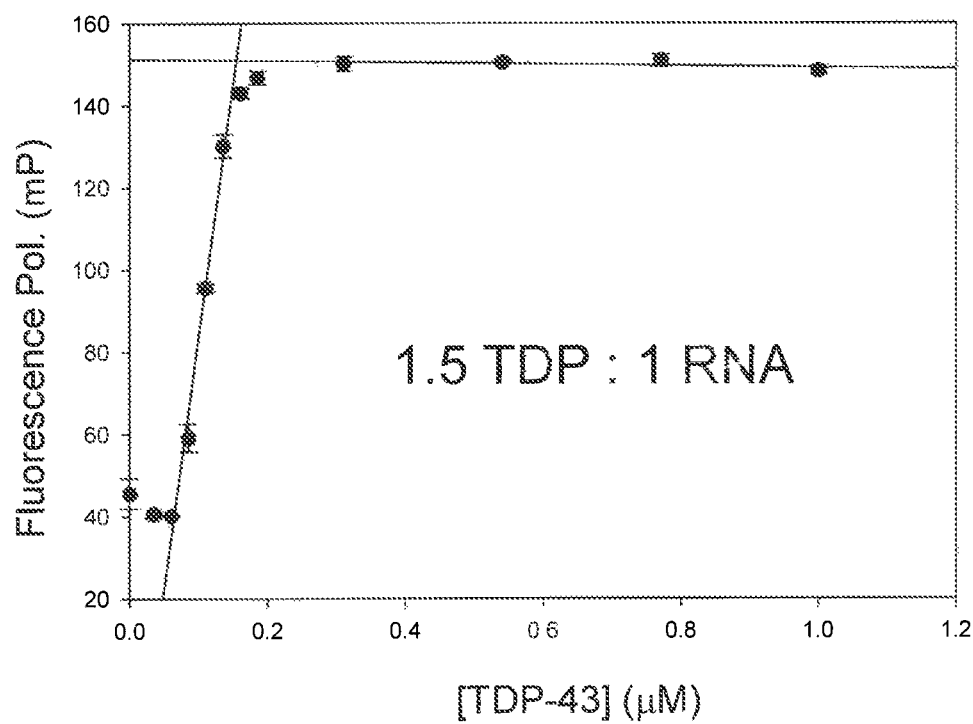
Figure 9D:
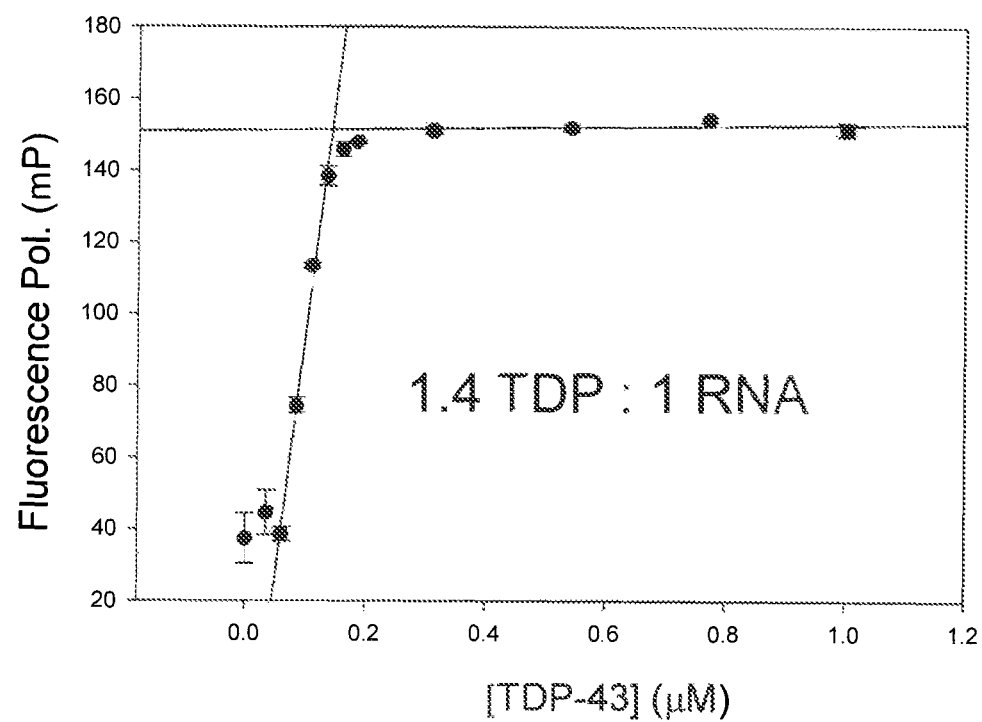

Plasmids:

Polynucleotides encoding human full-length TDP-43 (1-414 of SEQ ID NO:94) and its truncations residues 101-265 and residues 220-414 of SEQ ID NO:94 were amplified using standard procedures and subcloned into a modified pET19-b (Novagen) vector resulting in 6xHis and SUMO tags at the N-terminus of the protein encoded by the amplified polynucleotides. A schematic representation of the 6xHis SUMO tagged recombinant polypeptides is shown in FIG. 8B.

Protein Expression and Purification:

6xHis/SUMO tagged TDP-43 expression plasmids were transformed into BL21(DE3) STAR *Escherichia coli* (Invitrogen). Bacterial cultures were grown to an OD600 of 1.0 at 37° C. and induced with 1 mM IPTG for 16 h at 18° C. After pelleting, cells were lysed by microfluidization in purification buffer with protease inhibitors (40 mM HEPES (pH 7.5), 1.5 M KSCN, and 1 mM tris(2-carboxyethyl)phosphine (TCEP), 1 mM PMSF, 5 µM pepstatin, 1 mM benzamine, 10 µM bestatin, 10 µM E-64, 20 µM leupeptin, 1.5 µM aprotinin). To generate properly folded full-length TDP-43, TDP-43 (101-265) and TDP-43 (220-414), the corresponding 6xHis-SUMO tagged fusions proteins were purified on Ni-NTA agarose resin (Qiagen) following the manufacturer's instructions, using purification buffer for binding and washing. Bound proteins were eluted from Ni-NTA resin with the same buffer containing 250 mM imidazole and further purified on a preparative S200 size exclusion column (GE Healthcare) following the manufacturer's instructions using purification buffer. Fractions containing monomeric TDP-43 proteins were pooled, and reformulated in a buffer containing 40 mM HEPES (pH 75), 400 mM arginine, 1 mM TCEP by dialysis. 6xHis-SUMO-TDP43 (101-265) was additionally purified using the same purification strategy but altering buffer compositions by substituting 1.5 M KSCN with 0.5M KCl. To prepare unfolded 6xHis-TDP-43, cells were lysed by microfluidization in a Tris-imidazole buffer (50 mM Tris (pH 7.5), 20 mM imidazole, 150 mM NaCl) with protease inhibitors. The insoluble pellet was washed sequentially with the following buffers containing protease inhibitors: B-PER buffer (Pierce) containing 2 mM MgCl2, followed by Tris-imidazole buffer. Washed pellets were next solubilized in 8 M urea, 20 mM sodium phosphate (pH 7.8). Urea soluble material was then purified on Ni-NTA agarose resin following the manufacturer's instructions, using denaturing washing and elution conditions. Sedimentation and diffusion coefficients determination (FIG. 8C) as well as SDS-PAGE separation (FIG. 8A) were carried out by standard methods. (Laue, T. et al, (1992) in Analytical Ultracentrifugation in Biochemistry and Polymer Science (Harding, S. E., ed) Royal Society of Chemistry, Cambridge, UK).

Capture ELISA:

96 well plates (Thermo Fisher Scientific) were coated with anti 6xHis mouse monoclonal antibody (Clontech) diluted to a concentration of 1 µg/ml in PBS buffer (137 mM NaCl, 8.05 mM Na2HPO4, 1.5 mM KH2PO4, 2.7 mM KCl, pH 7.4) at 4° C. overnight. Non-specific binding sites were blocked for 1 hr at RT with PBS containing 1% BSA (Sigma) and 0.05% TWEEN-20 (Fisher Scientific), 6xHis-SUMO-TDP43 proteins at a concentration of 1.7 µM were allowed to bind to antibody-coated plates for 1 hr at RT in PBS buffer containing 1% BSA, 300 mM arginine and 0.1% PEG 5000, pH 7.5. Plates were incubated for 1 hr at RT with human antibodies of present invention, titrated in a three-fold dilution series, followed by HRP conjugated anti-human IgG Fc γ (Jackson ImmunoResearch) in phosphate buffered saline TWEEN containing 1% BSA. HRP activity was measured in a standard colorimetric assay. EC50 values were calculated using a four-parameter logistic curve fit on Softmax pro software (Molecular Devices).

RNA Binding Assay:

Equilibrium binding affinities of TDP-43 constructs for RNA were determined using fluorescence polarization. 5'TYETM fluorophore labeled RNA substrates, specific RNA (TYETM-UGUGUGUGUGUG) (SEQ ID NO: 312) and RNA control (TYETM-UUUUUUUUUUUU) (SEQ ID NO: 313) (integrated DNA Technologies), were incubated at a concentration of 5 nM for 30 min at 25° C. with TDP-43 (final concentrations 0 to 20 µM) in incubation buffer as indicated. Fluorescence polarization was measured with the plate reader fluorometer Envision (PerkinElmer) at each concentration of TDP-43 in a 96 well plate format with an excitation at 645 nm and emission at 665. $K_d$s were calculated using the quadratic equation for tight binding (Morrison equation) using Sigmaplot (Systat Software Inc.). To determine the stoichiometry of RNA/TDP-43 binding, the same fluorescence polarization experimental set up was used with the addition of 95 nM of unlabeled RNA of the same sequence for a total 100 nM RNA concentration (>7x higher than the previously determined $K_d$ values). Stoichiometries were calculated by measuring the intercept of two straight lines, one fit using data points of the partially bound state, and the other using data points of the fully bound state.

The recombinant full-length TDP-43 was monomeric by sedimentation analysis (FIG. 8C) in buffer containing 400 mM arginine. A minimum of 300 mM arginine was maintained in analytical assays when monomeric native TDP-43 was desired, because aggregation was observed at lower arginine concentrations. Consistent with arginine not adversely affecting TDP-43 activity, our recombinant, full-length TDP-43 binds an RNA of previously established specific sequence (UGUGUGUGUGUG (SEQ ID NO:312)) with at least 30 fold higher affinity than to a generic unspecific sequence (UUUUUUUUUUUU: (SEQ ID NO:313)) (FIG. 9).

We also purified a 6×His SUMO tagged fragment of TDP-43 comprising amino acid residues 101-265 of SEQ ID NO: 94 from which the C-terminal domain (amino acids 265 to 414) known to mediate aggregation was removed. The 6×His/SUMO tagged 101-265 truncated TDP-43 fragment, purified with or without chaotropes maintained a binding affinity to the specific RNA sequence very similar to the previously reported $K_D$ (~14 nM) in spite of the very different analytical methods used (FIG. 9). See, Kou Nucleic Acids Res. 2009, 37:1799-808. The stoichiometry of RNA TDP-43 binding was also the same regardless of purification strategy, indicating that there was no significant difference in the denatured protein population between the two preparations (FIG. 9). Together, these data indicated that the purified recombinant pure full length TDP-43 was in its native folding state.

We measured the binding affinity of the human-derived TDP-43 specific antibodies provided herein to properly folded 6×His SUMO tagged TDP-43 using a capture ELISA in which native TDP-43 was immobilized without direct adsorption on the surface of the ELISA plate. This was achieved by immobilizing an anti 6×His antibody which then captured native TDP-43. Binding to the anti 6×His tag by folded 6×His/SUMO tagged full-length human TDP-43 was achieved at 300 mM arginine concentration, ensuring a monomeric state of TDP-43. After this immobilization step, binding by human antibodies was tested in regular buffers without interference of TDP-43 aggregation. An example of the titration curves generated is shown in FIG. 10, Table 8 summarizes affinities ($EC_{50}$ [nM]) to folded, full length 6×His SUMO tagged TDP-43, or to a 6×His/SUMO tagged truncation construct containing the C-terminal, aggregation prone region of TDP-43 (residues 220-414 of SEQ ID NO: 94) by this capture ELISA method.

TABLE 8

$EC_{50}$ [nM] binding of human-derived TDP-43 antibodies to properly folded recombinant 6xHis/SUMO tagged full length TDP-43 and 6xHis/SUMO tagged truncated TDP-43 comprising residues 220-414.

| Antibody | full length TDP-43 | TDP-43 residues 220-414 |
|---|---|---|
| NI-205.41D1 | 0.07 | 0.10 |
| NI-205.51C1 | 1.1 | no binding |
| NI-205.21G2 | 3.6 | no binding |
| NI-205.1A9 | >98 | no binding |
| NI-205.3F10 | >90 | no binding |
| NI-205.14W3 | 7.4 | 1.6 |
| NI-205.98H6 | 46 | 20 |
| NI-205.44B2 | >125 | 33.5 |
| NI-205.9E12A | no binding | — |
| NI-205.8A2 | 34 | 4.6 |
| NI-205.15F12 | 16.3 | 9.7 |
| NI-205.10D3 | >90 | 20.5 |
| NI-205.38H2 | >120 | no binding |
| NI-205.29E11 | >100 | >97 |
| NI-205.9E12D | no binding | no binding |
| NI-205.31C11 | 21.1 | no binding |
| NI-205.113C4 | no binding | no binding |
| NI-205.25F3 | >120 | >100 |
| NI-205.10H7 | 30.9 | 6.45 |

TABLE 8-continued $EC_{50}$ [nM] binding of human-derived TDP-43 antibodies to properly folded recombinant 6xHis/SUMO tagged full length TDP-43 and 6xHis/SUMO tagged truncated TDP-43 comprising residues 220-414.

| Antibody | full length TDP-43 | TDP-43 residues 220-414 |
|---|---|---|
| NI-205.8C10 | no binding | — |
| NI-205.87E7 | no binding | no binding |
| NI-205.21G1 | 4.4 | 0.33 |
| NI-205.31D2 | 41.0 | 19.4 |
| NI-205.14H5 | >100 | — |
| NI-205.36D5 | >72.0 | >60 |
| NI-205.19G5 | no binding | — |
| NI-205.68G5 | no binding | — |
| NI-205.8F8 | >94 | — |
| NI-205.58E11 | no binding | — |
| NI-205.20A1 | no binding | — |

Example 10

Assessment of Human-Derived TDP-43 Antibody Binding to TDP-43 in FTLD-U Case and Control Hippocampal Tissues Human cortical, hippocampal, and spinal cord FTLD-U and control tissues were obtained from the IDIBAPS Biobank (Banc de Teixits Neurologics, Barcelona). Immunohistochemistry was performed on 5 µm thick paraffin embedded sections using EDTA-based epitope retrieval prior to conducting the otherwise standard immunohistochemical procedures with Elite ABC kits (Vector Laboratories) with DAB (Thermo Scientific). Immunohistochemistry was performed using the human TDP-43 antibodies of the invention at 5004 concentration. Control stainings were done using mouse monoclonal antibody 2E2 against human TDP-43 (Abnova), rabbit polyclonal antibody p409/p410 raised against TDP-43 p409/p410 (CosmoBio), and rabbit polyclonal antibody p409/p410 raised against TDP-43 p409/p410 (CosmoBio).

The capacity of the human derived anti-TDP-43 antibodies described herein to recognize native and pathological forms of TDP-43 was characterized by immunohistochemistry experiments on human FTLD-U case (10) and control (7) hippocampal tissues. TDP-43 is a predominantly nuclear protein which shuttles to and from the cytoplasm. Under pathological conditions it accumulates in the nucleus and particularly in the cytoplasm, and the pathology is typically characterized/classified based on cellular localization; NCI—neuronal cytoplasmic inclusion, NII—neuronal intranuclear inclusion, and dystrophic neuritic pathology (review Mackenzie et al., Lancet Neurology, 9: 995-1007 (2010)). In FTLD-U and ALS patient tissues, the protein is also found to be phosphorylated. The human TDP-43 binding characteristics of the antibodies disclosed herein were compared to that of commercially available antibodies commonly used to diagnose cases post-mortem. The 2E2-D3 control antibody (epitope mapped to aa205-222; Zhang et al., Neurosci. Lett., 434:170-174 (2008)) recognized nuclear and cytoplasmic TDP-43 accumulation in hippocampal pyramidal neurons (FIG. 11A) and granule cells (FIG. 11B), as well as TDP-43 in dystrophic neurites (FIG. 11C). On control case tissues, 2E2-D3 recognized predominantly nuclear TDP-43. The phosphorylation specific antibody, p403/p404 (raised against CNGGFGS(p)S(p)MDSK (SEQ ID NO:324); Hasegawa et al., Ann Neurol, 64(1):60-70 (2008)) recognized (FIG. 11D) cytoplasmic TDP-43 in pyramidal cells, (FIG.

11E) nuclear and cytoplasmic accumulation in granule cells, as well as (FIG. 11F) TDP-43 in dystrophic neurites. A second phosphorylation specific antibody, p409/p410 (raised against CMDSKS(p)S(p)GWGM (SEQ ID NO:325); Hasegawa et al., Ann Neurol, 64(1):60-70 (2008)) bound to TDP-43 accumulating in the nucleus and cytoplasm of (FIG. 11G) pyramidal cells and (FIG. 11H) granule cells, as well as (FIG. 11I) TDP-43 in dystrophic neurites.

The human-derived anti-TDP-43 antibodies described herein displayed various staining patterns, including binding to nuclear, cytoplasmic, and neuritic forms of TDP-43. Several of the human-derived anti-TDP-43 antibodies described herein specifically bound to disease forms of TDP-43, compared to staining on control case tissues from healthy individuals. (FIG. 11, and Table 9). For example, antibodies NI-205.68G5, NI-205.14W3, NI-205.21G1, and NI-205.41D1, selectively bound to pathological forms, i.e. to neuritic TDP-43, and nuclear and cytoplasmic TDP-43 in binding to control case tissues (compare for NI-205.41D1 staining in FTLD-U patient tissues (FIG. 11Y) and control case tissue (FIG. 11Z)).

Antibody (FIG. 11J) NI-205.10D3 bound predominantly to nuclear TDP-43, while (FIG. 11K) NI-205.8C10 bound to TDP-43 in cytoplasm and axons. Unlike the control anti-TDP-43 antibodies analyzed, a sub-set of the human anti-TDP-43 antibodies reported herein bound predominantly cytoplasmic TDP-43, rather than nuclear TDP-43. Antibodies that bound predominantly cytoplasmic TDP-43 include (FIG. 11L) NI-205.15F12, (FIG. 11M) NI-205.8A2, (FIG. 11N) NI-205.3F10, (FIG. 11O) NI-205.21G2, (FIG. 11P) NI-205.8F8, (FIG. 11Q) NI-205.31C11, (FIG. 11R) NI-205.36D5, (FIG. 11S) NI-205.31D2, (FIG. 11T) NI-205.10H7, and (FIG. 11U) NI-205.14H5. Antibodies (FIG. 11V) NI-205.68G5, (FIG. 11W) NI-205.14W3, (FIG. 11X) NI-205.21G1, and (FIG. 11Y) NI-205.41D1 bound to neuritic TDP-43 and TDP-43 accumulating in the nucleus and cytoplasm in hippocampal granule cells.

TABLE 9

Assessment of human-derived TDP-43 antibody binding to TDP-43 in FTLD-U case and control hippocampal tissues. Case and control samples were also stained with 2E2-D3, p403/p404, p409/p410 control anti-TDP-43 antibodies.

| Antibody | Antibody Staining by Immunohistochemistry | |
|---|---|---|
| | FTLD-U Case tissue | Control tissue |
| NI-205.41D1 | cytoplasmic and nuclear in granule cells + neuritic | no binding |
| NI-205.51C1 | no binding | ND |
| NI-205.21G2 | cytoplasmic | ND |
| NI-205.1A9 | no binding | ND |
| NI-205.3F10 | cytoplasmic | cytoplasmic |
| NI-205.14W3 | cytoplasmic and nuclear in granule cells + neuritic | no binding, cytoplasmic in neurons (in some cases) |
| NI-205.98H6 | no binding | ND |
| NI-205.44B2 | no binding | ND |
| NI-205.9E12A | no binding | ND |
| NI-205.8A2 | cytoplasmic | cytoplasmic |
| NI-205.15F12 | cytoplasmic in granule cells | ND |
| NI-205.10D3 | nuclear | nuclear |
| NI-205.38H2 | no binding | ND |
| NI-205.29E11 | no binding | ND |
| NI-205.9E12D | no binding | ND |
| NI-205.31C11 | cytoplasmic | cytoplasmic |
| NI-205.113C4 | no binding | ND |
| NI-205.25F3 | no binding | ND |
| NI-205.10H7 | cytoplasmic | cytoplasmic |
| NI-205.8C10 | cytoplasmic + axonal (one case) | no binding |
| NI-205.87E7 | no binding | ND |
| NI-205.21G1 | cytoplasmic and and nuclear in granule cells + neuritic | no binding |
| NI-205.31D2 | cytoplasmic | cytoplasmic |
| NI-205.14H5 | cytoplasmic | cytoplasmic |
| NI-205.36D5 | cytoplasmic | cytoplasmic |
| NI-205.19G5 | no binding | ND |
| NI-205.68G5 | cytoplasmic + neuritic (one case) | ND |
| NI-205.8F8 | cytoplasmic | cytoplasmic |
| NI-205.58E11 | no binding | ND |
| NI-205.20A1 | no binding | ND |
| 2E2-D3 | Nuclear, cytoplasmic and neuritic | Nuclear (cytoplasmic in some controls) |
| p403/p404 | Nuclear, cytoplasmic and neuritic | no binding |
| p409/p410 | Nuclear, cytoplasmic and neuritic | No binding |

ND—not determined hippocampal granule cells. Antibodies NI-205.14W3, NI-205.21G1, and NI-205.41D1 specifically bound to pathological forms of TDP-43 in FTLD-U patient tissues without The screen for human anti-TDP-43 antibodies using denatured recombinant TDP-43 and TDP-43 390-414 peptide phosphorylated at residues S409 and S410 resulted in the generation of antibodies that cover most natural and disease-related epitopes of human TDP-43. The human anti-TDP-43 antibodies disclosed herein identify new and interesting epitopes of TDP-43, and provide novel conformational information specific to the disease process of TDP-43 proteinpathies. For example, the NI-205.14W3, NI-205.2101, and NI-205.41D1 bound to TDP-43 with high affinity and were specific to pathological forms of TDP-43 on FTLD-U tissues in comparison to control cases. While these three antibodies had similar pathological TDP-43 specific staining pattern in immunohistochemistry, they recognized distinct epitopes in the aggregation prone C-terminal region of TDP-43: NI-41D1 bound to a discontinuous epitope in the C-terminal portion of TDP-43 and NI-21G1 bound to a phosphorylation prone region of TDP-43. Additionally, the NI-205.14H5 and NI-205.31D2 antibodies had high affinity for TDP-43 phosphorylated at one or both of residues S409 and S410, and specifically stained cytoplasmic TDP-43 in immunohistochemistry. Furthermore, NI-205.21G2 and NI-205.51C1 also demonstrated high affinity for TDP-43, and bound to epitopes N-terminal to the predicted caspase cleavage site, with NI-205.51C1 binding to RNA-recognition motif 2 (RRM2). NI-205.10D3 specifically stained nuclear TDP-43 in both FTLD-U and control case tissues, suggesting that it bound to endogenous/native forms of TDP-43.

Example 11

Acute Brain Penetration Study

TDP-43_G348C, transgenic mice (Swarup et al., Brain 134 (2011), 2610-2626) are intraperitoneally injected with 30 mg/kg human anti-TDP-43 antibody or equal volume of PBS at day 1 and day 4. At day 5, mice are perfused under anesthesia with PBS containing 1 Unit/ml heparin. Blood, brain and spinal cord are collected for analyses. Right hemisphere of the brain is frozen at −80° C., left hemisphere of the brain and the spinal cord are post fixed in 10% neutralized formalin at 4° C. for two days before being embedded in paraffin block and sectioned. Plasma is stored at −80° C. in aliquots.

Brain protein extraction: brain protein fractions are extracted using standard experimental methods, for example, frozen right hemisphere is weighed and homogenized in 5 volumes (5 mL/g of wet tissue) of a solution containing 50 mM NaCl, 0.2% diethylamine, protease inhibitors (Roche Diagnostics GmbH) and phosphatase inhibitor (Roche Diagnostics GmbH), Samples are then transferred to polycarbonate tubes and added another 5 volume of homogenization solution, and kept on ice for 30 min. Soluble fraction is then collected after centrifugation at 100,000 g, 4° C. for 30 min. This soluble fraction is used in human IgG assay. The pellet is re-suspended in 3 volumes of PBS with protease and phosphatase inhibitor. After centrifugation at 16,000 g, 4° C. for 30 min, supernatants and pellets are stored separately at −80° C. for further insoluble TDP-43 extraction.

Human antibody and TDP-43 is detected and quantitated in the brain protein extracts using standard experimental methods. For example, human IgG-specific sandwich ELISA: 2 µg/ml of goat anti-human IgG Fab (Jackson) in 50 mM carbonate ELISA coating buffer (pH9.6) is used as capture antibody. Half-area 96-well microtitre plates are coated with 30 µl/well with capture antibody at 4° C. over night. The plate is then washed 4 times with PBS containing 0.1% TWEEN 20 before incubating with 50 µl/well PBS containing 2% BSA at room temperature for one hour. Soluble fractions of brain extracts, plasma samples and human antibody standard are diluted in PBS containing 2% BSA and 0.1% TWEEN 20. 30 µl of the diluted samples are added into each well and incubated at room temperature for one hour. The plate is then washed with 200 µl/well PBS containing 0.1% TWEEN 20 for four times before incubated with HRP-conjugated donkey anti-human Fcγ (Jackson, diluted at 1:10,000 in PBS containing 2% BSA and 0.1% TWEEN 20) at room temperature for one hour. The plate is then washed with 200 µl/well PBS containing 0.1% TWEEN 20 for four times before adding 20 µl/well TMB (1:20 in 10 mM citrate solution pH=4.1). The reaction is then stopped by adding 10 µl 1M H2SO4 to each well. Antibody standard curve is obtained from serial dilutions of control antibody. Antibody concentrations in plasma and brain samples are calculated according to the standards. Brain human IgG level is then converted to µg antibody/gram fresh brain tissue.

Neuronal penetration of the administered human anti-TDP-43 antibody is detected by immunohistological staining of the brain tissue sections obtained from human anti-TDP-43 antibody treated and control animals. For example, free-floating tissue sections are washed in Tris-TRITON pH7.4 (50 mM Tris, 150 mM NaCl, 0.05% TRITON X-100), incubated in 1% H2O2 PBS for 30 min, and incubated with a blocking solution containing 2% normal goat- and horse serum in Tris-TRITON and with additional 0.2% TritonTRITON X-100 for 1 h at room temperature. The sections are then incubated with biotinylated donkey anti-human IgG (H+L) (Jackson Immunoresearch Labs, 709-065-149) at 1:200 in blocking solution for 16 h at 4° C. with agitation at 100 rpm to detect neuronal human IgG. The tissue-bound biotinylated antibody is visualized by peroxidase chromogenic reaction using the VECTASTAIN Elite ABC kit (Vector Laboratories, PK6100, 1:100). The enzymatic reaction is stopped with ice cold PBS and the sections is washed in PBS 3 times. The sections are then mounted on glass slides and air dried over night before they are counterstained with hemalum solution (Carl Roth GmbH+Co. T865.1). After dehydration steps, the slides are covered with coverslips before being scanned with the Olympus dotSlide 2.1 virtual microscopy system. Neuronal anti-human IgG staining observed in the antibody treated animals, but not in the control animals, indicates that the human anti-TDP-43 antibody enters the neurons.

Example 12

Chronic Study with Anti-TDP-43 Antibodies

TDP-43_G348C transgenic mice (Swamp et al., Brain 134 (2011), 2610-2626) are intraperitoneally injected with 10 mg/kg, 3 mg/kg of antibody solution, or equal volume of PBS control. Each treatment group has 20-25 mice. The treatment is carried out once a week for 26 weeks. Alternatively, the treatment is carried out twice a week for 13 weeks. Body weight is monitored every two weeks. Mice are perfused under anesthesia at the end of the treatment period. Brain, spinal cord and blood is collected. Half brain and spinal cord are post-fixed in 10% formalin for three days before being embedded in paraffin block. 4-6 µm thick sections cut from these tissue blocks are used for immunohistochemistry studies. The other half brain is weighted and deep frozen at −80° C. for biochemical analyses.

Drug effects are evaluated by comparing the level and distribution of TDP-43, including the level and distribution of pathological forms of TDP-43 in antibody treated and control animals using immunohistochemistry. Tissue samples obtained from antibody treated and control animals are stained with an anti-TDP-43 antibody, e.g., an anti-TDP-43 antibody specific for pathological forms of TDP-43, using standard histological methods. In one embodiment; the antibody used in the histochemical analysis is the same as the antibody administered to the animals. In another embodiment, the antibody used in the histochemical analysis is different from the antibody administered to the animals. Therapeutic efficacy of the human anti-TDP-43 antibodies disclosed herein is indicated by a reduction in the level, or absence of pathological forms of TDP-43 in antibody treated animals relative to control animals.

Drug effects are also evaluated by comparing the level of TDP-43, including the level of pathological forms of TDP-43 in antibody treated and control animals using ELISA or Western-blot. Therapeutic efficacy of the human anti-TDP-43 antibodies disclosed herein is indicated by a reduction in the level, or absence of pathological forms of TDP-43 in antibody treated animals relative to control animals.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method of reducing the accumulation of pathological TDP-43 deposits or reducing pathological TAR-DNA-binding protein 43 kDa (TDP-43) distribution in a human subject in need thereof, comprising administering to the subject an effective amount of an anti-TDP-43 monoclonal antibody comprising a heavy chain variable (VH) region comprising the amino acid sequences of SEQ ID NO:131 (VH CDR1), SEQ ID NO:132 (VH CDR2), and SEQ ID NO:133 (VH CDR3) and a light chain variable (VL) region comprising the amino acid sequences of SEQ ID NO:135 (VL CDR1), SEQ ID NO:136 (VL CDR2), and SEQ ID NO:137 (VL CDR3).

2. The method of claim 1, wherein the VH is at least 80%, 85%, 90%, 95%, 96%, 97%, 98%, or 99% identical to the amino acid sequence of SEQ ID NO:130.

3. The method of claim 1, wherein the VH comprises the amino acid sequence of SEQ ID NO:130.

4. The method of claim 1, wherein the VL is at least 80%, 85%, 90%, 95%, 96%, 97%, 98%, or 99% identical to the amino acid sequence of SEQ ID NO:134.

5. The method of claim 1, wherein the VL comprises the amino acid sequence of SEQ ID NO:134.

6. The method of claim 1, wherein the VH comprises the amino acid sequence of SEQ ID NO:130 and the VL comprises the amino acid sequence of SEQ ID NO:134.

7. The method of claim 1, wherein the antibody is a human antibody, humanized antibody, chimeric antibody, or murinized antibody.

8. The method of claim 1, wherein the antibody is an antigen binding antibody fragment.

9. The method of claim 8, wherein the antigen binding antibody fragment is selected from the group consisting of a single chain Fv fragment (scFv), a F(ab') fragment, a F(ab) fragment, and a F(ab')2 fragment.

10. The method of claims 1, wherein the antibody is attached to a drug.

11. The method of any one of claims 1 to 9, wherein the antibody is a component of a composition comprising a pharmaceutically acceptable carrier.

12. The method of claim 11, further comprising administering an additional agent useful for treating a TDP-43 proteinopathy.

13. The method of claim 1, wherein the subject is suffering from a TDP-43 proteinopathy selected from the group consisting of argyrophilic grain disease, Alzheimer's disease, amyotrophic lateral sclerosis (ALS), ALS-Parkinsonism dementia complex of Guam, corticobasal degeneration, Dementia with Lewy bodies, Huntington's disease, Lewy body disease, motor neuron disease, frontotemporal lobar degeneration (FTLD), frontotemporal dementia, frontotemporal lobar degeneration with ubiquitin-positive inclusions, hippocampal sclerosis, inclusion body myopathy, inclusion body myositis, Parkinson's disease, Parkinson's disease dementia, Parkinson-dementia complex in Kii peninsula and Pick's disease.

14. The method of claim 13, wherein the subject is suffering from Alzheimer's disease.

15. The method of claim 14, wherein the VH comprises the amino acid sequence of SEQ ID NO:130 and the VL comprises the amino acid sequence of SEQ ID NO:134.

16. The method of claim 13, wherein the subject is suffering from amyotrophic lateral sclerosis (ALS).

17. The method of claim 16, wherein the VH comprises the amino acid sequence of SEQ ID NO:130 and the VL comprises the amino acid sequence of SEQ ID NO:134.

18. The method of claim 13, wherein the subject is suffering from frontotemporal lobar degeneration (FTLD).

19. The method of claim 18, wherein the VH comprises the amino acid sequence of SEQ ID NO:130 and the VL comprises the amino acid sequence of SEQ ID NO:134.

20. The method of claim 13, wherein the subject is suffering from Parkinson's disease.

21. The method of claim 20, wherein the VH comprises the amino acid sequence of SEQ ID NO:130 and the VL comprises the amino acid sequence of SEQ ID NO:134.

22. A method of reducing the number or frequency of TAR-DNA-binding protein 43kDa (TDP-43) positive inclusion-positive neurons in the brain or spinal cord in a human subject in need thereof, comprising administering to the subject an effective amount of an anti-TDP-43 monoclonal antibody, comprising
a heavy chain variable (VH) region comprising the amino acid sequences of SEQ ID NO:131 (VH CDR1); SEQ ID NO:132 (VH CDR2), and SEQ ID NO:133 (VH CDR3)
and a light chain variable (VL) region comprising the amino acid sequences of SEQ ID NO:135 (VL CDR1), SEQ ID NO:136 (VL CDR2), and SEQ ID NO:137 (VL CDR3).

23. The method of claim 22, wherein the subject is suffering from Alzheimer's disease.

24. The method of claim 23, wherein the VH comprises the amino acid sequence of SEQ ID NO:130 and the VL comprises the amino acid sequence of SEQ ID NO:134.

25. The method of claim 22, wherein the subject is suffering from amyotrophic lateral sclerosis (ALS).

26. The method of claim 25, wherein the VH comprises the amino acid sequence of SEQ ID NO:130 and the VL comprises the amino acid sequence of SEQ ID NO:134.

27. The method of claim 22, wherein the subject is suffering from frontotemporal lobar degeneration (FTLD).

28. The method of claim 27, wherein the VH comprises the amino acid sequence of SEQ ID NO:130 and the VL comprises the amino acid sequence of SEQ ID NO:134.

29. The method of claim 22, wherein the subject is suffering from Parkinson's disease.

30. The method of claim 29, wherein the VH comprises the amino acid sequence of SEQ ID NO:130 and the VL comprises the amino acid sequence of SEQ ID NO:134.

31. The method of claim 22, wherein the VH comprises the amino acid sequence of SEQ ID NO:130 and the VL comprises the amino acid sequence of SEQ ID NO:134.

32. A method of reducing the amount or concentration of neuritic TAR-DNA-binding protein 43kDa (TDP-43) protein in the brain or spinal cord in a human subject in need thereof, comprising administering to the subject an effective amount of an anti-TDP-43 monoclonal antibody comprising
a heavy chain variable (VH) region comprising the amino acid sequences of SEQ ID NO:131 (VH CDR1), SEQ ID NO:132 (VH CDR2), and SEQ ID NO:133 (VH CDR3)
and a light chain variable (VL) region comprising the amino acid sequences of SEQ ID NO:135 (VL CDR1), SEQ ID NO:136 (VL CDR2), and SEQ ID NO:137 (VL CDR3).

33. The method of claim 32, wherein the VH comprises the amino acid sequence of SEQ ID NO:130 and the VL comprises the amino acid sequence of SEQ ID NO:134.

* * * * *

UNITED STATES PATENT AND TRADEMARK OFFICE
CERTIFICATE OF CORRECTION

PATENT NO. : 9,587,014 B2  
APPLICATION NO. : 14/354404  
DATED : March 7, 2017  
INVENTOR(S) : Nitsch et al.

Page 1 of 1

It is certified that error appears in the above-identified patent and that said Letters Patent is hereby corrected as shown below:

On the Title Page

Column 2  
Item (56), Other Publications, Line 19, delete "http:/" and insert -- http:// --.

In the Claims

Column 243  
Claim 1, Line 67, delete "TDP-43" and insert -- TAR-DNA-binding protein 43 kDa (TDP-43) --.

Columns 243-244  
Claim 1, line bridging columns 243-244, delete "TAR-DNA-binding protein 43 kDa (TDP-43)" and insert -- TDP-43 --.

Column 245  
Claim 10, Line 30, delete "claims" and insert -- claim --.

Column 246  
Claim 22, Line 14, delete "antibody," and insert -- antibody --.  
Claim 22, Line 16, delete "(VH CDR1);" and insert -- (VH CDR1), --.

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*